US012760000B2

(12) United States Patent
Beausoleil et al.

(10) Patent No.: US 12,760,000 B2
(45) Date of Patent: Oct. 13, 2026

(54) PYRIDAZINE DERIVATIVES AS MODULATORS OF NLRP3 INFLAMMASOME AND RELATED METHODS

(71) Applicant: Neumora Therapeutics, Inc., Watertown, MA (US)

(72) Inventors: Anne-Marie Beausoleil, Redwood City, CA (US); Ryan Hudson, Weston, MA (US)

(73) Assignee: Neumora Therapeutics, Inc., Watertown, MA (US)

( * ) Notice: Subject to any disclaimer, the term of this patent is extended or adjusted under 35 U.S.C. 154(b) by 260 days.

(21) Appl. No.: 18/724,789

(22) PCT Filed: Dec. 28, 2022

(86) PCT No.: PCT/US2022/082499

§ 371 (c)(1),
(2) Date: Jun. 27, 2024

(87) PCT Pub. No.: WO2023/129987

PCT Pub. Date: Jul. 6, 2023

(65) Prior Publication Data

US 2025/0074888 A1 Mar. 6, 2025

Related U.S. Application Data

(60) Provisional application No. 63/341,955, filed on May 13, 2022, provisional application No. 63/294,619, filed on Dec. 29, 2021.

(51) Int. Cl.

*C07D 401/12* (2006.01)
*A61K 31/501* (2006.01)
*A61K 31/55* (2006.01)
*C07D 403/12* (2006.01)

(52) U.S. Cl.

CPC .......... *C07D 401/12* (2013.01); *A61K 31/501* (2013.01); *A61K 31/55* (2013.01); *C07D 403/12* (2013.01)

(58) Field of Classification Search

CPC .. C07D 401/12; C07D 403/12; A61K 31/501; A61K 31/55; A61P 25/00
USPC .................................................... 514/217.05
See application file for complete search history.

(56) References Cited

U.S. PATENT DOCUMENTS

| | | | |
|---|---|---|---|
| 8,173,667 B2 | 5/2012 | Feuerbach et al. |
| 2020/0361898 A1 | 11/2020 | Farady et al. |
| 2021/0275526 A1 | 9/2021 | Babu et al. |
| 2023/0159526 A1 | 5/2023 | Dorich et al. |
| 2024/0166610 A1 | 5/2024 | Wu et al. |
| 2024/0391881 A1 | 11/2024 | Huang et al. |
| 2024/0391895 A1 | 11/2024 | Yu et al. |
| 2025/0002470 A1 | 1/2025 | Xu et al. |
| 2025/0018002 A1 | 1/2025 | Mouritzen et al. |
| 2025/0084092 A1 | 3/2025 | Inagaki et al. |
| 2025/0092051 A1 | 3/2025 | Ye et al. |
| 2025/0163060 A1 | 5/2025 | Murphy |

FOREIGN PATENT DOCUMENTS

| | | |
|---|---|---|
| CN | 115350274 A | 11/2022 |
| CN | 115381802 A | 11/2022 |
| CN | 118056822 A | 5/2024 |
| CN | 118064351 A | 5/2024 |
| CN | 118161434 A | 6/2024 |
| CN | 118161517 A | 6/2024 |
| CN | 118166086 A | 6/2024 |
| CN | 118178362 A | 6/2024 |
| CN | 118178391 A | 6/2024 |
| CN | 118178400 A | 6/2024 |
| CN | 118403040 A | 7/2024 |
| CN | 118403059 A | 7/2024 |
| CN | 118406145 A | 7/2024 |
| CN | 118414428 A | 7/2024 |
| CN | 118416046 A | 8/2024 |
| CN | 118416171 A | 8/2024 |
| CN | 118436588 A | 8/2024 |
| CN | 118436783 A | 8/2024 |

(Continued)

OTHER PUBLICATIONS

U.S. Appl. No. 18/316,994, filed May 12, 2023.
U.S. Appl. No. 18/880,470, filed Dec. 31, 2024.

*Primary Examiner* — James H Alstrum-Acevedo
*Assistant Examiner* — Sahar Inam
(74) *Attorney, Agent, or Firm* — Seed IP Law Group LLP

(57) ABSTRACT

Compounds are provided for modulating NLRP3 inflammasome generally, or for treating a NLRP3 inflammasome dependent condition more specifically, by contacting the NLRP3 inflammasome or administering to a subject in need thereof, respectively, an effective amount of a compound having structure (I): or a pharmaceutically acceptable salt, isomer, hydrate, solvate or isotope thereof, wherein $R^1$, $R^2$, $R^3$, $R^4$, $R^5$, $R^8$, $R^9$, $R^{10}$, $R^{11}$, $R^{12}$, and $R^{13}$ are as defined herein. Pharmaceutical compositions containing such compounds, as well as the compounds themselves, are also provided.

(I)

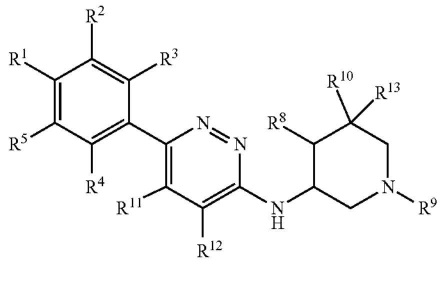

15 Claims, No Drawings

(56) References Cited

FOREIGN PATENT DOCUMENTS

| | | | | |
|---|---|---|---|---|
| CN | 118450892 | A | 8/2024 | |
| CN | 118453562 | A | 8/2024 | |
| CN | 118460662 | A | 8/2024 | |
| CN | 118806745 | A | 10/2024 | |
| CN | 118806777 | A | 10/2024 | |
| CN | 118806876 | A | 10/2024 | |
| CN | 118806901 | A | 10/2024 | |
| CN | 118831052 | A | 10/2024 | |
| CN | 118831176 | A | 10/2024 | |
| CN | 118834823 | A | 10/2024 | |
| CN | 118834946 | A | 10/2024 | |
| CN | 119258179 | A | 1/2025 | |
| CN | 119278897 | A | 1/2025 | |
| CN | 119280203 | A | 1/2025 | |
| CN | 119280209 | A | 1/2025 | |
| CN | 119280247 | A | 1/2025 | |
| CN | 119286732 | A | 1/2025 | |
| CN | 119286937 | A | 1/2025 | |
| CN | 119286975 | A | 1/2025 | |
| CN | 119300833 | A | 1/2025 | |
| CN | 119638773 | A | 3/2025 | |
| EP | 4461729 | A1 | 11/2024 | |
| EP | 4610258 | A1 | 9/2025 | |
| EP | 4613749 | A1 | 9/2025 | |
| EP | 4644380 | A1 | 11/2025 | |
| EP | 4656635 | A1 | 12/2025 | |
| NZ | 743147 | A | 3/2021 | |
| TW | 2025019659 | A | 5/2025 | |
| WO | WO-2020234715 | A1 * | 11/2020 | .............. A61P 25/00 |
| WO | 2021193897 | A1 | 9/2021 | |
| WO | 2022135567 | A1 | 6/2022 | |
| WO | 2022166890 | A1 | 8/2022 | |
| WO | 2022216971 | A1 | 10/2022 | |
| WO | 2022219546 | A1 | 10/2022 | |
| WO | 2022237780 | A1 | 11/2022 | |
| WO | 2022237781 | A1 | 11/2022 | |
| WO | 2022237782 | A1 | 11/2022 | |
| WO | 2022238347 | A1 | 11/2022 | |
| WO | 2022253936 | A1 | 12/2022 | |
| WO | 2023003002 | A1 | 1/2023 | |
| WO | 2023278438 | A1 | 1/2023 | |
| WO | 2023028534 | A1 | 3/2023 | |
| WO | 2023051761 | A1 | 4/2023 | |
| WO | 2023066377 | A1 | 4/2023 | |
| WO | 2023088856 | A1 | 5/2023 | |
| WO | 2023088987 | A1 | 5/2023 | |
| WO | 2023118366 | A1 | 6/2023 | |
| WO | 2023220408 | A1 | 11/2023 | |
| WO | 2023232917 | A1 | 12/2023 | |
| WO | 2024006559 | A1 | 1/2024 | |
| WO | 2024121086 | A1 | 6/2024 | |
| WO | 2024121184 | A1 | 6/2024 | |
| WO | 2024123982 | A1 | 6/2024 | |
| WO | 2024138045 | A1 | 6/2024 | |
| WO | 2024157205 | A1 | 8/2024 | |
| WO | 2024157953 | A1 | 8/2024 | |
| WO | 2024160690 | A1 | 8/2024 | |
| WO | 2024160691 | A1 | 8/2024 | |
| WO | 2024160692 | A1 | 8/2024 | |
| WO | 2024160693 | A1 | 8/2024 | |
| WO | 2024160694 | A1 | 8/2024 | |
| WO | 2024217442 | A1 | 10/2024 | |
| WO | 2024218100 | A1 | 10/2024 | |
| WO | 2025009945 | A1 | 1/2025 | |
| WO | 2025045961 | A1 | 3/2025 | |
| WO | 2025058329 | A1 | 3/2025 | |
| WO | 2025059069 | A1 | 3/2025 | |
| WO | 2025059165 | A1 | 3/2025 | |
| WO | 2025059481 | A1 | 3/2025 | |
| WO | 2025067343 | A1 | 4/2025 | |
| WO | 2025067411 | A1 | 4/2025 | |
| WO | 2025106863 | A1 | 5/2025 | |

* cited by examiner

PYRIDAZINE DERIVATIVES AS MODULATORS OF NLRP3 INFLAMMASOME AND RELATED METHODS

BACKGROUND

Technical Field

The invention relates to modulators of NLRP3 inflammasome, to products containing the same, as well as to methods of their use and preparation.

Description of the Related Art

The NOD-like receptor protein 3 (NLRP3) is a key protein that interacts with, apoptosis-associated speck-like protein (ASC) and procaspase-1 to form the NLRP3 inflammasome. The activation of the NLRP3 inflammasome produces inflammatory mediators, such as interleukin-1β (IL-1β) and interleukin-18 (IL-18), thereby contributing to the activation of the innate immune system. The dysregulation of innate immunity contributes to various diseases.

The innate immune response protects the host from invading microorganisms. The formation of the NLRP3 inflammasome activates caspase-1, which leads to the maturation and secretion of IL-1β and IL-18, cleavage of gasdermin-D and, finally the initiation of cell death via pyroptosis. The system is alerted to the presence of the invading microorganism by cytokine release and is working to resolve the inflammation by eliminating the infected cells.

However, nonmicrobial compounds of either endogenous or exogenous origin are also effective inducers of NLRP3 inflammation, allergic responses, or other forms of inflammation. For example, NLRP3 may be implicated in Parkinson's disease and/or Alzheimer's disease, suggesting that misfolded proteins form aggregates that lead to the activation of the NLRP3 inflammasome. Environmental particulates such as inhaled asbestos and silica also activate NLRP3 inflammasome, and the high levels of IL-1β are involved in the development of asbestosis and silicosis, two progressive pulmonary diseases leading to fibrosis.

Emerging studies have revealed the involvement of increased production of IL-1β and IL-18 by the NLRP3 inflammasome can contribute to the onset and progression of various diseases such as neuroinflammation-related disorders, for example, brain infection, acute injury, multiple sclerosis, Alzheimer's disease, and neurodegenerative diseases; cardiovascular diseases, cardiovascular risk reduction, atherosclerosis, type I and type II diabetes and related complications, inflammatory skin diseases, acne, hidradenitis suppurativa, asthma, age-related macular degeneration, or cancer related diseases. Those disorders that are immune or inflammatory in nature are usually difficult to diagnose or treat efficiently.

Accordingly, there is a need in the art for compounds that modulate the NLRP3 inflammasome for the purpose of treating diseases in which modulation of the NLRP3 inflammasome would be beneficial. The present invention fulfills these needs and provides other advantages as evident from the following description.

BRIEF SUMMARY

In an embodiment a compound is provided having structure (I):

(I)

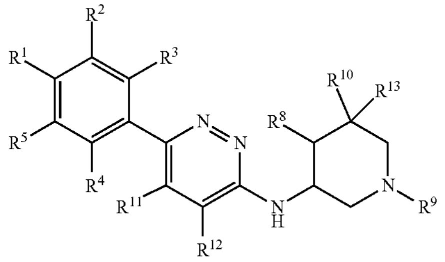

or a pharmaceutically acceptable salt, isomer, hydrate, solvate or isotope thereof, wherein $R^1$, $R^2$, $R^3$, $R^4$, $R^5$, $R^8$, $R^9$, $R^{10}$, $R^{11}$, $R^{12}$, and $R^{13}$ are as defined herein.

In another embodiment, pharmaceutical compositions are provided comprising a carrier or excipient and a compound having structure (I), or a pharmaceutically acceptable salt, isomer, hydrate, solvate or isotope thereof.

In a further embodiment, a method is provided for treating a NLRP3 inflammasome-dependent condition by administering to a subject in need thereof an effective amount of a compounds of structure (I), or a pharmaceutically acceptable salt, isomer, hydrate, solvate or isotope thereof, or a pharmaceutical composition comprising the same. In some embodiments, the NLRP3 inflammasome-dependent condition is a neuroinflammation-related disorder or a neurodegenerative disease.

DETAILED DESCRIPTION

Definitions

As used herein, the following terms have the meaning defined below, unless the context indicates otherwise.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "one", "a", "an" and "the" include plural references unless the context clearly dictates otherwise.

"Modulating" NLRP3 inflammasome means that the compound interacts with NLRP3 in a manner such that it blocks its ATPase function and the downstream formation of the NLRP3 inflammasome complex. In the above context, the compound acts to inhibit, or block, activation of the NLRP3 inflammasome and therefore the compound can also be described as an inhibitor.

NLRP3 refers to NOD-Like Receptor Protein 3. NLRP3 is a protein-coding gene, and an exemplary sequence may be found at https://www.uniprot.org/uniprot/Q96P20. NLRP3 functions as an ATPase that is auto-inhibited under normal conditions. NLRP3, unlike other inflammasomes, requires a two step activation process, which can be triggered by a variety of pathogen-associated molecular patterns (PAMPs) and damage-associated molecular patterns (DAMPs). The first step primes the NLRP3 inflammasome via recognition of PAMPs, DAMPs, or pathological species via pattern recognition receptors (PRRs) (e.g. Toll-like receptors). Priming increases NLRP3, pro-IL1β, and pro-IL18 expression. Activation of NLRP3 is triggered by a second signal, such as ATP, $K^+$ efflux, other cellular stress, or pathological species, which leads to ATP hydrolysis and activation of the enzyme. This activation leads to oligomerization of the inflammasome complex, resulting in auto-cleavage and activation of caspase-1. Active caspase-1 then cleaves pro-IL1β and pro-IL18. Active IL1β and IL18 then are released from the cell through a gasdermin D pore, and release of such cytokines triggers a downstream inflammatory response and cell death via pyroptosis.

"Effective amount" refers to a quantity of a specified agent sufficient to achieve a desired effect in a subject being treated with that agent. Ideally, an effective amount of an agent is an amount sufficient to inhibit or treat the disease without causing substantial toxicity in the subject. The effective amount of an agent will be dependent on the subject being treated, the severity of the affliction, and the manner of administration of the pharmaceutical composition. Methods of determining an effective amount of the disclosed compound sufficient to achieve a desired effect in a subject will be understood by those of skill in the art in light of this disclosure.

"Alkyl" means a saturated or unsaturated straight chain or branched alkyl group having from 1 to 8 carbon atoms, in some embodiments from 1 to 6 carbon atoms, in some embodiments from 1 to 4 carbon atoms, and in some embodiments from 1 to 3 carbon atoms. Examples of saturated straight chain alkyl groups include, but are not limited to, methyl, ethyl, n-propyl, n-butyl, n-pentyl-, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups.

"Halo" or "halogen" refers to fluorine, chlorine, bromine, and iodine (i.e., F, Cl, Br, and I).

"Hydroxyl" refers to —OH.

"Cyano" refers to —CN.

"Carboxyl" refers to —C(O)OH.

"Haloalkyl" refers to alkyl as defined above with one or more hydrogen atoms replaced with halogen. Examples of haloalkyl groups include, but are not limited to, $—CF_3$, $—CHF_2$, and the like.

"Cyanoalkyl" refers to cyano as described above joined by way of an alkyl as described above (i.e., -alkyl-CN). Examples of cyanoalkyl groups include, but are not limited to

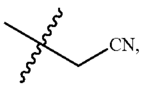 [SMILES: *CC#N]

and the like.

"Alkoxy" refers to alkyl as defined above joined by way of an oxygen atom (i.e., —O-alkyl, or in certain embodiments $—OC_{1-6}$ alkyl). Examples of alkoxy groups include, but are not limited to, methoxy, ethoxy, n-propoxy, n-butoxy, isopropoxy, sec-butoxy, tert-butoxy, and the like.

"Haloalkoxy" refers to haloalkyl as defined above joined by way of an oxygen atom (i.e., —O-haloalkyl). Examples of haloalkoxy groups include, but are not limited to, $—OCF_3$, and the like.

"Cycloalkyl" refers to non-aromatic ring moieties containing 3 or more ring members. In some embodiments, cycloalkyl includes 3 to 5 ring members. For example, cycloalkyl includes cyclopropyl, cyclobutyl, and cyclopentyl.

"Heterocycle" refers to aromatic and non-aromatic ring moieties containing 3 or more ring members, of which one or more is a heteroatom such as, but not limited to, N, O, S, or P. In some embodiments, heterocyclyl include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein.

Heterocyclyl groups also include fused ring species including those having fused aromatic and non-aromatic groups. A heterocyclyl group also includes polycyclic ring systems containing a heteroatom such as, but not limited to, quinuclidyl, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Isomer" is used herein to encompass all chiral, diastereomeric or racemic forms of a structure (also referred to as a stereoisomer, as opposed to a structural or positional isomer), unless a particular stereochemistry or isomeric form is specifically indicated. Such compounds can be enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention. The isomers resulting from the presence of a chiral center comprise a pair of nonsuperimposable-isomers that are called "enantiomers." Single enantiomers of a pure compound are optically active (i.e., they are capable of rotating the plane of plane polarized light and designated R or S).

"Isolated optical isomer" means a compound which has been substantially purified from the corresponding optical isomer(s) of the same formula. For example, the isolated isomer may be at least about 80%, at least 80% or at least 85% pure by weight. In other embodiments, the isolated isomer is at least 90% pure or at least 98% pure, or at least 99% pure by weight.

"Substantially enantiomerically or diastereomerically" pure means a level of enantiomeric or diastereomeric enrichment of one enantiomer with respect to the other enantiomer or diastereomer of at least about 80%, and more specifically in excess of 80%, 85%, 90%, 95%, 98%, 99%, 99.5% or 99.9%.

The terms "racemate" and "racemic mixture" refer to an equal mixture of two enantiomers. A racemate is labeled "(±)" because it is not optically active (i.e., will not rotate plane-polarized light in either direction since its constituent enantiomers cancel each other out). All compounds with an asterisk (*) adjacent to a tertiary or quaternary carbon are optically active isomers, which may be purified from the respective racemate and/or synthesized by appropriate chiral synthesis.

A "hydrate" is a compound that exists in combination with water molecules. The combination can include water in stoichiometric quantities, such as a monohydrate or a dihydrate, or can include water in random amounts. As the term is used herein a "hydrate" refers to a solid form; that is, a compound in a water solution, while it may be hydrated, is not a hydrate as the term is used herein.

A "solvate" is similar to a hydrate except that a solvent other that water is present. For example, methanol or ethanol can form an "alcoholate", which can again be stoichiometric or non-stoichiometric. As the term is used herein a "solvate" refers to a solid form; that is, a compound in a solvent solution, while it may be solvated, is not a solvate as the term is used herein.

"Isotope" refers to atoms with the same number of protons but a different number of neutrons, and an isotope of a compound of structure (I) includes any such compound wherein one or more atoms are replaced by an isotope of that atom. For example, carbon 12, the most common form of carbon, has six protons and six neutrons, whereas carbon 13 has six protons and seven neutrons, and carbon 14 has six protons and eight neutrons. Hydrogen has two stable isotopes, deuterium (one proton and one neutron) and tritium (one proton and two neutrons). While fluorine has a number of isotopes, fluorine-19 is longest-lived. Thus, an isotope of a compound having the structure of structure (I) includes, but not limited to, compounds of structure (I) wherein one or more carbon 12 atoms are replaced by carbon-13 and/or carbon-14 atoms, wherein one or more hydrogen atoms are replaced with deuterium and/or tritium, and/or wherein one or more fluorine atoms are replaced by fluorine-19.

"Salt" generally refers to an organic compound, such as a carboxylic acid or an amine, in ionic form, in combination with a counter ion. For example, salts formed between acids in their anionic form and cations are referred to as "acid addition salts". Conversely, salts formed between bases in the cationic form and anions are referred to as "base addition salts."

The term "pharmaceutically acceptable" refers an agent that has been approved for human consumption and is generally non-toxic. For example, the term "pharmaceutically acceptable salt" refers to nontoxic inorganic or organic acid and/or base addition salts (see, e.g., Lit et al., Salt Selection for Basic Drugs, Int. J. Pharm., 33, 201-217, 1986) (incorporated by reference herein).

Pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N'dibenzylethylenediamine, chloroprocaine, choline, diethanolamine, ethylenediamine, meglumine (N-methylglucamine), and procaine.

Pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aromatic aliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, hippuric, malonic, oxalic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, βhydroxybutyric, salicylic, galactaric, and galacturonic acid.

The compounds of the disclosure (i.e., compounds of structure (I) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also included.

Although pharmaceutically unacceptable salts are not generally useful as medicaments, such salts may be useful, for example as intermediates in the synthesis of compounds having the structure of Formula I, for example in their purification by recrystallization.

As used herein, the phrase "NLRP3 inflammasome dependent condition" means a condition wherein modulating NLRP3 provides a medical benefit to the patient or subject.

In some embodiments, is provided a method of modulating NLRP3 inflammasome activity by contacting NLRP3 inflammasome with an effective amount of a compound as described herein, or a pharmaceutically acceptable salt, isomer, hydrate, solvate or isotope thereof, or a pharmaceutical composition comprising the same.

In some embodiments, is provided a method of treating a NLRP3 inflammasome dependent condition by administering to a subject in need thereof an effective amount of a compound as described herein, or a pharmaceutically acceptable salt, isomer, hydrate, solvate or isotope thereof, or a pharmaceutical composition comprising the same. In certain embodiments, the NLRP3 inflammasome dependent condition is neuroinflammation-related disorders or neurodegenerative diseases.

In some embodiments, the NLRP3 inflammasome dependent condition is inflammation, an inflammatory disease, an immune disease, cancer, infections including viral infections; central nervous system diseases, metabolic diseases, cardiovascular diseases, respiratory diseases, liver diseases, renal diseases, ocular diseases, skin diseases, psychological diseases or blood diseases.

In one embodiment, the NLRP3 inflammasome dependent condition is neuroinflammation-related disorders or neurodegenerative diseases.

In one embodiment, the NLRP3 inflammasome dependent condition is neuroinflammation-related disorders or neurodegenerative diseases.

In one embodiment, the invention provides a method for inhibiting NLRP3 inflammasome with an effective amount of a pharmaceutical composition as described herein.

In another embodiment, the invention provides a method of treating a NLRP3 inflammasome dependent condition by administering to a subject in need thereof an effective amount of a pharmaceutical composition as described herein. In certain embodiments, the NLRP3 inflammasome dependent condition is a neuroinflammation-related disorder(s) or a neurodegenerative disease(s).

As used herein the phrase "inflammation" refers to inflammation, including inflammation occurring as a result of an inflammatory disorder, e.g. an autoinflammatory disease, inflammation occurring as a symptom of a non-inflammatory disorder, inflammation occurring as a result of infection, or inflammation secondary to trauma, injury or autoimmunity. Examples of inflammation that may be treated or prevented include inflammatory responses occurring in connection with, or as a result of:

(a) a skin condition such as contact hypersensitivity, bullous pemphigoid, sunburn, psoriasis, atopical dermatitis, contact dermatitis, allergic contact dermatitis, seborrhoetic dermatitis, lichen planus, scleroderma, pemphigus, epidermolysis bullosa, urticaria, erythemas, or alopecia;

(b) a joint condition such as osteoarthritis, systemic juvenile idiopathic arthritis, adult-onset Still's disease, relapsing polychondritis, rheumatoid arthritis, juvenile chronic arthritis, crystal induced arthropathy (e.g. pseudo-gout, gout), or a seronegative spondyloarthropathy (e.g. ankylosing spondylitis, psoriatic arthritis or Reiter's disease);

(c) a muscular condition such as polymyositis or myasthenia gravis;

(d) a gastrointestinal tract condition such as inflammatory bowel disease (including Crohn's disease and ulcerative colitis), gastric ulcer, coeliac disease, proctitis, pancreatitis, eosinopilic gastro-enteritis, mastocytosis, antiphospholipid syndrome, or a food-related allergy which may have effects remote from the gut (e.g., migraine, rhinitis or eczema);

(e) a respiratory system condition such as chronic obstructive pulmonary disease (COPD), asthma (including bronchial, allergic, intrinsic, extrinsic or dust asthma, and particularly chronic or inveterate asthma, such as late asthma and airways hyper-responsiveness), bronchitis, rhinitis (including acute rhinitis, allergic rhinitis, atrophic rhinitis, chronic rhinitis, rhinitis caseosa, hypertrophic rhinitis, rhinitis pumlenta, rhinitis sicca, rhinitis medicamentosa, membranous rhinitis, seasonal rhinitis e.g. hay fever, and vasomotor rhinitis), sinusitis, idiopathic pulmonary fibrosis (IPF), sarcoidosis, farmer's lung, silicosis, asbestosis, adult respiratory distress syndrome, hypersensitivity pneumonitis, or idiopathic interstitial pneumonia;

(f) a vascular condition such as atherosclerosis, Behcet's disease, vasculitides, or Wegener's granulomatosis;

(g) an immune condition, e.g. autoimmune condition, such as systemic lupus erythematosus (SLE), Sjogren's syndrome, systemic sclerosis, Hashimoto's thyroiditis, type I diabetes, idiopathic thrombocytopenia purpura, or Graves disease;

(h) an ocular condition such as uveitis, allergic conjunctivitis, or vernal conjunctivitis;

(i) a nervous condition such as multiple sclerosis or encephalomyelitis;

(j) an infection or infection-related condition, such as Acquired Immunodeficiency Syndrome (AIDS), acute or chronic bacterial infection, acute or chronic parasitic infection, acute or chronic viral infection, acute or chronic fungal infection, meningitis, hepatitis (A, B or C, or other viral hepatitis), peritonitis, pneumonia, epiglottitis, malaria, dengue hemorrhagic fever, leishmaniasis, streptococcal myositis, *Mycobacterium tuberculosis, Mycobacterium avium intracellulare, Pneumocystis carinii* pneumonia, orchitis/epidydimitis, *legionella*, Lyme disease, influenza A, epstein-barr virus, viral encephalitis/aseptic meningitis, or pelvic inflammatory disease;

(k) a renal condition such as mesangial proliferative glomerulonephritis, nephrotic syndrome, nephritis, glomerular nephritis, acute renal failure, uremia, or nephritic syndrome;

(l) a lymphatic condition such as Castleman's disease;

(m) a condition of, or involving, the immune system, such as hyper IgE syndrome, lepromatous leprosy, familial hemophagocytic lymphohistiocytosis, or graft versus host disease;

(n) a hepatic condition such as chronic active hepatitis, non-alcoholic steatohepatitis (NASH), alcohol-induced hepatitis, non-alcoholic fatty liver disease (NAFLD), alcoholic fatty liver disease (AFLD), alcoholic steatohepatitis (ASH) or primary biliary cirrhosis;

(o) a cancer, including those cancers listed herein below;

(p) a burn, wound, trauma, haemorrhage or stroke;

(q) radiation exposure; and/or (r) obesity; and/or (s) pain such as inflammatory hyperalgesia.

As used herein the phrase "an inflammatory disease" means for example, inflammation occurring as a result of an inflammatory disorder, e.g. an autoinflammatory disease, such as cryopyrin-associated periodic syndromes (CAPS), Muckle-Wells syndrome (MWS), familial cold autoinflammatory syndrome (FCAS), familial Mediterranean fever (FMF), neonatal onset multisystem inflammatory disease (NOMID), Majeed syndrome, pyogenic arthritis, pyoderma gangrenosum and acne syndrome (PAPA), adult-onset Still's disease (AOSD), haploinsufficiency of A20 (HA20), pediatric granulomatous arthritis (PGA), PLCG2-associated antibody deficiency and immune dysregulation (PLAID), PLCG2-associated autoinflammatory, antibody deficiency and immune dysregulation (APLAID), or sideroblastic anaemia with B-cell immunodeficiency, periodic fevers and developmental delay (SIFD).

As used herein the phrase "an immune disease" means for example, auto-immune diseases, such as acute disseminated encephalitis, Addison's disease, ankylosing spondylitis, antiphospholipid antibody syndrome (APS), anti-synthetase syndrome, aplastic anemia, autoimmune adrenalitis, autoimmune hepatitis, autoimmune oophoritis, autoimmune polyglandular failure, autoimmune thyroiditis, Coeliac disease, Crohn's disease, type 1 diabetes (T1D), Goodpasture's syndrome, Graves' disease, Guillain-Barre syndrome (GBS), Hashimoto's disease, idiopathic thrombocytopenic purpura, Kawasaki's disease, lupus erythematosus including systemic lupus erythematosus (SLE), multiple sclerosis (MS) including primary progressive multiple sclerosis (PPMS), secondary progressive multiple sclerosis (SPMS) and relapsing remitting multiple sclerosis (RRMS), myasthenia gravis, opsoclonus myoclonus syndrome (OMS), optic neuritis, Ord's thyroiditis, pemphigus, pernicious anaemia, polyarthritis, primary biliary cirrhosis, rheumatoid arthritis (RA), psoriatic arthritis, juvenile idiopathic arthritis or Still's disease, refractory gouty arthritis, Reiter's syndrome, Sjogren's syndrome, systemic sclerosis a systemic connective tissue disorder, Takayasu's arteritis, temporal arteritis, warm autoimmune hemolytic anemia, Wegener's granulomatosis, alopecia universalis, Beliefs disease, Chagas' disease, dysautonomia, endometriosis, hidradenitis suppurativa (HS), interstitial cystitis, neuromyotonia, psoriasis, sarcoidosis, scleroderma, ulcerative colitis, Schnitzler syndrome, macrophage activation syndrome, Blau syndrome, giant cell arteritis, vitiligo or vulvodynia.

As used herein the phrase "cancer" means for example, lung cancer, renal cell carcinoma, non-small cell lung carcinoma (NSCLC), Langerhans cell histiocytosis (LCH), myeloproliferative neoplams (MPN), pancreatic cancer, gastric cancer, myelodysplastic syndrome (MDS), leukaemia including acute lymphocytic leukaemia (ALL) and acute myeloid leukaemia (AML), promyelocytic leukemia (APML, or APL), adrenal cancer, anal cancer, basal and squamous cell skin cancer, bile duct cancer, bladder cancer, bone cancer, brain and spinal cord tumours, breast cancer, cervical cancer, chronic lymphocytic leukaemia (CLL), chronic myeloid leukaemia (CML), chronic myelomonocytic leukaemia (CMML), colorectal cancer, endometrial cancer, oesophagus cancer, Ewing family of tumours, eye cancer, gallbladder cancer, gastrointestinal carcinoid tumours, gastrointestinal stromal tumour (GIST), gestational trophoblastic disease, glioma, Hodgkin lymphoma, Kaposi sarcoma, kidney cancer, laryngeal and hypopharyngeal cancer, liver cancer, lung carcinoid tumour, lymphoma including cutaneous T cell lymphoma, malignant mesothelioma, melanoma skin cancer, Merkel cell skin cancer, multiple myeloma, nasal cavity and paranasal sinuses cancer, nasopharyngeal cancer, neuroblastoma, non-Hodgkin lymphoma, non-small cell lung cancer, oral cavity and oropharyngeal cancer, osteosarcoma, ovarian cancer, penile cancer, pituitary tumours, prostate cancer, retinoblastoma, rhabdomyosarcoma, salivary gland cancer, skin cancer, small cell lung cancer, small intestine cancer, soft tissue sarcoma, stomach cancer, testicular cancer, thymus cancer, thyroid cancer including anaplastic thyroid cancer, uterine sarcoma, vaginal cancer, vulvar cancer, Waldenstrom macroglobulinemia, and Wilms tumour.

As used herein the phrase "infections including viral infections" means for example, viral infections (e.g. from influenza virus, human immunodeficiency virus (HIV), alphavirus (such as Chikungunya and Ross River virus), flaviviruses (such as Dengue virus and Zika virus), herpes viruses (such as Epstein Barr Virus, cytomegalovirus, Varicella-zoster virus, and KSHV), poxyiruses (such as vaccinia virus (Modified vaccinia virus Ankara) and Myxoma virus), adenoviruses (such as Adenovirus 5), or papillomavirus), bacterial infections (e.g. from *Staphylococcus aureus, Helicobacter pylori, Bacillus anthracis, Bordatella pertussis, Burkholderia pseudomallei, Corynebacterium diptheriae, Clostridium tetani, Clostridium botulinum, Streptococcus pneumoniae, Streptococcus pyogenes, Listeria monocytogenes, Hemophilus influenzae, Pasteurella multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickettsia rickettsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* or *Yersinia pestis*), fungal infections (e.g. from *Candida* or *Aspergillus* species), protozoan infections (e.g. from *Plasmodium, Babesia, Giardia, Entamoeba, Leishmania* or Trypanosomes), helminth infections (e.g. from *schistosoma*, roundworms, tapeworms or flukes), and prion infections.

As used herein the phrase "central nervous system diseases" means for example, Parkinson's disease, Alzheimer's disease, Frontotemporal dementia, dementia, motor neuron disease, Huntington's disease, cerebral malaria, brain injury from pneumococcal meningitis, intracranial aneurysms, traumatic brain injury, multiple sclerosis, and amyotrophic lateral sclerosis.

As used herein the phrase "neuroinflammation-related diseases" means for example, multiple sclerosis, brain infection, acute injury, neurodegenerative disease, Parkinson's disease or Alzheimer's disease.

As used herein the phrase "neurodegenerative disease" means for example, Alzheimer's disease, Parkinson's disease, multiple sclerosis, or amyotrophic lateral sclerosis.

In one embodiment, neurodegenerative diseases are characterized by deep involvement of cell mediating neuroinflammatory processes.

As used herein the phrase "metabolic diseases" means for example, type 2 diabetes (T2D), atherosclerosis, obesity, gout, and pseudo-gout.

As used herein the phrase "cardiovascular diseases" means for example, hypertension, ischaemia, reperfusion injury including post-MI ischemic reperfusion injury, stroke including ischemic stroke, transient ischemic attack, myocardial infarction including recurrent myocardial infarction, heart failure including congestive heart failure and heart failure with preserved ejection fraction, embolism, aneurysms including abdominal aortic aneurysm, cardiovascular risk reduction (CvRR), and pericarditis including Dressler's syndrome.

As used herein the phrase "respiratory diseases" means for example, chronic obstructive pulmonary disorder (COPD), asthma such as allergic asthma and steroid-resistant asthma, asbestosis, silicosis, nanoparticle induced inflammation, cystic fibrosis, and idiopathic pulmonary fibrosis.

As used herein the phrase "liver diseases" means for example, non-alcoholic fatty liver disease (NAFLD) and nonalcoholic steatohepatitis (NASH) including advanced fibrosis stages F3 and F4, alcoholic fatty liver disease (AFLD), and alcoholic steatohepatitis (ASH).

As used herein the phrase "renal diseases" means for example, acute kidney disease, hyperoxaluria, chronic kidney disease, oxalate nephropathy, nephrocalcinosis, glomerulonephritis, and diabetic nephropathy;

As used herein the phrase "ocular diseases" means for example, diseases of the ocular epithelium, age-related macular degeneration (AMD) (dry and wet), uveitis, corneal infection, diabetic retinopathy, optic nerve damage, dry eye, and glaucoma.

As used herein the phrase "skin diseases" means for example, dermatitis such as contact dermatitis and atopic dermatitis, contact hypersensitivity, sunburn, skin lesions, hidradenitis suppurativa (HS), other cyst-causing skin diseases, and acne conglobate.

As used herein the phrase "psychological diseases" means for example, depression, and psychological stress.

As used herein the phrase "blood diseases" means for example, sickle cell disease.

As used herein, the term "administration" refers to providing a compound, or a pharmaceutical composition comprising the compound as described herein. The compound or composition can be administered by another person to the subject or it can be self-administered by the subject. Non-limiting examples of routes of administration are oral, parenteral (e.g., intravenous), or topical.

As used herein, the term "treatment" refers to an intervention that ameliorates a sign or symptom of a disease or pathological condition. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A prophylactic treatment is a treatment administered to a subject who does not exhibit signs of a disease or exhibits only early signs, for the purpose of decreasing the risk of developing pathology. A therapeutic treatment is a treatment administered to a subject after signs and symptoms of the disease have developed.

As used herein, the term "subject" refers to an animal (e.g., a mammal, such as a human). A subject to be treated according to the methods described herein may be one who has been diagnosed with a NLRP3 inflammasome dependent condition, such as inflammation, an inflammatory disease, an immune disease, cancer, infections including viral infections; central nervous system diseases, metabolic diseases, cardiovascular diseases, respiratory diseases, liver diseases, renal diseases, ocular diseases, skin diseases, psychological diseases or blood diseases.

Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition. The term "patient" may be used interchangeably with the term "subject." A subject may refer to an adult or pediatric subject.

Compounds

As detailed above, the present disclosure provides compounds showing significant activity as NLRP3 inflammasome antagonists (i.e., as NLRP3 inflammasome inhibitors).

Accordingly, in one embodiment, a compound is provided having structure (A):

(A)

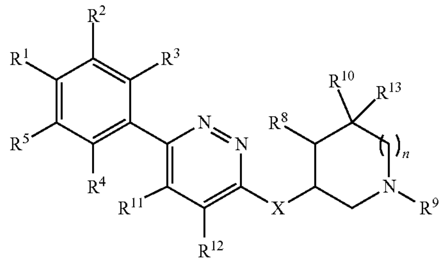

or a pharmaceutically acceptable salt, isomer, hydrate, solvate or isotope thereof, wherein:

X is O or $NR^{15}$;

$R^1$ is H, OH, $CF_3$, $CHF_2$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2;

wherein if $R^1$ is F, X is $NR^{15}$ and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

Accordingly, in one embodiment, a compound is provided having structure (A):

(A)

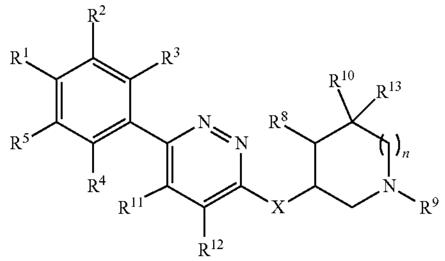

or a pharmaceutically acceptable salt, isomer, hydrate, solvate or isotope thereof, wherein:

X is O or $NR^{15}$;

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl; $R^{15}$ is H, $C_{1-6}$ alkyl, or $C_{3-5}$ cycloalkyl;

n is 1 or 2;

wherein if $R^1$ is F, X is $NR^{15}$ and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

Accordingly, in one embodiment, a compound is provided having structure (A):

(A)

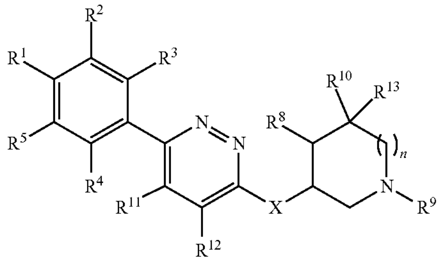

or a pharmaceutically acceptable salt, isomer, hydrate, solvate or isotope thereof, wherein:

X is O or $NR^{15}$;

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$, or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl; $R^{15}$ is H, $C_{1-6}$ alkyl, or $C_{3-5}$ cycloalkyl;

n is 1 or 2;

wherein if $R^1$ is F, X is $NR^{15}$ and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

Accordingly, in one embodiment, a compound is provided having structure (A):

(A)

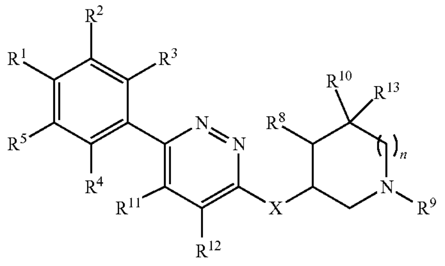

or a pharmaceutically acceptable salt, isomer, hydrate, solvate or isotope thereof, wherein:

X is O or $NR^{15}$;

$R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$, or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl; $R^{15}$ is H, $C_{1-6}$ alkyl, or $C_{3-5}$ cycloalkyl;

n is 1 or 2;

wherein if $R^1$ is F, X is $NR^{15}$ and $R^2$, $R^3$, $R^4$, $R^5$, $R^8$, $R^{11}$ and $R^{12}$ are each H, then $R^9$ is not ethyl; and wherein if $R^1$ is $CH_3$, then $R^9$ is not H.

In one embodiment, a compound is provided having structure (A'):

(A')

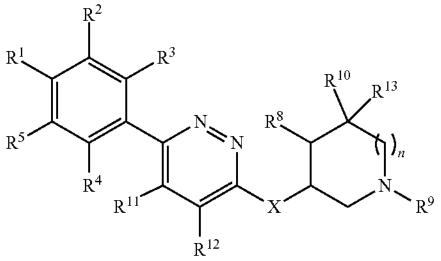

or a pharmaceutically acceptable salt, isomer, hydrate, solvate or isotope thereof, wherein:

(1) X is O or $NR^{15}$;

$R^1$ is F;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2;

(2) X is O or $NR^{15}$;

$R^1$ is H or methyl;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2; or (3) X is O or $NR^{15}$;

$R^1$ is OH, $CF_3$, $CHF_2$, $C_{2-6}$ alkyl, $C_{3-5}$ cycloalkyl, CN, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;
$R^{15}$ is H or $C_{1-6}$ alkyl; and
n is 1 or 2.

In one embodiment, a compound is provided having structure (A'):

(A')

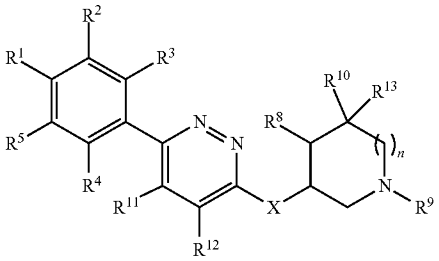

or a pharmaceutically acceptable salt, isomer, hydrate, solvate or isotope thereof, wherein:

(1) X is O or $NR^{15}$;
$R^1$ is F;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2;
(2) X is O or $NR^{15}$;
$R^1$ is H or methyl;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2; or
(3) X is O or $NR^{15}$;
$R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl, or $C_{3-5}$ cycloalkyl; and
n is 1 or 2.

In one embodiment, a compound is provided having structure (A'):

(A')

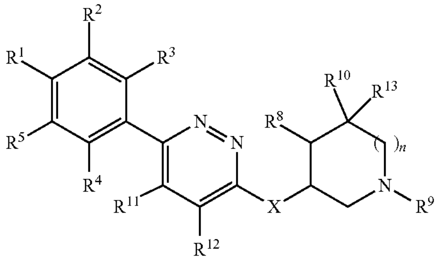

or a pharmaceutically acceptable salt, isomer, hydrate, solvate or isotope thereof, wherein:

(1) X is O or $NR^{15}$;
$R^1$ is F;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2;
(2) X is O or $NR^{15}$;
$R^1$ is H or methyl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2; or
(3) X is O or $NR^{15}$;
$R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl, or $C_{3-5}$ cycloalkyl; and
n is 1 or 2.

In one embodiment, a compound is provided having structure (A'):

(A')

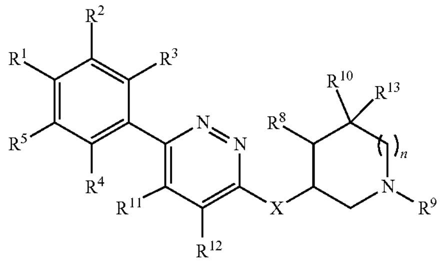

or a pharmaceutically acceptable salt, isomer, hydrate, solvate or isotope thereof, wherein:

(1) X is O or $NR^{15}$;
$R^1$ is F;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2;
(2) X is O or $NR^{15}$;
$R^1$ is H or methyl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2;
(3) X is O or $NR^{15}$;
$R^1$ is $CF_3$ or Cl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl, or $C_{3-5}$ cycloalkyl; and
n is 1 or 2; or
(4) X is O or $NR^{15}$;
$R^1$ is OH, $CHF_2$, $C_{2-6}$ alkyl, $C_{3-5}$ cycloalkyl, CN, $C_{1-6}$ cyanoalkyl, C(O)OH, $OC_{1-6}$ alkyl or $OCF_3$;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl, or $C_{3-5}$ cycloalkyl; and
n is 1 or 2.

In one embodiment, a compound is provided having structure (A'):

(A')

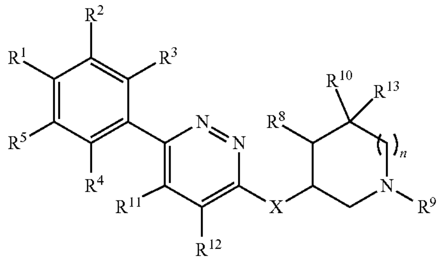

or a pharmaceutically acceptable salt, isomer, hydrate, solvate or isotope thereof, wherein:

(1) X is O or $NR^{15}$;
$R^1$ is F;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or halo;
$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2;
(2) X is O or $NR^{15}$;
$R^1$ is methyl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or halo;
$R^{11}$ and $R^{12}$ are each, independently, H, halo, $CF_3$, $C_{1-6}$ alkyl, CN, OH or $OC_{1-6}$ alkyl;
$R^{15}$ is H, $C_{1-6}$ alkyl or $C_{3-5}$ cycloalkyl;
n is 1 or 2; or
(3) X is O or $NR^{15}$;
$R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl, or $C_{3-5}$ cycloalkyl; and n is 1 or 2.

In one embodiment, a compound is provided having structure (B):

(B)

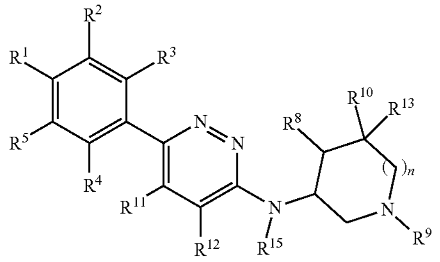

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (B):

(B)

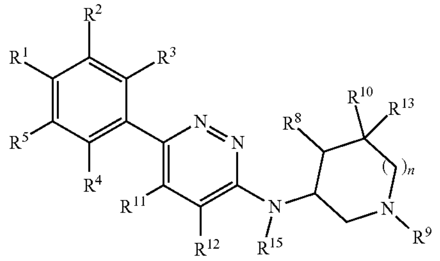

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (B):

(B)

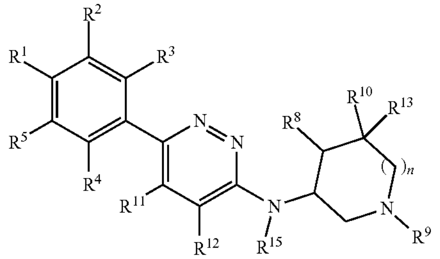

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (B):

(B)

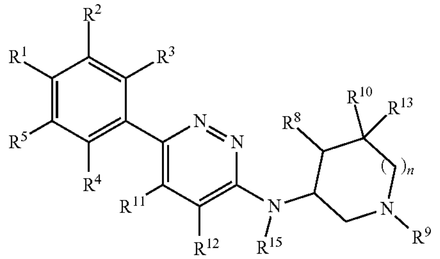

or a pharmaceutically acceptable salt, isomer, hydrate, solvate or isotope thereof, wherein:

$R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (B'):

(B')

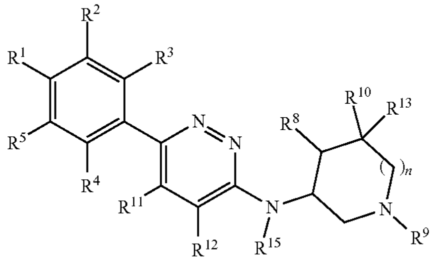

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl;

n is 1 or 2; or (3) $R^1$ is OH, $CF_3$, $CHF_2$, $C_{2-6}$ alkyl, $C_{3-5}$ cycloalkyl, CN, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl; and n is 1 or 2.

In one embodiment, a compound is provided having structure (B'):

(B')

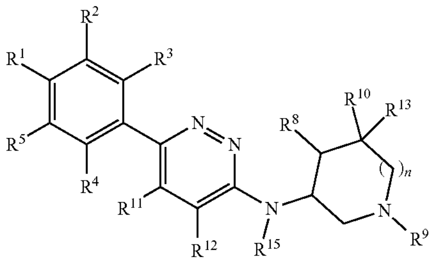

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl, $C_{3-5}$ cycloalkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2; or (3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl; and n is 1 or 2.

In one embodiment, a compound is provided having structure (B'):

(B')

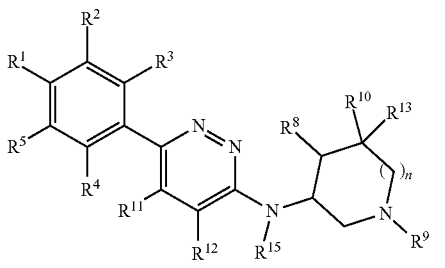

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl, $C_{3-5}$ cycloalkyl;

n is 1 or 2;

(2) $R^1$ is H or methyl;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2; or (3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl; and n is 1 or 2.

In one embodiment, a compound is provided having structure (B'):

(B')

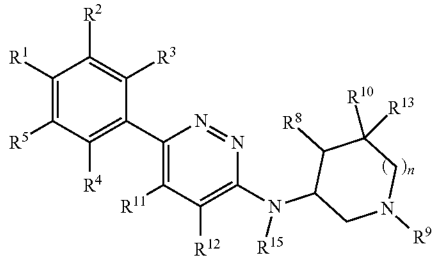

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl, $C_{3-5}$ cycloalkyl;

n is 1 or 2;

(2) $R^1$ is H or methyl;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

(3) $R^1$ is $CF_3$ or Cl;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl; and n is 1 or 2; or (4) $R^1$ is OH, $CHF_2$, $C_{2-6}$ alkyl, $C_{3-5}$ cycloalkyl, CN, $C_{1-6}$ cyanoalkyl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl; and n is 1 or 2.

In one embodiment, a compound is provided having structure (B'):

(B')

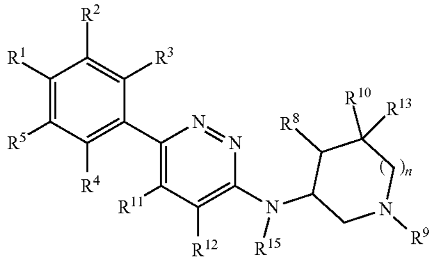

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl, $C_{3-5}$ cycloalkyl;

n is 1 or 2;

(2) $R^1$ is methyl;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2; or (3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl; and n is 1 or 2.

In one embodiment, a compound is provided having structure (C):

(C)

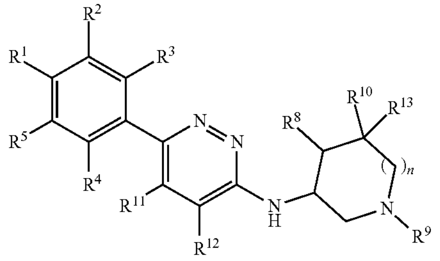

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (C):

(C)

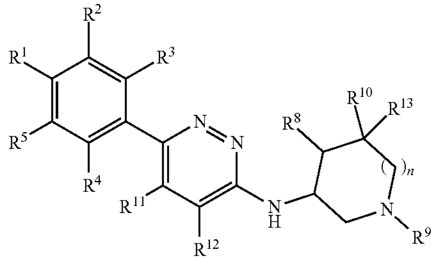

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (C):

(C)

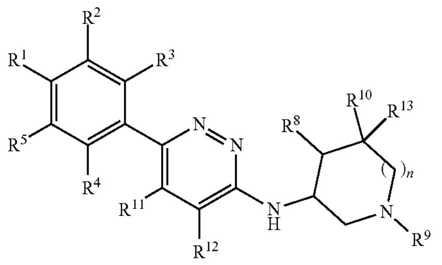

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (C):

(C)

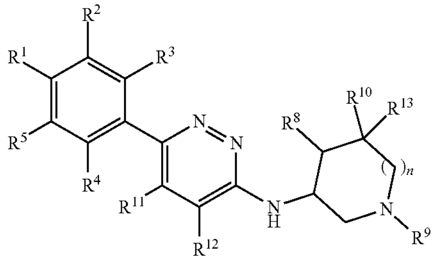

or a pharmaceutically acceptable salt, isomer, hydrate, solvate or isotope thereof, wherein:

$R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

In one embodiment, a compound is provided having structure (C'):

(C')

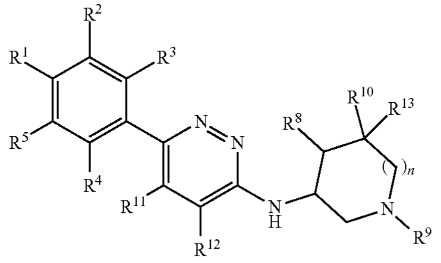

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2; or (3) $R^1$ is OH, $CF_3$, $CHF_2$, $C_{2-6}$ alkyl, $C_{3-5}$ cycloalkyl, CN, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

In one embodiment, a compound is provided having structure (C'):

(C')

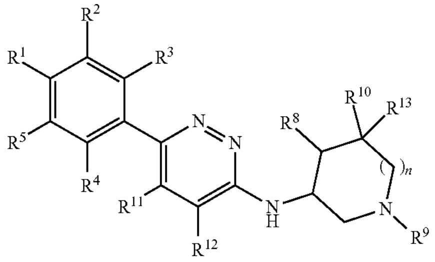

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2; or (3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

In one embodiment, a compound is provided having structure (C'):

(C')

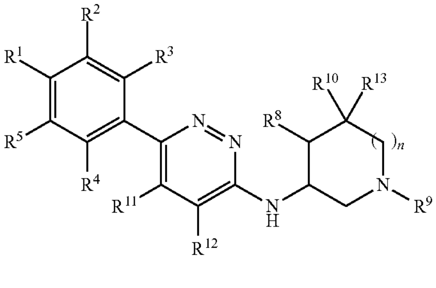

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

(2) $R^1$ is H or methyl;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2; or (3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

In one embodiment, a compound is provided having structure (C'):

(C')

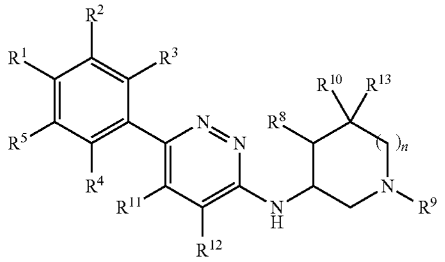

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl;
n is 1 or 2;
(2) $R^1$ is H or methyl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or F;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl;
n is 1 or 2;
(3) $R^1$ is $CF_3$ or Cl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or F;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl; and
n is 1 or 2; or
(4) $R^1$ is OH, $CHF_2$, $C_{2-6}$ alkyl, $C_{3-5}$ cycloalkyl, CN, $C_{1-6}$ cyanoalkyl, C(O)OH, $OC_{1-6}$ alkyl or $OCF_3$;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or F;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl; and
n is 1 or 2; or In one embodiment, a compound is provided having structure (C'):

(C')

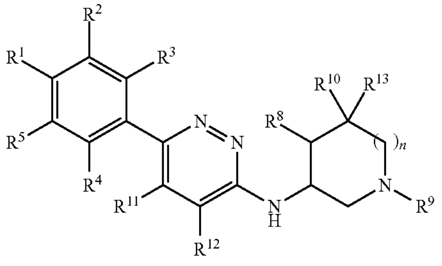

or a pharmaceutically acceptable salt, isomer, hydrate, solvate or isotope thereof, wherein:
(1) $R^1$ is F;
$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^8$ is H or F;
$R^9$ is H, $C_{3-5}$ cycloalkyl, methyl or $C_{3-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl;
n is 1 or 2;
(2) $R^1$ is methyl;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or F;
$R^9$ is $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl;
n is 1 or 2; or
(3) $R^1$ is OH, $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;
$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;
$R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl;
$R^8$ is H or F;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;
$R^{11}$ and $R^{12}$ are each, independently, H, F, Cl, $CF_3$, $C_{1-6}$ alkyl, CN, OH or $OC_{1-6}$ alkyl; and
n is 1 or 2.

In one embodiment, a compound is provided having structure (D):

(D)

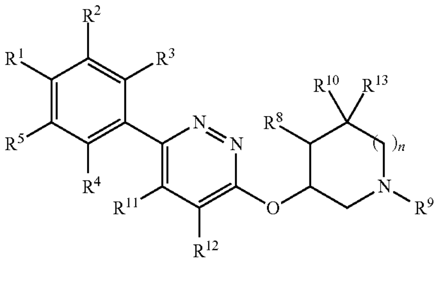

or a pharmaceutically acceptable salt, isomer, hydrate, solvate or isotope thereof, wherein:
$R^1$ is H, OH, $CF_3$, $CHF_2$, $C_{1-6}$ alkyl, $C_{3-5}$ cycloalkyl, CN, F, Cl, $OC_{1-6}$ alkyl or $OCF_3$;
$R^2$, $R^3$, $R^4$, and $R^5$ are independently H, $CF_3$, $CHF_2$, $C_{1-6}$ alkyl, CN, F, Cl, $OCF_3$, $OC_{1-6}$ alkyl or $C_{3-5}$ cycloalkyl;
$R^8$ is H or F;
$R^9$ is H, $C_{3-5}$ cycloalkyl, or $C_{1-6}$ alkyl optionally substituted with one or more $R^{9'}$;
$R^{9'}$ is OH, F, $CHF_2$, $CF_3$ or $C_{3-5}$ cycloalkyl;
$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

In one embodiment, a compound is provided having structure (D):

(D)

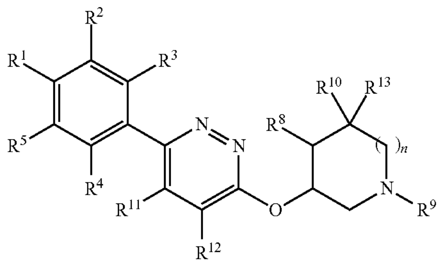

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

In one embodiment, a compound is provided having structure (I):

(I)

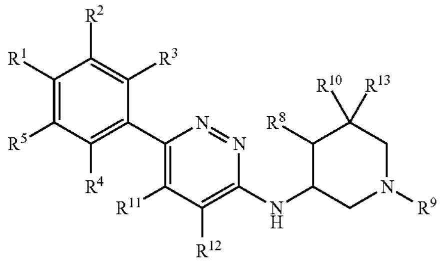

or a pharmaceutically acceptable salt, isomer, hydrate, solvate or isotope thereof, wherein:

$R^1$ is H, $CF_3$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $C_{1-6}$ alkyl, CN, F, Cl or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (1):

(I)

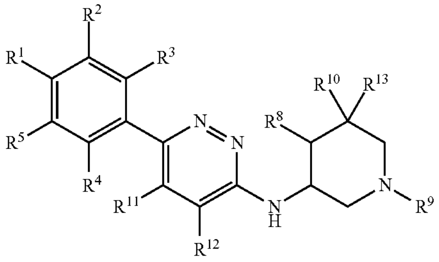

or a pharmaceutically acceptable salt, isomer, hydrate, solvate or isotope thereof, wherein:

$R^1$ is H, $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $C_{1-6}$ alkyl, CN, F, Cl, C(O)OH or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (1):

(I)

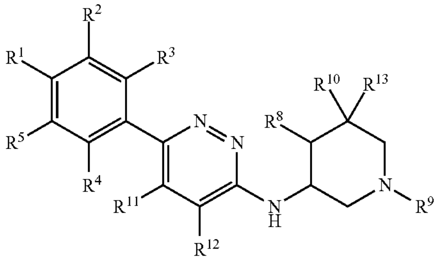

or a pharmaceutically acceptable salt, isomer, hydrate, solvate or isotope thereof, wherein:

$R^1$ is H, $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, $OC_{2-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (I):

(I)

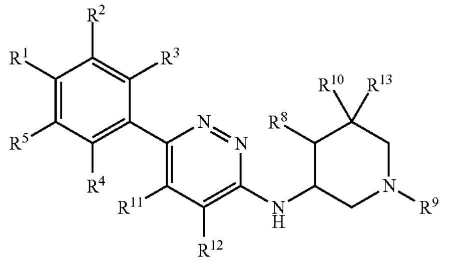

or a pharmaceutically acceptable salt, isomer, hydrate, solvate or isotope thereof, wherein:

$R^1$ is $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, $OC_{2-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (I):

(I)

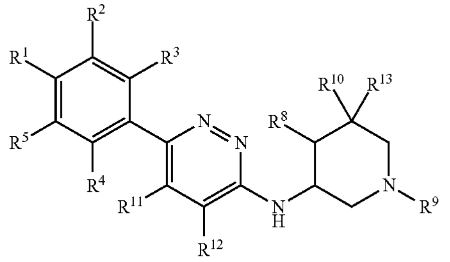

or a pharmaceutically acceptable salt, isomer, hydrate, solvate or isotope thereof, wherein:

$R^1$ is H, $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (I):

(I)

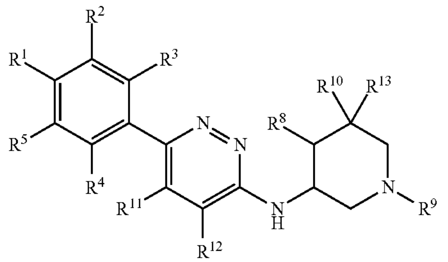

or a pharmaceutically acceptable salt, isomer, hydrate, solvate or isotope thereof, wherein:

$R^1$ is $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, CI or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

In one embodiment, a compound is provided having structure (I'):

(I')

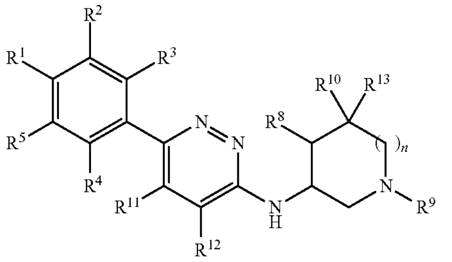

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl or $OC_{1-6}$ alkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, F, Cl or $OC_{1-6}$ alkyl;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

n is 1 or 2; or (3) $R^1$ is $CF_3$, $CHF_2$, $C_{2-6}$ alkyl, $C_{3-5}$ cycloalkyl, CN, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2.

In one embodiment, a compound is provided having structure (I'):

(I')

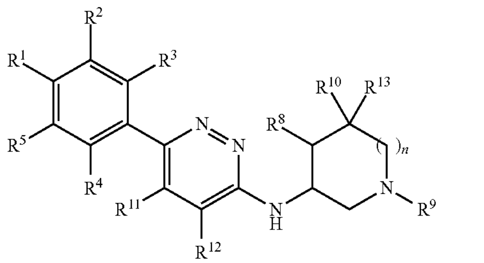

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl;

n is 1 or 2;

(2) $R^1$ is H or methyl;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

n is 1 or 2; or (3) $R^1$ is $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2.

In one embodiment, a compound is provided having structure (I'):

(I')

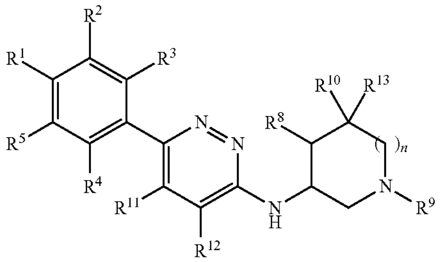

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl;

n is 1 or 2;

(2) $R^1$ is H or methyl;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

n is 1 or 2; or (3) $R^1$ is $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2.

In one embodiment, a compound is provided having structure (I'):

(I')

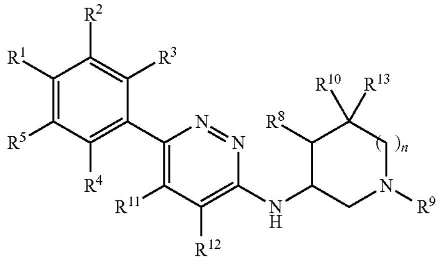

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl;

n is 1 or 2;

(2) $R^1$ is H or methyl;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

n is 1 or 2;

(3) $R^1$ is $CF_3$ or Cl;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2; or (4) $R^1$ is $CHF_2$, $C_{2-6}$ alkyl, $C_{3-5}$ cycloalkyl, CN, $C_{1-6}$ cyanoalkyl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2.

In one embodiment, a compound is provided having structure (I'):

(I')

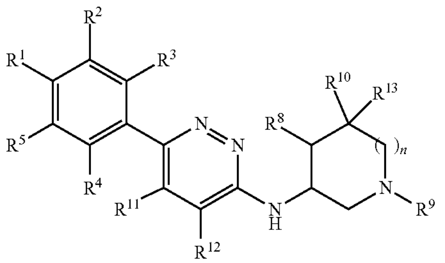

or a pharmaceutically acceptable salt, isomer, hydrate, solvate or isotope thereof, wherein:

(1) $R^1$ is F;

$R^2$, $R^3$, $R^4$, and $R^5$ are independently H, $CF_3$, $CHF_2$, $C_{1-6}$ alkyl, CN, F, Cl, C(O)OH or $OC_{1-6}$ alkyl;

$R^8$ is H or F;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl;

n is 1 or 2;

(2) $R^1$ is methyl;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, Cl or $C_{1-6}$ alkyl;

n is 1 or 2; or (3) $R^1$ is $CF_3$, $CHF_2$, $C_{2-6}$ alkyl, $C_{3-5}$ cycloalkyl, CN, $C_{1-6}$ cyanoalkyl, Cl, C(O)OH, $OC_{1-6}$ alkyl or $OCF_3$;

$R^2$ and $R^5$ are independently H, $CF_3$, $C_{1-6}$ alkyl, CN, F, Cl, C(O)OH or $OC_{1-6}$ alkyl;

$R^3$ and $R^4$ are independently H, $CF_3$, $C_{1-6}$ alkyl, CN, F, Cl or C(O)OH;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $OCH_3$, $C_{1-6}$ alkyl or CN;

$R^{12}$ is H, $CF_3$, OH, Cl or $C_{1-6}$ alkyl; and n is 1 or 2.

In another embodiment, a compound is provided having the following structure:

(Ia)

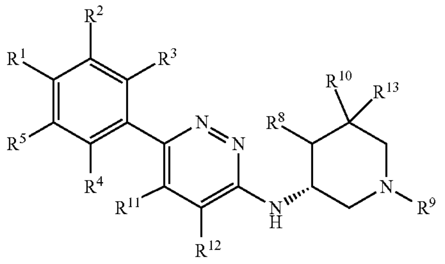

or a pharmaceutically acceptable salt, isomer, hydrate, solvate or isotope thereof, wherein:

$R^1$ is $CF_3$, $C_{1-6}$ alkyl, $C_{3-5}$ cycloalkyl, CN, F, or $OCF_3$;

$R^9$ is $C_{1-6}$ alkyl optionally substituted with one or more $R^{9'}$; and wherein $R^{9'}$ is F or $C_{3-5}$ cycloalkyl.

In another embodiment, a compound is provided having the following structure:

(Ia)

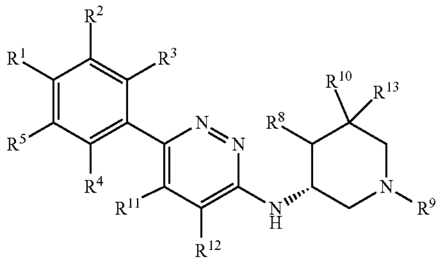

or a pharmaceutically acceptable salt, isomer, hydrate, solvate or isotope thereof, wherein:

$R^1$ is $CF_3$, $C_{1-6}$ alkyl, $C_{3-5}$ cycloalkyl, CN, $C_{1-6}$ cyanoalkyl, F, C(O)OH or $OCF_3$;

$R^9$ is $C_{1-6}$ alkyl optionally substituted with one or more $R^{9'}$; and wherein $R^{9'}$ is F or $C_{3-5}$ cycloalkyl.

In one embodiment, a compound is provided having the following structure:

(Ia')

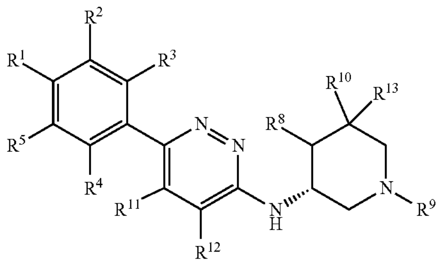

or a pharmaceutically acceptable salt, isomer, hydrate, solvate or isotope thereof.

In one embodiment, a compound is provided having the following structure:

(Ia')

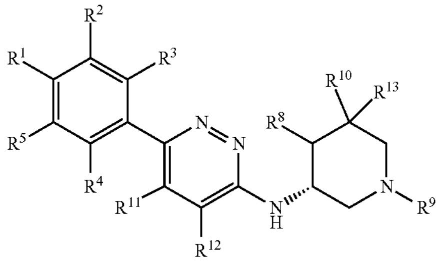

or a pharmaceutically acceptable salt, isomer, hydrate, solvate or isotope thereof, wherein:

$R^1$ is $CF_3$ or F.

In one embodiment, a compound is provided having the following structure:

(Ia")

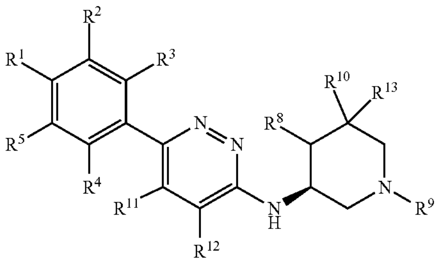

or a pharmaceutically acceptable salt, isomer, hydrate, solvate or isotope thereof.

In one embodiment, a compound is provided having the following structure:

(Ia")

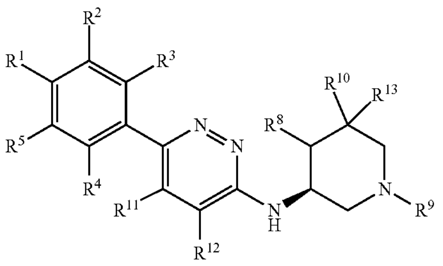

or a pharmaceutically acceptable salt, isomer, hydrate, solvate or isotope thereof, wherein:

$R^1$ is $CF_3$ or F.

In another embodiment, a compound is provided having the following structure:

(Ib)

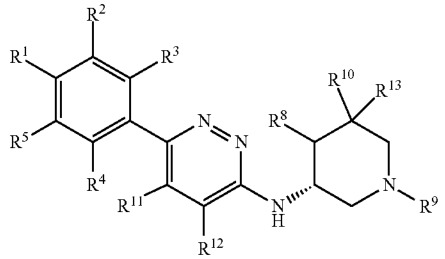

or a pharmaceutically acceptable salt, isomer, hydrate, solvate or isotope thereof, wherein:

X is O or $NR^{15}$;

$R^1$ is H, OH, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

one of $R^3$ or $R^4$ is $CHF_2$ and the other is H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F, X is $NR^{15}$ and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

Accordingly, in one embodiment, a compound is provided having structure (II):

(II)

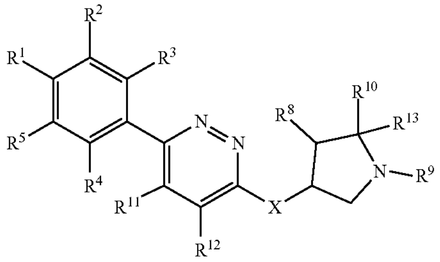

or a pharmaceutically acceptable salt, isomer, hydrate, solvate or isotope thereof, wherein:

X is O or $NR^{15}$;

$R^1$ is OH, $CF_3$, $CHF_2$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$ or $OC_{1-6}$ alkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl; and wherein if $R^1$ is F and $R^2$, $R^3$, $R^4$, $R^5$, $R^8$, $R^{11}$ and $R^{12}$ are each H, then $R^9$ is not tert-butyl.

Accordingly, in one embodiment, a compound is provided having structure (II):

(II)

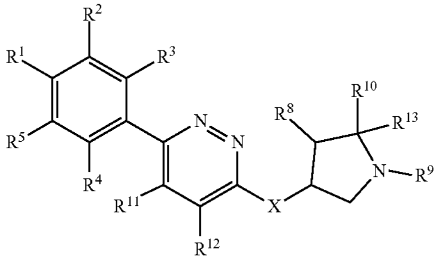

or a pharmaceutically acceptable salt, isomer, hydrate, solvate or isotope thereof, wherein:

X is O or $NR^{15}$;

$R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$ or $OC_{1-6}$ alkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H or $C_{1-6}$ alkyl; and wherein if $R^1$ is F and $R^2$, $R^3$, $R^4$, $R^5$, $R^8$, $R^{11}$ and $R^{12}$ are each H, then $R^9$ is not tert-butyl.

In one embodiment, a compound is provided having structure (II'):

(II')

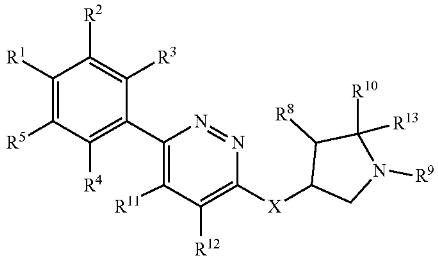

or a pharmaceutically acceptable salt, isomer, hydrate, solvate or isotope thereof, wherein:

(1) $R^1$ is F;

X is O or $NR^{15}$;

$R^2$, $R^3$, $R^4$, and $R^5$ are independently H, $CF_3$, $CHF_2$, $C_{1-6}$ alkyl, CN, F, Cl or $OC_{1-6}$ alkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or halo;

$R^{11}$ is H, $CF_3$, $OCH_3$, $C_{1-6}$ alkyl or CN;

$R^{12}$ is H, $CF_3$, OH, Cl or $C_{1-6}$ alkyl;

$R^{15}$ is H or $C_{1-6}$ alkyl;

(2) $R^1$ is OH, $CF_3$, $CHF_2$, $C_{1-6}$ alkyl, $C_{3-5}$ cycloalkyl, CN, F, Cl, $OC_{1-6}$ alkyl or $OCF_3$;

X is O or $NR^{15}$;

$R^2$, $R^3$, $R^4$, and $R^5$ are independently H, $CF_3$, $CHF_2$, $C_{1-6}$ alkyl, CN, F, Cl or $OC_{1-6}$ alkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or halo;

$R^{11}$ is H, $CF_3$, $OCH_3$, $C_{1-6}$ alkyl or CN;

$R^{12}$ is H, $CF_3$, OH, Cl or $C_{1-6}$ alkyl; and $R^{15}$ is H or $C_{1-6}$ alkyl.

In one embodiment, a compound is provided having structure (II'):

(II')

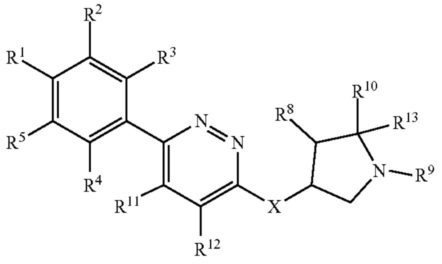

or a pharmaceutically acceptable salt, isomer, hydrate, solvate or isotope thereof, wherein:

(1) $R^1$ is F;

X is O or $NR^{15}$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH or $OC_{1-6}$ alkyl;

$R^8$ is H or halo;

$R^9$ is H, $C_{3-5}$ cycloalkyl, methyl or $C_{3-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or halo;

$R^{11}$ is H, $CF_3$, $OCH_3$, $C_{1-6}$ alkyl or CN;

$R^{12}$ is H, $CF_3$, OH, Cl or $C_{1-6}$ alkyl;

$R^{15}$ is H or $C_{1-6}$ alkyl;

(2) $R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

X is O or $NR^{15}$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH or $OC_{1-6}$ alkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or halo;

$R^{11}$ is H, $CF_3$, $OCH_3$, $C_{1-6}$ alkyl or CN;

$R^{12}$ is H, $CF_3$, OH, Cl or $C_{1-6}$ alkyl; and $R^{15}$ is H or $C_{1-6}$ alkyl.

In one embodiment, a compound is provided having the following structure (IIa'):

(IIa')

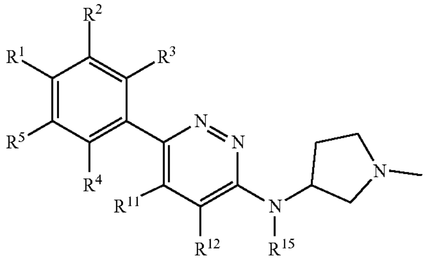

or a pharmaceutically acceptable salt, isomer, hydrate, solvate or isotope thereof, wherein:

$R^1$ is $CF_3$ or F.

In some embodiments, X is O.

In other embodiments, X is $NR^{15}$.

In some embodiments, when X is $NR^{15}$; $R^1$ is $CH_3$, $CF_3$, or Cl; and one of $R^3$ or $R^4$ is $CHF_2$ or $OCH_3$ then either (1) the other of $R^3$ or $R^4$ is not H or (2) $R^2$ or $R^5$ is not H.

In some embodiments, when X is NH; $R^1$ is $CH_3$, $CF_3$, or Cl; and one of $R^3$ or $R^4$ is $CHF_2$ or $OCH_3$ then either (1) the other of $R^3$ or $R^4$ is not H or (2) $R^2$ or $R^5$ is not H.

In some embodiments, $R^{11}$ is H, halo, $CF_3$, $C_{1-6}$ alkyl, CN, OH or $OC_{1-6}$ alkyl.

In some embodiments, $R^{12}$ is H, halo, $CF_3$, $C_{1-6}$ alkyl, CN, OH or $OC_{1-6}$ alkyl.

In some embodiments, $R^{11}$ and $R^{12}$ are each, independently, is H, halo, $CF_3$, $C_{1-6}$ alkyl, CN, OH or $OC_{1-6}$ alkyl.

In some embodiments, $R^{11}$ and $R^{12}$ are each, independently, is H, halo, $CF_3$, $C_{1-6}$ alkyl, CN, OH or $OC_{1-6}$ alkyl.

In another embodiment, $R^{11}$ and $R^{12}$ are not H.

In some embodiments, $R^{11}$ is F, $CF_3$, $C_{1-6}$ alkyl, OH, $OC_{1-6}$ alkyl or CN and $R^{12}$ is H.

In some embodiments, $R^{11}$ is F, $CF_3$, $C_{1-6}$ alkyl, $OC_{1-6}$ alkyl or CN and $R^{12}$ is H.

In some embodiments, $R^{11}$ is methyl and $R^{12}$ is H.

In some embodiments, $R^{11}$ is OH and $R^{12}$ is H.

In some embodiments, $R^{11}$ is $CF_3$ and $R^{12}$ is H.

In some embodiments, $R^{11}$ is $CF_3$, $C_{1-6}$ alkyl, or CN and $R^{12}$ is H.

In other embodiments, $R^{11}$ is H and $R^{12}$ is F, $CF_3$, CN, $OC_{1-6}$ alkyl, Cl or $C_{1-6}$ alkyl.

In some embodiments, $R^{11}$ is H and $R^{12}$ is methyl.

In some embodiments, $R^{11}$ is H and $R^{12}$ is $CF_3$.

In other embodiments, $R^{11}$ is H and $R^{12}$ is Cl or $C_{1-6}$ alkyl.

In yet other embodiments, both $R^{11}$ and $R^{12}$ are H.

In some embodiments, both $R^{11}$ and $R^{12}$ are not H.

In some embodiments, $R^{11}$ or $R^{12}$ is OH.

In some embodiments, $R^{11}$ is methyl and $R^{12}$ is OH.

In some embodiments, $R^{11}$ or $R^{12}$ is $OCH_3$.

In some embodiments, $R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$.

In some embodiments, $R^1$ is OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$.

In some embodiments, $R^1$ is H, OH, $CHF_2$, $C_{2-6}$ alkyl, $C_{3-5}$ cycloalkyl, CN, $C_{1-6}$ cyanoalkyl, F, C(O)OH, $OC_{1-6}$ alkyl or $OCF_3$.

In some embodiments, $R^1$ is OH, $CHF_2$, $C_{2-6}$ alkyl, $C_{3-5}$ cycloalkyl, CN, $C_{1-6}$ cyanoalkyl, F, C(O)OH, $OC_{1-6}$ alkyl or $OCF_3$.

In some embodiments, $R^1$ is H, OH, $CHF_2$, $C_{3-5}$ cycloalkyl, CN, $C_{1-6}$ cyanoalkyl, F, C(O)OH, $OC_{1-6}$ alkyl or $OCF_3$.

In some embodiments, $R^1$ is OH, $CHF_2$, $C_{3-5}$ cycloalkyl, CN, $C_{1-6}$ cyanoalkyl, F, C(O)OH, $OC_{1-6}$ alkyl or $OCF_3$.

In other embodiments, $R^1$ is H, $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$.

In other embodiments, $R^1$ is $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$.

In other embodiments, $R^1$ is $CF_3$, $C_{1-6}$ alkyl, $C_{3-5}$ cycloalkyl, CN, $C_{1-6}$ cyanoalkyl, F, C(O)OH or $OCF_3$.

In other embodiments, $R^1$ is $CF_3$, CN, $C_{1-6}$ cyanoalkyl, F or $OCF_3$.

In certain embodiments, $R^1$ is $CF_3$, or F.

In some embodiments, $R^1$ is H.

In one embodiment, $R^1$ is $CF_3$.

In one embodiment, $R^1$ is $CHF_2$.

In another embodiment, $R^1$ is F.

In some embodiments, $R^1$ is Cl.

In other embodiments, $R^1$ is $OCF_3$.

In some embodiments, $R^1$ is CN.

In other embodiments, $R^1$ is OH.

In some embodiments, $R^1$ is C(O)OH.

In some embodiments, $R^1$ is $C_{1-6}$ alkyl.

In certain embodiments, $R^1$ is methyl.

In certain embodiments, $R^1$ is ethyl.

In certain embodiments, $R^1$ is isopropyl.

In some embodiments, $R^1$ is $C_{1-6}$ cyanoalkyl.

In certain embodiments, $R^1$ is

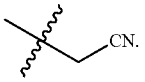 [SMILES: *CC#N]

In some embodiments, $R^1$ is $OC_{1-6}$ alkyl.

In certain embodiments, $R^1$ is $OCH_3$.

In some embodiments, $R^1$ is $C_{3-5}$ cycloalkyl.

In certain embodiments, $R^1$ is cyclopropyl.

In certain embodiments, $R^1$ is cyclobutyl.

In some embodiments, $R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl; and $R^3$ and $R^4$ are independently H, $CF_3$, $C_{1-6}$ alkyl, CN, $C_{1-6}$ cyanoalkyl, F, Cl, C(O)OH, $OCF_3$, $OC_{2-6}$ alkyl or $C_{3-5}$ cycloalkyl.

In some embodiments, $R^2$ and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl; and $R^3$ and $R^4$ are independently H, $CF_3$, $C_{1-6}$ alkyl, CN, $C_{1-6}$ cyanoalkyl, F, Cl, C(O)OH, $OCF_3$ or $C_{3-5}$ cycloalkyl.

In some embodiments, $R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl.

In some embodiments, $R^2$, $R^3$, $R^4$, and $R^5$ are independently H, $CF_3$, $C_{1-6}$ alkyl, CN, $C_{1-6}$ cyanoalkyl, F, Cl, C(O)OH, $OCF_3$, $OC_{2-6}$ alkyl or $C_{3-5}$ cycloalkyl.

In some embodiments, $R^2$, $R^3$, $R^4$, and $R^5$ are independently H, $CF_3$, $C_{1-6}$ alkyl, CN, $C_{1-6}$ cyanoalkyl, F, Cl, C(O)OH, $OCF_3$, or $C_{3-5}$ cycloalkyl.

In other embodiments, $R^2$, $R^3$, $R^4$, and $R^5$ are independently H, $CF_3$, $CHF_2$, $C_{1-6}$ alkyl, CN, F, Cl, C(O)OH, $OCF_3$, $OC_{1-6}$ alkyl or $C_{3-5}$ cycloalkyl.

In certain embodiments, $R^2$, $R^3$, $R^4$, and $R^5$ are independently H, $CF_3$, $C_{1-6}$ alkyl, CN, F, Cl, C(O)OH or $OC_{1-6}$ alkyl.

In one embodiment, $R^2$ and $R^5$ are independently H, $C_{1-6}$ alkyl, F, Cl, $CF_3$ or CN.

In some embodiments, $R^2$ is H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl.

In other embodiments, $R^2$ is H, $CF_3$, $CHF_2$, $C_{1-6}$ alkyl, CN, F, Cl, C(O)OH, $OCF_3$, $OC_{1-6}$ alkyl or $C_{3-5}$ cycloalkyl.

In certain embodiments, $R^2$ is H, $CF_3$, $C_{1-6}$ alkyl, CN, F, Cl, C(O)OH or $OC_{1-6}$ alkyl.

In one embodiment, $R^2$ is H.

In other embodiments, $R^2$ is $C_{1-6}$ alkyl.

In certain embodiments, $R^2$ is methyl.

In certain embodiments, $R^2$ is ethyl.

In certain embodiments, $R^2$ is isopropyl. In some embodiments, $R^2$ is $C_{1-6}$ cyanoalkyl.

In certain embodiments, $R^2$ is

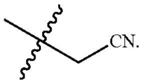 [SMILES: *CC#N]

In some embodiments, $R^2$ is F.

In yet another embodiment, $R^2$ is Cl.

In some embodiments, $R^2$ is Br.

In yet another embodiment, $R^2$ is I.

In one embodiment, $R^2$ is $CF_3$.

In another embodiment, $R^2$ is $CHF_2$.

In some embodiments, $R^2$ is $OCF_3$.

In yet other embodiments, $R^2$ is $OC_{1-6}$ alkyl.

In certain embodiments, $R^2$ is $OCH_3$.

In another embodiment, $R^2$ is CN.

In certain embodiments, $R^2$ is C(O)OH.

In some embodiments, $R^2$ is $C_{3-5}$ cycloalkyl.

In certain embodiments, $R^2$ is cyclopropyl.

In certain embodiments, $R^2$ is cyclobutyl.

In some embodiments, $R^5$ is H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl.

In other embodiments, $R^5$ is H, $CF_3$, $CHF_2$, $C_{1-6}$ alkyl, CN, F, Cl, C(O)OH, $OCF_3$, $OC_{1-6}$ alkyl or $C_{3-5}$ cycloalkyl.

In certain embodiments, $R^5$ is H, $CF_3$, $C_{1-6}$ alkyl, CN, F, Cl, C(O)OH or $OC_{1-6}$ alkyl.

In some embodiments, $R^5$ is H.

In yet other embodiments, $R^5$ is $C_{1-6}$ alkyl.

In certain embodiments, $R^5$ is methyl.

In certain embodiments, $R^5$ is ethyl.

In certain embodiments, $R^5$ is isopropyl. In some embodiments, $R^5$ is $C_{1-6}$ cyanoalkyl.

In certain embodiments, $R^5$ is

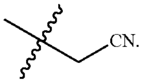 [SMILES: *CC#N]

In one embodiment, $R^5$ is F.

In another embodiment, $R^5$ is Cl.

In one embodiment, $R^5$ is Br.

In another embodiment, $R^5$ is I.

In some embodiments, $R^5$ is $CF_3$.

In another embodiment, $R^5$ is $CHF_2$.

In yet other embodiments, $R^5$ is $OCF_3$.

In yet other embodiments, $R^5$ is CN.

In some embodiments, $R^5$ is $OC_{1-6}$ alkyl.

In certain embodiments, $R^5$ is $OCH_3$.

In certain embodiments, $R^5$ is C(O)OH.

In some embodiments, $R^5$ is $C_{3-5}$ cycloalkyl.

In certain embodiments, $R^5$ is cyclopropyl.

In certain embodiments, $R^5$ is cyclobutyl.

In one embodiment, $R^3$ are $R^4$ are independently H, $CF_3$, $C_{1-6}$ alkyl, CN, F or Cl.

In some embodiments, $R^3$ is H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl.

In other embodiments, $R^3$ is H, $CF_3$, $CHF_2$, $C_{1-6}$ alkyl, CN, F, Cl, C(O)OH, $OCF_3$, $OC_1$-alkyl or $C_{3-5}$ cycloalkyl.

In certain embodiments, $R^3$ is H, $CF_3$, $C_{1-6}$ alkyl, CN, F, Cl, C(O)OH or $OC_{1-6}$ alkyl.

In one embodiment, $R^3$ is H.

In another embodiment, $R^3$ is $CF_3$.

In another embodiment, $R^3$ is $CHF_2$.

In some embodiments, $R^3$ is $C_{1-6}$ alkyl.

In certain embodiments, $R^3$ is methyl.

In certain embodiments, $R^3$ is ethyl.

In certain embodiments, $R^3$ is isopropyl. In some embodiments, $R^3$ is $C_{1-6}$ cyanoalkyl.

In certain embodiments, $R^3$ is

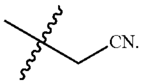 [SMILES: *CC#N]

In other embodiments, $R^3$ is CN.

In yet other embodiments, $R^3$ is F.

In one embodiment, $R^3$ is Cl.

In one embodiment, $R^3$ is Br.

In one embodiment, $R^3$ is I.

In some embodiments, $R^3$ is $OC_{1-6}$ alkyl.

In certain embodiments, $R^3$ is $OCH_3$.

In certain embodiments, $R^3$ is C(O)OH.

In some embodiments, $R^3$ is $C_{3-5}$ cycloalkyl.

In certain embodiments, $R^3$ is cyclopropyl.

In certain embodiments, $R^3$ is cyclobutyl.

In some embodiments, $R^4$ is H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl.

In other embodiments, $R^4$ is H, $CF_3$, $CHF_2$, $C_{1-6}$ alkyl, CN, F, Cl, C(O)OH, $OCF_3$, $OC_1$-alkyl or $C_{3-5}$ cycloalkyl.

In certain embodiments, $R^4$ is H, $CF_3$, $C_{1-6}$ alkyl, CN, F, Cl, C(O)OH or $OC_{1-6}$ alkyl.

In one embodiment, $R^4$ is H.

In another embodiment, $R^4$ is $CF_3$.

In another embodiment, $R^4$ is $CHF_2$.

In some embodiments, $R^4$ is $C_{1-6}$ alkyl.

In certain embodiments, $R^4$ is methyl.

In certain embodiments, $R^4$ is ethyl.

In certain embodiments, $R^4$ is isopropyl. In some embodiments, $R^4$ is $C_{1-6}$ cyanoalkyl.

In certain embodiments, $R^4$ is

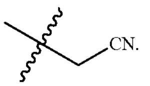 [SMILES: *CC#N]

In one embodiment, $R^4$ is CN.

In another embodiment, $R^4$ is F.

In yet another embodiment, $R^4$ is Cl.

In another embodiment, $R^4$ is Br.

In yet another embodiment, $R^4$ is I.

In some embodiments, $R^4$ is $OC_{1-6}$ alkyl.

In certain embodiments, $R^4$ is $OCH_3$.

In certain embodiments, $R^4$ is C(O)OH.

In some embodiments, $R^4$ is $C_{3-5}$ cycloalkyl.

In certain embodiments, $R^4$ is cyclopropyl.

In certain embodiments, $R^4$ is cyclobutyl.

In one embodiment, $R^8$ is H.

In another embodiment, $R^8$ is F.

In another embodiment, $R^8$ is Cl.

In another embodiment, $R^8$ is Br.

In another embodiment, $R^8$ is I.

In some embodiments, $R^9$ is H, $C_{3-5}$ cycloalkyl, or $C_{1-6}$ alkyl optionally substituted with one or more $R^{9'}$.

In some embodiments, $R^9$ is $C_{3-5}$ cycloalkyl, or $C_{1-6}$ alkyl optionally substituted with one or more $R^{9'}$.

In one embodiment, $R^9$ is H.

In another embodiment, $R^9$ is not H.

In yet another embodiment, $R^9$ is $C_{1-6}$ alkyl.

In certain embodiments, $R^9$ is methyl.

In certain embodiments, $R^9$ is $CD_3$.

In certain embodiments, $R^9$ is ethyl.

In certain embodiments, $R^9$ is isopropyl.

In one embodiment, $R^9$ is $C_{1-6}$ alkyl optionally substituted with one or more F.

In certain embodiments, $R^9$ is $—CH_2CH_2F$.

In certain embodiments, $R^9$ is $—CH_2CHF_2$.

In certain embodiments, $R^9$ is $—CH_2CF_3$.

In some embodiments, $R^9$ is $C_{3-5}$ cycloalkyl.

In certain embodiments, $R^9$ is cyclopropyl.

In some embodiments, $R^9$ is $C_{1-6}$ alkyl optionally substituted with one or more $C_{3-5}$ cycloalkyl.

In certain embodiments, $R^9$ is

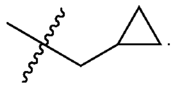 [SMILES: *CC1CC1]

In some embodiments, $R^9$ is $C_{1-6}$ alkyl optionally substituted with one or more OH.

In certain embodiments, $R^9$ is

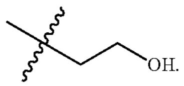 [SMILES: *CCO]

In another embodiment, $R^{10}$ and $R^{13}$ are both H.

In one embodiment, $R^{10}$ and $R^{13}$ are both halo. In another embodiment, $R^{10}$ is H and $R^{13}$ is halo.

In one embodiment, $R^{10}$ and $R^{13}$ are both F. In another embodiment, $R^{10}$ is H and $R^{13}$ is F.

In some embodiments, $R^{10}$ is H.

In some embodiments, $R^{10}$ is F.

In some embodiments, $R^{10}$ is Cl.

In some embodiments, $R^{10}$ is Br.

In some embodiments, $R^{10}$ is I.

In some embodiments, $R^{13}$ is H.

In some embodiments, $R^{13}$ is F.

In some embodiments, $R^{13}$ is Cl.

In some embodiments, $R^{13}$ is Br.

In some embodiments, $R^{13}$ is I.

In some embodiments, $R^{15}$ is H.

In other embodiments, $R^{15}$ is $C_{1-6}$ alkyl.

In certain embodiments, $R^{15}$ is methyl.

In certain embodiments, $R^{15}$ is ethyl.

In certain embodiments, $R^{15}$ is isopropyl.

In certain embodiments, $R^{15}$ is $C_{3-5}$ cycloalkyl.

In certain embodiments, $R^{15}$ is cyclopropyl.

In certain embodiments, $R^{15}$ is cyclobutyl.

In certain embodiments, $R^{15}$ is cyclopentyl.

In certain embodiments, n is 1.

In certain embodiments, n is 2.

In one embodiment, a compound is selected from one of the compounds listed in Table 1, or a pharmaceutically acceptable salt, isomer, hydrate, solvate or isotope thereof.

TABLE 1

Representative compounds having Structure (I)

| Structure | Cpd No. |
|---|---|
| 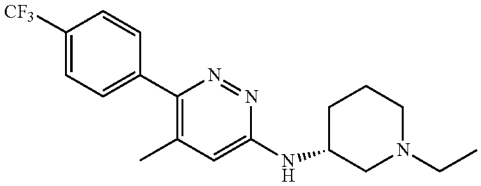 [SMILES: CCN1CCC[C@@H](Nc2cc(C)c(-c3ccc(C(F)(F)F)cc3)nn2)C1] | 1 |
| 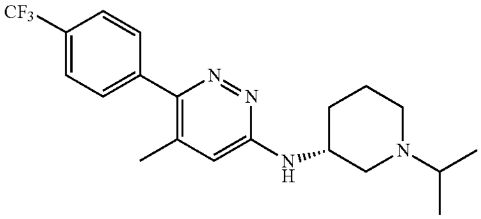 [SMILES: Cc1cc(N[C@@H]2CCCN(C(C)C)C2)nnc1-c1ccc(C(F)(F)F)cc1] | 2 |
| 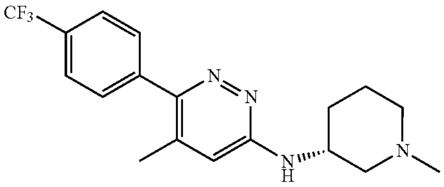 [SMILES: Cc1cc(N[C@@H]2CCCN(C)C2)nnc1-c1ccc(C(F)(F)F)cc1] | 3 |
| 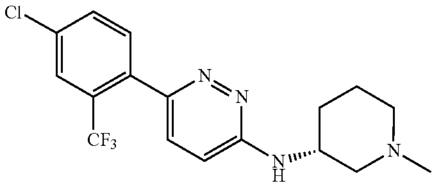 [SMILES: CN1CCC[C@@H](Nc2ccc(-c3ccc(Cl)cc3C(F)(F)F)nn2)C1] | 4 |
| 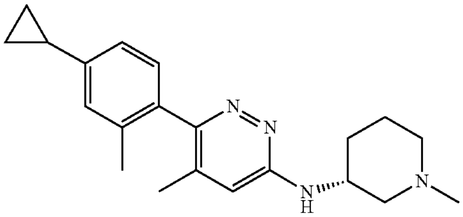 [SMILES: Cc1cc(C2CC2)ccc1-c1nnc(N[C@@H]2CCCN(C)C2)cc1C] | 5 |
| 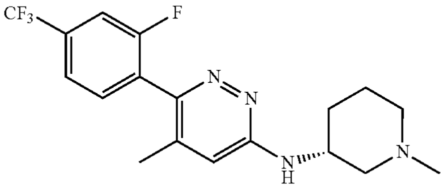 [SMILES: Cc1cc(N[C@@H]2CCCN(C)C2)nnc1-c1ccc(C(F)(F)F)cc1F] | 6 |

TABLE 1-continued
| Representative compounds having Structure (I) | |
|---|---|
| Structure | Cpd No. |
| 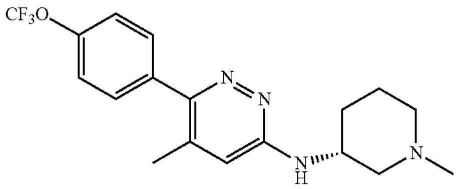 | 7 |
| 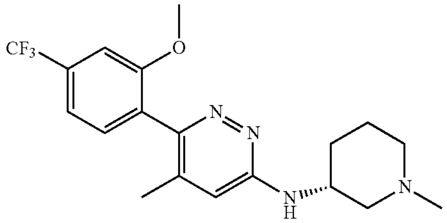 [SMILES: COc1cc(C(F)(F)F)ccc1-c1nnc(N[C@@H]2CCCN(C)C2)cc1C] | 8 |
| 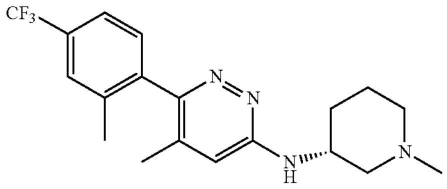 [SMILES: Cc1cc(C(F)(F)F)ccc1-c1nnc(N[C@@H]2CCCN(C)C2)cc1C] | 9 |
| 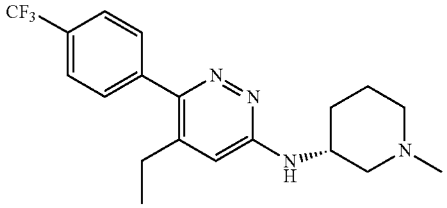 [SMILES: CCc1cc(N[C@@H]2CCCN(C)C2)nnc1-c1ccc(C(F)(F)F)cc1] | 10 |
| 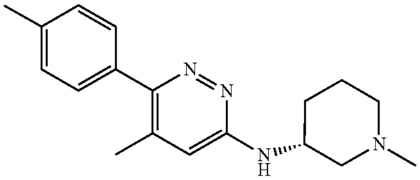 | 11 |
| 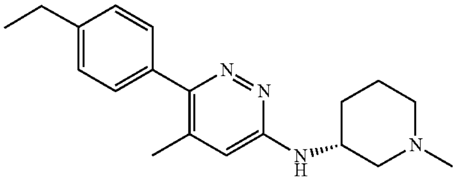 [SMILES: CCc1ccc(-c2nnc(N[C@@H]3CCCN(C)C3)cc2C)cc1] | 12 |
| 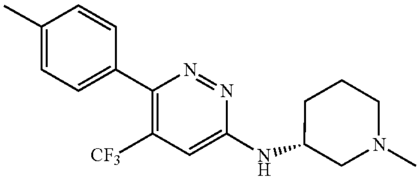 | 13 |

TABLE 1-continued
| Representative compounds having Structure (I) | |
|---|---|
| Structure | Cpd No. |
| 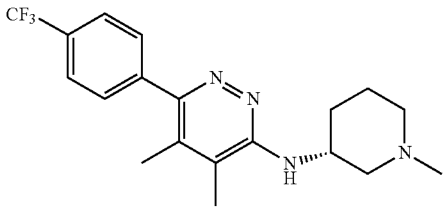 [SMILES: Cc1c(N[C@@H]2CCCN(C)C2)nnc(-c2ccc(C(F)(F)F)cc2)c1C] | 14 |
| 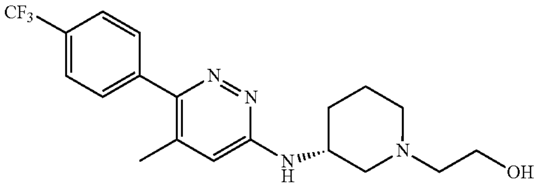 [SMILES: Cc1cc(N[C@@H]2CCCN(CCO)C2)nnc1-c1ccc(C(F)(F)F)cc1] | 15 |
| 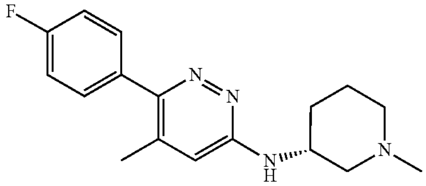 [SMILES: Cc1cc(N[C@@H]2CCCN(C)C2)nnc1-c1ccc(F)cc1] | 16 |
| 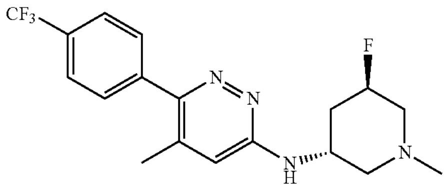 [SMILES: Cc1cc(N[C@@H]2C[C@@H](F)CN(C)C2)nnc1-c1ccc(C(F)(F)F)cc1] | 17 |
| 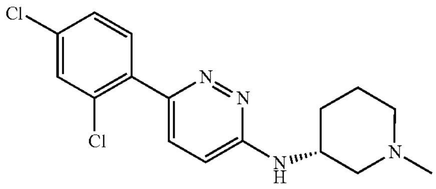 [SMILES: CN1CCC[C@@H](Nc2ccc(-c3ccc(Cl)cc3Cl)nn2)C1] | 18 |
| 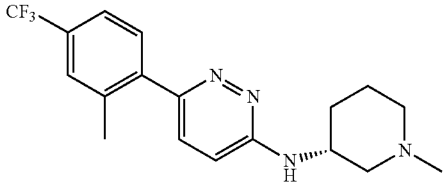 [SMILES: Cc1cc(C(F)(F)F)ccc1-c1ccc(N[C@@H]2CCCN(C)C2)nn1] | 19 |
| 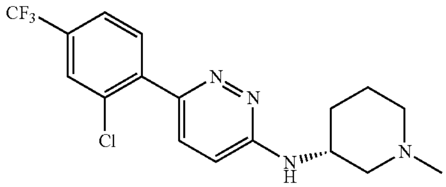 [SMILES: CN1CCC[C@@H](Nc2ccc(-c3ccc(C(F)(F)F)cc3Cl)nn2)C1] | 20 |

TABLE 1-continued
| Representative compounds having Structure (I) | |
|---|---|
| Structure | Cpd No. |
| 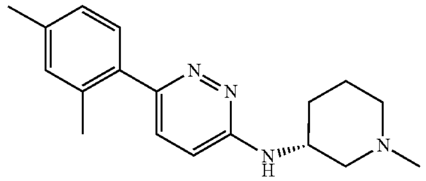 | 21 |
| 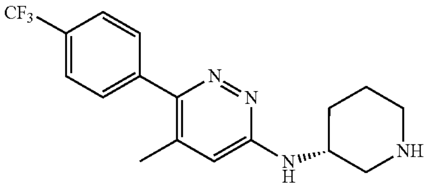 [SMILES: Cc1cc(N[C@@H]2CCCNC2)nnc1-c1ccc(C(F)(F)F)cc1] | 22 |
| 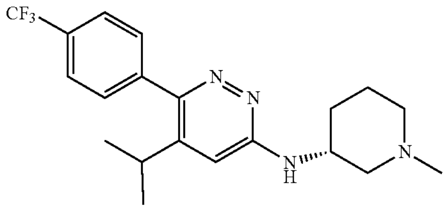 [SMILES: CC(C)c1cc(N[C@@H]2CCCN(C)C2)nnc1-c1ccc(C(F)(F)F)cc1] | 23 |
| 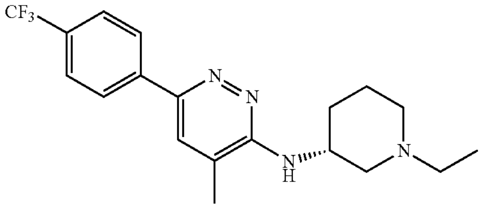 [SMILES: CCN1CCC[C@@H](Nc2nnc(-c3ccc(C(F)(F)F)cc3)cc2C)C1] | 24 |
| 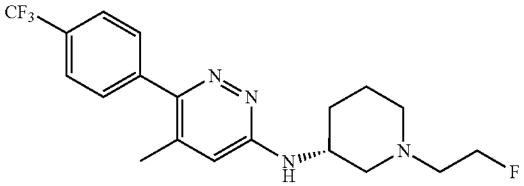 [SMILES: Cc1cc(N[C@@H]2CCCN(CCF)C2)nnc1-c1ccc(C(F)(F)F)cc1] | 25 |
| 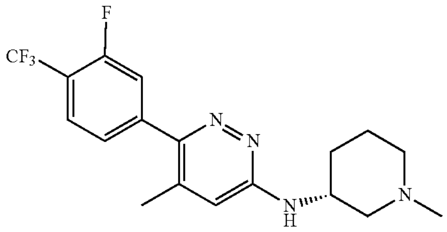 [SMILES: Cc1cc(N[C@@H]2CCCN(C)C2)nnc1-c1ccc(C(F)(F)F)c(F)c1] | 26 |
| 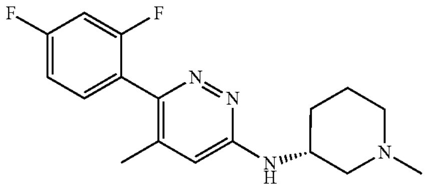 [SMILES: Cc1cc(N[C@@H]2CCCN(C)C2)nnc1-c1ccc(F)cc1F] | 27 |

TABLE 1-continued
| Representative compounds having Structure (I) | |
|---|---|
| Structure | Cpd No. |
| 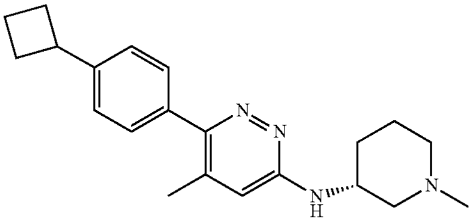 [SMILES: Cc1cc(N[C@@H]2CCCN(C)C2)nnc1-c1ccc(C2CCC2)cc1] | 28 |
| 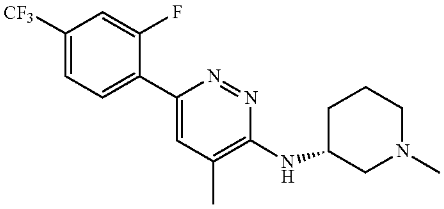 [SMILES: Cc1cc(-c2ccc(C(F)(F)F)cc2F)nnc1N[C@@H]1CCCN(C)C1] | 29 |
| 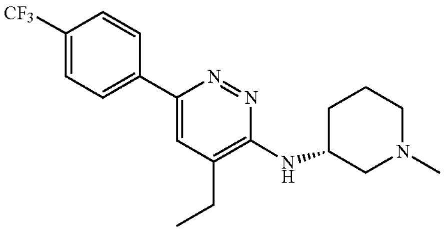 [SMILES: CCc1cc(-c2ccc(C(F)(F)F)cc2)nnc1N[C@@H]1CCCN(C)C1] | 30 |
| 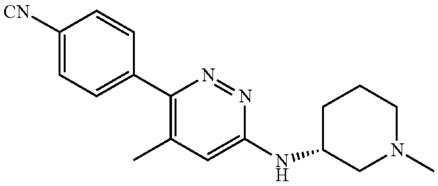 | 31 |
| 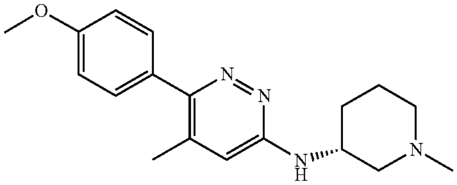 | 32 |
| 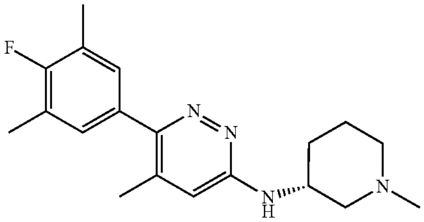 [SMILES: Cc1cc(N[C@@H]2CCCN(C)C2)nnc1-c1cc(C)c(F)c(C)c1] | 33 |
| 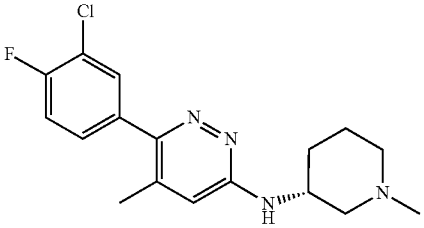 [SMILES: Cc1cc(N[C@@H]2CCCN(C)C2)nnc1-c1ccc(F)c(Cl)c1] | 34 |

TABLE 1-continued
Representative compounds having Structure (I)
| Structure | Cpd No. |
| --- | --- |
| 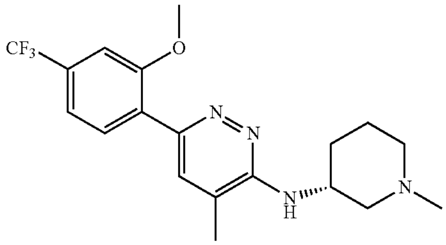 [SMILES: COc1cc(C(F)(F)F)ccc1-c1cc(C)c(N[C@@H]2CCCN(C)C2)nn1] | 35 |
| 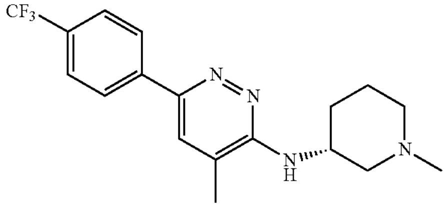 [SMILES: Cc1cc(-c2ccc(C(F)(F)F)cc2)nnc1N[C@@H]1CCCN(C)C1] | 36 |
| 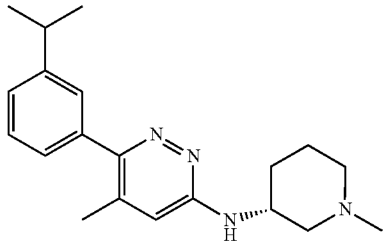 [SMILES: Cc1cc(N[C@@H]2CCCN(C)C2)nnc1-c1cccc(C(C)C)c1] | 37 |
| 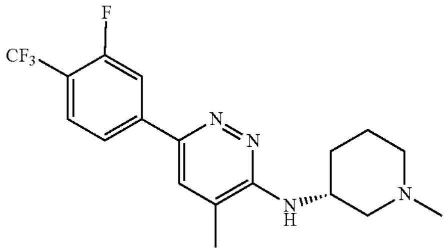 [SMILES: Cc1cc(-c2ccc(C(F)(F)F)c(F)c2)nnc1N[C@@H]1CCCN(C)C1] | 38 |
| 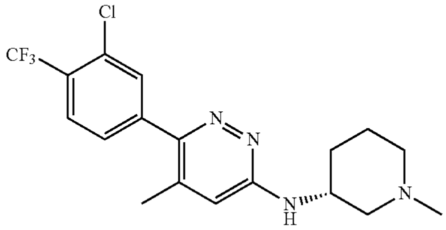 | 39 |
| 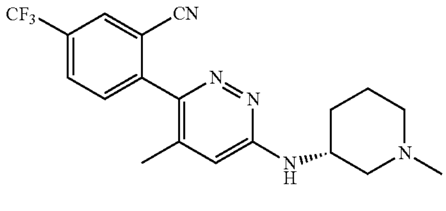 [SMILES: Cc1cc(N[C@@H]2CCCN(C)C2)nnc1-c1ccc(C(F)(F)F)cc1C#N] | 40 |

TABLE 1-continued
Representative compounds having Structure (I)
| Structure | Cpd No. |
|---|---|
| 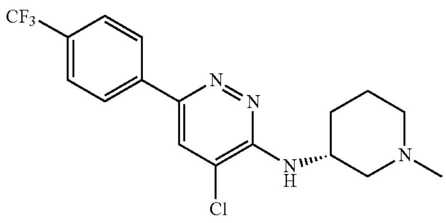 [SMILES: CN1CCC[C@@H](Nc2nnc(-c3ccc(C(F)(F)F)cc3)cc2Cl)C1] | 41 |
| 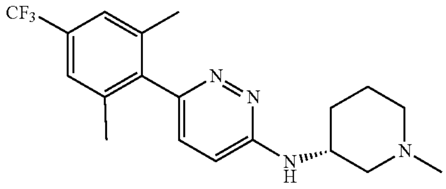 [SMILES: Cc1cc(C(F)(F)F)cc(C)c1-c1ccc(N[C@@H]2CCCN(C)C2)nn1] | 42 |
| 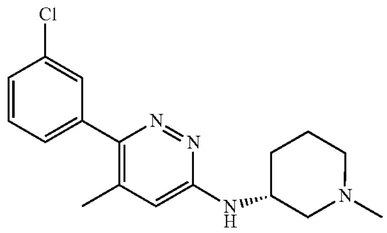 | 43 |
| 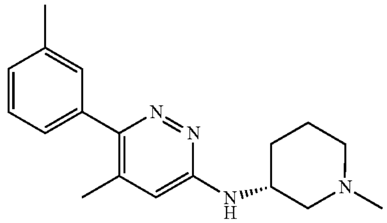 [SMILES: Cc1cccc(-c2nnc(N[C@@H]3CCCN(C)C3)cc2C)c1] | 44 |
| 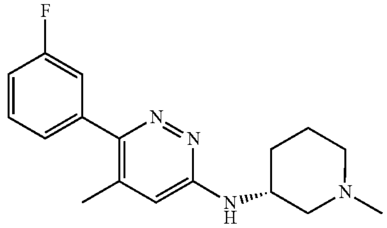 [SMILES: Cc1cc(N[C@@H]2CCCN(C)C2)nnc1-c1cccc(F)c1] | 45 |
| 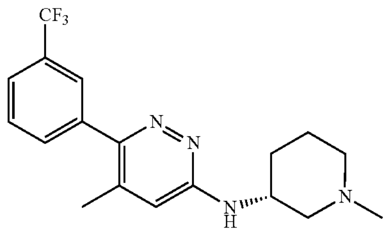 | 46 |

TABLE 1-continued
| Representative compounds having Structure (I) | |
|---|---|
| Structure | Cpd No. |
| 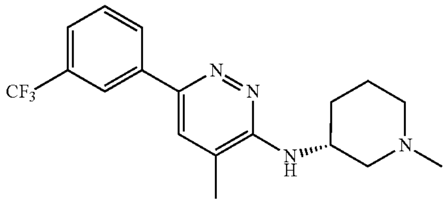 [SMILES: Cc1cc(-c2cccc(C(F)(F)F)c2)nnc1N[C@@H]1CCCN(C)C1] | 47 |
| 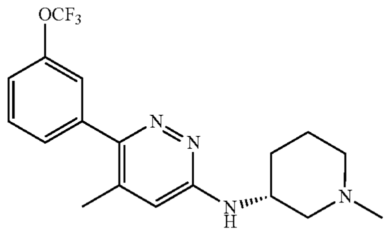 [SMILES: Cc1cc(N[C@@H]2CCCN(C)C2)nnc1-c1cccc(OC(F)(F)F)c1] | 48 |
| 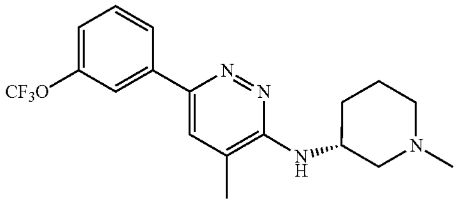 | 49 |
| 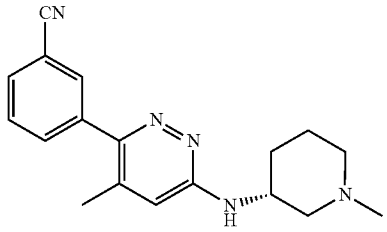 | 50 |
| 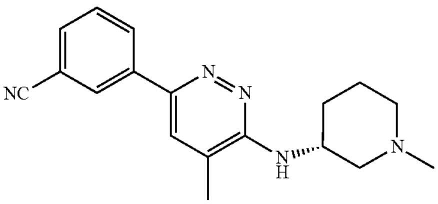 [SMILES: Cc1cc(-c2cccc(C#N)c2)nnc1N[C@@H]1CCCN(C)C1] | 51 |
| 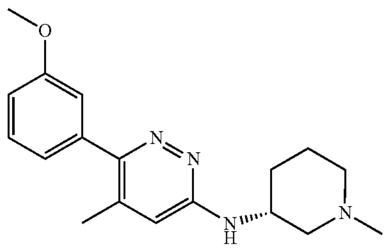 | 52 |

TABLE 1-continued
| Representative compounds having Structure (I) | |
|---|---|
| Structure | Cpd No. |
| 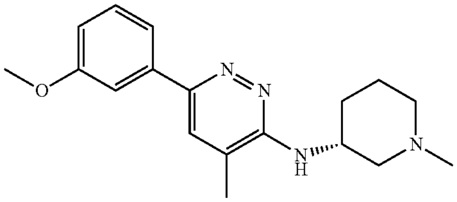 | 53 |
| 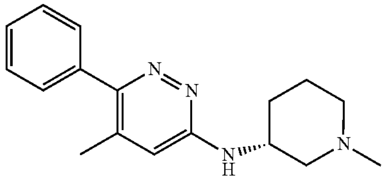 [SMILES: Cc1cc(N[C@@H]2CCCN(C)C2)nnc1-c1ccccc1] | 54 |
| 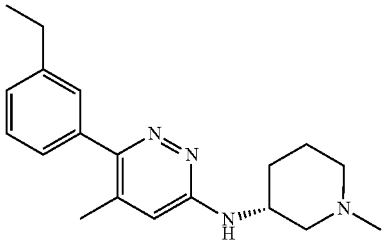 [SMILES: CCc1cccc(-c2nnc(N[C@@H]3CCCN(C)C3)cc2C)c1] | 55 |
| 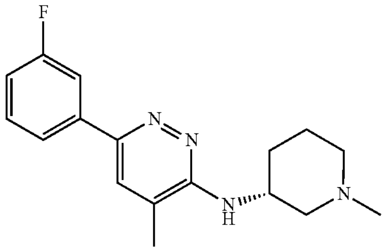 [SMILES: Cc1cc(-c2cccc(F)c2)nnc1N[C@@H]1CCCN(C)C1] | 56 |
| 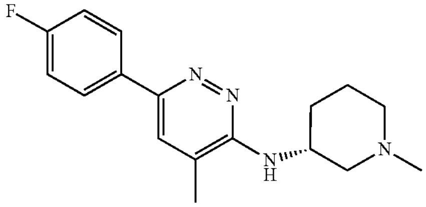 [SMILES: Cc1cc(-c2ccc(F)cc2)nnc1N[C@@H]1CCCN(C)C1] | 57 |
| 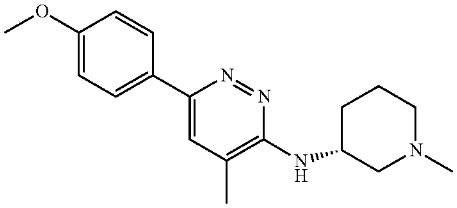 | 58 |
| 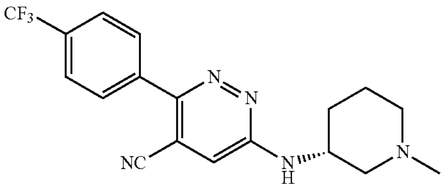 [SMILES: CN1CCC[C@@H](Nc2cc(C#N)c(-c3ccc(C(F)(F)F)cc3)nn2)C1] | 59 |

TABLE 1-continued
| Representative compounds having Structure (I) | |
|---|---|
| Structure | Cpd No. |
| 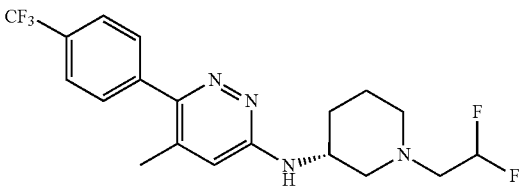 [SMILES: Cc1cc(N[C@@H]2CCCN(CC(F)F)C2)nnc1-c1ccc(C(F)(F)F)cc1] | 60 |
| 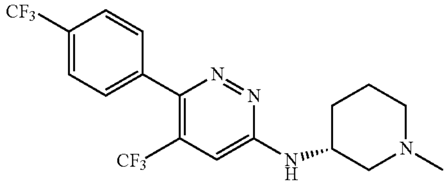 [SMILES: CN1CCC[C@@H](Nc2cc(C(F)(F)F)c(-c3ccc(C(F)(F)F)cc3)nn2)C1] | 61 |
| 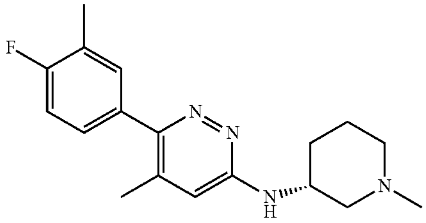 [SMILES: Cc1cc(-c2nnc(N[C@@H]3CCCN(C)C3)cc2C)ccc1F] | 62 |
| 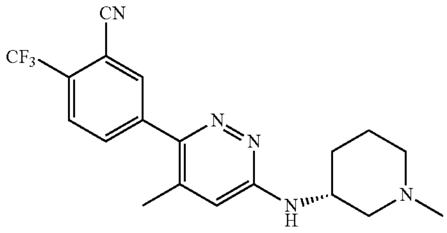 [SMILES: Cc1cc(N[C@@H]2CCCN(C)C2)nnc1-c1ccc(C(F)(F)F)c(C#N)c1] | 63 |
| 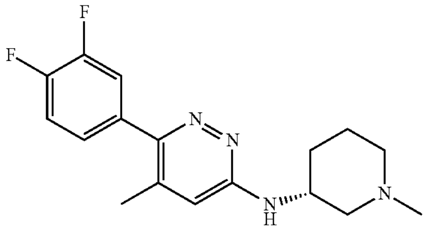 | 64 |
| 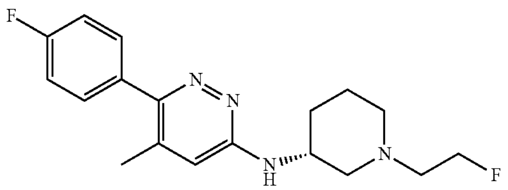 [SMILES: Cc1cc(N[C@@H]2CCCN(CCF)C2)nnc1-c1ccc(F)cc1] | 65 |
| 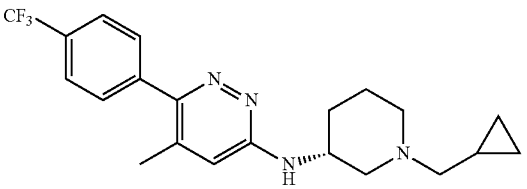 [SMILES: Cc1cc(N[C@@H]2CCCN(CC3CC3)C2)nnc1-c1ccc(C(F)(F)F)cc1] | 66 |

TABLE 1-continued
| Representative compounds having Structure (I) | |
|---|---|
| Structure | Cpd No. |
| 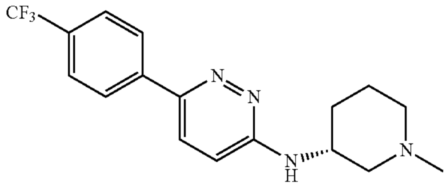 [SMILES: CN1CCC[C@@H](Nc2ccc(-c3ccc(C(F)(F)F)cc3)nn2)C1] | 67 |
| 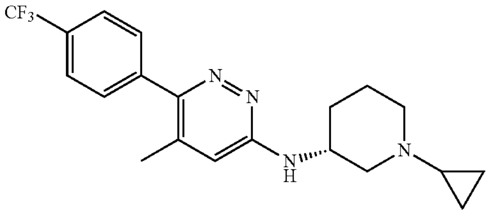 [SMILES: Cc1cc(N[C@@H]2CCCN(C3CC3)C2)nnc1-c1ccc(C(F)(F)F)cc1] | 68 |
| 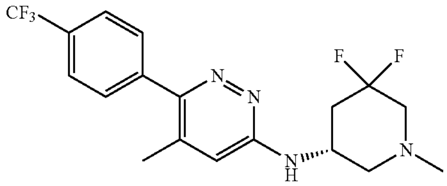 [SMILES: Cc1cc(N[C@H]2CN(C)CC(F)(F)C2)nnc1-c1ccc(C(F)(F)F)cc1] | 69 |
| 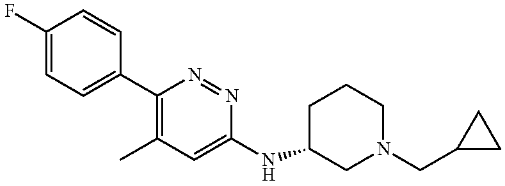 [SMILES: Cc1cc(N[C@@H]2CCCN(CC3CC3)C2)nnc1-c1ccc(F)cc1] | 70 |
| 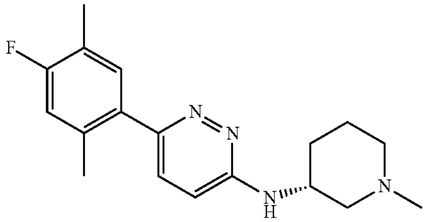 [SMILES: Cc1cc(-c2ccc(N[C@@H]3CCCN(C)C3)nn2)c(C)cc1F] | 71 |
| 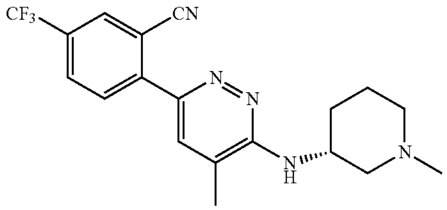 [SMILES: Cc1cc(-c2ccc(C(F)(F)F)cc2C#N)nnc1N[C@@H]1CCCN(C)C1] | 72 |
| 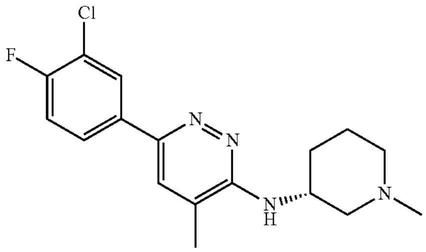 [SMILES: Cc1cc(-c2ccc(F)c(Cl)c2)nnc1N[C@@H]1CCCN(C)C1] | 73 |

TABLE 1-continued
| Representative compounds having Structure (I) | |
|---|---|
| Structure | Cpd No. |
| 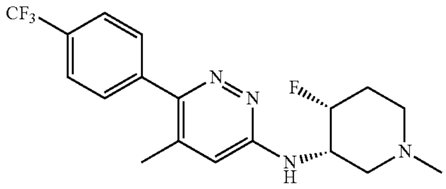 [SMILES: Cc1cc(N[C@H]2CN(C)CC[C@H]2F)nnc1-c1ccc(C(F)(F)F)cc1] | 74 |
| 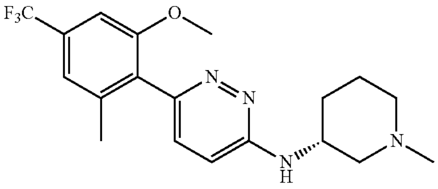 [SMILES: COc1cc(C(F)(F)F)cc(C)c1-c1ccc(N[C@@H]2CCCN(C)C2)nn1] | 75 |
| 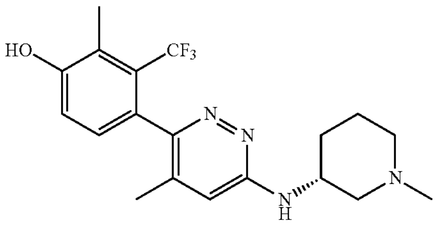 [SMILES: Cc1cc(N[C@@H]2CCCN(C)C2)nnc1-c1ccc(O)c(C)c1C(F)(F)F] | 76 |
| 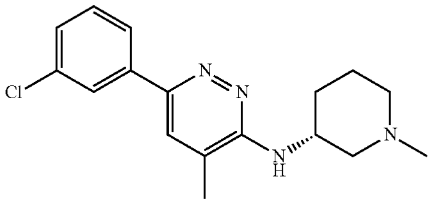 [SMILES: Cc1cc(-c2cccc(Cl)c2)nnc1N[C@@H]1CCCN(C)C1] | 77 |
| 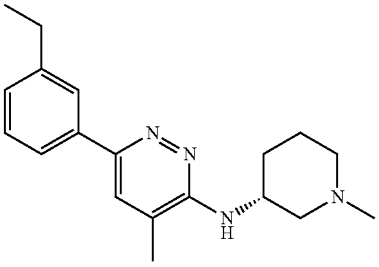 [SMILES: CCc1cccc(-c2cc(C)c(N[C@@H]3CCCN(C)C3)nn2)c1] | 78 |
| 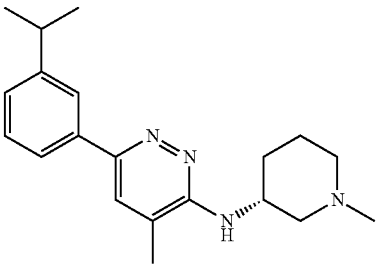 [SMILES: Cc1cc(-c2cccc(C(C)C)c2)nnc1N[C@@H]1CCCN(C)C1] | 79 |

TABLE 1-continued
| Representative compounds having Structure (I) | |
|---|---|
| Structure | Cpd No. |
| 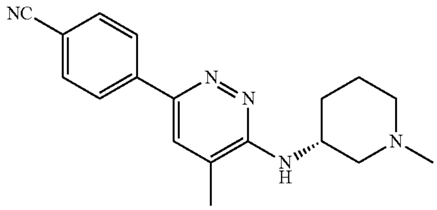 [SMILES: Cc1cc(-c2ccc(C#N)cc2)nnc1N[C@@H]1CCCN(C)C1] | 80 |
| 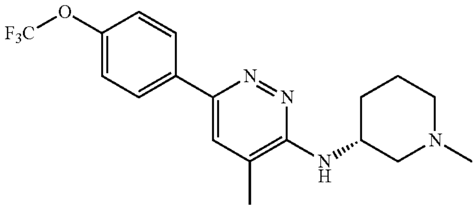 [SMILES: Cc1cc(-c2ccc(OC(F)(F)F)cc2)nnc1N[C@@H]1CCCN(C)C1] | 81 |
| 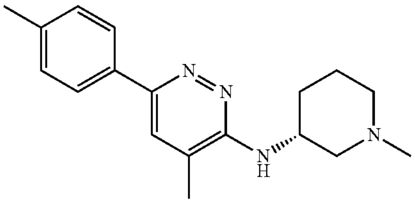 | 82 |
| 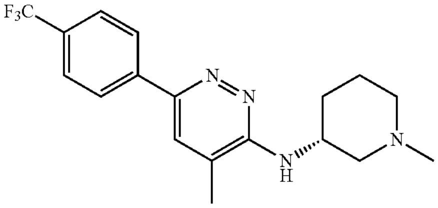 [SMILES: Cc1cc(-c2ccc(C(F)(F)F)cc2)nnc1N[C@@H]1CCCN(C)C1] | 83 |
| 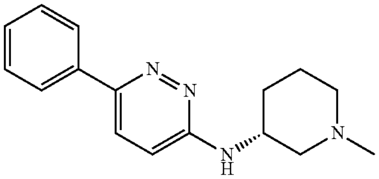 [SMILES: CN1CCC[C@@H](Nc2ccc(-c3ccccc3)nn2)C1] | 84 |
| 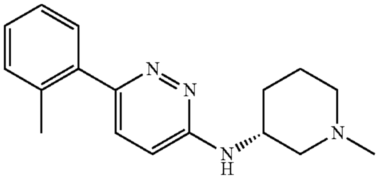 [SMILES: Cc1ccccc1-c1ccc(N[C@@H]2CCCN(C)C2)nn1] | 85 |
| 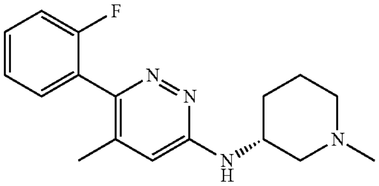 [SMILES: Cc1cc(N[C@@H]2CCCN(C)C2)nnc1-c1ccccc1F] | 86 |

TABLE 1-continued
| Representative compounds having Structure (I) | |
| --- | --- |
| Structure | Cpd No. |
| 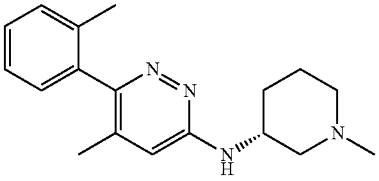 [SMILES: Cc1ccccc1-c1nnc(N[C@@H]2CCCN(C)C2)cc1C] | 87 |
| 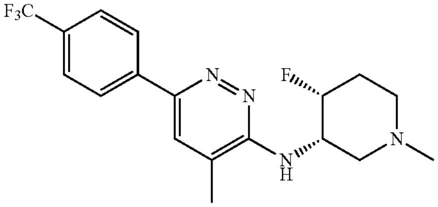 [SMILES: Cc1cc(-c2ccc(C(F)(F)F)cc2)nnc1N[C@H]1CN(C)CC[C@H]1F] | 88 |
| 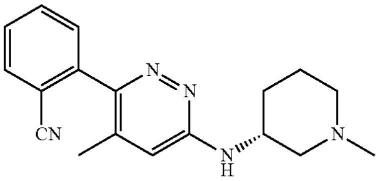 [SMILES: Cc1cc(N[C@@H]2CCCN(C)C2)nnc1-c1ccccc1C#N] | 89 |
| 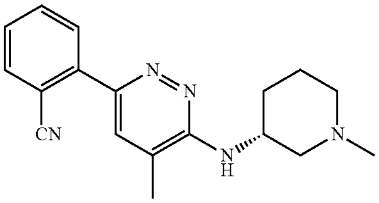 [SMILES: Cc1cc(-c2ccccc2C#N)nnc1N[C@@H]1CCCN(C)C1] | 90 |
| 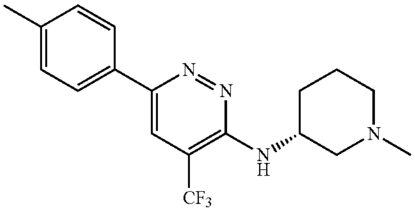 | 91 |
| 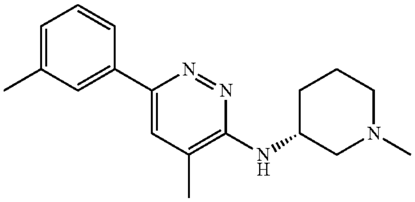 | 92 |
| 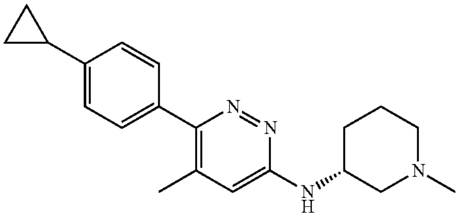 [SMILES: Cc1cc(N[C@@H]2CCCN(C)C2)nnc1-c1ccc(C2CC2)cc1] | 93 |

TABLE 1-continued
| Representative compounds having Structure (I) | |
|---|---|
| Structure | Cpd No. |
| 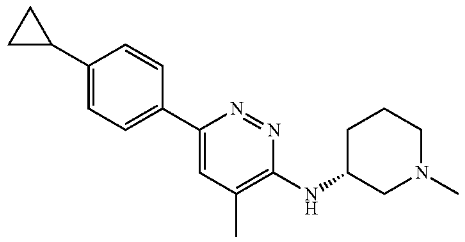 [SMILES: Cc1cc(-c2ccc(C3CC3)cc2)nnc1N[C@@H]1CCCN(C)C1] | 94 |
| 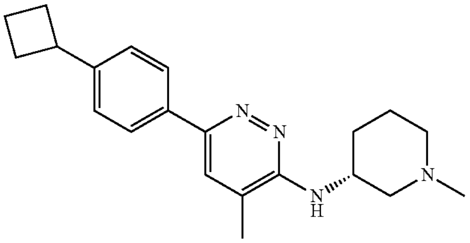 [SMILES: Cc1cc(-c2ccc(C3CCC3)cc2)nnc1N[C@@H]1CCCN(C)C1] | 95 |
| 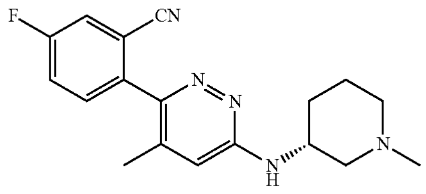 [SMILES: Cc1cc(N[C@@H]2CCCN(C)C2)nnc1-c1ccc(F)cc1C#N] | 96 |
| 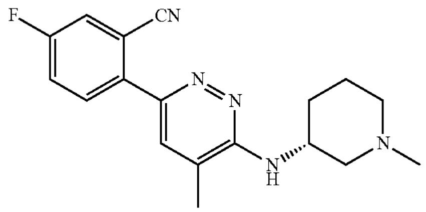 [SMILES: Cc1cc(-c2ccc(F)cc2C#N)nnc1N[C@@H]1CCCN(C)C1] | 97 |
| 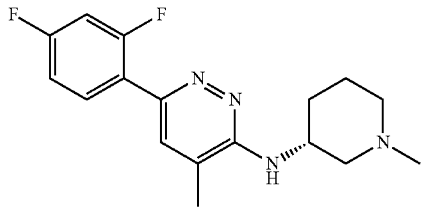 [SMILES: Cc1cc(-c2ccc(F)cc2F)nnc1N[C@@H]1CCCN(C)C1] | 98 |
| 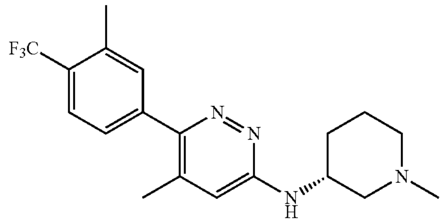 [SMILES: Cc1cc(-c2nnc(N[C@@H]3CCCN(C)C3)cc2C)ccc1C(F)(F)F] | 99 |

TABLE 1-continued
| Representative compounds having Structure (I) | |
|---|---|
| Structure | Cpd No. |
| 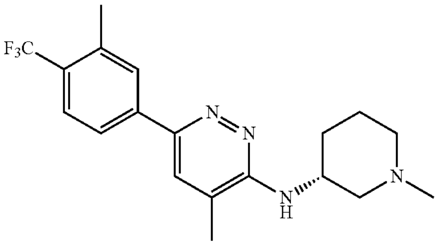 [SMILES: Cc1cc(-c2cc(C)c(N[C@@H]3CCCN(C)C3)nn2)ccc1C(F)(F)F] | 100 |
| 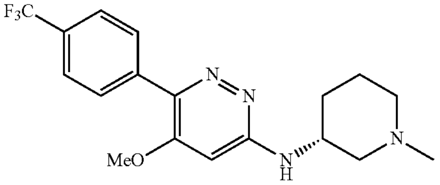 [SMILES: COc1cc(N[C@@H]2CCCN(C)C2)nnc1-c1ccc(C(F)(F)F)cc1] | 101 |
| 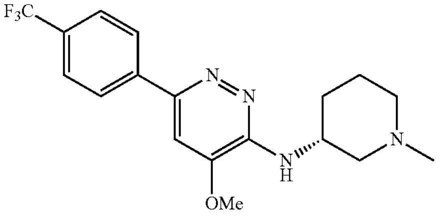 [SMILES: COc1cc(-c2ccc(C(F)(F)F)cc2)nnc1N[C@@H]1CCCN(C)C1] | 102 |
| 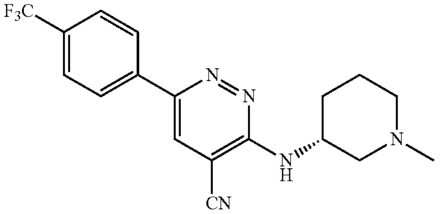 [SMILES: CN1CCC[C@@H](Nc2nnc(-c3ccc(C(F)(F)F)cc3)cc2C#N)C1] | 103 |
| 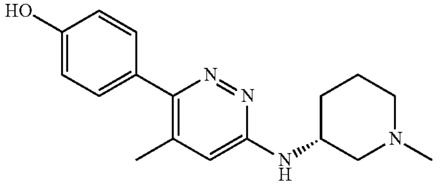 [SMILES: Cc1cc(N[C@@H]2CCCN(C)C2)nnc1-c1ccc(O)cc1] | 104 |
| 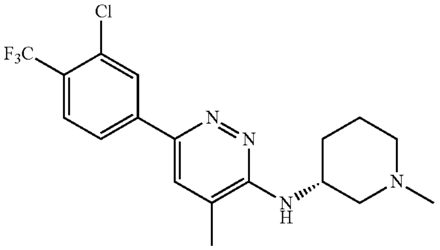 [SMILES: Cc1cc(-c2ccc(C(F)(F)F)c(Cl)c2)nnc1N[C@@H]1CCCN(C)C1] | 105 |

TABLE 1-continued
Representative compounds having Structure (I)
| Structure | Cpd No. |
|---|---|
| 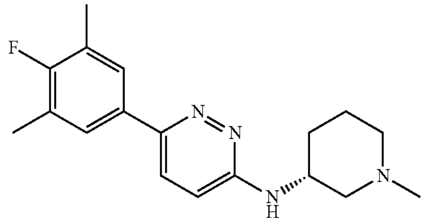 [SMILES: Cc1cc(-c2ccc(N[C@@H]3CCCN(C)C3)nn2)cc(C)c1F] | 106 |
| 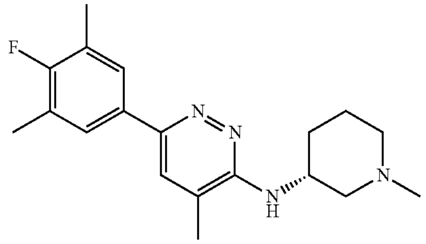 [SMILES: Cc1cc(-c2cc(C)c(F)c(C)c2)nnc1N[C@@H]1CCCN(C)C1] | 107 |
| 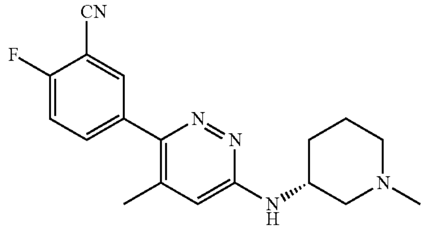 [SMILES: Cc1cc(N[C@@H]2CCCN(C)C2)nnc1-c1ccc(F)c(C#N)c1] | 108 |
| 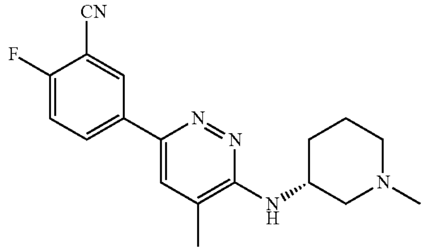 [SMILES: Cc1cc(-c2ccc(F)c(C#N)c2)nnc1N[C@@H]1CCCN(C)C1] | 109 |
| 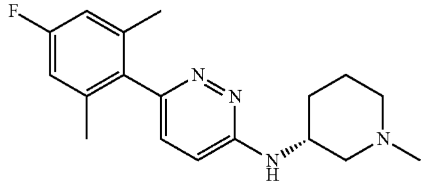 [SMILES: Cc1cc(F)cc(C)c1-c1ccc(N[C@@H]2CCCN(C)C2)nn1] | 110 |
| 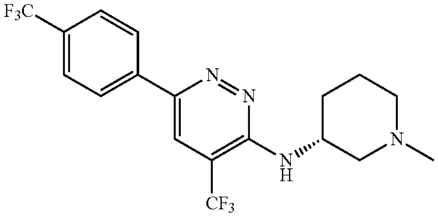 [SMILES: CN1CCC[C@@H](Nc2nnc(-c3ccc(C(F)(F)F)cc3)cc2C(F)(F)F)C1] | 111 |

TABLE 1-continued
| Representative compounds having Structure (I) | |
|---|---|
| Structure | Cpd No. |
| 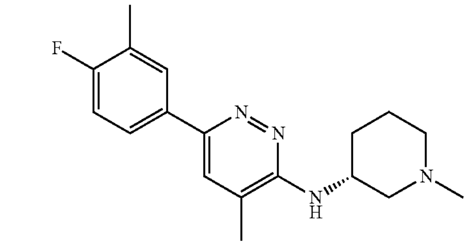 [SMILES: Cc1cc(-c2cc(C)c(N[C@@H]3CCCN(C)C3)nn2)ccc1F] | 112 |
| 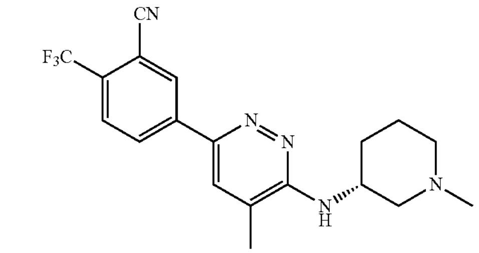 [SMILES: Cc1cc(-c2ccc(C(F)(F)F)c(C#N)c2)nnc1N[C@@H]1CCCN(C)C1] | 113 |
| 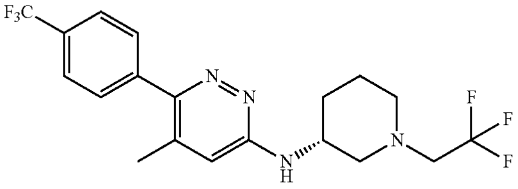 [SMILES: Cc1cc(N[C@@H]2CCCN(CC(F)(F)F)C2)nnc1-c1ccc(C(F)(F)F)cc1] | 114 |
| 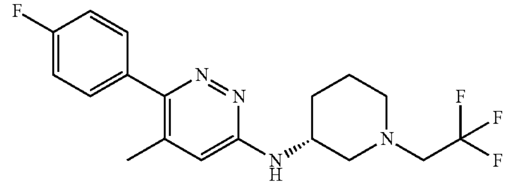 [SMILES: Cc1cc(N[C@@H]2CCCN(CC(F)(F)F)C2)nnc1-c1ccc(F)cc1] | 115 |
| 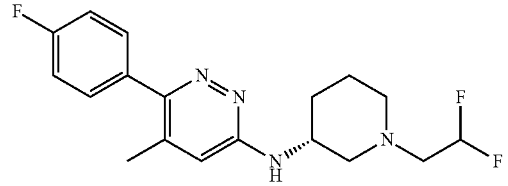 [SMILES: Cc1cc(N[C@@H]2CCCN(CC(F)F)C2)nnc1-c1ccc(F)cc1] | 116 |
| 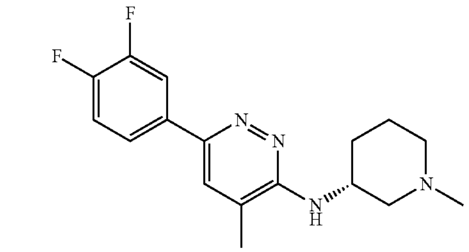 [SMILES: Cc1cc(-c2ccc(F)c(F)c2)nnc1N[C@@H]1CCCN(C)C1] | 117 |

TABLE 1-continued
| Representative compounds having Structure (I) | |
|---|---|
| Structure | Cpd No. |
| 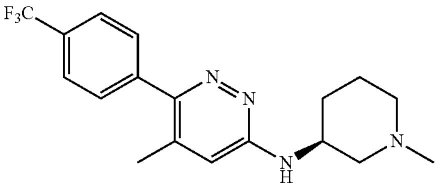 [SMILES: Cc1cc(N[C@H]2CCCN(C)C2)nnc1-c1ccc(C(F)(F)F)cc1] | 118 |
| 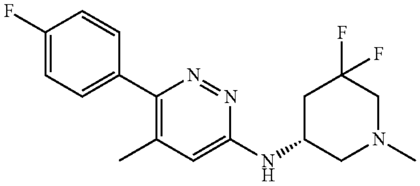 [SMILES: Cc1cc(N[C@H]2CN(C)CC(F)(F)C2)nnc1-c1ccc(F)cc1] | 119 |
| 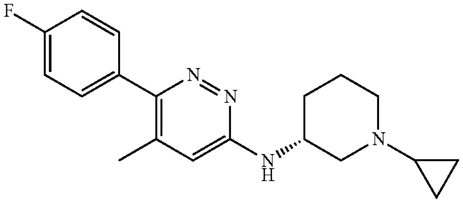 [SMILES: Cc1cc(N[C@@H]2CCCN(C3CC3)C2)nnc1-c1ccc(F)cc1] | 120 |
| 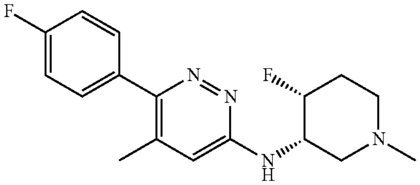 [SMILES: Cc1cc(N[C@H]2CN(C)CC[C@H]2F)nnc1-c1ccc(F)cc1] | 121 |
| 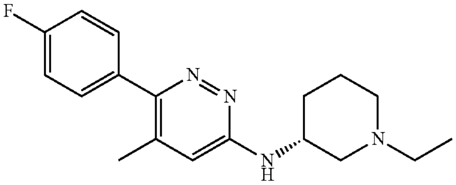 [SMILES: CCN1CCC[C@@H](Nc2cc(C)c(-c3ccc(F)cc3)nn2)C1] | 122 |
| 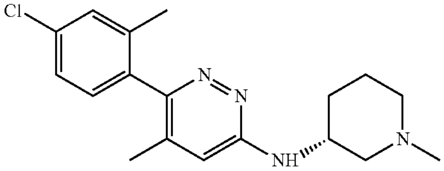 [SMILES: Cc1cc(Cl)ccc1-c1nnc(N[C@@H]2CCCN(C)C2)cc1C] | 123 |
| 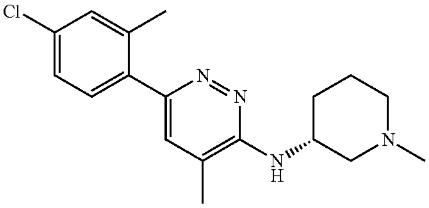 [SMILES: Cc1cc(Cl)ccc1-c1cc(C)c(N[C@@H]2CCCN(C)C2)nn1] | 124 |

TABLE 1-continued
| Representative compounds having Structure (I) | |
| --- | --- |
| Structure | Cpd No. |
| 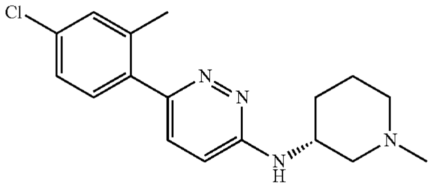 [SMILES: Cc1cc(Cl)ccc1-c1ccc(N[C@@H]2CCCN(C)C2)nn1] | 125 |
| 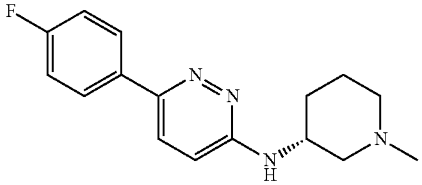 [SMILES: CN1CCC[C@@H](Nc2ccc(-c3ccc(F)cc3)nn2)C1] | 126 |
| 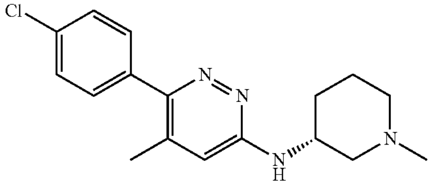 [SMILES: Cc1cc(N[C@@H]2CCCN(C)C2)nnc1-c1ccc(Cl)cc1] | 127 |
| 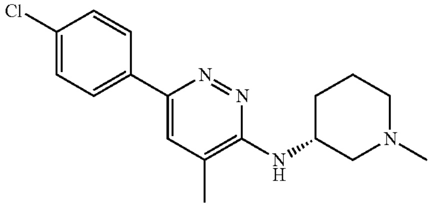 [SMILES: Cc1cc(-c2ccc(Cl)cc2)nnc1N[C@@H]1CCCN(C)C1] | 128 |
| 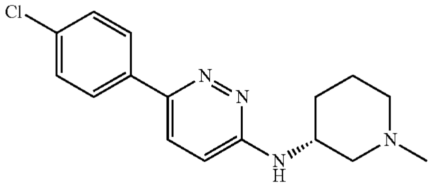 [SMILES: CN1CCC[C@@H](Nc2ccc(-c3ccc(Cl)cc3)nn2)C1] | 129 |
| 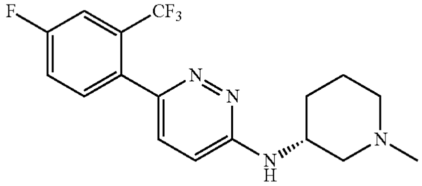 [SMILES: CN1CCC[C@@H](Nc2ccc(-c3ccc(F)cc3C(F)(F)F)nn2)C1] | 130 |
| 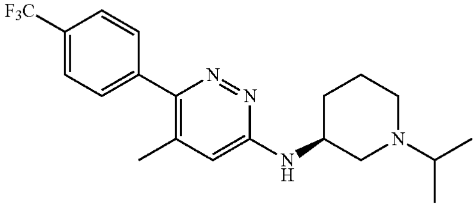 [SMILES: Cc1cc(N[C@H]2CCCN(C(C)C)C2)nnc1-c1ccc(C(F)(F)F)cc1] | 131 |

TABLE 1-continued
Representative compounds having Structure (I)
| Structure | Cpd No. |
| --- | --- |
| 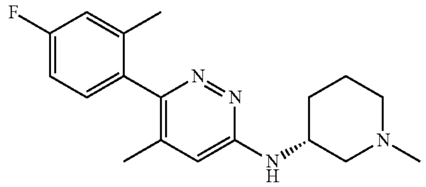 [SMILES: Cc1cc(F)ccc1-c1nnc(N[C@@H]2CCCN(C)C2)cc1C] | 132 |
| 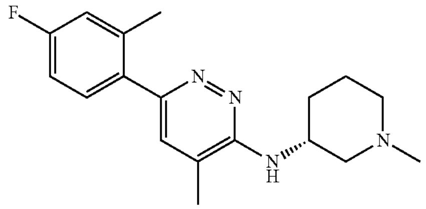 [SMILES: Cc1cc(F)ccc1-c1cc(C)c(N[C@@H]2CCCN(C)C2)nn1] | 133 |
| 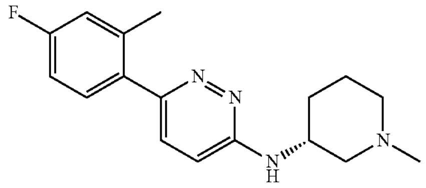 [SMILES: Cc1cc(F)ccc1-c1ccc(N[C@@H]2CCCN(C)C2)nn1] | 134 |
| 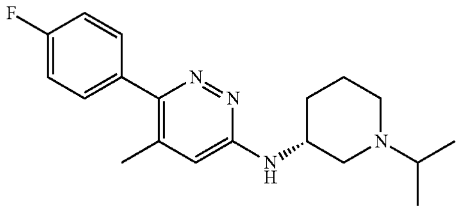 [SMILES: Cc1cc(N[C@@H]2CCCN(C(C)C)C2)nnc1-c1ccc(F)cc1] | 135 |
| 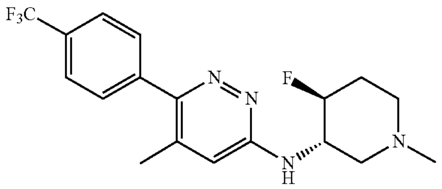 [SMILES: Cc1cc(N[C@H]2CN(C)CC[C@@H]2F)nnc1-c1ccc(C(F)(F)F)cc1] | 136 |
| 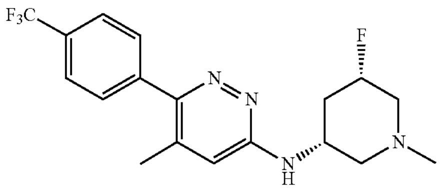 [SMILES: Cc1cc(N[C@@H]2C[C@H](F)CN(C)C2)nnc1-c1ccc(C(F)(F)F)cc1] | 137 |
| 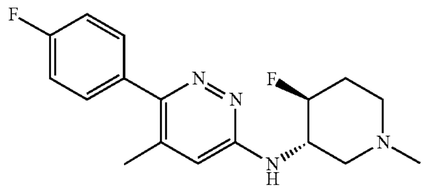 [SMILES: Cc1cc(N[C@H]2CN(C)CC[C@@H]2F)nnc1-c1ccc(F)cc1] | 138 |

TABLE 1-continued
| Representative compounds having Structure (I) | |
|---|---|
| Structure | Cpd No. |
| 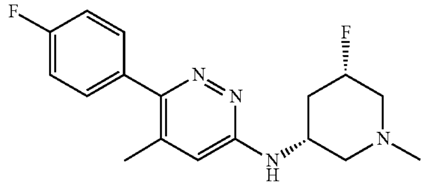 [SMILES: Cc1cc(N[C@@H]2C[C@H](F)CN(C)C2)nnc1-c1ccc(F)cc1] | 139 |
| 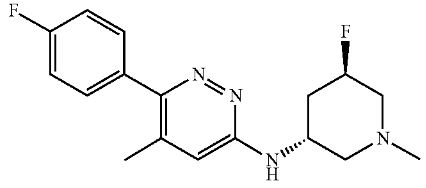 [SMILES: Cc1cc(N[C@@H]2C[C@@H](F)CN(C)C2)nnc1-c1ccc(F)cc1] | 140 |
| 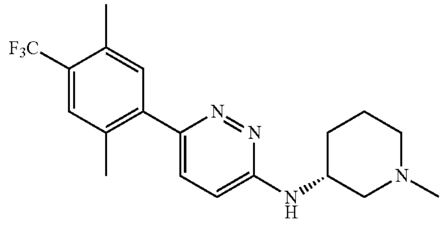 [SMILES: Cc1cc(C(F)(F)F)c(C)cc1-c1ccc(N[C@@H]2CCCN(C)C2)nn1] | 141 |
| 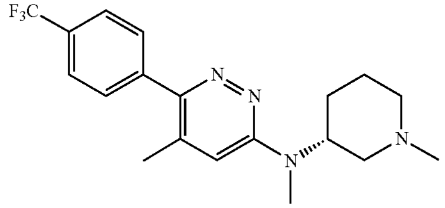 [SMILES: Cc1cc(N(C)[C@@H]2CCCN(C)C2)nnc1-c1ccc(C(F)(F)F)cc1] | 142 |
| 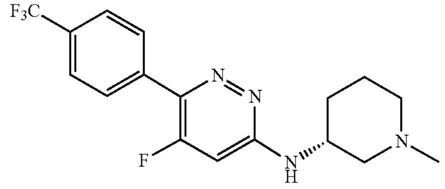 [SMILES: CN1CCC[C@@H](Nc2cc(F)c(-c3ccc(C(F)(F)F)cc3)nn2)C1] | 143 |
| 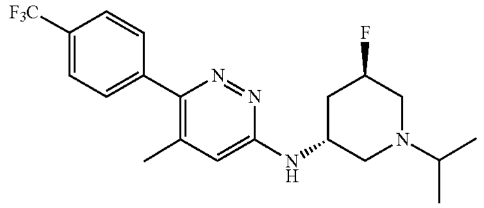 [SMILES: Cc1cc(N[C@@H]2C[C@@H](F)CN(C(C)C)C2)nnc1-c1ccc(C(F)(F)F)cc1] | 144 |
| 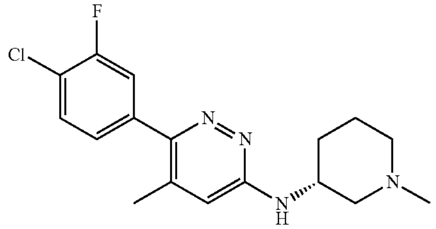 [SMILES: Cc1cc(N[C@@H]2CCCN(C)C2)nnc1-c1ccc(Cl)c(F)c1] | 145 |

TABLE 1-continued
Representative compounds having Structure (I)
| Structure | Cpd No. |
|---|---|
| 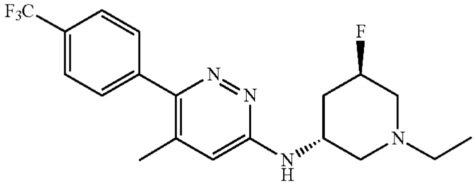 [SMILES: CCN1C[C@H](F)C[C@@H](Nc2cc(C)c(-c3ccc(C(F)(F)F)cc3)nn2)C1] | 146 |
| 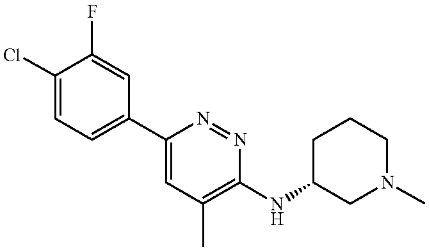 [SMILES: Cc1cc(-c2ccc(Cl)c(F)c2)nnc1N[C@@H]1CCCN(C)C1] | 147 |
| 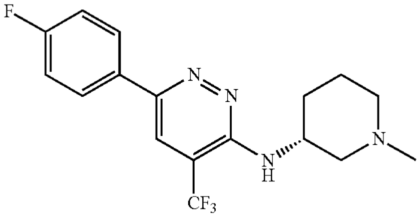 [SMILES: CN1CCC[C@@H](Nc2nnc(-c3ccc(F)cc3)cc2C(F)(F)F)C1] | 148 |
| 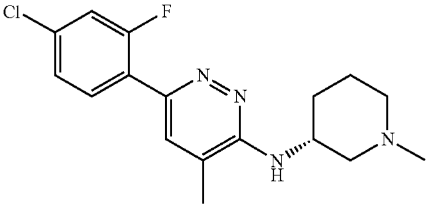 [SMILES: Cc1cc(-c2ccc(Cl)cc2F)nnc1N[C@@H]1CCCN(C)C1] | 149 |
| 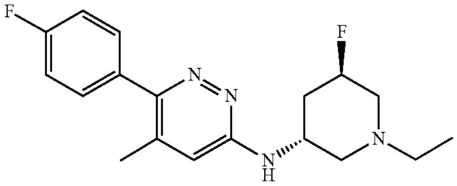 [SMILES: CCN1C[C@H](F)C[C@@H](Nc2cc(C)c(-c3ccc(F)cc3)nn2)C1] | 150 |
| 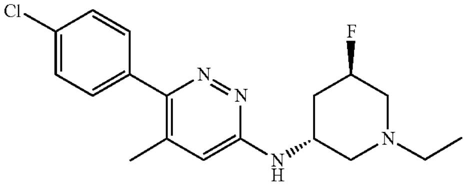 [SMILES: CCN1C[C@H](F)C[C@@H](Nc2cc(C)c(-c3ccc(Cl)cc3)nn2)C1] | 151 |
| 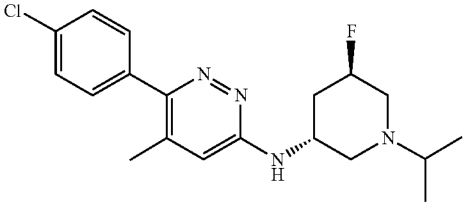 [SMILES: Cc1cc(N[C@@H]2C[C@@H](F)CN(C(C)C)C2)nnc1-c1ccc(Cl)cc1] | 152 |

TABLE 1-continued
Representative compounds having Structure (I)
| Structure | Cpd No. |
|---|---|
| 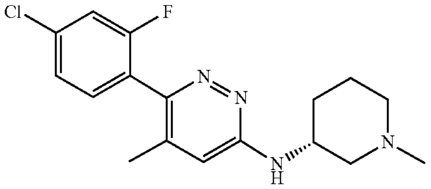 [SMILES: Cc1cc(N[C@@H]2CCCN(C)C2)nnc1-c1ccc(Cl)cc1F] | 153 |
| 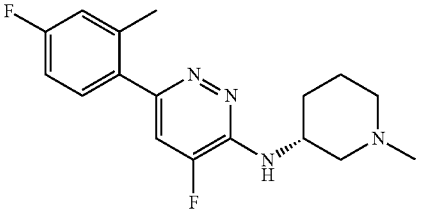 [SMILES: Cc1cc(F)ccc1-c1cc(F)c(N[C@@H]2CCCN(C)C2)nn1] | 154 |
| 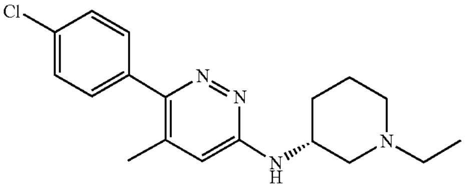 [SMILES: CCN1CCC[C@@H](Nc2cc(C)c(-c3ccc(Cl)cc3)nn2)C1] | 155 |
| 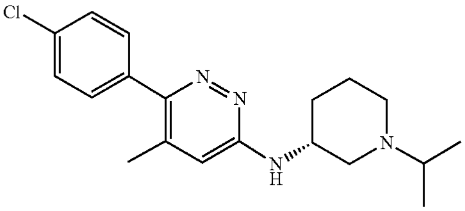 [SMILES: Cc1cc(N[C@@H]2CCCN(C(C)C)C2)nnc1-c1ccc(Cl)cc1] | 156 |
| 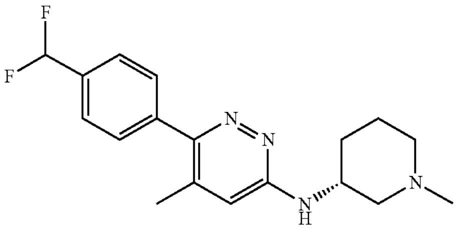 [SMILES: Cc1cc(N[C@@H]2CCCN(C)C2)nnc1-c1ccc(C(F)F)cc1] | 157 |
| 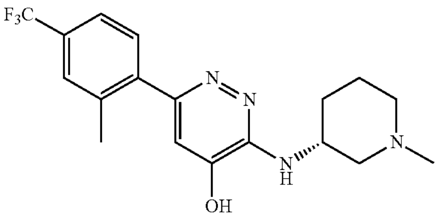 [SMILES: Cc1cc(C(F)(F)F)ccc1-c1cc(O)c(N[C@@H]2CCCN(C)C2)nn1] | 158 |
| 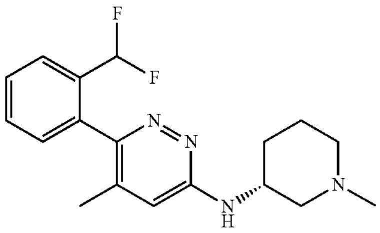 [SMILES: Cc1cc(N[C@@H]2CCCN(C)C2)nnc1-c1ccccc1C(F)F] | 159 |

TABLE 1-continued
| Representative compounds having Structure (I) | |
|---|---|
| Structure | Cpd No. |
| 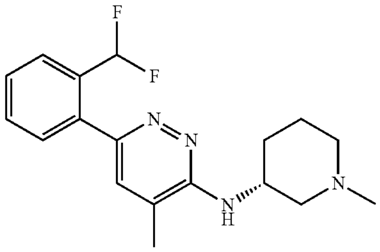 [SMILES: Cc1cc(-c2ccccc2C(F)F)nnc1N[C@@H]1CCCN(C)C1] | 160 |
| 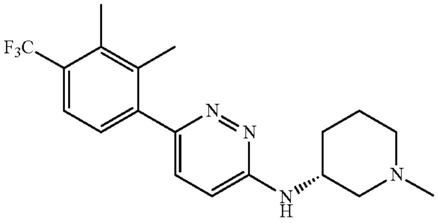 [SMILES: Cc1c(-c2ccc(N[C@@H]3CCCN(C)C3)nn2)ccc(C(F)(F)F)c1C] | 161 |
| 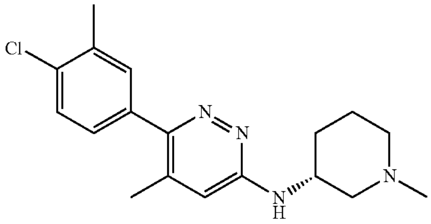 [SMILES: Cc1cc(-c2nnc(N[C@@H]3CCCN(C)C3)cc2C)ccc1Cl] | 162 |
| 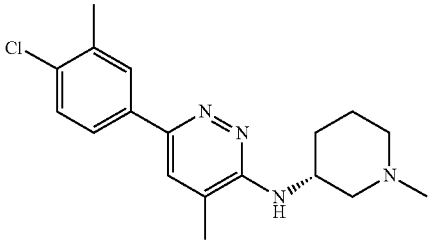 [SMILES: Cc1cc(-c2cc(C)c(N[C@@H]3CCCN(C)C3)nn2)ccc1Cl] | 163 |
| 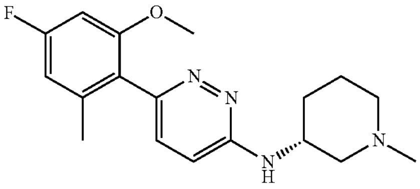 [SMILES: COc1cc(F)cc(C)c1-c1ccc(N[C@@H]2CCCN(C)C2)nn1] | 164 |
| 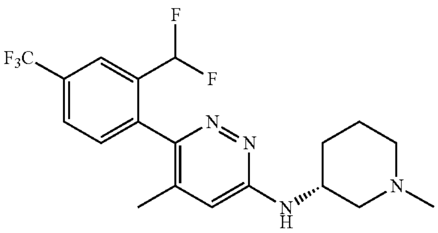 [SMILES: Cc1cc(N[C@@H]2CCCN(C)C2)nnc1-c1ccc(C(F)(F)F)cc1C(F)F] | 165 |

TABLE 1-continued
Representative compounds having Structure (I)
| Structure | Cpd No. |
| --- | --- |
| 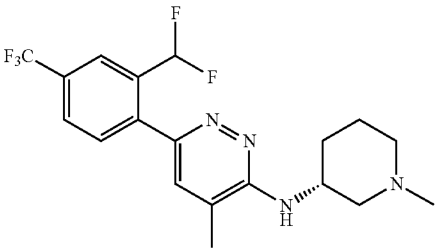 [SMILES: Cc1cc(-c2ccc(C(F)(F)F)cc2C(F)F)nnc1N[C@@H]1CCCN(C)C1] | 166 |
| 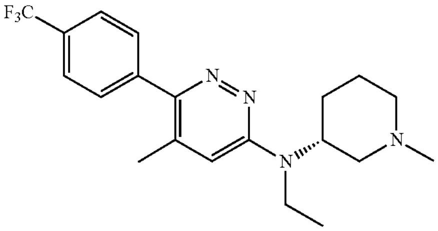 [SMILES: CCN(c1cc(C)c(-c2ccc(C(F)(F)F)cc2)nn1)[C@@H]1CCCN(C)C1] | 167 |
| 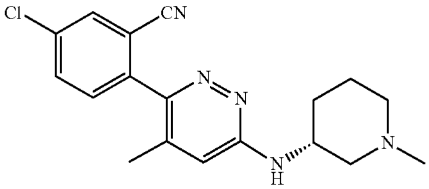 [SMILES: Cc1cc(N[C@@H]2CCCN(C)C2)nnc1-c1ccc(Cl)cc1C#N] | 168 |
| 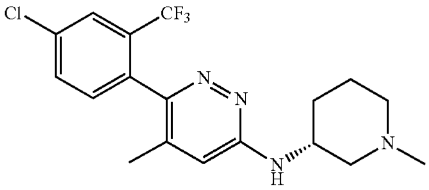 | 169 |
| 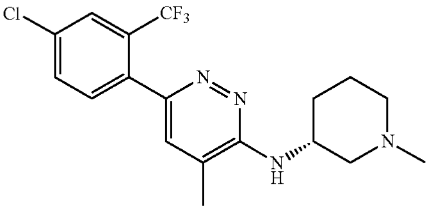 | 170 |
| 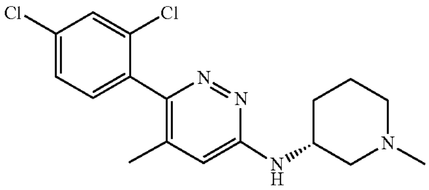 [SMILES: Cc1cc(N[C@@H]2CCCN(C)C2)nnc1-c1ccc(Cl)cc1Cl] | 171 |
| 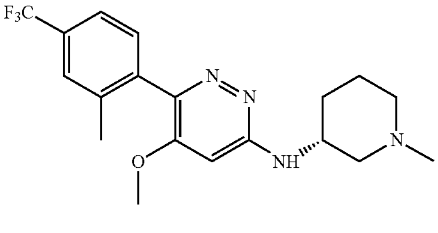 [SMILES: COc1cc(N[C@@H]2CCCN(C)C2)nnc1-c1ccc(C(F)(F)F)cc1C] | 172 |

TABLE 1-continued
| Representative compounds having Structure (I) | |
|---|---|
| Structure | Cpd No. |
| 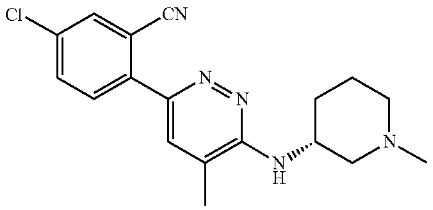 [SMILES: Cc1cc(-c2ccc(Cl)cc2C#N)nnc1N[C@@H]1CCCN(C)C1] | 173 |
| 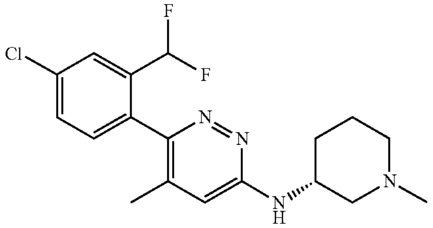 [SMILES: Cc1cc(N[C@@H]2CCCN(C)C2)nnc1-c1ccc(Cl)cc1C(F)F] | 174 |
| 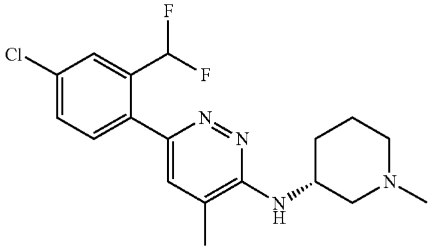 [SMILES: Cc1cc(-c2ccc(Cl)cc2C(F)F)nnc1N[C@@H]1CCCN(C)C1] | 175 |
| 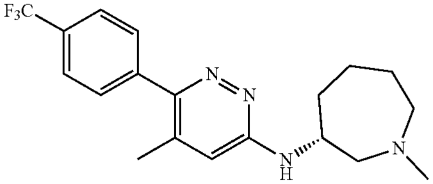 [SMILES: Cc1cc(N[C@@H]2CCCCN(C)C2)nnc1-c1ccc(C(F)(F)F)cc1] | 176 |
| 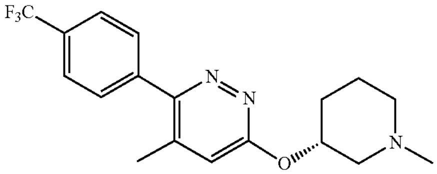 [SMILES: Cc1cc(O[C@@H]2CCCN(C)C2)nnc1-c1ccc(C(F)(F)F)cc1] | 177 |
| 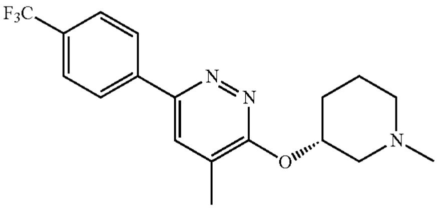 [SMILES: Cc1cc(-c2ccc(C(F)(F)F)cc2)nnc1O[C@@H]1CCCN(C)C1] | 178 |
| 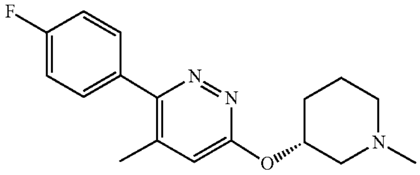 [SMILES: Cc1cc(O[C@@H]2CCCN(C)C2)nnc1-c1ccc(F)cc1] | 179 |

TABLE 1-continued
| Representative compounds having Structure (I) | |
|---|---|
| Structure | Cpd No. |
| 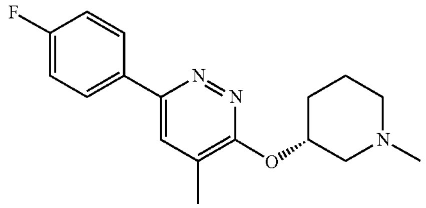 [SMILES: Cc1cc(-c2ccc(F)cc2)nnc1O[C@@H]1CCCN(C)C1] | 180 |
| 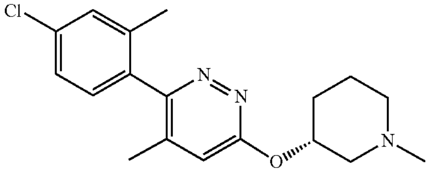 [SMILES: Cc1cc(Cl)ccc1-c1nnc(O[C@@H]2CCCN(C)C2)cc1C] | 181 |
| 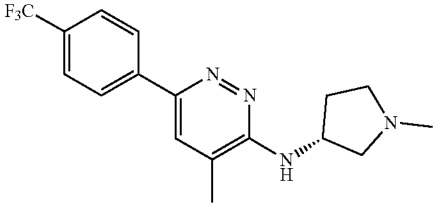 [SMILES: Cc1cc(-c2ccc(C(F)(F)F)cc2)nnc1N[C@@H]1CCN(C)C1] | 182 |
| 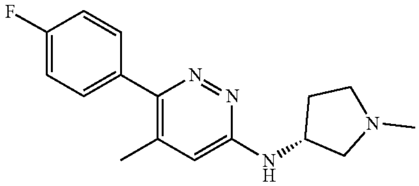 [SMILES: Cc1cc(N[C@@H]2CCN(C)C2)nnc1-c1ccc(F)cc1] | 183 |
| 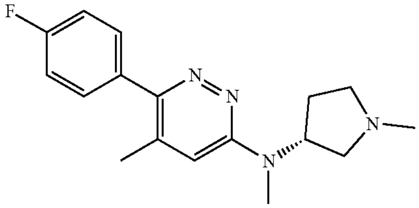 [SMILES: Cc1cc(N(C)[C@@H]2CCN(C)C2)nnc1-c1ccc(F)cc1] | 184 |
| 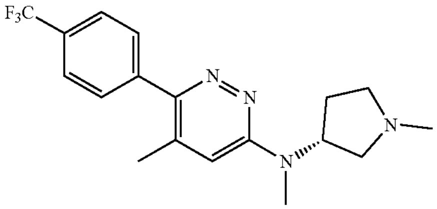 [SMILES: Cc1cc(N(C)[C@@H]2CCN(C)C2)nnc1-c1ccc(C(F)(F)F)cc1] | 185 |
| 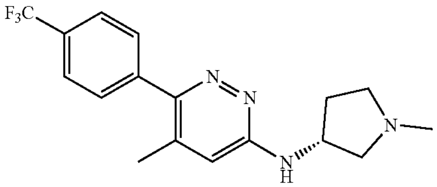 [SMILES: Cc1cc(N[C@@H]2CCN(C)C2)nnc1-c1ccc(C(F)(F)F)cc1] | 186 |

TABLE 1-continued
| Representative compounds having Structure (I) | |
|---|---|
| Structure | Cpd No. |
| 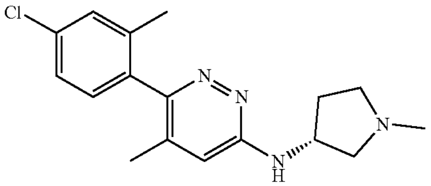 [SMILES: Cc1cc(Cl)ccc1-c1nnc(N[C@@H]2CCN(C)C2)cc1C] | 187 |
| 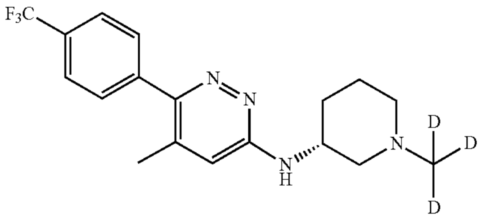 [SMILES: [2H]C([2H])([2H])N1CCC[C@@H](Nc2cc(C)c(-c3ccc(C(F)(F)F)cc3)nn2)C1] | 188 |
| 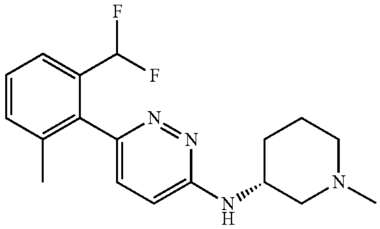 [SMILES: Cc1cccc(C(F)F)c1-c1ccc(N[C@@H]2CCCN(C)C2)nn1] | 189 |
| 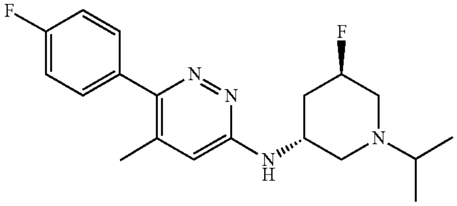 [SMILES: Cc1cc(N[C@@H]2C[C@@H](F)CN(C(C)C)C2)nnc1-c1ccc(F)cc1] | 190 |
| 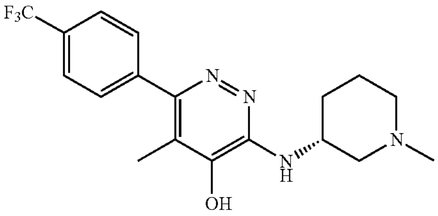 [SMILES: Cc1c(-c2ccc(C(F)(F)F)cc2)nnc(N[C@@H]2CCCN(C)C2)c1O] | 191 |
| 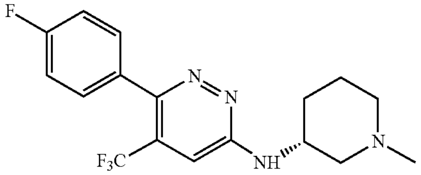 [SMILES: CN1CCC[C@@H](Nc2cc(C(F)(F)F)c(-c3ccc(F)cc3)nn2)C1] | 192 |
| 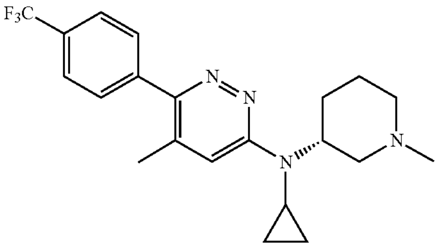 [SMILES: Cc1cc(N(C2CC2)[C@@H]2CCCN(C)C2)nnc1-c1ccc(C(F)(F)F)cc1] | 193 |

TABLE 1-continued
| Representative compounds having Structure (I) | |
|---|---|
| Structure | Cpd No. |
| 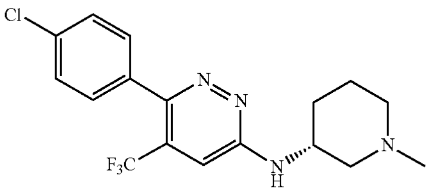 [SMILES: CN1CCC[C@@H](Nc2cc(C(F)(F)F)c(-c3ccc(Cl)cc3)nn2)C1] | 194 |
| 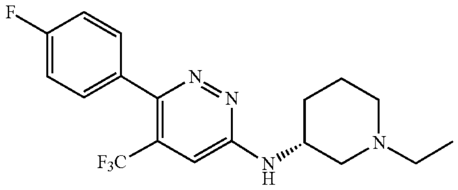 [SMILES: CCN1CCC[C@@H](Nc2cc(C(F)(F)F)c(-c3ccc(F)cc3)nn2)C1] | 195 |
| 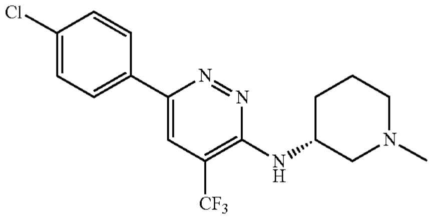 [SMILES: CN1CCC[C@@H](Nc2nnc(-c3ccc(Cl)cc3)cc2C(F)(F)F)C1] | 196 |
| 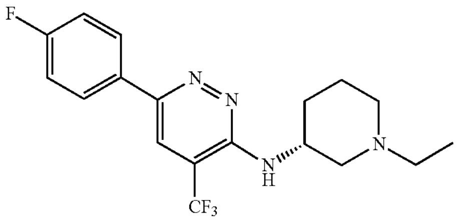 [SMILES: CCN1CCC[C@@H](Nc2nnc(-c3ccc(F)cc3)cc2C(F)(F)F)C1] | 197 |
| 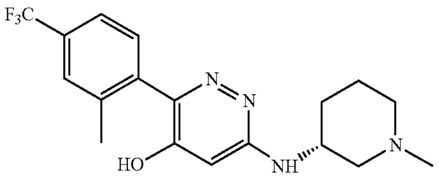 [SMILES: Cc1cc(C(F)(F)F)ccc1-c1nnc(N[C@@H]2CCCN(C)C2)cc1O] | 198 |
| 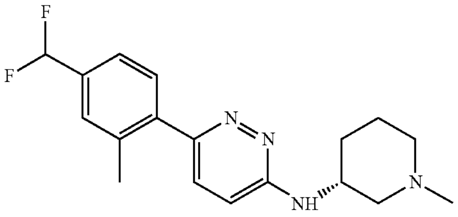 [SMILES: Cc1cc(C(F)F)ccc1-c1ccc(N[C@@H]2CCCN(C)C2)nn1] | 199 |
| 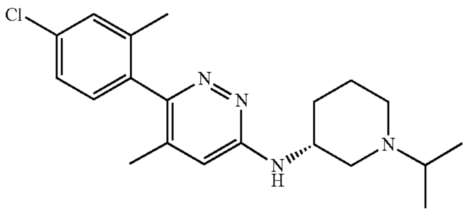 [SMILES: Cc1cc(Cl)ccc1-c1nnc(N[C@@H]2CCCN(C(C)C)C2)cc1C] | 200 |

TABLE 1-continued
| Representative compounds having Structure (I) | |
|---|---|
| Structure | Cpd No. |
| 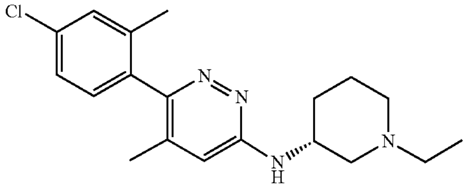 [SMILES: CCN1CCC[C@@H](Nc2cc(C)c(-c3ccc(Cl)cc3C)nn2)C1] | 201 |
| 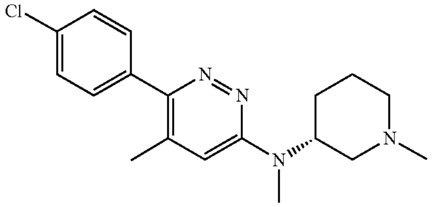 [SMILES: Cc1cc(N(C)[C@@H]2CCCN(C)C2)nnc1-c1ccc(Cl)cc1] | 202 |
| 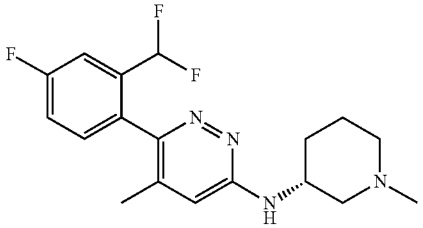 [SMILES: Cc1cc(N[C@@H]2CCCN(C)C2)nnc1-c1ccc(F)cc1C(F)F] | 203 |
| 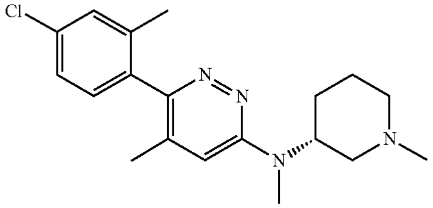 [SMILES: Cc1cc(Cl)ccc1-c1nnc(N(C)[C@@H]2CCCN(C)C2)cc1C] | 204 |
| 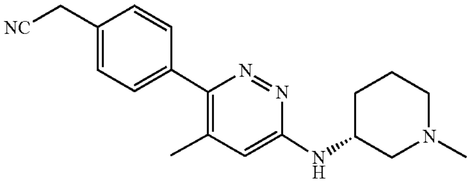 [SMILES: Cc1cc(N[C@@H]2CCCN(C)C2)nnc1-c1ccc(CC#N)cc1] | 205 |
| 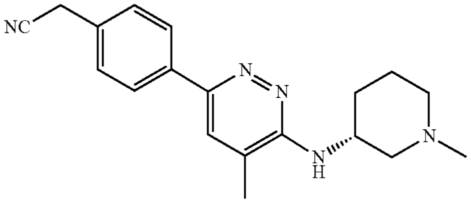 [SMILES: Cc1cc(-c2ccc(CC#N)cc2)nnc1N[C@@H]1CCCN(C)C1] | 206 |
| 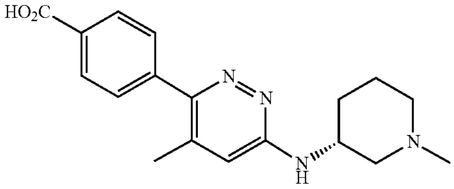 [SMILES: Cc1cc(N[C@@H]2CCCN(C)C2)nnc1-c1ccc(C(=O)O)cc1] | 207 |

TABLE 1-continued

| Representative compounds having Structure (I) | |
|---|---|
| Structure | Cpd No. |
| 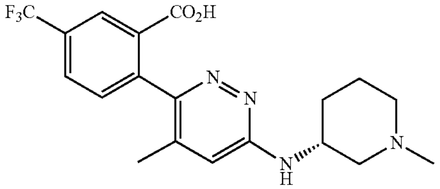 [SMILES: Cc1cc(N[C@@H]2CCCN(C)C2)nnc1-c1ccc(C(F)(F)F)cc1C(=O)O] | 208 |
| 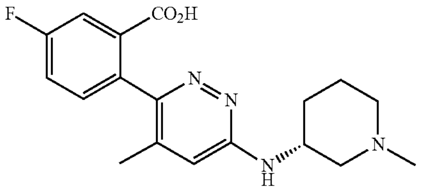 [SMILES: Cc1cc(N[C@@H]2CCCN(C)C2)nnc1-c1ccc(F)cc1C(=O)O] | 209 |
| 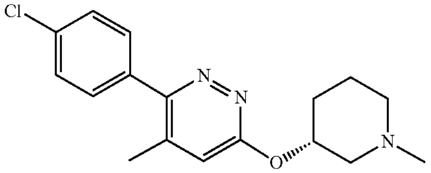 [SMILES: Cc1cc(O[C@@H]2CCCN(C)C2)nnc1-c1ccc(Cl)cc1] | 210 |

Pharmaceutical Compositions

In certain embodiments, the invention provides a pharmaceutical composition comprising a compound of structure (I), or a pharmaceutically acceptable salt, isomer, hydrate, solvate or isotope thereof, together with at least one pharmaceutically acceptable carrier, diluent, or excipient. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose, and polyvinylpyrrolidone. Similarly, the carrier or diluent can include any sustained release material known in the art, such as glyceryl monostearate or glyceryl distearate, alone or mixed with a wax.

As used herein, the term "pharmaceutical composition" refers to a composition containing one or more of the compounds described herein, or a pharmaceutically acceptable isomer, racemate, hydrate, solvate, isotope or salt thereof, formulated with a pharmaceutically acceptable carrier, which can also include other additives, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for administration to a pediatric subject (e.g., solution, syrup, suspension, elixir, powder for reconstitution as suspension or solution, dispersible/effervescent tablet, chewable tablet, lollipop, freezer pops, troches, oral thin strips, orally disintegrating tablet, orally disintegrating strip, and sprinkle oral powder or granules); or in any other formulation described herein. Conventional procedures and ingredients for the selection and preparation of suitable formulations are described, for example, in Remington: The Science and Practice of Pharmacy, 21st Ed., Gennaro, Ed., Lippencott Williams & Wilkins (2005) and in The United States Pharmacopeia: The National Formulary (USP 36 NF31), published in 2013.

In some embodiments, the pharmaceutical composition comprising a compound of structure (I) or a pharmaceutically acceptable salt, isomer, hydrate, solvate or isotope thereof, with at least one pharmaceutically acceptable carrier, diluent, or excipient further comprises a second therapeutic agent.

As used herein, the term "pharmaceutically acceptable carrier" refers to any ingredient other than the disclosed compounds, or a pharmaceutically acceptable isomer, racemate, hydrate, solvate, isotope or salt thereof (e.g., a carrier capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The formulations can be mixed with auxiliary agents which do not deleteriously react with the active compounds. Such additives can include wetting agents, emulsifying and suspending agents, salt for influencing osmotic pressure, buffers and/or coloring substances, preserving agents, sweetening agents, or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal, or parenteral, including intravenous, subcutaneous and/or intramuscular. In one embodiment, the route of administration is oral. In another embodiment, the route of administration is topical.

Dosage forms can be administered once a day, or more than once a day, such as twice or thrice daily. Alternatively, dosage forms can be administered less frequently than daily, such as every other day, or weekly, if found to be advisable by a prescribing physician or drug's prescribing information. Dosing regimens include, for example, dose titration to the extent necessary or useful for the indication to be treated, thus allowing the patient's body to adapt to the treatment, to minimize or avoid unwanted side effects associated with the treatment, and/or to maximize the therapeutic effect of the present compounds. Other dosage forms include delayed or controlled-release forms. Suitable dosage regimens and/or forms include those set out, for example, in the latest edition of the Physicians' Desk Reference, incorporated herein by reference.

In one embodiment, the invention provides an oral pharmaceutical composition comprising structure (I) or a pharmaceutically acceptable salt, isomer, hydrate, solvate or isotope thereof, together with at least one pharmaceutically acceptable oral carrier, diluent, or excipient. In another embodiment, the invention provides a topical pharmaceutical composition comprising a compound of structure (I) or a pharmaceutically acceptable salt, isomer, hydrate, solvate or isotope thereof, together with at least one pharmaceutically acceptable topical carrier, diluent, or excipient.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation. In some embodiments, the composition is formulated into a pediatric dosage form suitable for treating a pediatric subject.

In certain embodiments, the invention provides a compound having structure (I) or a pharmaceutically acceptable salt, isomer, hydrate, solvate or isotope thereof. Such compounds can be synthesized using standard synthetic techniques known to those skilled in the art. For example, compounds of the present invention can be synthesized using appropriately modified synthetic procedures set forth in the following Examples and Reaction Schemes.

To this end, the reactions, processes, and synthetic methods described herein are not limited to the specific conditions described in the following experimental section, but rather are intended as a guide to one with suitable skill in this field. For example, reactions may be carried out in any suitable solvent, or other reagents to perform the transformation[s] necessary. Generally, suitable solvents are protic or aprotic solvents which are substantially non-reactive with the reactants, the intermediates or products at the temperatures at which the reactions are carried out (i.e., temperatures which may range from the freezing to boiling temperatures). A given reaction may be carried out in one solvent or a mixture of more than one solvent. Depending on the particular reaction, suitable solvents for a particular work-up following the reaction may be employed.

All reagents, for which the synthesis is not described in the experimental part, are either commercially available, or are known compounds or may be formed from known compounds by known methods by a person skilled in the art. The compounds and intermediates produced according to the methods of the invention may require purification. Purification of organic compounds is well known to a person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using purpose-made or prepacked silica gel cartridges and eluents such as gradients of solvents such as heptane, ether, ethyl acetate, acetonitrile, ethanol and the like. In some cases, the compounds may be purified by preparative HPLC using methods as described.

Purification methods as described herein may provide compounds of the present invention which possess a sufficiently basic or acidic functionality in the form of a salt, such as, in the case of a compound of the present invention which is sufficiently basic, a trifluoroacetate or formate salt, or, in the case of a compound of the present invention, which is sufficiently acidic, an ammonium salt. A salt of this type can either be transformed into its free base or free acid form, respectively, by various methods known to a person skilled in the art, or be used as salts in subsequent biological assays. It is to be understood that the specific form of a compound of the present invention as isolated and as described herein is not necessarily the only form in which said compound can be applied to a biological assay in order to quantify the specific biological activity.

Chemical names were generated using the ChemDraw naming software (Version 17.0.0.206) by PerkinElmer Informatics, Inc. In some cases, generally accepted names of commercially available reagents were used in place of names generated by the naming software.

EXAMPLES

General Methods $^1H$ NMR (400 MHz) spectra were obtained in solution of deuterochloroform ($CDCl_3$), deuteromethanol ($CD_3OD$) or dimethyl sulfoxide-$D_6$ (DMSO). HPLC retention times, purities, and mass spectra (LCMS) were obtained using Shimadzu LCMS 2010 (Shim-pack XR-ODS 3.0*30 mm 2.2 μm) operating in ES (+) ionization mode. Flow Rate: 0.8 mL/min, Acquire Time: 3 min, Wavelength: UV220, Oven, Temp.: 50° C.

The following additional abbreviations are used: ethyl acetate (EtOAc), N,N-diisopropylethylamine (DIEA), water ($H_2O$), hydrochloridric acid (HCl), methanol (MeOH), dimethyl sulfoxide (DMSO), silica gel ($SiO_2$), trifluoroacetic acid (TFA), 1-methyl-2-pyrrolidinone (NMP), cesium fluoride (CsF), (2,2'-bis(diphenylphosphino)-1,1'-binaphthyl (BINAP), palladium(II) acetate ($Pd(OAc)_2$), [1,1'-bis(diphenylphosphino)ferrocene]dichloropalladium(II) (Pd(dppf)$Cl_2$), potassium carbonate ($K_2CO_3$), sodium sulfate ($Na_2SO_4$), cesium carbonate ($Cs_2CO_3$), ammonia ($NH_3$), tetrahydrofuran (THF), dichloromethane (DCM), acetonitrile (MeCN or ACN), retention time (RT), molecular weight (MW), room temperature (rt), hour (h), volume/volume (v/v), proton nuclear magnetic resonance ($^1$HNMR), formic acid (FA), sodium hydride (NaH), formaldehyde (HCHO), acetic acid (AcOH), (2-Dicyclohexylphosphino-2',4',6'-triisopropyl-1,1'-biphenyl)[2-(2'-amino-1,1'-biphenyl)]palladium(II) methanesulfonate (XPhosPdG3), degree Celsius (° C.), milligram (mg), gram (g), millimole (mmol), milliliter (mL), polyethylene (PE), molar (M), sodium bicarbonate ($NaHCO_3$), potential of hydrogen (pH), sodium cyanoborohydride ($NaBH_3CN$), preparative high-performance liquid chromatography (prep-HPLC), normal (N).

Example 1

Intermediate General Synthetic Route A

General Scheme 1

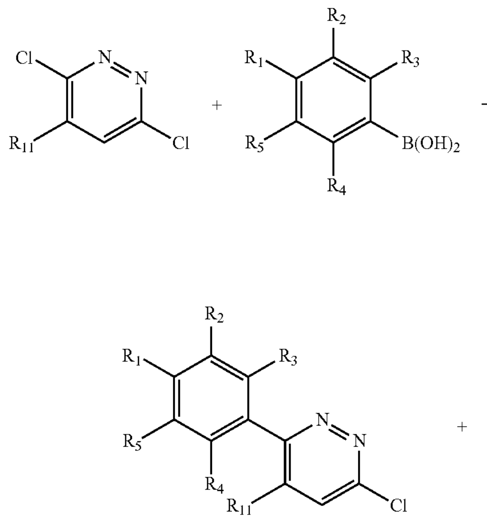

-continued

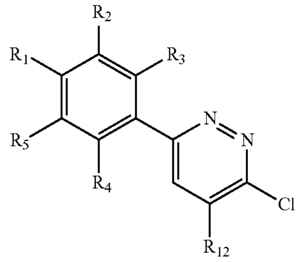

Synthesis of 6-chloro-4-methyl-3-(4-(trifluoromethyl)phenyl)pyridazine and 3-chloro-4-methyl-6-(4-(trifluoromethyl)phenyl)pyridazine

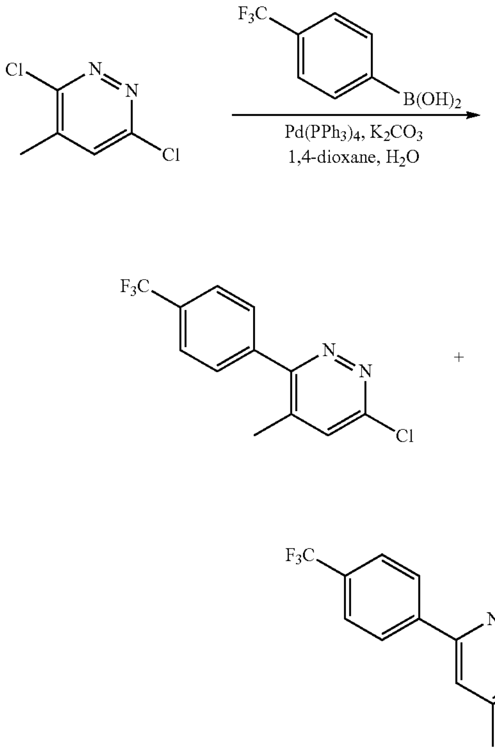

To a solution of 3,6-dichloro-4-methyl-pyridazine (6000 mg, 36.8 mmol) and [4-(trifluoromethyl)phenyl]boronic acid (6996 mg, 36.8 mmol) in 1,4-dioxane (72 mL) were added Pd(dppf)$Cl_2$ (1800 mg, 2.46 mmol), $K_2CO_3$ (15.24 g, 110 mmol) and $H_2O$ (24 mL) under nitrogen atmosphere. The resulting mixture was stirred at 80° C. for 2 h. The mixture was then diluted with water (80 mL) and extracted with EtOAc (4×50 mL). The combined organic layer was washed with brine (50 mL), dried over $Na_2SO_4$ and concentrated under reduced pressure to afford crude residue. The crude was purified by Combi-flash (silica gel, 330 g, 0-15% ethyl acetate in petrol ether) twice to afford desired products 6-chloro-4-methyl-3-[4-(trifluoromethyl)phenyl]pyridazine (1800 mg, 17.94%) and 6-chloro-4-methyl-3-[4-(trifluoromethyl)phenyl]pyridazine (660 mg, 6.58%) in a ~3:1 ratio.

Example 2

General Synthetic Route B

General Scheme 2

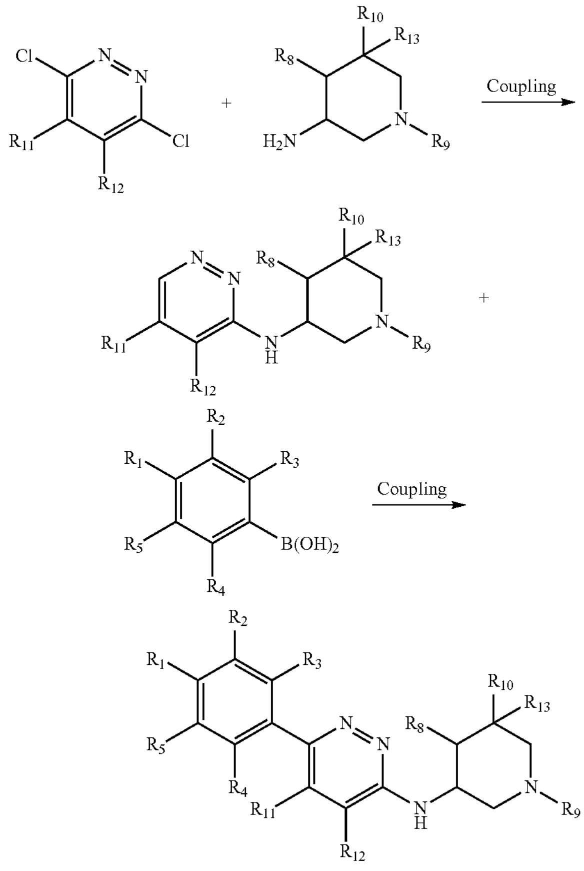

more generally,

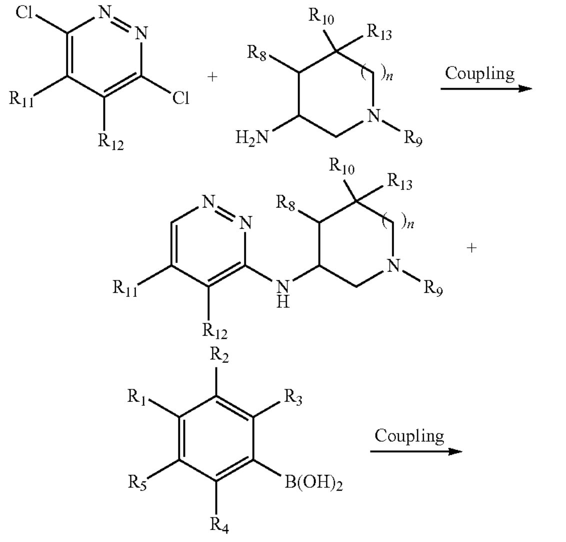

-continued

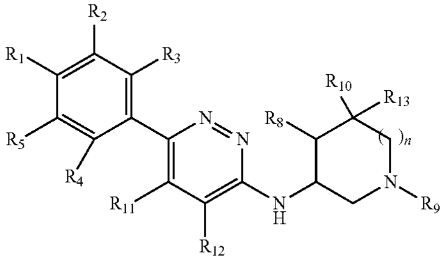

n is 0, 1, or 2

Synthesis of (R)-5-methyl-N-(1-methylpiperidin-3-yl)-6-(4-(trifluoromethyl)phenyl)-pyridazin-3-amine

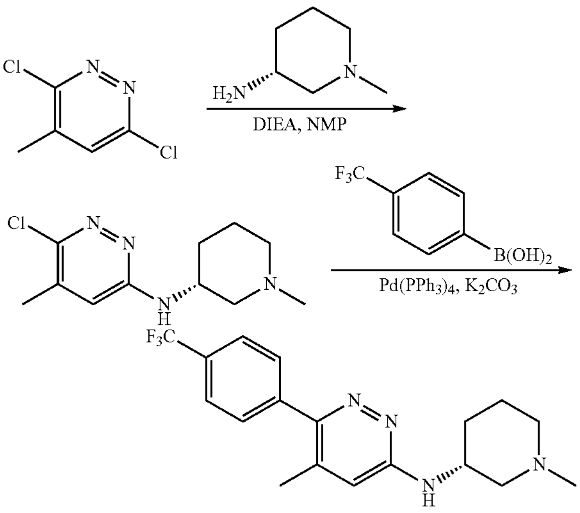

Synthesis of (R)-6-chloro-5-methyl-N-(1-methylpiperidin-3-yl)pyridazin-3-amine

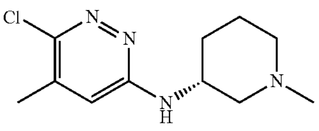

To a solution of 3,6-dichloro-4-methyl-pyridazine (8.56 g, 52.5 mmol) in NMP (50 mL) were added (3R)-1-methylpiperidin-3-amine (5.0 g, 43.8 mmol) and DIEA (11 mL, 65.7 mmol). The resulting mixture was stirred at 110° C. for 14 h under nitrogen atmosphere. The mixture was then poured into water (100 mL) and extracted with EtOAc (3×100 mL). The organic layers were combined, dried over anhydrous $Na_2SO_4$ and concentrated under reduced pressure to afford crude residue. The crude was purified by silica gel column chromatography (4.6% MeOH in DCM) to afford desired product (R)-6-chloro-5-methyl-N-(1-methylpiperidin-3-yl)pyridazin-3-amine (5.30 g) as yellow solid.

Synthesis of (R)-5-methyl-N-(1-methylpiperidin-3-yl)-6-(4-(trifluoromethyl)phenyl)-pyridazin-3-amine (Compound No. 3)

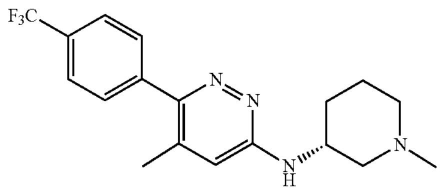 [SMILES: Cc1cc(N[C@@H]2CCCN(C)C2)nnc1-c1ccc(C(F)(F)F)cc1]

To a mixture of 4,4,5,5-tetramethyl-2-[4-(trifluoromethyl) phenyl]-1,3,2-dioxaborolane (1.70 g, 6.23 mmol) and (R)-6-chloro-5-methyl-N-(1-methylpiperidin-3-yl)pyridazin-3-amine (1.0 g, 4.15 mmol) in 1,4-dioxane (30 mL) were added Pd(dppf)$Cl_2$ (0.460 g, 0.623 mmol) and CsF (1.89 g, 12.5 mmol). The resulting mixture was stirred at 90° C. for 14 h under nitrogen atmosphere. The mixture was then filtered over Celite, and the filtrate cake was washed with EtOAc (30 mL). The filtrate was poured into water (30 mL) and was extracted with EtOAc (3×30 mL). The organic layers were combined, washed with brine (30 mL), dried over anhydrous $Na_2SO_4$ and concentrated under reduced pressure to afford crude residue. The crude was purified by silica gel column chromatography (10% MeOH in DCM) to afford impure desired product (R)-5-methyl-N-(1-methylpiperidin-3-yl)-6-(4-(trifluoromethyl)phenyl)pyridazin-3-amine (900 mg) as brown solid. The desired product was further purified by prep-HPLC (0.05% $NH_3$·$H_2O$ as additive) to afford pure desired product (R)-5-methyl-N-(1-methylpiperidin-3-yl)-6-(4-(trifluoromethyl)phenyl)-pyridazin-3-amine (339 mg, 23.2% yield) as a brown solid.

Example 3

General Synthetic Route C

General Scheme 3

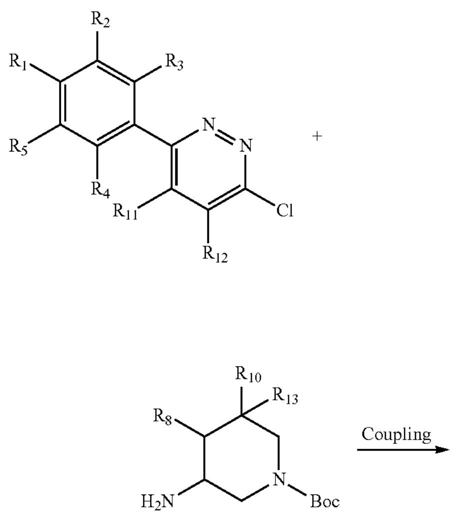

-continued

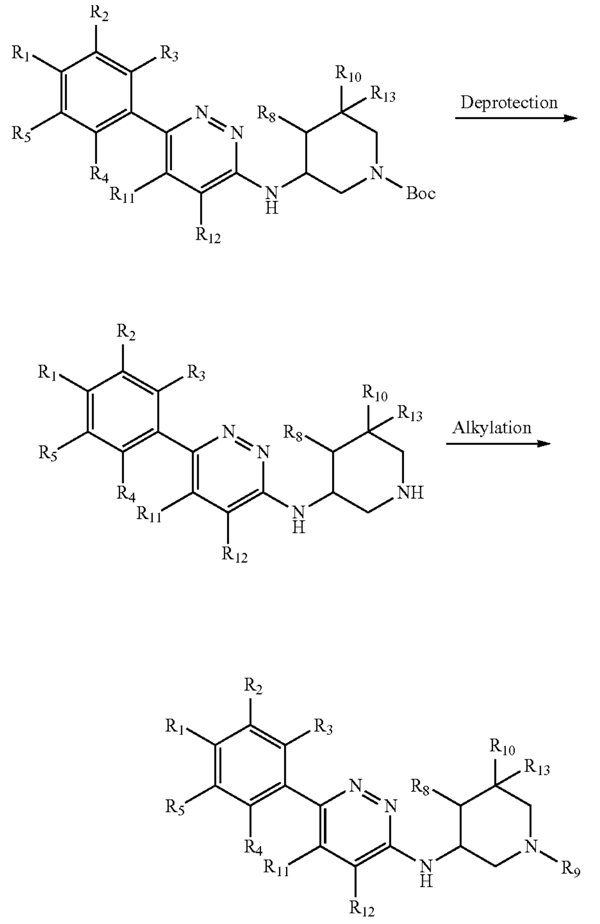

more generally,

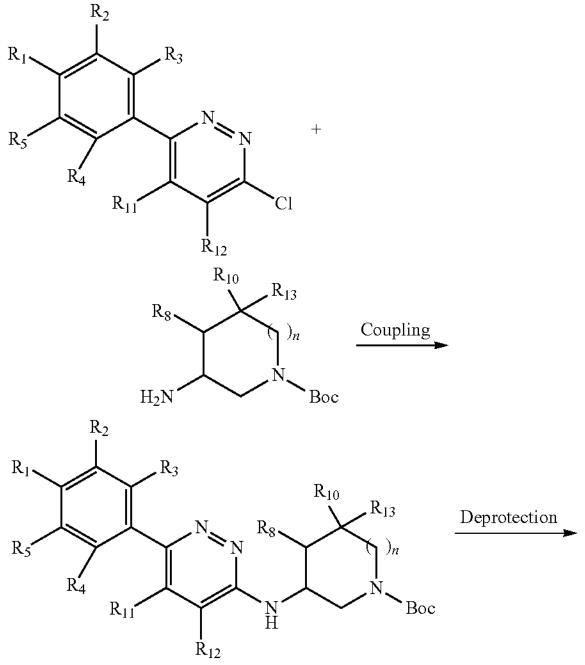

-continued

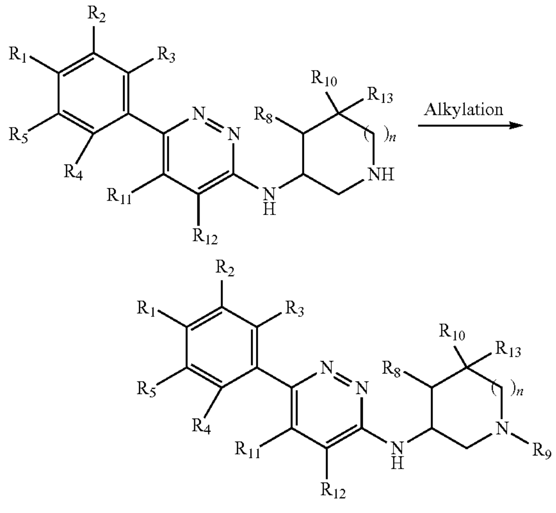

Synthesis of (R)-2-(3-((5-methyl-6-(4-(trifluoromethyl)phenyl)pyridazin-3-yl)amino)-piperidin-1-yl) ethan-1-ol

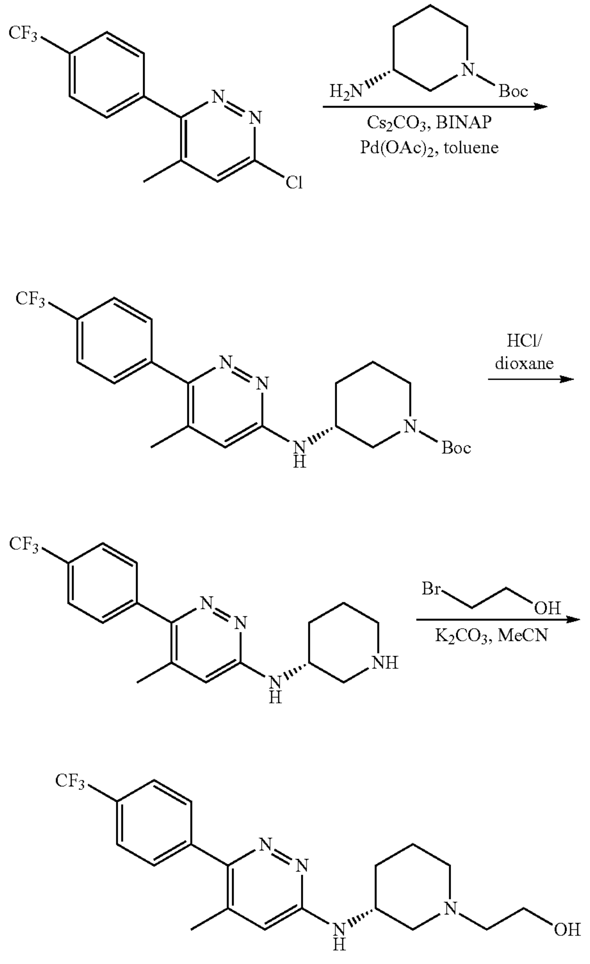

Synthesis of tert-butyl (3R)-3-[[5-methyl-6-[4-(trifluoromethyl)phenyl]pyridazin-3-yl]-amino]piperidine-1-carboxylate

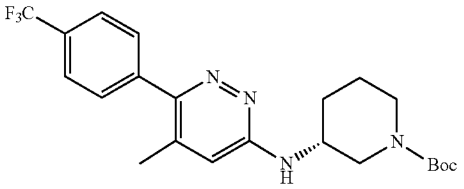 [SMILES: Cc1cc(N[C@@H]2CCCN(C(=O)OC(C)(C)C)C2)nnc1-c1ccc(C(F)(F)F)cc1]

To a mixture of tert-butyl (3R)-3-aminopiperidine-1-carboxylate (294 mg, 1.47 mmol) and 6-chloro-4-methyl-3-[4-(trifluoromethyl)phenyl]pyridazine (200 mg, 0.734 mmol) in toluene (2.6 mL) were added $Cs_2CO_3$ (478 mg, 1.47 mmol, 2 eq), BINAP (64 mg, 0.103 mmol, 0.14 eq) and $Pd(OAc)_2$ (12 mg, 0.0534 mmol, 0.07 eq). The resulting mixture was stirred at 105 ℃ for 16 h under nitrogen atmosphere. The mixture was then diluted with water (8 mL) and extracted with EtOAc (4×8 mL). The combined organic layer was dried over anhydrous $Na_2SO_4$ and concentrated under reduced pressure to afford crude residue. The crude was purified by Combi-flash (silica gel, 12 g, 10%-100% ethyl acetate in petrol ether) to afford desired product tert-butyl (3R)-3-[[5-methyl-6-[4-(trifluoromethyl)phenyl] pyridazin-3-yl]amino]piperidine-1-carboxylate (160 mg, 49.97%) as a yellow solid.

Synthesis of 5-methyl-N-[(3R)-3-piperidyl]-6-[4-(trifluoromethyl)phenyl]pyridazin-3-amine

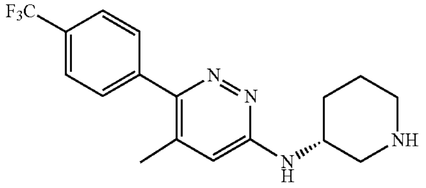 [SMILES: Cc1cc(N[C@@H]2CCCNC2)nnc1-c1ccc(C(F)(F)F)cc1]

To a solution of tert-butyl (3R)-3-[[5-methyl-6-[4-(trifluoromethyl)phenyl]-pyridazin-3-yl]amino]piperidine-1-carboxylate (160 mg, 0.367 mmol) in 1,4-dioxane (2 mL) was added HCl in dioxane (2.0 mL, 8.00 mmol, 4 M). The resulting mixture was stirred at 25 ℃ for 16 h. The mixture was then concentrated under reduced pressure and basified with $NH_3 \cdot H_2O$ (27%) until pH~8. The mixture was concentrated under reduced pressure to afford crude residue. The crude was purified by prep-HPLC (column: Phenomenex C18 80*30 mm*5 um; mobile phase: [water (ammonia hydroxide v/v)-ACN]; B %: 5%-95%, 10 min) to afford desired product 5-methyl-N-[(3R)-3-piperidyl]-6-[4-(trifluoromethyl)phenyl]-pyridazin-3-amine (26 mg, 21.48%) as a white solid.

Synthesis of 2-[(3R)-3-[[5-methyl-6-[4-(trifluoromethyl)phenyl]pyridazin-3-yl]amino]-1-piperidyl]ethanol (Compound No. 15)

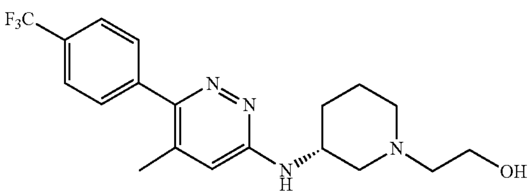 [SMILES: Cc1cc(N[C@@H]2CCCN(CCO)C2)nnc1-c1ccc(C(F)(F)F)cc1]

To a mixture of 5-methyl-N-[(3R)-3-piperidyl]-6-[4-(trifluoromethyl)-phenyl]pyridazin-3-amine (80 mg, 0.238 mmol) and 2-bromoethanol (30 mg, 0.240 mmol) in MeCN (1 mL) was added $K_2CO_3$ (65 mg, 0.471 mmol). The mixture was stirred at 25 ⍰ for 16 h under nitrogen atmosphere. The resulting mixture was then diluted with water (4 mL) and extracted with EtOAc (6×4 mL). The combined organic layer was concentrated under reduced pressure to afford crude residue. The crude was purified by prep-HPLC (column: Boston Prime C18 150*30 mm*5 um; mobile phase: [water (ammonia hydroxide v/v)-ACN]; B %: 24%-64%, 9 min) to afford desired product 2-[(3R)-3-[[5-methyl-6-[4-(trifluoromethyl)phenyl]pyridazin-3-yl]amino]-1-piperidyl]ethanol (32 mg, 32.73%) as a white solid.

Example 4

General Synthetic Route D

General Scheme 5

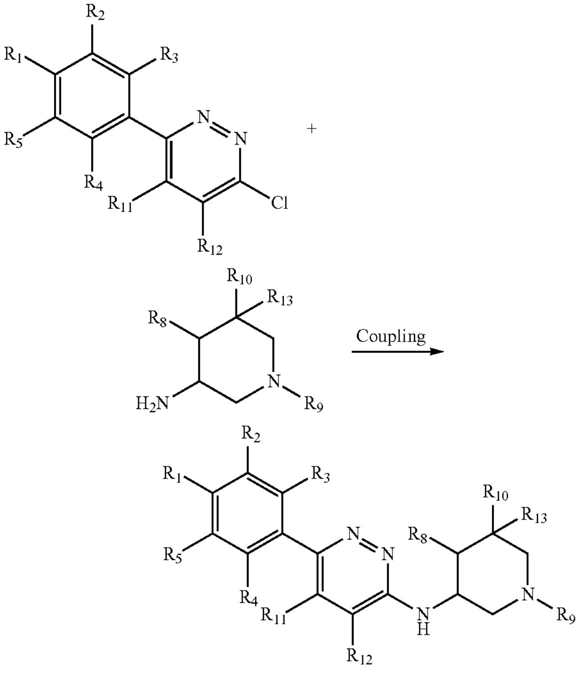

more generally,

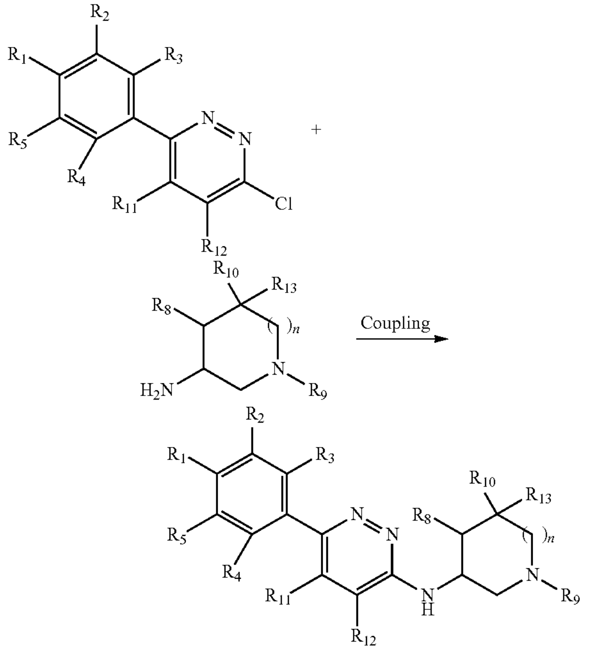

n is 0, 1, or 2

Synthesis of N-((3S,4R)-4-fluoro-1-methylpiperidin-3-yl)-5-methyl-6-(4-(trifluoromethyl)-phenyl)pyridazin-3-amine (Compound No. 74)

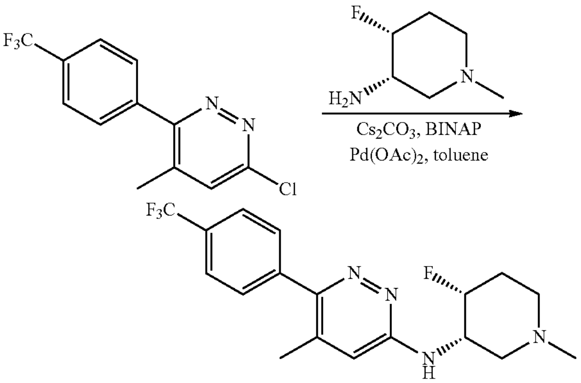

To a mixture of 6-chloro-4-methyl-3-(4-(trifluoromethyl)phenyl)pyridazine (120 mg, 0.440 mmol) and (3S,4R)-4-fluoro-1-methyl-piperidin-3-amine;hydrochloride (96 mg, 0.569 mmol) in toluene (1.6 mL) were added BINAP (40 mg, 0.0642 mmol), $Cs_2CO_3$ (288 mg, 0.884 mmol), $Pd(OAc)_2$ (12 mg, 0.0534 mmol) under nitrogen atmosphere. The resulting mixture was stirred at 105° C. for 16 h. The mixture was then diluted with water (5 mL) and extracted with EtOAc (3×5 mL). The combined organic layer was dried over anhydrous $Na_2SO_4$ and concentrated to afford crude residue. The crude was purified by prep-HPLC (Boston Prime C18 150*30 mm*5 um; mobile phase: water (0.05% ammonia hydroxide v/v)-ACN; B %: 31-71%, 9 min) to afford desired product N-[(3S,4R)-4-fluoro-1-methyl-3-piperidyl]-5-methyl-6-[4-(trifluoromethyl)phenyl]pyridazin-3-amine (2.4 mg, 1.45%) as a white solid.

Example 5
General Synthetic Route E
General Scheme 6
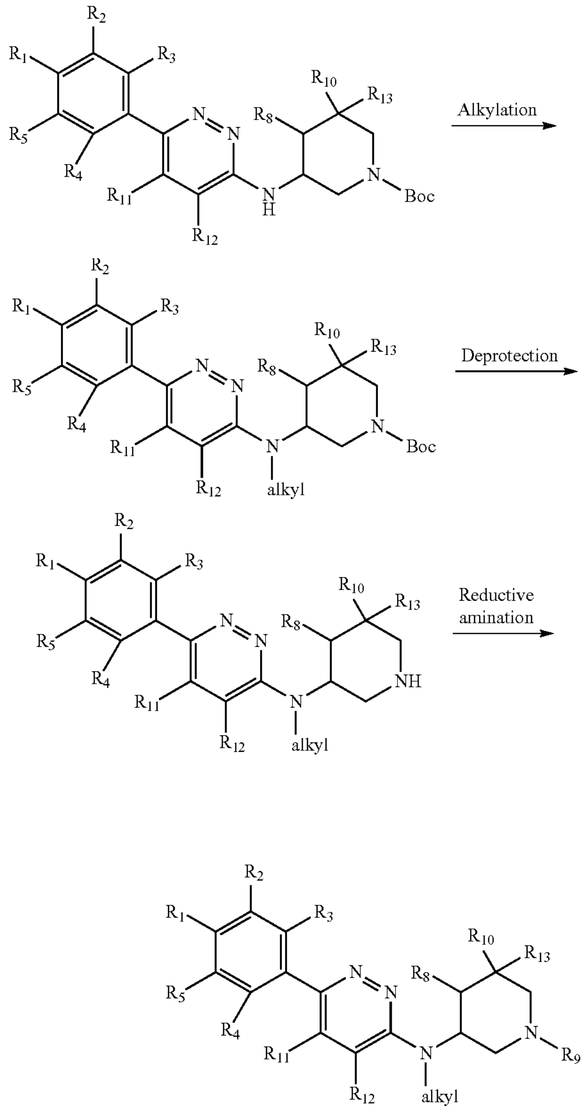
n is 0, 1, or 2
more generally,
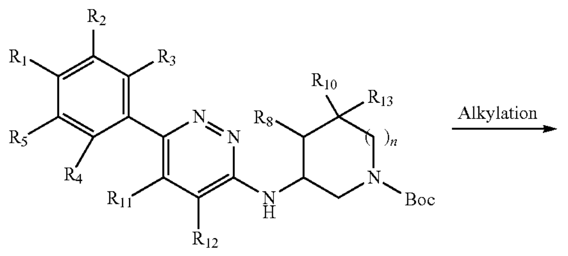
-continued
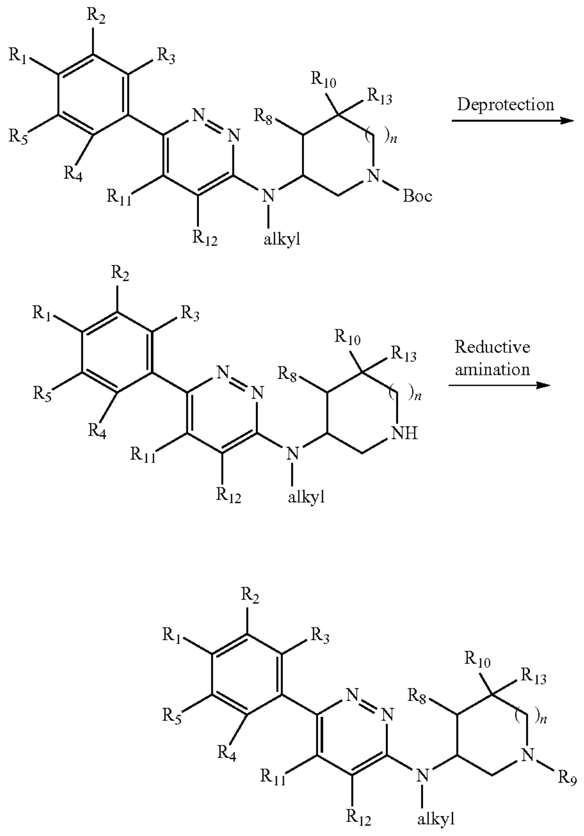
n is 0, 1, or 2
Synthesis of (R)—N,5-dimethyl-N-(1-methylpiperidin-3-yl)-6-(4-(trifluoromethyl)phenyl)pyridazin-3-amine
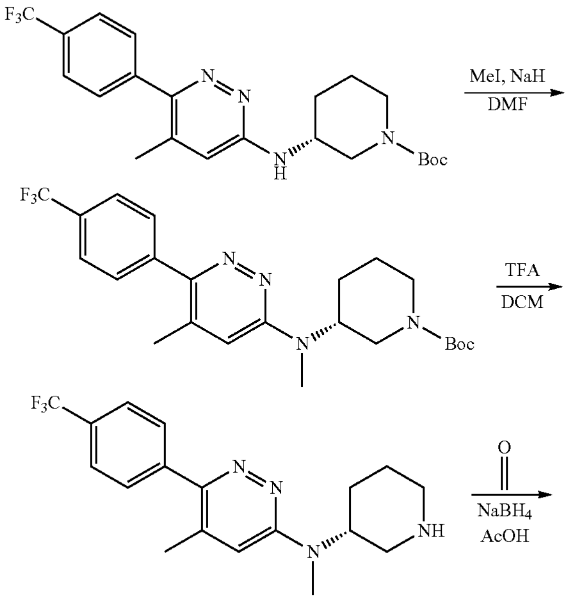

-continued

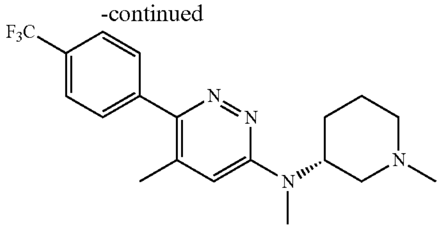

Synthesis of tert-butyl (R)-3-(methyl(5-methyl-6-(4-(trifluoromethyl)phenyl)pyridazin-3-yl)amino)piperidine-1-carboxylate

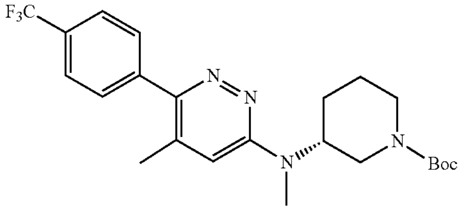 [SMILES: Cc1cc(N(C)[C@@H]2CCCN(C(=O)OC(C)(C)C)C2)nnc1-c1ccc(C(F)(F)F)cc1]

To a solution of tert-butyl (R)-3-((5-methyl-6-(4-(trifluoromethyl)phenyl)pyridazin-3-yl)amino)piperidine-1-carboxylate (73 mg, 0.167 mmol) in DMF (5 mL) was added NaH (6.0 mg, 0.251 mmol) at 0° C. under nitrogen atmosphere. The mixture was stirred for 20 min at 0° C. Iodomethane (47 mg, 0.335 mmol) was then added and the resulting mixture was stirred at 25° C. for an additional 16 h. The mixture was concentrated under reduced pressure to afford crude residue. The crude was purified by column chromatography ($SiO_2$, Petroleum ether/Ethyl acetate, 2:1 to 1:1) to afford impure desired product tert-butyl (R)-3-(methyl(5-methyl-6-(4-(trifluoromethyl)phenyl)pyridazin-3-yl)amino)piperidine-1-carboxylate (425 mg) as yellow liquid.

Synthesis of (R)—N,5-dimethyl-N-(piperidin-3-yl)-6-(4-(trifluoromethyl)phenyl)pyridazin-3-amine

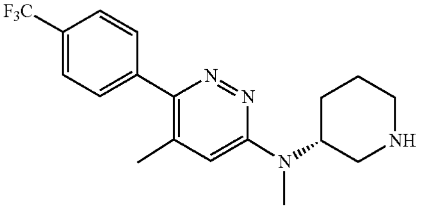 [SMILES: Cc1cc(N(C)[C@@H]2CCCNC2)nnc1-c1ccc(C(F)(F)F)cc1]

To a solution of tert-butyl (R)-3-(methyl(5-methyl-6-(4-(trifluoromethyl)phenyl)pyridazin-3-yl)amino)piperidine-1-carboxylate (425 mg, 0.943 mmol) in DCM (2 mL) was added TFA (1.0 mL, 13.2 mmol). The mixture was stirred at 25° C. for 1 h under nitrogen atmosphere. The mixture was concentrated under reduced pressure to afford crude residue, (R)—N,5-dimethyl-N-(piperidin-3-yl)-6-(4-(trifluoromethyl)phenyl)pyridazin-3-amine, which was used without purification for the next step.

Synthesis of (R)—N,5-dimethyl-N-(1-methylpiperidin-3-yl)-6-(4-(trifluoromethyl)phenyl)pyridazin-3-amine (Compound No. 142)

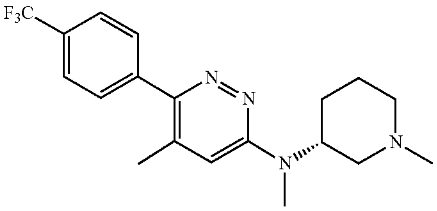 [SMILES: Cc1cc(N(C)[C@@H]2CCCN(C)C2)nnc1-c1ccc(C(F)(F)F)cc1]

To a solution of (R)—N,5-dimethyl-N-(piperidin-3-yl)-6-(4-(trifluoromethyl)phenyl)pyridazin-3-amine (425 mg, 1.21 mmol)) in DCE (2 mL) was added formaldehyde (73 mg, 2.43 mmol). AcOH (7.3 mg, 0.121 mmol) was then added dropwise, and the resulting mixture was stirred at 25° C. for 2 h. Sodium cyanoborohydride (113 mg, 1.82 mmol) was added, and the mixture was stirred at 25° C. for an additional 16 h. The mixture was concentrated under reduced pressure to afford crude residue. The crude was purified by column chromatography (SiO2, dichloromethane/methanol=5:1) to afford desired product (R)—N,5-dimethyl-N-(1-methylpiperidin-3-yl)-6-(4-(trifluoromethyl)phenyl)pyridazin-3-amine (291 mg, 53%) as yellow solid.

Example 6

General Synthetic Route F

General Scheme 7

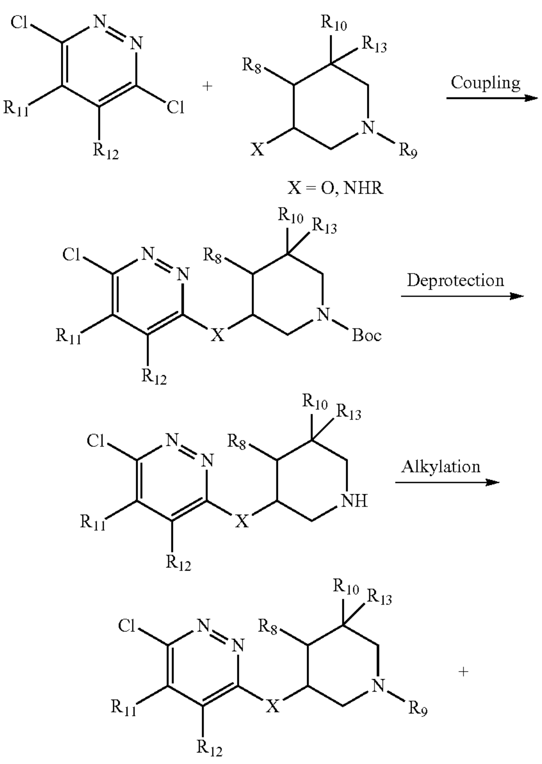

-continued

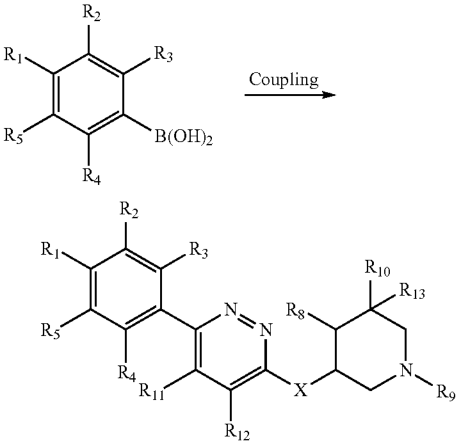

more generally,

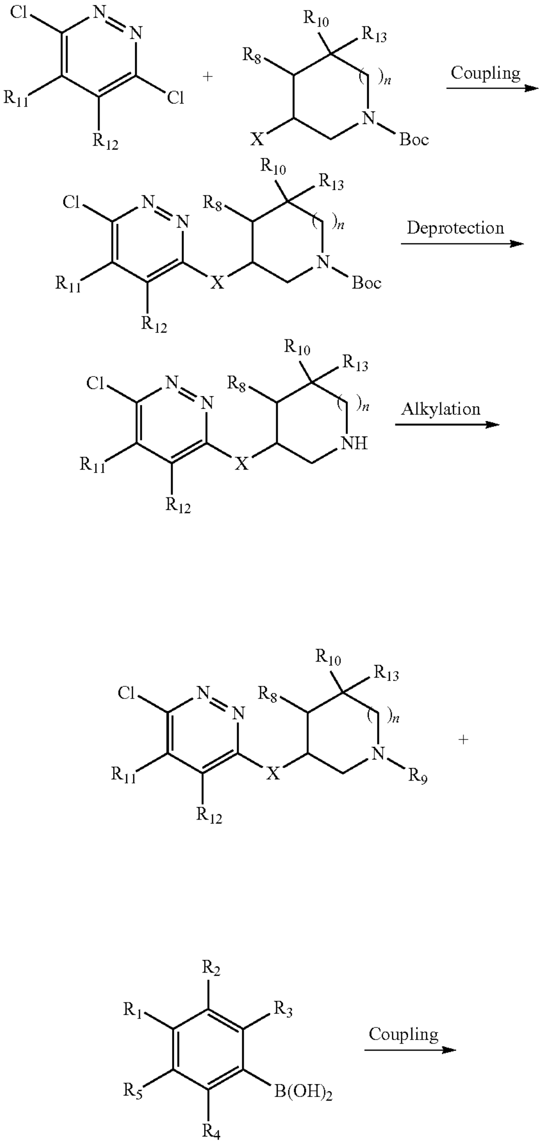

-continued

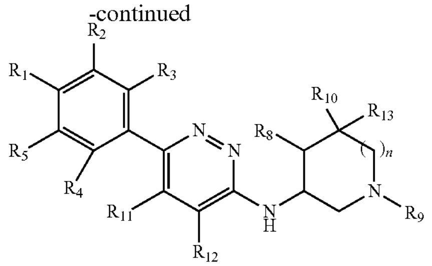

X is O, NHR n is 0, 1, or 2

Synthesis of (R)-4-methyl-6-((1-methylpiperidin-3-yl)oxy)-3-(4-(trifluoromethyl)phenyl)pyridazine

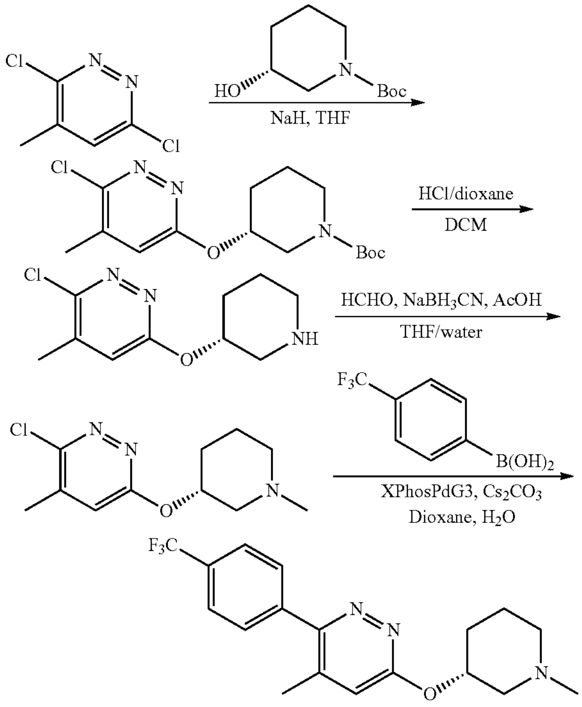

Synthesis of tert-butyl (R)-3-((6-chloro-5-methylpyridazin-3-yl)oxy)piperidine-1-carboxylate

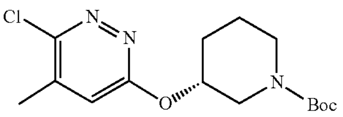 [SMILES: Cc1cc(O[C@@H]2CCCN(C(=O)OC(C)(C)C)C2)nnc1Cl]

To a mixture of (R)-tert-butyl 3-hydroxypiperidine-1-carboxylate (1.00 g, 4.97 mmol) in THF (10 mL) was added NaH (230 mg, 5.85 mmol) (60% in mineral oil) portionwise at 0° C. The mixture was stirred at 20° C. for 2 h under nitrogen atmosphere. 3,6-dichloro-4-methylpyridazine (830 mg, 5.07 mmol) was then added and the resulting mixture was stirred at 20° C. for an additional 14 h. The mixture was poured into water (30 mL) and was extracted with EtOAc (3×30 mL). The organic layers were combined, washed with brine (30 mL), dried over anhydrous $Na_2SO_4$ and concentrated under reduced pressure to afford crude residue. The crude residue was purified by silica gel column chromatography (30% EtOAc in PE) to afford desired product tert-butyl (R)-3-((6-chloro-5-methylpyridazin-3-yl)oxy)piperidine-1-carboxylate (1.27 g, 78% yield) as a yellow solid.

Synthesis of (R)-3-chloro-4-methyl-6-(piperidin-3-yloxy)pyridazine

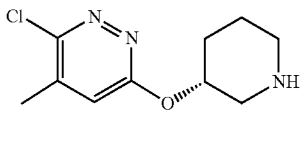

To a mixture of tert-butyl (R)-3-((6-chloro-5-methylpyridazin-3-yl)oxy)piperidine-1-carboxylate (11.6 g, 35.4 mmol) in DCM (110 mL) was added 4 M HCl in dioxane (100 mL). The mixture was stirred at 20° C. for 2 h. Saturated aqueous $NaHCO_3$ was then added to adjust pH~8-9. The resulting mixture was extracted with EtOAc (3×100 mL). The organic layers were combined, washed with brine (2×100 mL), dried over anhydrous $Na_2SO_4$ and concentrated under reduced pressure to afford crude product (R)-3-chloro-4-methyl-6-(piperidin-3-yloxy)pyridazine as an off-white solid, which was used without further purification.

Synthesis of (R)-3-chloro-4-methyl-6-((1-methylpiperidin-3-yl)oxy)pyridazine

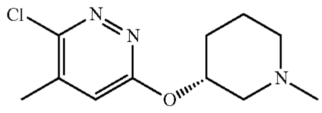

To a mixture of (R)-3-chloro-4-methyl-6-(piperidin-3-yloxy)pyridazine (6.95 g) in THF (50 mL) and water (5 mL) were added HCHO (2.48 g, 30.5 mmol) (37% in water), $NaBH_3CN$ (2.88 g, 45.8 mmol) and AcOH (1.83 g, 30.5 mmol). The mixture was stirred at 50° C. for 2 h under nitrogen atmosphere. The mixture was then poured into water (100 mL) and was extracted with EtOAc (3×100 mL). The organic layers were combined, washed with brine (2×100 mL), dried over anhydrous $Na_2SO_4$ and concentrated under reduced pressure to afford crude product (R)-3-chloro-4-methyl-6-((1-methylpiperidin-3-yl)oxy)pyridazine as brown oil which was used without further purification.

Synthesis of (R)-4-methyl-6-((1-methylpiperidin-3-yl)oxy)-3-(4-(trifluoromethyl)phenyl)pyridazine (Compound No. 177)

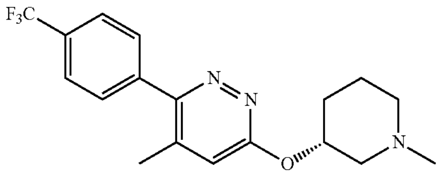

To a mixture of (R)-3-chloro-4-methyl-6-((1-methylpiperidin-3-yl)oxy)pyridazine (300 mg) in dioxane (3 mL) and water (0.3 mL) were added 4,4,5,5-tetramethyl-2-[4-(trifluoromethyl)phenyl]-1,3,2-dioxaborolane (405 mg, 1.49 mmol), XPhosPdG3 (105 mg, 0.124 mmol) and $Cs_2CO_3$ (1.21 g, 3.72 mmol). The mixture was stirred at 100° C. for 16 h under nitrogen atmosphere. The mixture was then poured into water (20 mL) and was extracted with EtOAc (3×30 mL). The organic layers were combined, washed with brine (2×30 mL), dried over anhydrous $Na_2SO_4$ and concentrated under reduced pressure to afford crude residue. The crude residue was purified by silica gel column chromatography (10% MeOH in DCM) followed by prep-HPLC (0.025% FA as additive) to afford desired product (R)-4-methyl-6-((1-methylpiperidin-3-yl)oxy)-3-(4-(trifluoromethyl)phenyl)pyridazine (10 mg, 2% yield) as an off-white solid.

Example 7

Synthesis of Representative Compounds

The Compounds listed in Table 2 below were prepared by procedures similar to the ones described in the representative schemes found in the Examples with appropriate variations in reactants, quanitites of reagents, protections and deprotections, solvents and reaction conditions. The characterization data of the compounds are also summarized herein in Table 2.

TABLE 2

| Cmpd No | General Synthetic Route | LCMS [M + H]+ | Characterization |
|---|---|---|---|
| 1 | B | 365.2 | 1HNMR (400 MHz, MeOD): δ 7.78 (d, J = 8.4 Hz, 2H), 7.68 (d, J = 8.0 Hz, 2H), 6.82 (s, 1H), 4.14-4.24 (m, 1H), 3.23-3.30 (m, 1H), 2.86-2.96 (m, 1H), 2.57-2.68 (m, 2H), 2.29-2.39 (m, 1H), 2.18-2.27 (m, 4H), 2.03-2.10 (m, 1H), 1.86-1.92 (m, 1H), 1.71-1.81 (m, 1H), 1.44-1.54 (m, 1H), 1.16 (t, J = 7.6 Hz, 3H) |
| 2 | B | 364.2 | 1HNMR (400 MHz, DMSO-d6): δ 7.78-7.83 (m, 2H), 7.72-7.77 (m, 2H), 6.74 (s, 1H), 6.69 (d, J = 8.0 Hz, 1H), 3.96-4.06 (m, 1H), 2.89-2.98 (m, 1H), 2.67-2.77 (m, 1H), 2.59-2.66 (m, 1H), 2.13-2.22 (m, 4H), 2.01-2.10 (m, 1H), 1.82-1.93 (m, 1H), 1.64-1.74 (m, 1H), 1.44-1.56 (m, 1H), 1.24-1.37 (m, 1H), 0.96 (dd, J = 6.54, 2.87 Hz, 6H) |

TABLE 2-continued

| Cmpd No | General Synthetic Route | LCMS [M + H]+ | Characterization |
|---|---|---|---|
| 3 | B | 351.2 | 1HNMR (400 MHz, DMSO-d6): δ 7.68-7.89 (m, 4H), 6.69-6.82 (m, 2H), 4.01-4.11 (m, 1H), 2.83-2.86 (m, 1H), 2.52-2.58 (m, 1H), 2.17 (s, 6H), 1.96-2.01 (m, 1H), 1.78-1.95 (m, 2H), 1.64-1.75 (m, 1H), 1.48-1.60 (m, 1H), 1.22-1.35 (m, 1H) |
| 4 | B | 371.2 | $^{1}$HNMR (400 MHz, DMSO-d6): δ 7.93 (d, J = 1.6 Hz, 1H), 7.86 (dd, J = 8.0, 2.0 Hz, 1H), 7.58 (d, J = 8.0 Hz, 1H), 7.35 (d, J = 9.2 Hz, 1H), 6.89-6.99 (m, 2H), 4.03-4.18 (m, 1H), 2.82-2.94 (m, 1H), 2.52-2.59 (m, 1H), 2.19 (s, 3H), 1.95-2.09 (m, 2H), 1.81-1.88 (m, 1H), 1.69-1.76 (m, 1H), 1.50-1.63 (m, 1H), 1.27-1.39 (m, 1H) |
| 5 | B | 336.48 | $^{1}$HNMR (400 MHz, DMSO-$d_6$): δ 7.37 (d, J = 8.0 Hz, 2H), 7.14 (d, J = 8.4 Hz, 2H), 6.69 (s, 1H), 6.57 (brd, J = 8.0 Hz, 1H), 4.02-4.06 (m, 1H), 2.85 (m, 1H), 2.52 (s, 1H), 2.17 (s, 3H), 2.13 (s, 3H), 1.94-1.99 (m, 2H), 1.81-1.89 (m, 2H), 1.68-1.72 (m, 1H), 1.49-1.57 (m, 1H), 1.22-1.33 (m, 1H), 0.96-1.00 (m, 2H), 0.70-0.74 (m, 2H) |
| 6 | B | 369.2 | 1HNMR (400 MHz, DMSO-d6) δ 7.81 (d, J = 10.0 Hz, 1H), 7.66-7.73 (m, 2H), 6.84 (brd, J = 8.0 Hz, 1H), 6.77 (s, 1H), 3.99-4.10 (m, 1H), 2.78-2.90 (m, 1H), 2.52-2.60 (m, 1H), (overlap with DMSO-d6 single), 2.17 (s, 3H), 1.95-2.10 (m, 4H), 1.79-1.93 (m, 2H), 1.66-1.74 (m, 1H), 1.47-1.59 (m, 1H), 1.24-1.36 (m, 1H) |
| 7 | B | 367.4 | $^{1}$HNMR (400 MHz, DMSO-d6): δ 7.65 (d, J = 8.4 Hz, 2H), 7.44 (d, J = 8.4 Hz, 2H), 6.74 (s, 1H), 6.69 (brd, J = 8.0 Hz, 1H), 4.01-4.09 (m, 1H), 2.85 (d, J = 10.4 Hz, 1H), 2.52-2.58 (m, 1H), 2.18 (s, 3H), 2.16 (s, 3H), 1.97-2.06 (m, 1H), 1.80-1.96 (m, 2H), 1.65-1.76 (m, 1H), 1.49-1.60 (m, 1H), 1.24-1.34 (m, 1H) |
| 8 | B | 381.2 | 1HNMR (400 MHz, DMSO-d6): δ 7.36-7.46 (m, 3H), 6.64-6.70 (m, 2H), 3.95-4.07 (m, 1H), 3.83 (s, 3H), 2.80-2.90 (m, 1H), 2.53-2.56 (m, 1H), 2.19 (s, 3H), 2.00-2.05 (m, 1H), 1.82-1.93 (m, 5H), 1.64-1.72 (m, 1H), 1.50-1.57 (m, 1H), 1.30-1.33 (m, 1H) |
| 9 | B | 365.3 | $^{1}$HNMR (400 MHz, DMSO-d6): δ 7.71 (s, 1H), 7.62 (d, J = 8.4 Hz, 1H), 7.40 (d, J = 8.0 Hz, 1H), 6.77 (s, 1H), 6.70 (brd, J = 8.0 Hz, 1H), 4.01-4.11 (m, 1H), 2.83-2.88 (m, 1H), 2.54-2.58 (m, 1H), 2.18 (s, 3H), 2.13 (s, 3H), 1.98-2.04 (m, 1H), 1.87-1.94 (m, 4H), 1.80-1.87 (m, 1H), 1.67-1.75 (m, 1H), 1.50-1.61 (m, 1H), 1.25-1.34 (m, 1H) |
| 10 | B | 365.2 | $^{1}$HNMR (400 MHz, DMSO-d6) δ = 7.82 (d, J = 8.0 Hz, 2H), 7.70 (d, J = 8.0 Hz, 2H), 6.83-6.73 (m, 2H), 4.03-4.15 (m, 1H), 2.79-2.91 (m, 1H), 2.59-2.53 (m, 3H), 2.18 (s, 3H), 2.00-2.07 (m, 1H), 1.92 (d, J = 2.0 Hz, 1H), 1.80-1.87 (m, 1H), 1.72-1.77 (m, 1H), 1.55 (dd, J = 9.6, 4.0 Hz, 1H), 1.25-1.35 (m, 1H), 1.02 (t, J = 7.6 Hz, 3H). |
| 11 | B | 297.3 | $^{1}$HNMR (400 MHz, DMSO-d6): δ 7.38 (d, J = 7.6 Hz, 2H), 7.25 (d, J = 7.6 Hz, 2H), 6.70 (s, 1H), 6.59 (brd, J = 8.4 Hz, 1H), 4.10-3.95 (m, 1H), 2.87-2.83 (m, 1H), 2.55-2.62 (m, 1H), 2.36 (s, 3H), 2.11-2.19 (m, 6H), 2.04-1.96 (m, 1H), 1.92-1.79 (m, 2H), 1.75-1.66 (m, 1H), 1.59-1.48 (m, 1H), 1.35-1.22 (m, 1H) |
| 12 | B | 311.4 | $^{1}$HNMR (400 MHz, DMSO-d6): δ 7.41 (d, J = 8.0 Hz, 2H), 7.29 (d, J = 8.0 Hz, 2H), 6.71 (s, 1H), 6.58 (brd, J = 8.0 Hz, 1H), 3.99-4.08 (m, 1H), 2.81-2.89 (m, 1H), 2.63-2.67 (m, 2H), 2.51-2.54 (m, 1H), 2.18 (s, 3H), 2.15 (s, 3H), 1.96-2.03 (m, 1H), 1.80-1.96 (m, 2H), 1.69-1.75 (m, 1H), 1.52-1.60 (m, 1H), 1.27-1.33 (m, 1H), 1.21-1.27 (m, 3H) |
| 13 | B | 351.5 | $^{1}$HNMR (400 MHz, DMSO-d6): δ 7.26-7.32 (m, 6H), 4.11-4.23 (m, 1H), 2.76-2.86 (m, 1H), 2.52-2.53 (m, 1H), 2.38 (s, 3H), 2.19 (s, 3H), 2.10-2.16 (m, 1H), 1.98-2.08 (m, 1H), 1.79-1.88 (m, 1H), 1.68-1.78 (m, 1H), 1.49-1.61 (m, 1H), 1.33-1.44 (m, 1H) |

TABLE 2-continued

| Cmpd No | General Synthetic Route | LCMS [M + H]+ | Characterization |
|---|---|---|---|
| 14 | B | 365.2 | $^1$HNMR (400 MHz, DMSO-d6): δ 7.81 (d, J = 8.4 Hz, 2H), 7.68 (d, J = 8.0 Hz, 2H), 5.77 (brd, J = 7.6 Hz, 1H), 4.15-4.36 (m, 1H), 2.85-2.97 (m, 1H), 2.57-2.65 (m, 1H), 2.19 (s, 3H), 2.10-2.15 (m, 6H), 1.85-1.97 (m, 3H), 1.66-1.75 (m, 1H), 1.53-1.61 (m, 1H), 1.40-1.48 (m, 1H) |
| 15 | C | 365.2 | 1HNMR (400 MHz, DMSO-d6) δ 7.78-7.84 (m, 2H), 7.72-7.77 (m, 2H), 6.67-6.81 (m, 2H), 4.37 (s, 1H), 3.98-4.12 (m, 1H), 3.44-3.55 (m, 2H), 2.86-2.98 (m, 1H), 2.58-2.70 (m, 1H), 2.38-2.43 (m, 2H), 2.09-2.22 (m, 4H), 1.98-2.08 (m, 1H), 1.75-1.87 (m, 1H), 1.61-1.74 (m, 1H), 1.45-1.59 (m, 1H), 1.27-1.45 (m, 1H) |
| 16 | B | 301.3 | $^1$HNMR (400 MHz, DMSO-d6): δ 7.55 (dd, J = 8.4, 1.6 Hz, 2H), 7.24-7.30 (m, 2H), 6.72 (s, 1H), 6.63 (d, J = 8.0 Hz), 4.01-4.07 (m, 1H), 2.82-2.85 (m, 1H), 2.52-2.53 (m, 1H)2.18 (s, 3H), 2.14 (s, 3H), 1.95-2.01 (m, 1H), 1.78-1.92 (m, 2H), 1.63-1.72 (m, 1H), 1.49-1.54 (m, 1H), 1.19-1.30 (m, 1H) |
| 17 | D | 369.2 | 1HNMR (400 MHz, DMSO-d6): δ 7.82 (d, J = 8.0 Hz, 2H), 7.76 (d, J = 8.4 Hz, 2H), 6.83 (d, J = 8.4 Hz, 1H), 6.74 (s, 1H), 4.93 (d, J = 46.8 Hz, 1H), 4.31-4.43 (m, 1H), 2.84-2.84 (m, 1H), 2.71-2.83 (m, 1H), 2.15-2.31 (m, 7H), 2.04-2.13 (m, 1H), 1.96 (t, J = 9.6 Hz, 1H), 1.57-1.76 (m, 1H) |
| 18 | B | 337.1 | $^1$HNMR (400 MHz, DMSO-$d_6$): δ 7.72-7.75 (m, 1H), 7.59-7.61 (m, 1H), 7.48-7.67 (m, 2H), 6.96 (d, J = 8.0 Hz, 1H), 6.91 (brd, J = 9.2 Hz, 1 H), 4.04-4.13 (m, 1H), 2.82-2.85 (m, 1H), 2.53-2.57 (m, 1H), 2.18 (s, 3H), 1.98-2.06 (m, 1H), 1.88-1.97 (m, 1H), 1.78-1.87 (m, 1H), 1.66-1.76 (m, 1H), 1.49-1.60 (m, 1H), 1.26-1.39 (m, 1H) |
| 19 | B | 351.2 | $^1$HNMR (400 MHz, DMSO-d6): δ = 7.69 (s, 1H), 7.61-7.66 (m, 1H), 7.56-7.61 (m, 1H), 7.46 (d, J = 9.2 Hz, 1H), 6.87-6.93 (m, 2H), 4.04-4.17 (m, 1H), 2.78-2.94 (m, 1H), 2.59-2.61 (m, 1H), 2.20 (s, 3H), 2.19 (s, 3H), 2.02-2.07 (m, 1H), 1.91-1.98 (m, 1H), 1.81-1.88 (m, 1H), 1.68-1.77 (m, 1H), 1.50-1.61 (m, 1H), 1.28-1.40 (m, 1H) |
| 20 | B | 371.2 | $^1$HNMR (400 MHz, DMSO-d6): δ 7.99 (s, 1H), 7.80-7.85 (m, 2H), 7.59 (d, J = 9.2 Hz, 1H), 7.04-7.09 (m, 1H), 6.94 (brd, J = 9.2 Hz, 1H), 4.05-4.16 (m, 1H), 2.83-2.95 (m, 1H), 2.59-2.64 (m, 1H), 2.19 (s, 3H), 1.93-2.10 (m, 2H), 1.82-1.90 (m, 1H), 1.71-1.79 (m, 1H), 1.53-1.64 (m, 1H), 1.30-1.41 (m, 1H) |
| 21 | B | 297.6 | $^1$HNMR (400 MHz, DMSO-$d_6$): δ 7.34 (d, J = 9.6 Hz, 1H), 7.23 (d, J = 7.6 Hz, 1H), 7.07-7.11 (m, 2H), 6.89 (d, J = 9.2 Hz, 1H), 6.72 (brd, J = 7.6 Hz, 1 H), 4.01-4.11 (m, 1H), 2.82-2.90 (m, 1H), 2.50-2.53 (m, 1H), 2.31 (s, 3H), 2.27 (s, 3H), 2.18 (s, 3H), 2.01-2.05 (m, 1H), 1.92-1.94 (m, 1H), 1.82-1.85 (m, 1H), 1.69-1.73 (m, 1H), 1.52-1.57 (m, 1H), 1.30-1.35 (m, 1H) |
| 22 | C | 337.2 | 1HNMR (400 MHz, DMSO-d6) δ 7.78-7.83 (m, 2H), 7.72-7.77 (m, 2H), 6.69-6.76 (m, 2H), 3.82-3.93 (m, 1H), 3.06-3.14 (m, 1H), 2.79 (d, J = 11.6 Hz, 1H), 2.43-2.49 (m, 2H), 2.31-2.41 (m, 1H), 2.17 (s, 3H), 1.89-2.00 (m, 1H), 1.59-1.72 (m, 1H), 1.34-1.51 (m, 2H) |
| 23 | B | 379.2 | $^1$HNMR (400 MHz, DMSO-$d_6$): δ 7.83 (d, J = 8.0 Hz, 2H), 7.66 (d, J = 8.0 Hz, 2H), 6.85 (s, 1H), 6.73 (brd, J = 8.0 Hz, 1H), 4.02-4.10 (m, 1H), 2.81-2.87 (m, 2H), 2.20 (s, 3H), 1.82-2.07 (m, 2H), 1.57-1.72 (m, 2H), 1.53-1.55 (m, 1H), 1.31-1.41 (m, 1H), 1.50-1.57 (m, 6H) |
| 24 | B | 365.2 | 1HNMR (400 MHz, MeOD): δ 8.09 (d, J = 8.0 Hz, 2H), 7.75 (d, J = 8.4 Hz, 2H), 7.71 (s, 1H), 4.41-4.52 (m, 1H), 3.04-3.14 (m, 1H), 2.66-2.75 (m, 1H), 2.45-2.58 (m, 2H), 2.20-2.37 (m, 5H), 1.95-2.05 (m, 1H), 1.78-1.88 (m, 1H), 1.68-1.78 (m, 1H), 1.53-1.66 (m, 1H), 1.14 (t, J = 7.19 Hz, 3H) |
| 25 | C | 383.2 | 1HNMR (400 MHz, DMSO-d6): δ 7.72-7.83 (m, 4H), 6.70-6.77 (m, 2H), 4.45-4.62 (m, 2H), 4.01-4.09 (m, 1H), 3.00-3.05 (m, 1H), 2.66-2.78 (m, 2H), 2.59-2.63 (m, 1H), 2.08-2.21 (m, 4H), 1.98-2.05 (m, 1H), 1.85-1.92 (m, 1H), 1.67-1.75 (m, 1H), 1.49-1.61 (m, 1H), 1.25-1.36 (m, 1H) |
| 26 | B | 369.3 | $^1$HNMR (400 MHz, DMSO-d6): δ 7.85 (t, J = 8.0 Hz, 1H), 7.68 (d, J = 12.0 Hz, 1H), 7.58 (d, J = 8.0 Hz, 1H), 6.83 (brd, J = 8.0 Hz, 1H), 6.75 (s, 1H), 4.05-4.07 (m, 1H), 2.83-2.85 (m, 1H), 2.53-2.57 (m, 1H), 2.17-2.20 (m, 6H), 1.91-2.00 (m, 1H), 1.88-1.84 (m, 2H), 1.69-1.71 (m, 1H), 1.53-1.55 (m, 1H), 1.31-1.34 (m, 1H) |

TABLE 2-continued

| Cmpd No | General Synthetic Route | LCMS [M + H]+ | Characterization |
|---|---|---|---|
| 27 | B | 319.2 | 1HNMR (400 MHz, DMSO-d6) δ 7.44-7.51 (m, 1H), 7.30-7.40 (m, 1H), 7.15-7.25 (m, 1H), 6.71-6.77 (m, 2H), 3.97-4.09 (m, 1H), 2.78-2.89 (m, 1H), 2.52-2.60 (m, 1H), (overlap with DMSO-d6 single), 2.17 (s, 3H), 1.94-2.05 (m, 4H), 1.78-1.92 (m, 2H), 1.65-1.74 (m, 1H), 1.47-1.59 (m, 1H), 1.22-1.35 (m, 1H) |
| 28 | B | 337.3 | $^1$HNMR (400 MHz, DMSO-$d_6$): δ 7.42 (d, J = 8.0 Hz, 2H), 7.31 (d, J = 8.0 Hz, 2H), 6.71 (s, 1H), 6.58 (brd, J = 8.0 Hz, 1H), 4.01-4.07 (m, 1H), 3.56-3.62 (m, 1H), 2.79-2.88 (m, 1H), 2.30-2.40 (m, 2H), 2.08-2.23 (m, 9H), 1.99-2.03 (m, 2H), 1.83-1.94 (m, 3H), 1.69-1.72 (m, 1H), 1.52-1.58 (m, 1H), 1.28-1.30 (m, 1H) |
| 29 | B | 369.2 | 1HNMR (400 MHz, DMSO-d6) δ 8.05-8.15 (m, 1H), 7.79 (d, J = 10.8 Hz, 1H), 7.69 (d, J = 8.0 Hz, 1H), 7.55 (s, 1H), 6.07 (brd, J = 7.6 Hz, 1H), 4.25-4.37 (m, 1H), 2.85-3.00 (m, 1H), 2.57-2.70 (m, 1H), 2.10-2.25 (m, 6H), 1.81-1.98 (m, 3H), 1.63-1.75 (m, 1H), 1.36-1.62 (m, 2H) |
| 30 | B | 365.2 | $^1$HNMR (400 MHz, DMSO-d6) δ = 8.09-8.30 (m, 2H), 7.78-7.87 (m, 2H), 7.73 (s, 1H), 6.04 (brd, J = 8.0 Hz, 1H), 4.23-4.44 (m, 1H), 2.85-3.01 (m, 1H), 2.65-2.55 (m, 3H), 2.19 (s, 3H), 1.85-2.02 (m, 3H), 1.64-1.75 (m, 1H), 1.50-1.61 (m, 1H), 1.39-1.47 (m, 1H), 1.21-1.25 (m, 3H) |
| 31 | B | 308.3 | $^1$HNMR (400 MHz, DMSO-$d_6$): δ 7.91 (d, J = 8.4 Hz, 2H), 7.73 (d, J = 8.0 Hz, 2H), 6.80 (brd, J = 8.0 Hz, 1H), 6.75 (s, 1H), 4.04-4.08 (m, 1H), 2.84-2.88 (m, 1H), 2.51-2.55 (m, 1H), 2.13-2.18 (m, 6H), 1.98-2.08 (m, 1H), 1.82-1.95 (m, 2H), 1.69-1.76 (m, 1H), 1.46-1.5 (m, 1H), 1.29-1.39 (m, 1H) |
| 32 | B | 313.3 | $^1$HNMR (400 MHz, DMSO-d6): δ 7.42 (d, J = 8.8 Hz, 2H), 7.00 (d, J = 8.4 Hz, 2H), 6.69 (s, 1H), 6.53 (brd, J = 8.0 Hz, 1H), 4.00-4.04 (m, 1H), 3.80 (s, 3H), 2.82-2.86 (m, 1H), 2.54-2.57 (m, 1H), 2.17 (s, 3H), 2.14 (s, 3H), 1.94-2.02 (m, 1H), 1.77-1.86 (m, 2H), 1.65-1.75 (m, 1H), 1.45-1.56 (m, 1H), 1.21-1.31 (m, 1H) |
| 33 | B | 329.4 | $^1$HNMR (400 MHz, DMSO-d6): δ 7.20 (d, J = 7.2 Hz, 2H), 6.70 (s, 1H), 6.60 (d, J = 8.0 Hz, 1H), 4.00-4.07 (m, 1H), 2.87-2.89 (m, 1H), 2.55-2.67 (m, 1H), 2.26 (s, 6H), 2.19 (s, 3H), 2.13 (s, 3H), 1.98-2.07 (m, 1H), 1.91-2.03 (m, 1H), 1.82-1.84 (m, 1H), 1.70-1.71 (m, 1H), 1.56-1.69 (m, 1H), 1.23-1.30 (m, 1H) |
| 34 | B | 335.2 | 1H NMR (400 MHz, DMSO-d6) δ 7.65-7.80 (m, 1H), 7.44-7.56 (m, 2H), 6.67-6.76 (m, 2H), 3.97-4.11 (m, 1 H), 2.75-2.95 (m, 1H), 2.52-2.60 (m, 1H), (overlap with DMSO-d6 signal), 2.12-2.20 (m, 6H), 1.95-2.05 (m, 1H), 1.77-1.93 (m, 2H), 1.64-1.74 (m, 1H), 1.46-1.61 (m, 1H), 1.20-1.35 (m, 1H) |
| 35 | B | 381.2 | 1HNMR (400 MHz, DMSO-d6): δ 7.82 (d, J = 8.0 Hz, 1H), 7.51 (s, 1H), 7.38-7.42 (m, 2H), 5.89 (brd, J = 8.0 Hz, 1H), 4.25-4.32 (m, 1H), 3.89 (s, 3H), 2.92-2.96 (m, 1H), 2.53-2.56 (m, 1H), 2.10-2.23 (m, 6H), 1.83-2.00 (m, 3H), 1.68-1.74 (m, 1H), 1.64-1.72 (m, 1H), 1.56-1.62 (m, 1H), 1.40-1.46 (m, 1H) |
| 36 | B | 351.2 | 1HNMR (400 MHz, DMSO-d6): δ 8.17-8.22 (m, 2H), 7.75-7.85 (m, 3H), 6.00 (brd, J = 7.6 Hz, 1H), 4.26-4.35 (m, 1H), 2.88-2.97 (m, 1H), 2.58-2.62 (m, 1H), 2.17 (d, J = 3.2 Hz, 6H), 1.81-1.99 (m, 3H), 1.67-1.70 (m, 1H), 1.50-1.60 (m, 1H), 1.37-1.47 (m, 1H). |
| 37 | B | 325.3 | 1HNMR (400 MHz, DMSO-d6) δ 7.24-7.39 (m, 4H), 6.71 (s, 1H), 6.60 (brd, J = 8.0 Hz, 1H), 3.97-4.11 (m, 1H), 2.90-3.00 (m, 1H), 2.80-2.89 (m, 1H), 2.10-2.25 (m, 6H), 1.92-2.05 (m, 1H), 1.77-1.89 (m, 2H), 1.63-1.76 (m, 1H), 1.45-1.60 (m, 1H), 1.26-1.36 (m, 1H), 1.24 (d, J = 7.2 Hz, 6H) |
| 38 | B | 369.3 | $^1$HNMR (400 MHz, DMSO-d6): δ 7.82-7.88-8.11 (m, 1H), 7.68 ( (d, J = 8.0 Hz, 1H), 7.58 (d, J = 8.0 Hz, 1H), 6.83 (brd, J = 8.0 Hz, 1H), 6.75 (s, 1H), 4.04-4.08 (m, 1H), 2.81-2.83 (m, 1H), 2.56-2.59 (m, 1H), 2.16-2.20 (m, 6H), 1.96-2.03 (m, 1H), 1.77-1.92 (m, 2H), 1.65-1.78 (m, 1H), 1.47-1.53 (m, 1H), 1.30-1.42 (m, 1H) |

TABLE 2-continued

| Cmpd No | General Synthetic Route | LCMS [M + H]+ | Characterization |
|---|---|---|---|
| 39 | B | 385.2 | 1H NMR (400 MHz, DMSO-d6) δ 7.85-7.97 (m, 2 H), 7.67-7.75 (m, 1H), 6.84 (brd, J = 7.6 Hz, 1H), 6.75 (s, 1H), 4.00-4.15 (m, 1H), 2.75-2.90 (m, 1H), 2.52-2.54 (m, 1H), (overlap with DMSO-d6 signal), 2.10-2.25 (m, 6H), 1.96-2.07 (m, 1H), 1.79-1.95 (m, 2H), 1.65-1.76 (m, 1H), 1.44-1.62 (m, 1H), 1.16-1.39 (m, 1H) |
| 40 | B | 376.3 | $^{1}$HNMR (400 MHz, DMSO-d6): δ 8.48 (s, 1H), 8.16 (dd, J = 8.0, 1.6 Hz, 1H), 7.89 (d, J = 8.0 Hz, 1H), 6.98 (brd, J = 8.0 Hz, 1H), 6.82 (s, 1H)3.98-, 4.20 (m, 1H), 2.84-2.87 (m, 1H), 2.52-2.58 (m, 1H), 2.19 (s, 3H), 2.09 (s, 3H), 1.99-2.05 (m, 1H), 1.90-1.97 (m, 1H), 1.81-1.88 (m, 1H), 1.68-1.77 (m, 1H), 1.55 (m, 1H), 1.32 (m, 1H) |
| 41 | B | 371.3 | $^{1}$HNMR (400 MHz, DMSO-d6): δ 8.32 (s, 1H), 8.27 (d, J = 8.0 Hz, 2H), 7.84 (d, J = 8.4 Hz, 2H), 6.54 (d, J = 7.6 Hz, 1H), 4.31-4.40 (m, 1H), 2.80 (d, J = 9.6 Hz1H), 2.48-2.51 (m, 1H), 2.21 (s, 3H), 2.08-2.18 (m, 2H), 1.76-1.84 (m, 1H), 1.65-1.73 (m, 1H), 1.52-1.61 (m, 2H). |
| 42 | B | 365.1 | 1HNMR (400 MHz, DMSO-d6): δ 7.51 (s,2H), 7.21 (d, J = 8.8 Hz, 1H), 6.94 (d, J = 9.2 Hz, 1H), 6.83 (d, J = 8.0 Hz, 1H), 4.04-4.15 (m, 1H), 2.86 (d, J = 8.4 Hz, 1H), 2.52-2.58 (m, 1H), 2.18 (s, 3H), 2.08 (s, 6H), 1.98-2.05 (m, 1H), 1.79-1.98 (m, 2H), 1.66-1.76 (m, 1H), 1.47-1.62 (m, 1H), 1.23-1.39 (m, 1H) |
| 43 | B | 317.1 | 1HNMR (400 MHz, DMSO-d6): δ 7.55 (s, 1H), 7.43-7.50 (m, 3H), 6.67-6.76 (m, 2H), 3.96-4.11 (m, 1H), 2.80-2.90 (m, 1H), 2.53-2.57 (m, 1H), 2.16 (d, J = 4.8 Hz, 6H), 1.77-2.05 (m, 3H), 1.63-1.72 (m, 1H), 1.47-1.59 (m, 1H), 1.22-1.35 (m, 1H) |
| 44 | B | 297.5 | $^{1}$HNMR (400 MHz, DMSO-$d_6$): δ 7.21-7.35 (m, 4H), 6.71 (s, 1H), 6.63 (d, J = 7.6 Hz, 1H), 4.06-4.08 (m, 1H), 2.87-3.01 (m, 1H), 2.58-2.69 (m, 1H), 2.37 (s, 3H), 2.25 (s, 3H), 2.06-2.17 (m, 4H), 1.92-2.02 (m, 1H), 1.83-1.91 (m, 1H), 1.68-1.78 (m, 1H), 1.50-1.62 (m, 1H), 1.22-1.39 (m, 1H) |
| 45 | B | 301.2 | 1HNMR (400 MHz, DMSO-d6) δ 7.18-7.54 (m, 4H), 6.60-6.81 (m, 2H), 3.95-4.10 (m, 1H), 2.70-2.95 (m, 1H), 2.51-2.58 (m, 1H), (overlap with DMSO-d6 signal), 2.10-2.25 (m, 6H), 1.79-2.06 (m, 3H), 1.60-1.75 (m, 1H), 1.40-1.59 (m, 1H), 1.20-1.39 (m, 1H) |
| 46 | B | 351.2 | 1HNMR (400 MHz, DMSO-d6): δ 7.66-7.86 (m, 4H), 6.73-6.77 (m, 2H), 4.02-4.10 (m, 1H), 2.83-2.87 (m, 1H), 2.53-2.56 (m, 1H), 2.18 (s, 6H), 1.66-1.92 (m, 3H), 1.51-1.56 (m, 1H), 1.30-1.3 (m, 1H), 1.25-1.29 (m, 1H) |
| 47 | B | 351.2 | 1HNMR (400 MHz, DMSO-d6): δ 8.27-8.38 (m, 2H), 7.88 (s, 1H), 7.67-7.76 (m, 2H), 5.99 (b, J = 7.6 Hz, 1H), 4.28-4.32 (m, 1H), 2.92-2.96 (m, 1H), 2.61-2.68 (m, 1H), 2.16-2.20 (m, 6H), 1.87-1.95 (m, 3H), 1.69-1.73 (m, 1H), 1.50-1.58 (m, 1H), 1.38-1.45 (m, 1H) |
| 48 | B | 351.2 | 1HNMR (400 MHz, DMSO-d6): δ 7.66-7.86 (m, 4H), 6.73-6.77 (m, 2H), 4.02-4.10 (m, 1H), 2.83-2.87 (m, 1H), 2.53-2.56 (m, 1H), 2.18 (s, 6H), 1.66-1.92 (m, 3H), 1.51-1.56 (m, 1H), 1.30-1.34 (m, 1H), 1.25-1.29 (m, 1H) |
| 49 | B | 351.2 | 1HNMR (400 MHz, DMSO-d6): δ 7.66-7.86 (m, 4H), 6.73-6.77 (m, 2H), 4.02-4.10 (m, 1H), 2.83-2.87 (m, 1H), 2.53-2.56 (m, 1H), 2.18 (s, 6H), 1.66-1.92 (m, 3H), 1.51-1.56 (m, 1H), 1.30-1.34 (m, 1H), 1.25-1.29 (m, 1H) |
| 50 | B | 308.2 | 1HNMR (400 MHz, DMSO-d6): δ 7.98 (t, J = 1.2 Hz, 1H), 7.84-7.90 (m, 2H), 7.64-7.70 (m, 1H), 6.71-6.79 (m, 2H), 3.99-4.12 (m, 1H), 2.84 (d, J = 9.2 Hz, 1H), 2.51-2.58 (m, 1H), 2.17 (s, 6H), 2.00 (t, J = 8.8 Hz, 1H), 1.77-1.95 (m, 2H), 1.64-1.73 (m, 1H), 1.48-1.60 (m, 1H), 1.23-1.37 (m, 1H) |
| 51 | B | 308.2 | 1HNMR (400 MHz, DMSO-d6): δ 8.39 (s, 1H), 8.33-8.38 (m, 1H), 7.80-7.88 (m, 2H), 7.67 (t, J = 8.0 Hz, 1H), 5.99 (d, J = 7.6 Hz, 1H), 4.23-4.35 (m, 1H), 2.92 (d, J = 8.4 Hz, 1H), 2.57-2.66 (m, 1H), 2.17 (d, J = 7.2 Hz, 6H), 1.83-1.98 (m, 3H), 1.66-1.75 (m, 1H), 1.49-1.61 (m, 1H), 1.35-1.47 (m, 1H) |
| 52 | B | 313.2 | 1HNMR (400 MHz, DMSO-d6): δ 7.35 (t, J = 7.6 Hz, 1H), 7.00-7.07 (m, 2H), 6.94-7.00 (m, 1H), 6.71 (s,1H), 6.61 (d, J = 8.0 Hz, 1H), 3.98-4.11 (m, 1H), 3.79 (s, 3H), 2.85 (d, J = 9.2 Hz, 1H), 2.51-2.57 (m, 1H), 2.16 (d, J = 11.2 Hz, 6H), 1.93-2.05 (m, 1H), 1.77-1.93 (m, 2H), 1.64-1.75 (m, 1H), 1.47-1.60 (m, 1H), 1.22-1.35 (m, 1H) |

TABLE 2-continued

| Cmpd No | General Synthetic Route | LCMS [M + H]+ | Characterization |
|---|---|---|---|
| 53 | B | 313.2 | 1HNMR (400 MHz, DMSO-d6): δ 7.72 (d, J = 0.8 Hz, 1H), 7.51-7.59 (m, 2H), 7.37 (t, J = 8.0 Hz, 1H), 6.90-6.98 (m, 1H), 5.85 (d, J = 8.0 Hz, 1H), 4.21-4.32 (m, 1H), 3.82 (s, 3H), 2.93 (d, J = 8.4 Hz, 1H), 2.58-2.66 (m, 1H), 2.17 (d, J = 12.4 Hz, 6H), 1.83-1.99 (m, 3H), 1.66-1.75 (m, 1H), 1.51-1.62 (m, 1H), 1.35-1.48 (m, 1H) |
| 54 | B | 283.2 | $^1$HNMR (400 MHz, DMSO-d6): δ 7.53-7.39 (m, 5H), 6.89-6.72 (m, 2H), 4.16-4.22 (m, 1H), 3.04-3.10 (m, 1H), 2.69-2.73 (m, 1H), 2.28-2.38 (m, 3H), 2.17 (s, 3H), 1.96-1.24 (m, 6H) |
| 55 | B | 311.2 | 1HNMR (400 MHz, DMSO-d6): δ 7.16-7.45 (m, 4H), 6.50-6.80 (m, 2H), 4.04 (brs, 1H), 2.84 (s, 1H), 2.65-2.67 (m, 3H), 2.15 (d, J = 11.6 Hz, 6H), 1.77-2.03 (m, 3H), 1.47-1.73 (m, 2H), 1.21-1.36 (m, 4H). |
| 56 | B | 301.2 | 1HNMR (400 MHz, DMSO-d6) δ 7.74-7.87 (m, 2H), 7.70 (s, 1H), 7.43-7.54 (m, 1H), 7.10-7.25 (m, 1H), 5.60-5.75 (m, 1H), 4.25-4.40 (m, 1H), 2.75-3.05 (m, 1H), 2.52-2.60 (m, 1H), (overlap with DMSO-d6 single), 2.10-2.25 (m, 6H), 1.98-2.12 (m, 2H), 1.82-1.93 (m, 1H), 1.67-1.77 (m, 1H), 1.38-1.65 (m, 2H) |
| 57 | B | 313.3 | $^1$HNMR (400 MHz, DMSO-d6): δ 8.02 (dd, J = 8.0, 1.6 Hz, 2H), 7.71 (s, 1H), 7.25-7.32 (m, 2H), 5.85 (brd, J = 8.0 Hz, 1H), 4.21-4.35 (m, 1H), 2.94-2.95 (m, 1H), 2.52-2.59 (m, 1H)2.20 (s, 3H), 2.16 (s, 3H), 1.85-1.97 (m, 3H), 1.69-1.76 (m, 1H), 1.61-1.52 (m, 1H), 1.36-1.46 (m, 1H) |
| 58 | B | 313.3 | $^1$HNMR (400 MHz, DMSO-d6): δ 7.92 (d, J = 8.4 Hz, 2H), 7.65 (s, 1H), 7.01 (d, J = 8.4 Hz, 2H), 5.74 (brd, J = 7.6 Hz, 1H), 4.20-4.28 (m, 1H), 3.80 (s, 3H), 2.92-2.96 (m, 1H), 2.64-2.57 (m, 1H), 2.12-2.21 (m, 6H), 1.83-1.98 (m, 3H), 1.66-1.76 (m, 1H), 1.35-1.60 (m, 2H) |
| 59 | B | 362.2 | $^1$HNMR (400 MHz, DMSO-d6): δ 8.0 ( (d, J = 8.4 Hz, 2H), 7.92 (d, J = 8.4 Hz, 2H), 7.54 (brd, J = 8.0 Hz, 1H), 7.43 (s, 1H), 4.24-4.04 (m, 1H), 2.85-2.70 (m, 1H), 2.54-2.53 (m, 1H), 2.20 (s, 3H), 2.14-2.02 (m, 2H), 1.86-1.78 (m, 1H), 1.75-1.67 (m, 1H), 1.61-1.50 (m, 1H), 1.45-1.33 (m, 1H) |
| 60 | C | 401.2 | 1HNMR (400 MHz, DMSO-d6) δ 7.72-7.86 (m, 4H), 6.70-6.81 (m, 2H), 5.97-6.31 (m, 1H), 3.97-4.12 (m, 1H), 3.01-3.12 (m, 1H), 2.68-2.83 (m, 3H), 2.09-2.27 (m, 5H), 1.82-1.93 (m, 1H), 1.64-1.76 (m, 1H), 1.48-1.58 (m, 1H), 1.26-1.36 (m, 1H) |
| 61 | B | 405.0 | $^1$HNMR (400 MHz, DMSO-d6): δ 8.33 (d, J = 8.4 Hz, 2H), 8.27 (s, 1H), 7.87 (d, J = 8.4 Hz, 2H), 6.33 (d, J = 7.6 Hz, 1H), 4.48-4.58 (m, 1H), 2.64-2.72 (m, 1H), 2.52-2.53 (m, 1H), 2.39-2.44 (m, 1H), 2.27-2.35 (m, 1H), 2.22 (s, 3H), 1.62-1.75 (m, 3H), 1.49-1.61 (m, 1H) |
| 62 | B | 315.1 | $^1$HNMR (400 MHz, DMSO-d6): δ 7.4-7.42 (m, 1H), 7.31-7.35 (m, 1H), 7.17-7.22 (m, 1H), 6.71 (s, 1H), 6.61 (d, J = 8.0 Hz, 1H), 4.03-4.05 (m, 1H), 2.84-2.86 (m, 1H), 2.50-2.53 (m, 1H), 2.29 (s, 3H), 2.17 (s, 3H), 2.14 (s, 3H), 1.98-2.02 (m, 1H), 1.81-1.91 (m, 2H), 1.68-1.73 (m, 1H), 1.52-1.56 (m, 1H), 1.23-1.36 (m, 1H) |
| 63 | B | 376.1 | $^1$HNMR (400 MHz, DMSO-d6): δ 8.34 (s, 1H), 8.09-8.12 (m, 2H), 6.90 (d, J = 7.6 Hz, 1H), 6.77 (s, 1H), 4.06-4.08 (m, 1H), 2.88-2.82 (m, 1H), 2.52-2.53 (m, 1H), 2.22 (s, 3H), 2.18 (s, 3H), 2.01-2.17 (m, 1H), 1.90-1.91 (m, 1H), 1.81-1.84 (m, 1H), 1.69-1.70 (m, 1H), 1.53-1.56 (m, 1H), 1.29-1.32 (m, 1H) |
| 64 | B | 319.1 | $^1$HNMR (400 MHz, DMSO-d6) δ : 7.56-7.60 (m, 1H), 7.49-7.51 (m, 1H), 7.36-7.37 (m, 1H), 6.70-6.72 (m, 2H), 4.03-4.05 (m, 1H), 2.82-2.85 (m, 1H), 2.62-2.52 (m, 1H), 2.16-2.17 (m, 6H), 1.98-2.01 (m, 1H), 1.81-1.89 (m, 2H), 1.68-1.70 (m, 1H), 1.52-1.54 (m, 1H), 1.27-1.30 (m, 1H) |
| 65 | C | 333.2 | 1HNMR (400 MHz, DMSO-d6): δ 7.49-7.62 (m, 2H), 7.23-7.29 (m, 2H), 6.55-6.78 (m, 2H), 4.43-4.63 (m, 2H), 3.96-4.09 (m, 1H), 3.01-3.05 (m, 1H), 2.57-2.76 (m, 3H), 1.81-2.17 (m, 6H), 1.47-1.77 (m, 2H), 1.21-1.34 (m, 1H) |
| 66 | C | 391.2 | 1HNMR (400 MHz, DMSO-d6) δ 7.69-7.90 (m, 4H), 6.67-6.85 (m, 2H), 4.05-4.17 (m, 1H), 2.97-3.13 (m, 1H), 2.70-2.86 (m, 1H), 2.14-2.29 (m, 5H), 1.83-2.12 (m, 3H), 1.65-1.78 (m, 1H), 1.44-1.63 (m, 1H), 1.19-1.40 (m, 1H), 0.74-0.96 (m, 1H), 0.37-0.52 (m, 2H), −0.02-0.15 (m, 2H). |

TABLE 2-continued

| Cmpd No | General Synthetic Route | LCMS [M + H]+ | Characterization |
|---|---|---|---|
| 67 | B | 337.1 | $^{1}$HNMR (400 MHz, DMSO-d6): δ 8.20 (d, J = 8.4 Hz, 2H), 7.89 (d, J = 9.2 Hz, 1H), 7.83 (d, J = 8.4 Hz, 2H), 6.94-7.02 (m, 2H), 4.05-4.19 (m, 1H), 2.76-2.93 (m, 1H), 2.53-2.57 (m, 1H), 2.19 (s, 3H), 2.01-2.09 (m, 1H), 1.92-2.00 (m, 1H), 1.80-1.89 (m, 1H), 1.68-1.77 (m, 1H), 1.49-1.61 (m, 1H), 1.29-1.40 (m, 1H) |
| 68 | B | 377.2 | 1HNMR (400 MHz, DMSO-d6): δ 7.81 (d, J = 8.0 Hz, 2H), 7.75 (d, J = 8.4 Hz, 2H), 6.74 (s, 1H), 6.69 (d, J = 7.6 Hz, 1H), 3.94-3.98 (m, 1H), 3.05-3.08 (m, 1H), 2.74-2.77 (m, 1H), 2.09-2.45 (m, 5H), 1.83-1.88 (m, 1H), 1.60-1.69 (m, 2H), 1.26-1.48 (m, 2H), 0.30-0.42 (m, 4H), |
| 69 | C | 387.2 | 1HNMR (400 MHz, DMSO-d6): δ 7.81-7.84 (m, 4H), 6.88 (brd, J = 8.0 Hz, 1H), 6.78 (s, 1H), 4.25-4.36 (m, 1H), 2.86-3.00 (m, 2H), 2.34-2.46 (m, 2H), 2.29 (s, 3H), 2.19 (s, 3H), 2.01-2.08 (m, 1H), 1.78-1.95 (m, 1H) |
| 70 | C | 341.2 | 1HNMR (400 MHz, DMSO-d6): δ 8.21 (brs, 1H), 7.52-7.57 (m, 2H), 7.27 (t, J = 8.8 Hz, 2H), 6.65-7.72 (m, 2H), 4.05-4.09 (m, 1H), 3.07-3.11 (m, 1H), 2.80-2.84 (m, 1H), 2.24-2.33 (m, 2H), 2.13-2.15 (m, 4H), 2.00-2.07 (m, 1H), 1.84-1.93 (m, 1H), 1.70-1.77 (m, 1H), 1.55-1.6 (m, 1H), 1.39-1.45 (m, 1H), 0.82-0.87 (m, 1H), 0.44-0.47 (m, 2H), 0.07-0.11 (m, 2H) |
| 71 | B | 315.1 | $^{1}$HNMR (400 MHz, DMSO-d6): δ 7.36 (d, J = 9.2 Hz, 1H), 7.25 (d, J = 8.0 Hz, 1H), 7.08 (d, J = 10.8 Hz, 1H), 6.89 (d, J = 9.2 Hz, 1H), 6.80 (d, J = 8.0 Hz, 1 H), 4.24-4.00 (m, 1H), 3.02-2.85 (m, 1H), 2.69-2.60 (m, 1H), 2.30-2.21 (m, 9H), 2.23-2.15 (m, 1H), 1.87-1.85 (m, 1H), 1.75-1.73 (m, 1H), 1.59-1.58 (m, 1H), 1.35-1.30 (m, 1H) |
| 72 | B | 376.3 | $^{1}$HNMR (400 MHz, DMSO-d6): δ 8.42 (s, 1H), 8.16 (d, J = 8.4, 1H), 8.04 (d, J = 8.0 Hz, 1 H), 7.70 (s, 1H), 6.27-6.16 (m, 1H), 4.40-4.31 (m, 1H), 2.86-2.98 (m, 1H), 2.53-2.65 (m, 1H), 2.17-2.20 (m, 6H), 1.90-1.98 (m, 3H), 1.68-1.73 (m, 1H), 1.54-1.62 (m, 1H), 1.42-1.46 (m, 1H) |
| 73 | B | 335.2 | 1H NMR (400 MHz, DMSO-d6) δ 8.10-8.28 (m, 1H), 7.93-8.09 (m, 1H), 7.70-7.88 (m, 1H), 7.45-7.61 (m, 2H), 5.85-6.05 (m, 1H), 4.21-4.35 (m, 1H), 2.62-3.00 (m, 1H), (overlap with DMSO-d6 signal), 2.09-2.24 (m, 7 H), 1.84-1.98 (m, 3H), 1.58-1.75 (m, 1H), 1.49-1.61 (m, 1H) |
| 74 | D | 369.2 | 1HNMR (400 MHz, DMSO-d6): δ 7.82 (d, J = 8.4 Hz, 2H), 7.75 (d, J = 8.4 Hz, 2H), 6.96 (d, J = 8.4 Hz, 1H), 6.87 (s, 1H), 4.92 (d, J = 48.8 Hz, 1H), 4.33-4.48 (m, 1H), 2.70-2.79 (m, 1H), 2.43-2.46 (m, 1H), 2.13-2.24 (m, 8H), 1.76-2.03 (m, 2H) |
| 75 | B | 381.2 | 1HNMR (400 MHz, DMSO-d6): δ 7.25 (s, 1H), 7.21 (s, 1H), 7.12 (d, J = 9.2 Hz, 1H), 6.84 (d, J = 9.2 Hz, 1H), 6.76 (d, J = 8.0 Hz, 1H), 4.00-4.11 (m, 1H), 3.71 (s, 3H), 2.81-2.91 (m, 1H), 2.53-2.57 (m, 1H), 2.44 (s, 3H), 2.19 (s, 3H), 1.98-2.08 (m, 1H), 1.89-1.97 (m, 1H), 1.80-1.88 (m, 1H), 1.67-1.76 (m, 1H), 1.49-1.61 (m, 1H), 1.24-1.35 (m, 1H) |
| 76 | B | 381.2 | 1HNMR (400 MHz, DMSO-d6): δ 8.19 (s, 1H), 7.34 (d, J = 8.0 Hz, 1H), 7.23 (d, J = 8.4 Hz, 1H), 6.87 (d, J = 8.0 Hz, 1H), 6.80 (s, 1H), 4.02-4.13 (m, 1H), 2.84-2.98 (m, 1H), 2.57-2.66 (m, 1H), 2.33 (s, 3H), 2.24 (s, 3H), 2.08-2.17 (m, 4H), 1.94-2.05 (m, 1H), 1.80-1.90 (m, 1H), 1.70-1.78 (m, 1H), 1.51-1.63 (m, 1H), 1.26-1.41 (m, 1H) |
| 77 | B | 317.2 | 1HNMR (400 MHz, DMSO-d6): δ 7.72-8.13 (m, 3H), 7.40-7.53 (m, 2H), 5.95 (brd, J = 7.2 Hz, 1H), 4.20-4.53 (m, 1H), 2.86-2.95 (m, 1H), 2.56-2.62 (m, 1H), 2.17 (brd, J = 10.8 Hz, 6H), 1.80-1.95 (m, 3H), 1.65-1.75 (m, 1H), 1.50-1.60 (m, 1H), 1.35-1.46 (m, 1H) |
| 78 | B | 311.2 | 1HNMR (400 MHz, DMSO-d6): δ 7.65-7.94 (m, 3H), 7.36 (t, J = 7.2 Hz, 1H), 7.22 (d, J = 7.2 Hz, 1H), 5.83 (b, J = 7.2 Hz, 1H), 4.17-4.35 (m, 1H), 2.91-2.94 (m, 1H), 2.63-2.74 (m, 3H), 2.15-2.18 (m, 6H), 1.81-2.02 (m, 3H), 1.65-1.69 (m, 1H), 1.53-1.57 (m, 1H), 1.33-1.45 (m, 1H), 1.20-1.24 (m, 3H) |

TABLE 2-continued

| Cmpd No | General Synthetic Route | LCMS [M + H]+ | Characterization |
| --- | --- | --- | --- |
| 79 | B | 325.2 | 1HNMR (400 MHz, DMSO-d6) δ 7.88 (s, 1H), 7.76 (d, J = 7.6 Hz, 1H), 7.71 (s, 1H), 7.37 (t, J = 7.6 Hz, 1H), 7.25 (d, J = 7.6 Hz, 1H), 5.83 (brd, J = 8.0 Hz, 1H), 4.17-4.34 (m, 1H), 2.89-3.02 (m, 2H), 2.56-2.68 (m, 1H), 2.10-2.25 (m, 6H), 1.82-1.98 (m, 3H), 1.63-1.75 (m, 1H), 1.49-1.61 (m, 1H), 1.35-1.47 (m, 1H), 1.25 (d, J = 6.8 Hz, 6H) |
| 80 | B | 308.3 | $^{1}$HNMR (400 MHz, DMSO-$d_6$): δ 8.21 (d, J = 8.0 Hz, 2H), 7.93 (d, J = 8.0 Hz, 2H), 7.86 (s, 1H), 6.07 (d, J = 7.6 Hz, 1H), 4.03-4.33 (m, 1H), 2.76-2.78 (m, 1H), 2.68-2.73 (m, 1H), 2.34-2.35 (m, 6H), 1.92-2.18 (m, 3H), 1.72-1.86 (m, 1H), 1.70-1.72 (m, 1H), 1.43-1.70 (m, 1H) |
| 81 | B | 367.3 | $^{1}$HNMR (400 MHz, DMSO-d6): δ 8.09-8.12 (m, 2H), 7.76 (s, 1H), 7.46 (d, J = 8.0 Hz, 2H), 5.92 (d, J = 8.0 Hz, 1H), 4.24-4.36 (m, 1H), 2.93 (d, J = 11.6 Hz, 1H), 2.61-2.66 (m, 1H), 2.16-2.21 (m, 6H), 1.85-2.00 (m, 3H), 1.67-1.75 (m, 1H), 1.51-1.63 (m, 1H), 1.38-1.48 (m, 1H) |
| 82 | B | 297.3 | $^{1}$HNMR (400 MHz, DMSO-d6): δ = 7.87 (d, J = 8.0 Hz, 2H), 7.67 (s, 1H), 7.27 (d, J = 8.0 Hz, 2H), 5.79 (brd, J = 8.0 Hz, 1H), 4.34-4.21 (m, 1H), 2.99-2.88 (m, 1H), 2.70-2.64 (m, 1H), 2.34 (s, 3H), 2.19 (s, 3H), 2.15 (s, 3H), 1.99-1.87 (m, 3H), 1.73-1.68 (m, 1H), 1.60-1.52 (m, 1H), 1.47-1.37 (m, 1H) |
| 83 | C | 337.1 | 1HNMR (400 MHz, DMSO-d6) δ 8.20 (d, J = 8.0 Hz, 2H), 7.78-7.83 (m, 3H), 5.99 (d, J = 8.0 Hz, 1H), 4.11-4.25 (m, 1H), 3.07-3.18 (m, 1H), 2.81 (d, J = 12.0 Hz, 1H), 2.41-2.49 (m, 3H), 2.18 (s, 3H), 1.90-2.01 (m, 1H), 1.35-1.71 (m, 3H) |
| 84 | B | 269.1 | 1HNMR (400 MHz, DMSO-d6): δ 7.92-7.99 (m, 2H), 7.78 (d, J = 9.2 Hz, 1H), 7.46 (t, J = 7.6 Hz, 2H), 7.35-7.41 (m, 1H), 6.92 (d, J = 9.2 Hz, 1H), 6.81 (d, J = 7.6 Hz, 1H), 4.02-4.15 (m, 1H), 2.86 (d, J = 8.4 Hz, 1H), 2.52-2.58 (m, 1H), 2.18 (s, 3H), 1.97-2.08 (m, 1H), 1.87-1.97 (m, 1H), 1.80-1.87 (m, 1H), 1.67-1.76 (m, 1H), 1.49-1.61 (m, 1H), 1.24-1.37 (m, 1H) |
| 85 | B | 283.5 | $^{1}$HNMR (400 MHz, DMSO-d6) δ = 7.41-7.25 (m, 5H), 6.91 (d, J = 9.2 Hz, 1H), 6.76 (brd, J = 8.0 Hz, 1 H), 3.99-4.20 (m, 1H), 2.85-2.91 (m, 1H), 2.51-2.58 (m, 1H), 2.31 (s, 3H), 2.19 (s, 3H), 2.00-2.07 (m, 1H), 1.90-1.98 (m, 1H), 1.81-1.89 (m, 1H), 1.69-1.76 (m, 1H), 1.50-1.60 (m, 1H), 1.27-1.38 (m, 1H) |
| 86 | B | 365.2 | 1HNMR (400 MHz, DMSO-d6) δ 7.25-7.55 (m, 4H), 6.68-6.80 (m, 2H), 3.90-4.10 (m, 1H), 2.75-2.95 (m, 1H), 2.52-2.61 (m, 1H), (overlap with DMSO-d6 single), 2.17 (s, 3H), 1.94-2.05 (m, 4H), 1.78-1.93 (m, 2H), 1.58-1.70 (m, 1H), 1.45-1.57 (m, 1H), 1.15-1.38 (m, 1H) |
| 87 | B | 297.2 | 1HNMR (400 MHz, DMSO-d6): δ 7.20-7.33 (m, 3H), 7.10-7.15 (m, 1H), 6.73 (s, 1H), 6.61-6.65 (m, 1H), 4.02-4.10 (m, 1H), 2.93-2.99 (s, 1H), 1.80-2.33 (m, 13H), 1.65-1.72 (m, 1H), 1.53-1.62 (m, 1H), 1.30-1.36 (m, 1) |
| 88 | D | 369.2 | 1HNMR (400 MHz, DMSO-d6): δ 8.23 (d, J = 8.4 Hz, 2H), 7.88 (s, 1H), 7.83 (d, J = 8.4 Hz, 2H), 6.03 (d, J = 8.4 Hz, 1H), 5.01 (d, J = 50.8 Hz, 1H), 4.46-4.65 (m, 1H), 2.79 (dd, J = 10.4, 4.4 Hz, 1H), 2.56-2.62 (m, 1H), 2.29-2.37 (m, 1H), 2.24 (d, J = 7.2 Hz, 6H), 2.12-2.21 (m, 1H), 1.79-2.06 (m, 2H) |
| 89 | B | 308.2 | 1HNMR (400 MHz, DMSO-d6): δ 7.96 (d, J = 7.2 Hz, 1H), 7.76-7.82 (m, 1H), 7.58-7.66 (m, 2H), 6.85 (brd, J = 8.4 Hz, 1H), 6.79 (s, 1H), 4.04-4.10 (m, 1H), 2.82-2.87 (m, 1H), 2.53-2.56 (m, 1H), 2.18 (s, 3H), 1.98-2.05 (m, 4H), 1.75-1.92 (m, 2H), 1.68-1.73 (m, 1H), 1.50-1.58 (m, 1H), 1.26-1.32 (m, 1H) |
| 90 | B | 308.2 | 1HNMR (400 MHz, DMSO-d6): δ 7.94 (d, J = 7.6 Hz, 1H), 7.78-7.81 (m, 2H), 7.55-7.63 (m, 2H), 6.06 (brd, J = 8.4 Hz, 1H), 4.28-4.33 (m, 1H), 2.90-2.94 (m, 1H), 2.59-2.62 (m, 1H), 2.16-2.22 (m, 6H), 1.85-2.00 (m, 3H), 1.66-1.75 (m, 1H), 1.52-1.60 (m, 1H), 1.40-1.45 (m, 1H) |
| 91 | B | 351.5 | $^{1}$HNMR (400 MHz, DMSO-d6): δ 8.10 (s, 1H), 7.98 (d, J = 8.0 Hz, 2H), 7.32 (d, J = 8.0 Hz, 2H), 6.09 (d, J = 8.0 Hz, 1H), 4.46-4.56 (m, 1H), 2.64-2.67 (m, 1H), 2.55-2.60 (m, 1H), 2.37 (s, 3H), 2.23-2.32 (m, 2H), 2.22 (s, 3H), 1.61-1.73 (m, 3H), 1.49-1.60 (m, 1H) |

TABLE 2-continued

| Cmpd No | General Synthetic Route | LCMS [M + H]+ | Characterization |
|---|---|---|---|
| 92 | B | 297.6 | $^1$HNMR (400 MHz, DMSO-$d_6$): δ 7.73-7.81 (m, 2H), 7.69 (s, 1H), 7.34 (t, J = 7.6 Hz, 1H), 7.19 (d, J = 7.6 Hz, 1H), 5.83 (brd, J = 7.6 Hz, 1H), 4.23-4.36 (m, 1H), 2.91-3.00 (m, 1H), 2.62-2.65 (m, 1H), 2.37 (s, 3H), 2.21 (s, 3H), 2.16 (s, 3H), 1.86-1.98 (m, 3H), 170-1.73 (m, 1H), 1.55-1.61 (m, 1H), 1.38-1.46 (m, 1H) |
| 93 | B | 323.3 | $^1$HNMR (400 MHz, DMSO-$d_6$): δ 7.37 (d, J = 8.0 Hz, 2H), 7.14 (d, J = 8.4 Hz, 2H), 6.69 (s, 1H), 6.57 (brd, J = 8.0 Hz, 1H), 4.02-4.06 (m, 1H), 2.85 (m, 1H), 2.52 (s, 1H), 2.17 (s, 3H), 2.13 (s, 3H), 1.94-1.99 (m, 2H), 1.81-1.89 (m, 2H), 1.68-1.72 (m, 1H), 1.49-1.57 (m, 1H), 1.22-1.33 (m, 1H), 0.96-1.00 (m, 2H), 0.70-0.74 (m, 2H) |
| 94 | B | 323.3 | $^1$HNMR (400 MHz, DMSO-$d_6$): δ 7.86 (d, J = 8.4 Hz, 2H), 7.68 (s, 1H), 7.16 (d, J = 8.4 Hz, 2H), 5.87 (brd, J = 7.6 Hz, 1H), 4.28-4.34 (m, 1H), 3.02 (m, 1H), 2.68-2.73 (m, 1H), 2.53-2.55 (m, 1H), 2.27 (s, 3H), 2.16 (s, 3H), 2.07 (m, 1H), 1.92-1.99 (m, 1H), 1.87-1.91 (m, 1H), 1.73-1.76 (m, 1H), 1.55-1.64 (m, 1H), 1.44-1.49 (m, 1H), 0.96-1.00 (m, 2H), 0.70-0.74 (m, 2H) |
| 95 | B | 337.3 | $^1$HNMR (400 MHz, DMSO-$d_6$): δ 7.91 (d, J = 8.0 Hz, 2H), 7.68 (s, 1H), 7.32 (d, J = 8.4 Hz, 2H), 5.80 (brd, J = 8.0 Hz, 1H), 4.25-4.31 (m, 1H), 3.52-3.61 (m, 1H), 2.92-2.95 (m, 1H), 2.61-2.63 (m, 1H), 2.30-2.30 (m, 2H), 2.20 (s, 3H), 2.16 (s, 3H), 2.08-2.13 (m, 1H), 1.80-2.03 (m, 6H), 1.68-1.74 (m, 1H), 1.55-1.59 (m, 1H), 1.40-1.46 (m, 1H) |
| 96 | B | 326.2 | 1HNMR (400 MHz, DMSO-d6): δ 7.95-8.00 (m, 1H), 7.65-7.70 (m, 2H), 6.87 (brd, J = 8.0 Hz, 1H), 6.78 (s, 1H), 4.05-4.09 (m, 1H), 2.81-2.86 (m, 1H), 2.43-2.46 (m, 1H), 2.18 (s, 3H), 1.98-2.06 (m, 4H), 1.80-1.88 (m, 2H), 1.66-1.72 (m, 1H), 1.50-1.61 (m, 1H), 1.30-1.38 (m, 1H) |
| 97 | B | 326.2 | 1HNMR (400 MHz, DMSO-d6): δ 7.91-7.98 (m, 1H), 7.80-7.88 (m, 1H), 7.66-7.72 (m, 1H), 7.58 (s, 1H), 6.07 (brd, J = 8.0 Hz, 1H), 4.28-4.35 (m, 1H), 2.90-2.94 (m, 1H), 2.60-2.65 (m, 1H), 2.15-2.20 (m, 6H), 1.85-1.98 (m, 3H), 1.65-1.77 (m, 1H), 1.50-1.60 (m, 1H), 1.40-1.48 (m, 1H) |
| 98 | B | 319.2 | 1HNMR (400 MHz, DMSO-d6) δ 7.82-7.94 (m, 1H), 7.45 (s, 1H), 7.32-7.40 (m, 1H), 7.15-7.25 (m, 1H), 5.94 (brd, J = 7.6Hz, 1H), 4.23-4.34 (m, 1H), 2.85-3.00 (m, 1H), 2.58-2.69 (m, 1H), 2.10-2.25 (m, 6H), 1.81-2.01 (m, 3H), 1.65-1.78 (m, 1H), 1.49-1.62 (m, 1H), 1.35-1.48 (m, 1H) |
| 99 | B | 365.1 | $^1$HNMR (400 MHz, DMSO-$d_6$): δ 7.73 (d, J = 8.0 Hz, 1H), 7.59 (s, 1H), 7.52 (d, J = 7.6 Hz, 1H), 6.65-6.80 (m, 2H), 3.96-4.12 (m, 1H), 2.82-2.86 (m, 1H), 2.52-2.58 (m, 4H), 2.17 (s, 6H), 1.95-2.05 (m, 1H), 1.78-1.94 (m, 2H), 1.65-1.75 (m, 1H), 1.47-1.60 (m, 1H), 1.24-1.36 (m, 1H) |
| 100 | B | 365.1 | $^1$HNMR (400 MHz, DMSO-$d_6$): δ 8.07 (s, 1H), 7.99 (d, J = 8.4 Hz, 1H), 7.81 (s, 1H), 7.74 (d, J = 8.0 Hz, 1H), 5.99 (brd, J = 7.6 Hz, 1H), 4.29-4.31 (m, 1H), 2.92-2.96 (m, 1H), 2.60-2.65 (m, 1H), 2.51-2.53 (m, 3H), 2.16-2.19 (m, 6H), 1.84-1.97 (m, 3H), 1.66-1.75 (m, 1H), 1.51-1.61 (m, 1H), 1.37-1.48 (m, 1H) |
| 101 | B | 367.2 | $^1$HNMR (400 MHz, DMSO-d6): δ 8.26 (d, J = 8.4 Hz, 2H), 7.76 (d, J = 8.0 Hz, 2H), 6.06 (brd, J = 7.6 Hz, 1H), 5.76 (s, 1H), 3.79 (s, 3H), 3.41-3.47 (m, 1H), 2.77-2.90. (m, 1H), 2.59-2.64 (m, 1H), 2.22 (s, 3H), 1.93-2.03 (m, 2H), 1.83-1.86 (m, 1H), 1.68-1.72 (m, 1H), 1.56-1.59 (m, 1H), 1.37-1.43 (m, 1H) |
| 102 | B | 367.2 | $^1$HNMR (400 MHz, $CDCl_3$-d6): δ 7.82 (d, J = 8.0 Hz, 2H), 7.61 (d, J = 8.4 Hz, 2H), 7.39-7.55 (m, 1H), 6.59 (s, 1H), 4.01-4.24 (m, 4H), 2.63-2.79 (m, 1H), 2.15-2.51 (m, 6H), 1.67-1.94 (m, 4H). |
| 103 | B | 362.3 | $^1$HNMR (400 MHz, DMSO-d6): δ 8.57 (s, 1H), 8.26 (d, J = 8.4 Hz, 2H), 7.87 (d, J = 8.4 Hz, 2H), 7.12-7.25 (m, 1H), 4.31-4.46 (m, 1H), 2.79-2.86 (m, 1H), 2.52-2.59 (m, 1H), 2.21 (s, 3H), 2.00-2.19 (m, 2H), 1.83 (m, 1H), 1.67-1.74 (m, 1H), 1.51-1.59 (m, 2H) |
| 104 | B | 299.3 | 1H NMR (400 MHz, DMSO-d6): δ 9.55 (brs, 1H), 7.31 (d, J = 8.4 Hz, 2H), 6.82 (d, J = 8.4 Hz, 2H), 6.68 (s, 1H), 6.51 (brd, J = 8.4 Hz, 1H), 3.99-4.08 (m, 1H), 2.84-2.94 (m, 1H), 2.59-2.63 (m, 1H), 2.19 (s, 3H), 2.17 (s, 3H), 1.95-2.03 (m, 1H), 1.78-1.85 (m, 2H), 1.62-1.70 (m, 1H), 1.48-1.58 (m, 1H), 1.18-1.28 (m, 1H). |

TABLE 2-continued

| Cmpd No | General Synthetic Route | LCMS [M + H]+ | Characterization |
|---|---|---|---|
| 105 | B | 385.2 | 1H NMR (400 MHz, DMSO-d6) δ 8.32 (s, 1H), 8.17 (d, J = 8.0 Hz, 1H), 7.85-7.98 (m, 2H), 6.10 (brd, J = 8.0 Hz, 1 H), 4.24-4.39 (m, 1H), 2.85-3.00 (m, 1H), 2.56-2.70 (m 1H), 2.14-2.23 (m, 6H), 1.82-1.99 (m, 3H), 1.65-1.76 (m, 1H), 1.50-1.62 (m, 1H), 1.35-1.48 (m, 1H) |
| 106 | B | 315.4 | $^1$HNMR (400 MHz, DMSO-d6): δ 7.68-7.75 (m, 3H), 6.89 (d, J = 9.2 Hz, 1H), 6.77 (brd, J = 8.0 Hz, 1 H), 4.06-4.08 (m, 1H), 2.84-2.86 (m, 1H), 2.52-2.57 (m, 1H), 2.28 (s, 6H), 2.17 (s, 3H), 1.97-2.02 (m, 1H), 1.82-1.91 (m, 2H), 1.68-1.72 (m, 1H), 1.53-1.56 (m, 1H), 1.24-1.31 (m, 1H) |
| 107 | B | 329.3 | $^1$HNMR (400 MHz, DMSO-d6): δ 7.68-7.73 (m, 3H), 5.82-5.86 (m, 1H), 4.27-4.28 (m, 1H), 3.00-3.02 (m, 1H), 2.60-2.67 (m, 1H), 2.28 (s, 6H), 2.25 (s, 3H), 2.15 (s, 3H), 2.02-2.07 (m, 1H), 1.95-2.01 (m, 1H), 1.87-1.89 (m, 1H), 1.71-1.72 (m, 1H), 1.52-1.60 (m, 1H), 1.44-1.46 (m, 1H) |
| 108 | B | 326.0 | $^1$HNMR (400 MHz, DMSO-d6): δ 8.09-8.10 (dd, J = 2.4, 6.4, 1H), 7.92-7.96 (m, 1H), 7.60-7.64 (m, 1H), 6.75-6.78 (m, 2H), 4.03-4.09 (m, 1H), 2.85-2.90 (m, 1H), 2.62-2.68 (m, 1H), 2.15-2.20 (m, 6H), 1.83-2.08 (m, 3H), 1.70-1.74 (m, 1H), 1.52-1.59 (m, 1H), 1.30-1.34 (m, 1H) |
| 109 | B | 326.4 | $^1$HNMR (400 MHz, DMSO-d6): δ 8.42-8.49 (m, 2H), 7.86 (s, 1H), 7.62-7.66 (m, 1H), 6.01 (d, J = 7.6 Hz, 1H), 4.27-4.35 (m, 1H), 2.93-2.95 (m, 1H), 2.62-2.68 (m, 1H), 2.16-2.20 (m, 6H), 1.87-1.97 (m, 3H), 1.69-1.74 (m, 1H), 1.55-1.58 (m, 1H), 1.40-1.44 (m, 1H) |
| 110 | B | 315.4 | $^1$HNMR (DMSO-d6): δ 7.15 (d, J = 9.2 Hz, 1H), 6.98 (d, J = 10.0 Hz, 2H), 6.90 (d, J = 9.2 Hz, 1H), 6.75 (d, J = 7.6 Hz, 1H), 4.02-4.09 (m, 1H), 2.83-2.86 (m, 1H), 2.54-2.69 (m, 1H), 2.18 (s, 3H), 1.93-1.99 (m, 8H), 1.82-1.85 (m, 1H), 1.70-1.72 (m, 1H), 1.53-1.56 (m, 1H), 1.32-1.50 (m, 1H) |
| 111 | B | 405.1 | $^1$HNMR (400 MHz, DMSO-d6): δ 7.86 (d, J = 8.4 Hz, 2H), 7.68 (d, J = 8.0 Hz, 2H), 7.47 (d, J = 8.0 Hz, 1H), 7.35 (s, 1H), 4.15-4.26 (m, 1H), 2.76-2.86 (m, 1H), 2.53-2.54 (m, 1H), 2.20 (s, 3H), 2.02-2.14 (m, 2H), 1.79-1.88 (m, 1H), 1.70-1.73 (m, 1H), 1.49-1.63 (m, 1H), 1.35-1.47 (m, 1H) |
| 112 | B | 315.1 | $^1$HNMR (400 MHz, DMSO-d6): δ 7.83-7.92 (m, 2H), 7.69 (s, 1H), 7.19-7.23 (m, 1H), 5.84 (d, J = 7.2 Hz, 1H), 4.23-4.29 (m, 1H), 2.93-2.95 (m, 1H), 2.61-2.63 (m, 1H), 2.30 (s, 3H), 2.16-2.19 (m, 6H), 1.86-1.95 (m, 3H), 1.69-1.72 (m, 1H), 1.55-1.57 (m, 1H), 1.40-1.45 (m, 1H) |
| 113 | B | 376.1 | $^1$HNMR (400 MHz, DMSO-d6): δ 8.73 (s, 1H), 8.56-8.58 (m, 1H), 8.10 (d, J = 8.4 Hz, 1H), 7.99 (s, 1H), 6.19 (d, J = 7.2 Hz, 1H), 4.29-4.37 (m, 1H), 2.95-2.99 (m, 1H), 2.54-2.65 (m, 1H), 2.22 (s, 3H), 2.19 (s, 3H), 1.98-2.04 (m, 3H), 1.90-1.91 (m, 1H), 1.71-1.88 (m, 1H), 1.46-1.56 (m, 1H) |
| 114 | C | 419.2 | 1HNMR (400 MHz, DMSO-d6) δ 7.57-7.95 (m, 4H), 6.62-6.90 (m, 2H), 3.97-4.14 (m, 1H), 3.09-3.28 (m, 3H), 2.75-2.90 (m, 1H), 2.34-2.45 (m, 1H), 2.10-2.30 (m, 4H), 1.83-1.99 (m, 1H), 1.47-1.76 (m, 2H), 1.16-1.39 (m, 1H) |
| 115 | C | 369.2 | 1HNMR (400 MHz, DMSO-d6) δ 7.48-7.62 (m, 2H), 7.27 (t, J = 9.2 Hz, 2H), 6.60-6.76 (m, 2H), 3.84-4.23 (m, 1H), 3.08-3.30 (m, 3H), 2.77-2.92 (m, 1H), 2.21-2.42 (m, 2H), 2.15 (s, 3H), 1.82-2.00 (m, 1H), 1.47-1.77 (m, 2H), 1.14-1.39 (m, 1H) |
| 116 | C | 351.1 | 1HNMR (400 MHz, DMSO-d6): δ 9.49-9.59 (m, 2H), 7.28 (t, J = 8.8 Hz, 2H), 6.57-6.75 (m, 2H), 5.95-6.32 (m, 1H), 4.00-4.01 (m, 1H), 3.03-3.11 (m, 1H), 2.70-2.84 (m, 3H), 2.19-2.28 (m, 1H), 2.08-2.17 (m, 4H), 1.83-1.92 (m, 1H), 1.65-1.76 (m, 1H), 1.45-1.61 (m, 1H), 1.23-1.33 (m, 1H) |
| 117 | B | 319.0 | $^1$HNMR (400 MHz, DMSO-d6): δ 8.02-8.06 (m, 1H), 7.78-7.86 (m, 1H), 7.78 (s, 1H), 7.51-7.54 (m, 1H), 5.94 (d, J = 8.0 Hz, 1H), 4.23-4.31 (m, 1H), 2.91-2.94 (m, 1H), 2.55-2.64 (m, 1H), 2.24 (s, 3H), 2.19 (s, 3H), 2.11-1.96 (m, 3H), 1.90-1.91 (m, 1H), 1.85-1.86 (m, 1H), 1.57-1.69 (m, 1H), 1.43-1.56 (m, 1H) |
| 118 | B | 351.2 | 1HNMR (400 MHz, DMSO-d6) δ 7.67-7.87 (m, 4H), 6.70-6.83 (m, 2H), 3.92-4.22 (m, 1H), 2.76-2.94 (m, 1H), 2.52-2.54 (m, 1H), 2.18 (s, 6H), 1.65-2.10 (m, 4H), 1.45-1.62 (m, 1H), 1.17-1.38 (m, 1H) |

TABLE 2-continued

| Cmpd No | General Synthetic Route | LCMS [M + H]+ | Characterization |
|---|---|---|---|
| 119 | C | 337.2 | 1HNMR (400 MHz, DMSO-d6) δ 7.50-7.59 (m, 2H), 7.28 (t, J = 8.8 Hz, 2H), 6.69-6.80 (m, 2H), 4.18-4.40 (m, 1H), 2.85-3.02 (m, 2H), 2.33-2.46 (m, 2H), 2.29 (s, 3H), 2.29 (s, 3H), 1.97-2.06 (m, 1H), 1.73-1.95 (m, 1H) |
| 120 | C | 327.2 | 1HNMR (400 MHz, DMSO-d6): δ 7.52-7.57 (m, 2H), 7.24-7.30 (m, 2H), 6.71 (s, 1H), 6.57 (d, J = 8.0 Hz, 1H), 3.89-4.00 (m, 1H), 3.01-3.12 (m, 1H), 2.71-2.80 (m, 1H), 2.19-2.28 (m, 1H), 2.14 (s, 3H), 2.07-2.12 (m, 1H), 1.81-1.90 (m, 1H), 1.59-1.69 (m, 2H), 1.41-1.52 (m, 1H), 1.26-1.36 (m, 1H), 0.30-0.43 (m, 4H) |
| 121 | D | 319.2 | 1HNMR (400 MHz, DMSO-d6): δ 7.51-7.58 (m, 2H), 7.24-7.32 (m, 2H), 6.82-6.86 (m, 2H), 4.91 (d, J = 50.8 Hz, 1H), 4.30-4.47 (m, 1H), 2.71-2.74 (m, 1H), 2.54-2.56 (m, 1H), 2.10-2.22 (m, 8H), 1.79-2.02 (m, 2H) |
| 122 | B | 315.2 | 1HNMR (400 MHz, MSO-d6) δ 8.22 (brs, 1H), 7.49-7.61 (m, 2H), 7.27 (t, J = 8.8 Hz, 2H), 6.71-6.77 (m, 1H), 6.67 (d, J = 8.0 Hz, 1H), 4.00-4.10 (m, 1H), 2.94-3.06 (m, 1H), 2.64-2.80 (m, 1H), 2.38-2.45 (m, 2H), 2.06-2.19 (m, 4H), 1.93-2.03 (m, 1H), 1.81-1.92 (m, 1H), 1.67-1.78 (m, 1H), 1.46-1.62 (m, 1H), 1.27-1.38 (m, 1H), 1.02 (t, J = 7.2 Hz, 3H). |
| 123 | B | 331.1 | $^1$HNMR (400 MHz, DMSO-d6): δ 7.42 (s, 1H), 7.32 (d, J = 8.0 Hz, 1H), 7.18 (d, J = 8.0 Hz, 1H), 6.74 (s, 1H), 6.63 (d, J = 8.0 Hz, 1H), 3.98-4.10 (m, 1H), 2.80-2.92 (m, 1H), 2.53-2.54 (m, 1H), 2.18 (s, 3H), 1.97-2.06 (m, 4H), 1.78-1.88 (m, 5H), 1.66-1.76 (m, 1H), 1.48-1.60 (m, 1H), 1.21-1.36 (m, 1H) |
| 124 | B | 331.1 | $^1$HNMR (400 MHz, DMSO-d6): δ 7.28-7.42 (m, 4H), 5.83 (brd, J = 7.6Hz, 1H), 4.23-4.35 (m, 1H), 2.91-2.95 (m, 1H), 2.57-2.66 (m, 1H), 2.32 (s, 3H), 2.20 (s, 3H), 2.14 (s, 3H), 1.84-2.00 (m, 3H), 1.66-1.76 (m, 1H), 1.51-1.62 (m, 1H), 1.37-1.48 (m, 1H) |
| 125 | B | 317.0 | $^1$HNMR (400 MHz, DMSO-$d_6$) δ 7.32-7.40 (m, 4H), 6.90 (d, J = 9.2 Hz, 1H), 6.82 (d, J = 8.0 Hz, 1H), 4.08-4.11 (m, 1H), 2.81-2.88 (m, 1H), 2.52-2.52 (m, 1H), 2.30 (s, 3H), 2.18 (s, 3H), 1.99-2.09 (m, 1H), 1.88-1.98 (m, 1H), 1.79-1.86 (m, 1H), 1.67-1.76 (m, 1H), 1.49-1.59 (m, 1H), 1.28-1.38 (m, 1H) |
| 126 | B | 287.1 | $^1$HNMR (DMSO-d6): δ 7.99-8.02 (m, 2H), 7.78 (d, J = 9.2 Hz, 1H), 7.27-7.32 (m, 2H), 6.92 (d, J = 9.2 Hz, 1H), 6.81 (d, J = 7.6 Hz, 1H), 4.06-4.13 (m, 1H), 2.81-2.88 (m, 1H), 2.52-2.54 (m, 1H), 2.18 (s, 3H), 1.98-2.09 (m, 1H), 1.81-1.85 (m, 2H), 1.70-1.72 (m, 1H), 1.52-1.56 (m, 1H), 1.23-1.32 (m, 1H) |
| 127 | B | 317.0 | $^1$HNMR (400 MHz, DMSO-d6): δ 7.50-7.55 (m, 4H), 6.66-6.72 (m, 2H), 4.03-4.08 (m, 1H), 2.88-2.81 (m, 1H), 2.55-2.60 (m, 1H), 2.15-2.20 (m, 6H), 1.97-2.02 (m, 1H), 1.81-1.89 (m, 2H), 1.68-1.69 (m, 1H), 1.52-1.55 (m, 1H), 1.30-1.32 (m, 1H) |
| 128 | B | 317.2 | $^1$HNMR (400 MHz, DMSO-d6): δ 8.01 (d, J = 8.4 Hz, 2H), 7.74 (s, 1H), 7.52 (d, J = 8.8 Hz, 2H), 5.91 (d, J = 8.0 Hz, 1H), 4.25-4.32 (m, 1H), 2.91-2.93 (m, 1H), 2.60-2.65 (m, 1H), 2.15-2.19 (m, 6H), 1.85-1.93 (m, 3H), 1.68-1.71 (m, 1H), 1.57-1.67 (m, 1H), 1.36-1.42 (m, 1H) |
| 129 | B | 303.2 | $^1$HNMR (400 MHz, DMSO-d6): δ 8.00 (d, J = 8.4 Hz, 2H), 7.81 (d, J = 8.6 Hz, 1H), 7.53 (d, J = 8.8 Hz, 2H), 6.90-6.95 (m, 2H), 4.01-4.11 (m, 1H), 2.84 (d, J = 1.6 Hz, 1H), 2.53-2.56 (m, 1H), 2.18 (s, 3H), 2.10-2.00 (m, 1H), 1.94 (s, 1H), 1.88-1.80 (m, 1H), 1.70 (d, J = 4.0Hz, 1H), 1.53-1.56 (m, 1H), 1.33 (s, 1H) |
| 130 | B | 355.1 | $^1$HNMR (400 MHz, DMSO-d6): δ 7.75-7.78 (m, 1H), 7.56-7.77 (m, 2H), 7.33 (d, J = 9.2 Hz, 1H), 6.89-6.97 (m, 2H), 3.93-2.91 (m, 1H), 2.78 (m, 1H), 2.54-2.56 (m, 1H), 2.19 (s, 3H), 1.89-2.09 (m, 2H), 1.68-1.87 (m, 2H), 1.53-1.56 (m, 1H), 1.22-1.39 (m, 1H) |
| 131 | B | 379.2 | 1HNMR (400 MHz, DMSO-d6) δ 8.15 (brs, 0.3H), 7.67-7.89 (m, 4H), 6.76-6.97 (m, 2H), 4.10-4.33 (m, 1H), 3.20-3.24 (m, 1H), 2.91-3.09 (m, 2H), 2.53-2.65 (m, 1H), 2.36-2.45 (m, 1H), 2.19 (s, 3H), 1.78-2.00 (m, 2H), 1.32-1.73 (m, 2H), 1.11 (d, J = 6.4 Hz, 6H). |

TABLE 2-continued

| Cmpd No | General Synthetic Route | LCMS [M + H]+ | Characterization |
|---|---|---|---|
| 132 | B | 315.1 | $^1$HNMR (400 MHz, DMSO-d6): δ 7.14-7.24 (m, 2H), 7.06-7.11 (m, 1H), 6.73 (s, 1H), 6.63 (d, J = 8.0 Hz, 1H), 4.01-4.07 (m, 1H), 2.79-2.94 (m, 1H), 2.51-2.58 (m, 1H), 2.19 (s, 3H), 1.98-2.07 (m, 4H), 1.81-1.94 (m, 5H), 1.67-1.76 (m, 1H), 1.49-1.62 (m, 1H), 1.25-1.35 (m, 1H) |
| 133 | B | 315.2 | $^1$HNMR (400 MHz, DMSO-d6): δ 7.37 (dd, J = 8.4, 6.2 Hz, 1H), 7.29 (s, 1H), 7.06-7.23 (m, 2H), 5.82 (brd, J = 7.6 Hz, 1H), 4.22-4.33 (m, 1H), 2.88-2.95 (m, 1H), 2.61-2.66 (m, 1H), 2.31 (s, 3H), 2.20 (s, 3H), 2.14 (s, 3H), 1.85-2.01 (m, 3H), 1.67-1.76 (m, 1H), 1.63-1.51 (m, 1H), 1.38-1.48 (m, 1H) |
| 134 | B | 301.1 | $^1$HNMR (400 MHz, DMSO-d6): δ 7.34-7.38 (m, 2H), 7.08-7.25 (m, 2H), 6.87-6.92 (m, 1H), 6.78 (brd, J = 7.6 Hz, 1H), 3.99-4.15 (m, 1H), 2.92-2.81 (m, 1H), 2.53-2.54 (m, 1H), 2.30 (s, 3H), 2.18 (s, 3H), 2.00-2.09 (m, 1H), 1.87-1.97 (m, 1H), 1.78-1.87 (m, 1H), 1.68-1.76 (m, 1H), 1.49-1.62 (m, 1H), 1.26-1.37 (m, 1H) |
| 135 | B | 329.2 | 1HNMR (400 MHz, DMSO-d6): δ 7.50-7.59 (m, 2H), 7.27 (t, J = 8.8 Hz, 2H), 6.71 (s, 1H), 6.57 (brd, J = 8.0 Hz, 1H), 3.92-4.07 (m, 1H), 2.87-2.99 (m, 1H), 2.68-2.78 (m, 1H), 2.59-2.66 (m, 1H), 2.12-2.22 (m, 4H), 2.00-2.08 (m, 1H), 1.80-1.90 (m, 1H), 1.64-1.74 (m, 1H), 1.44-1.55 (m, 1H), 1.23-1.34 (m, 1H), 0.93-0.99 (m, 6H) |
| 136 | D | 369.0 | 1H NMR (400 MHz, DMSO-d6): δ 8.13 (s, 1H), 7.80-7.85 (m, 2H), 7.73-7.78 (m, 2H), 7.04 (d, J = 8.0 Hz, 1H), 6.83 (s, 1H), 6.53 (s, 1H), 4.47-4.67 (m, 1H), 4.27-4.36 (m, 1H), 2.84-2.93 (m, 1H), 2.55-2.66 (m, 1H), 2.17-2.24 (m, 7H), 2.04-2.13 (m, 2H), 1.74-1.82 (m, 1H). |
| 137 | D | 369.0 | 1H NMR (400 MHz, DMSO-d6): δ 8.13 (s, 1H), 7.69-7.87 (m, 4H), 6.73-6.86 (m, 2H), 4.62 -4.85 (m, 1H), 4.08-4.20 (m, 1H), 2.88-3.02 (m, 2H), 2.25-2.35 (m, 4H), 2.19 (s, 3H), 2.04-2.14 (m, 1H), 1.83-1.95 (m, 1H), 1.44-1.57 (m, 1H) |
| 138 | D | 319.1 | 1H NMR (400 MHz, DMSO-d6): δ 7.52-7.57 (m, 2H), 7.24-7.31 (m, 2H), 6.90 (d, J = 8.0 Hz, 1H), 6.80 (s, 1H), 4.46-4.67 (m, 1H), 4.22-4.35 (m, 1H), 2.82-2.90 (m, 1H), 2.56-2.60 (m, 2H), 2.14-2.22 (m, 7H), 2.01-2.10 (m, 2H), 1.72-1.83 (m, 1H) |
| 139 | D | 319.0 | 1H NMR (400 MHz, DMSO-d6): δ 7.48-7.63 (m, 2H), 7.22-7.32 (m, 2H), 6.66-6.76 (m, 2H), 4.60-4.83 (m, 1H), 4.06-4.17 (m, 1H), 2.85-3.01 (m, 2H), 2.22-2.36 (m, 4H), 2.15 (s, 3H), 2.02-2.10 (m, 1H), 1.79-1.89 (m, 1H), 1.42-1.55 (m, 1H) |
| 140 | D | 319.2 | 1H NMR (400 MHz, DMSO-d6) δ 7.50-7.65 (m, 2H), 7.27 (t, J = 9.2 Hz, 2H), 6.61-6.79 (m, 2H), 4.73-5.07 (m, 1H), 4.25-4.45 (m, 1H), 2.70-2.94 (m, 2H), 2.01-2.29 (m, 8H), 1.88-2.00 (m, 1H), 1.52-1.77 (m, 1H). |
| 141 | B | 365.2 | 1H NMR (400 MHz, DMSO-d6): δ 8.18 (s, 1H), 7.60 (s, 1H), 7.42-7.47 (m, 2H), 6.89-6.95 (m, 2H), 4.08-4.17 (m, 1H), 2.87-2.93 (m, 1H), 2.55-2.60 (m, 1H), 2.45 (s, 3H), 2.34 (s, 3H), 2.22 (s, 3H), 2.07-2.15 (m, 1H), 1.96-2.03 (m, 1H), 1.82-1.88 (m, 1H), 1.71-1.77 (m, 1H), 1.54-1.61 (m, 1H), 1.30-1.41 (m, 1H) |
| 142 | E | 365.2 | $^1$HNMR (400 MHz, DMSO-d6) δ 7.76-7.87 (m, 4H), 7.03 (s, 1H), 4.61-4.72 (m, 1H), 2.98 (s, 3H), 2.72-2.75 (m, 2H), 2.27 (s, 3H), 2.20 (s, 3H), 2.01-2.11 (m, 1H), 1.81-1.89 (m, 1H), 1.74-1.69 (m, 2H), 1.55-1.66 (m, 2H) |
| 143 | B | 355.2 | 1H NMR (400 MHz, DMSO-d6) δ 8.02 (d, J = 8.0 Hz, 2H), 7.86 (d, J = 8.0 Hz, 2H), 7.32 (d, J = 7.6 Hz, 1H), 6.83 (brd, J = 14.0 Hz, 1H), 4.04-4.25 (m, 1H), 2.70-2.95 (m, 1H), 2.54-2.62 (m, 1H, overlap with DMSO-$d_6$ signal), 2.20 (s, 3H), 1.99-2.15 (m, 2H), 1.77-1.86 (m, 1H), 1.66-1.75 (m, 1H), 1.50-1.60 (m, 1H), 1.31-1.43 (m, 1H). |
| 144 | D | 397.3 | 1H NMR (400 MHz, DMSO-d6) δ 7.81 (d, J = 8.0 Hz, 2H), 7.75 (d, J = 8.0 Hz, 2H), 6.70-6.78 (m, 2H), 4.77-5.05 (m, 1H), 4.16-3.38 (m, 1H), 2.88-2.97 (m, 1H), 2.71-2.85 (m, 2H), 2.43-2.46 (m, 1H, overlap with DMSO-$d_6$ signal), 2.18 (s, 3H), 2.02-2.16 (m, 2H), 1.59-1.81 (m, 1H), 0.89-1.01 (m, 6H). |

TABLE 2-continued

| Cmpd No | General Synthetic Route | LCMS [M + H]+ | Characterization |
|---|---|---|---|
| 145 | B | 335.0 | 1H NMR (400 MHz, DMSO-d6) δ 7.63-7.69 (m, 1H), 7.56-7.60 (m, 1H), 7.37-7.42 (m, 1H), 6.75 (brd, J = 8.0 Hz, 1H), 6.73 (s, 1H), 3.98-4.12 (m, 1H), 2.80-2.88 (m, 1H), 2.52-2.58 (m, 1H), 2.15-2.19 (m, 6H), 1.96-2.05 (m, 1H), 1.78-1.94 (m, 2H), 1.66-1.74 (m, 1H), 1.48-1.59 (m, 1H), 1.34 - 1.23 (m, 1H) |
| 146 | D | 383.2 | 1H NMR (400 MHz, DMSO-d6) δ 7.72-7.85 (m, 4H), 6.80 (d, J = 8.0 Hz, 1H), 6.7 (s, 1H), 4.82-5.04 (m, 1H), 4.29-4.42 (m, 1H), 2.92-3.02 (m, 1H), 2.79-2.91 (m, 1H), 2.38-2.45 (m, 2H, overlap with DMSO-$d_6$ signal), 2.26-2.37 (m, 1H), 2.18 (s, 3H), 2.05-2.14 (m, 1H), 1.90-2.04 (m, 1H), 1.58-1.78 (m, 1H), 1.00 (t, J = 7.2 Hz, 3H). |
| 147 | B | 335.0 | 1H NMR (400 MHz, DMSO-d6) δ 8.01 (d, J = 11.2 Hz, 1H), 7.89 (d, J = 7.6 Hz, 1H), 7.81 (s, 1H), 7.65-7.71 (m, 1H), 6.00 (brd, J = 7.6 Hz, 1H), 4.24-4.35 (m, 1H), 2.89-2.98 (m, 1H), 2.59-2.68 (m, 1H), 2.15-2.20 (m, 6H), 1.85-1.96 (m, 3H), 1.66 -1.73 (m, 1H), 1.53-1.61 (m, 1H), 1.38-1.47 (m, 1H) |
| 148 | B | 355.1 | 1H NMR (400 MHz, DMSO-d6): δ 8.10-8.18 (m, 3H), 7.34 (t, J = 8.8 Hz, 2H), 6.16 (d, J = 7.6 Hz, 1H), 4.47-4.56 (m, 1H), 2.64-2.72 (m, 1H), 2.54-2.56 (m, 1H), 2.36-2.43 (m, 1H), 2.28-2.34 (m, 1H), 2.21 (s, 3H), 1.62-1.74 (m, 3H), 1.50-1.60 (m, 1H) |
| 149 | B | 335.1 | 1H NMR (400 MHz, DMSO-d6): δ 7.89 (t, J = 8.4 Hz, 1H), 7.50-7.58 (m, 1H), 7.49 (s, 1H), 7.42 (dd, J = 8.4, 1.6 Hz, 1H), 5.99 (d, J = 8.0 Hz, 1H), 4.24-4.37 (m, 1H), 2.89-2.97 (m, 1H), 2.58-2.70 (m, 1H), 2.20 (s, 3H), 2.15 (s, 3H), 1.84-1.98 (m, 3H), 1.66-1.77 (m, 1H), 1.51-1.61 (m, 1H), 1.36-1.49 m (m, 1H) |
| 150 | D | 333.1 | 1H NMR (400 MHz, DMSO-d6) δ 7.43-7.64 (m, 2H), 7.28 (t, J = 7.2 Hz, 2H), 6.59-6.83 (m, 2H), 4.76-5.10 (m, 1H), 4.27-4.41 (m, 1H), 2.76-3.03 (m, 2H), 2.37-2.45 (m, 2H, overlap with DMSO-$d_6$ signal), 2.23-2.36 (m, 1H), 2.04-2.18 (m, 4H), 1.88-2.02 (m, 1H), 1.54-1.80 (m, 1H), 1.00 (t, J = 7.2 Hz, 3H). |
| 151 | D | 349.2 | 1H NMR (400 MHz, DMSO-d6): δ 7.49-7.56 (m, 4H), 6.70-6.75 (m, 2H), 4.92 (d, J = 49.2 Hz, 1H), 4.25-4.39 (m, 1H), 2.80-3.02 (m, 2H), 2.37-2.45 (m, 2H), 2.22-2.34 (m, 1H), 2.16 (s, 3H), 2.04-2.13 (m, 1H), 1.92-2.02 (m, 1H), 1.57-1.77 (m, 1H), 1.00 (t, J = 7.2 Hz, 3H). |
| 152 | D | 363.1 | 1H NMR (400 MHz, DMSO-d6): δ 7.41-7.69 (m 4H), 6.55-6.85 (m, 2H), 4.90 (d, J = 48.4 Hz, 1H), 4.26-4.45 (m, 1H), 2.70-3.03 (m, 3H), 2.00-2.20 (m, 5H), 1.51-1.85 (m, 2H), 0.85-1.11 (m, 6H). |
| 153 | B | 335.3 | 1H NMR (400 MHz, DMSO-d6): δ 7.57 (dd, J = 9.6, 1.6 Hz, 1H), 7.38-7.51 (m, 2H), 6.69-6.87 (m, 2H), 3.99-4.14 (m, 1H), 2.82-2.91 (m, 1H), 2.50-2.60 (m, 1H), 2.19 (s, 3H), 1.95-2.05 (m, 4H), 1.79-1.95 (m, 2H), 1.67-1.76 (m, 1H), 1.47-1.63 (m, 1H), 1.22-1.38 (m, 1H) |
| 154 | B | 319.2 | 1H NMR (400 MHz, DMSO-d6) δ 8.16 (brs, 1H), 7.31-7.36 (m, 1H), 7.11-7.24 (m, 3H), 6.79 (d, J = 12.8 Hz, 1H), 4.10-4.17 (m, 1H), 2.90-2.99 (m, 1H), 2.59-2.68 (m, 1H), 2.13-2.45 (m, 8H), 1.72-1.88 (m, 2H), 1.53-1.62 (m, 1H), 1.33-1.42 (m, 1H). |
| 155 | B | 331.1 | 1H NMR (400 MHz, DMSO-d6) δ 7.47-7.56 (m, 4H), 6.71 (s, 1H), 6.66 (d, J = 8.0 Hz, 1H), 3.96-4.08 (m, 1H), 2.89-3.03 (m, 1H), 2.60-2.72 (m, 1H), 2.33 (q, J = 7.2 Hz, 2H), 2.15 (s, 3H), 1.93-2.03 (m, 1H), 1.81-1.92 (m, 2H), 1.65-1.74 (m, 1H), 1.46-1.58 (m, 1H), 1.23-1.35 (m, 1H), 0.99 (t, J = 6.8 Hz, 3H). |
| 156 | B | 345.3 | 1H NMR (400 MHz, DMSO-d6) δ 7.48-7.56 (m, 4H), 6.71 (s, 1H), 6.62 (t, J = 8.0 Hz, 1H), 3.92-4.07 (m, 1H), 2.87-2.96 (m, 1H), 2.68-2.76 (m, 1H), 2.58-2.66 (m, 1H), 2.17-2.22 (m, 1H), 2.19 (s, 1H), 2.15 (s, 3H), 2.00-2.18 (m, 1H), 1.79-1.90 (m, 1H), 1.64-1.73 (m, 1H), 1.44-1.56 (m, 1H), 1.24-1.35 (m, 1H), 0.92-0.99 (m, 6H). |
| 157 | B | 333.1 | 1H NMR (400 MHz, DMSO-d6) δ 8.18 (s, 1H), 7.63-7.68 (m, 4H), 6.92-7.30 (m, 1H), 6.67-6.85 (m, 2H), 4.00-4.15 (m, 1H), 2.86-2.99 (m, 1H), 2.24 (s, 3H), 1.93-2.19 (m, 6H), 1.79-1.88 (m, 1H), 1.68-1.77 (m, 1H), 1.47-1.63 (m, 1H), 1.25-1.37 (m, 1H). |

TABLE 2-continued

| Cmpd No | General Synthetic Route | LCMS [M + H]+ | Characterization |
|---|---|---|---|
| 158 | B | 367.1 | 1H NMR (400 MHz, DMSO-d6): δ 12.52 (brs, 1H), 7.78 (d, J = 8.8 Hz, 1H), 7.63-7.73 (m, 1H), 7.53-7.62 (m, 1H), 6.21-6.36 (m, 1H), 5.89-6.04 (m, 1H), 3.75-3.89 (m, 1H), 2.62-2.72 (m, 1H), 2.29-2.40 (m, 4H), 2.11-2.24 (m, 5H), 1.47-1.71 (m, 4H). |
| 159 | B | 333.1 | 1H NMR (400 MHz, DMSO-d6) δ 7.68-7.79 (d, J = 6.4 Hz, 1H), 7.52-7.66 (m, 2H), 7.32-7.44 (d, J = 6.4 Hz, 1H), 6.53-6.92 (m, 3H), 3.91-4.21 (m, 1H), 2.81-2.94 (m, 1H), 2.55-2.62 (m, 1H, overlap with DMSO-$d_6$ signal), 2.19 (s, 3H), 1.79-2.08 (m, 6H), 1.64-1.77 (m, 1H), 1.46-1.62 (m, 1H), 1.25-1.35 (m, 1H). |
| 160 | B | 333.1 | 1H NMR (400 MHz, DMSO-d6) δ 7.78 (d, J = 7.6 Hz, 1H), 7.16-7.69 (m, 5H), 5.96 (d, J = 8.0 Hz, 1H). 4.17-4.42 (m, 1H), 2.91-2.99 (m, 1H), 2.61-2.69 (m, 1H), 2.13-2.25 (m, 6H), 1.83-2.06 (m, 3H), 1.69-1.79 (m, 1H), 1.37-1.64 (m, 2H). |
| 161 | B | 365.1 | 1H NMR (400 MHz, DMSO-d6): δ 8.28 (s, 0.1H), 7.60 (d, J = 8.0 Hz, 1H), 7.32-7.37 (m, 2H), 6.93 (d, J = 9.6 Hz, 1H), 6.87 (d, J = 7.6 Hz, 1H), 4.06-4.15 (m, 1H), 2.81-2.89 (m, 1H), 2.54-2.59 (m, 1H), 2.40 (s, 3H), 2.22 (s, 3H), 2.19 (s, 3H), 2.00-2.08 (m, 1H), 1.91-1.99 (m, 1H), 1.81-1.88 (m, 1H), 1.68-1.76 (m, 1H), 1.50-1.59 (m, 1H), 1.28-1.38 (m, 1H) |
| 162 | B | 330.9 | 1H NMR (400 MHz, DMSO-d6): δ 7.45-7.50 (m, 2H), 7.32-7.36 (m, 1H), 6.71 (s, 1H), 6.65 (d, J = 8.0 Hz, 1H), 3.99-4.07 (m, 1H), 2.81-2.87 (m, 1H), 2.52-2.58 (m, 1H), 2.38 (s, 3H), 2.17 (s, 3H), 2.15 (s, 3H), 1.96-2.03 (m, 1H), 1.80-1.91 (m, 2H), 1.67-1.73 (m, 1H), 1.49-1.58 (m, 1H), 1.23-1.34 (m, 1H) |
| 163 | B | 331.1 | 1H NMR (400 MHz, DMSO-d6): δ 7.99 (d, J = 1.6 Hz, 1H), 7.83 (dd, J = 8.4, 2.0 Hz, 1H), 7.73 (s, 1H), 7.48 (d, J = 8.4 Hz, 1H), 5.89 (d, J = 8.0 Hz, 1H), 4.23-4.33 (m, 1H), 2.92-2.98 (m, 1H), 2.61-2.67 (m, 1H), 2.40 (s, 3H), 2.20 (s, 3H), 2.16 (s, 3H), 1.85-1.99 (m, 3H), 1.67-1.73 (m, 1H), 1.50-1.62 (m, 1H), 1.37-1.48 (m, 1H) |
| 164 | B | 331.0 | 1H NMR (400 MHz, DMSO-d6): δ 7.11 (d, J = 9.2 Hz, 1H), 6.81-6.89 (m, 2H), 6.75 (dd, J = 9.6, 2.0 Hz, 1H), 6.69 (d, J = 8.0 Hz, 1H), 4.00-4.11 (m, 1H), 3.68 (s, 3H), 2.83-2.90 (m, 1H), 2.54-2.56 (m, 1H), 2.19 (s, 3H), 2.04 (s, 4H), 1.89-1.97 (m, 1H), 1.80-1.88 (m, 1H), 1.67-1.76 (m, 1H), 1.51-1.60 (m, 1H), 1.27-1.36 (m, 1H) |
| 165 | B | 401.1 | 1H NMR (400 MHz, DMSO-d6) δ 7.98-8.05 (m, 2H), 7.69 (d, J = 8.4 Hz, 1H), 6.73-7.07 (m, 3H), 4.02-4.08 (m, 1H), 2.82-2.92 (m, 1H), 2.45-2.47 (m, 2H, overlap with DMSO-$d_6$ signal), 2.16-2.28 (m, 3H), 1.92-2.07 (m, 4H), 1.67-1.91 (m, 2H), 1.50-1.62 (m, 1H), 1.23-1.39 (m, 1H). |
| 166 | B | 401.1 | 1H NMR (400 MHz, DMSO-d6) δ 7.99-8.08 (m, 2H), 7.85 (d, J = 8.4 Hz, 1H), 7.28-7.57 (m, 2H), 6.19 (brs, 1H), 4.32-4.43 (m, 1H), 2.55-2.59 (m, 2H, overlap with DMSO-$d_6$ signal), 2.43-2.46 (m, 3H, overlap with DMSO-$d_6$ signal), 2.12-2.23 (m, 4H), 1.75-1.93 (m, 2H), 1.45-1.65 (m, 2H). |
| 167 | E | 379.1 | 1H NMR (400 MHz, DMSO-d6) δ 8.16 (brs, 1H), 7.76-7.85 (m, 4H), 6.97 (s, 1H), 4.60-4.72 (m, 1H), 3.47-3.76 (m, 2H, overlap with $H_2O$ signal), 2.73-2.82 (m, 2H), 2.26 (s, 3H), 2.22 (s, 3H), 2.01-2.08 (m, 1H), 1.84-1.90 (m, 1H), 1.71-1.78 (m, 2H), 1.54-1.65 (m, 2H), 1.14 (t, J = 6.8 Hz, 3H). |
| 168 | B | 342.1 | 1H NMR (400 MHz, DMSO-d6) δ 8.16 (d, J = 2.4 Hz, 1H), 7.86 (dd, J = 8.0, 2.4 Hz, 1H), 7.64 (d, J = 8.4 Hz, 1H), 6.89 (d, J = 8.0 Hz, 1H), 6.79 (s, 1H), 4.01-4.12 (m, 1H), 2.80-2.87 (m, 1H), 2.53-2.58 (m, 1H), 2.18 (s, 3H), 2.05 (s, 3H), 1.97-2.02 (m, 1H), 1.88-1.95 (m, 1H), 1.80-1.86 (m, 1H), 1.67-1.74 (m, 1H), 1.49-1.60 (m, 1H), 1.27-1.35 (m, 1H) |
| 169 | B | 385.1 | 1H NMR (400 MHz, DMSO-d6): δ 7.95 (d, J = 2.0 Hz, 1H), 7.85 (dd, J = 8.0, 2.0 Hz, 1H), 7.50 (d, J = 8.0 Hz, 1H), 6.72-6.77 (m, 2H), 4.03 (s, 1H), 2.80-2.88 (m, 1H), 2.51-2.54 (m, 1H), 2.18 (s, 3H), 1.96-2.05 (m, 1H), 1.87 (s, 3H), 1.76-1.85 (m, 2H), 1.67-1.73 (m, 1H), 1.47-1.59 (m, 1H), 1.17-1.36 (m, 1H). |

TABLE 2-continued

| Cmpd No | General Synthetic Route | LCMS [M + H]+ | Characterization |
|---|---|---|---|
| 170 | B | 385.0 | 1H NMR (400 MHz, DMSO-d6): δ 7.95 (s, 1H), 7.85 (d, J = 8.4 Hz, 1H), 7.57 (d, J = 8.0 Hz, 1H), 7.26 (s, 1H), 5.94 (d, J = 8.0 Hz, 1H), 4.21-4.34 (m, 1H), 2.87-2.97 (m, 1H), 2.51-2.58 (m, 1H), 2.20 (s, 3H), 2.14 (s, 3H), 1.85-1.98 (m, 3H), 1.67-1.76 (m, 1H), 1.51-1.63 (m, 1H), 1.38-1.49 (m, 1H). |
| 171 | B | 351.0 | 1H NMR (400 MHz, DMSO-d6): δ 8.20 (d, J = 1.2 Hz, 1H), 7.76 (d, J = 2.0 Hz, 1H), 7.53-7.56 (m, 1H), 7.42 (d, J = 8.0 Hz, 1H), 6.74-6.78 (m, 2H), 4.03-4.08 (m, 1H), 2.85-2.91 (m, 1H), 2.54-2.60 (m, 1H), 2.20 (s, 3H), 2.04 (s, 2H), 1.93 (s, 3H), 1..82-1.87 (m, 1H), 1.69-1.75 (m, 1H), 1.52-1.59 (m, H), 1.28-1.35 (m, 1H) |
| 172 | B | 381.1 | 1H NMR (400 MHz, DMSO-d6): δ 7.60 (s, 1H), 7.55 (d, J = 8.0 Hz, 1H), 7.41 (d, J = 8.0 Hz, 1H), 6.00 (d, J = 8.0 Hz, 1H), 5.70 (s, 1H), 3.72 (s, 3H), 3.44-3.49 (m, 1H), 2.79-2.85 (m, 1H), 2.58-2.62 (m, 1H), 2.26 (s, 3H), 2.21 (s, 3H), 1.92-2.02 (m, 2H), 1.83-1.88 (m, 1H), 1.66-1.73 (m, 1H), 1.53-1.61 (m, 1H), 1.35-1.43 (m, 1H). |
| 173 | B | 342.0 | 1H NMR (400 MHz, $CDCl_3$): δ 7.95 (d, J = 8.8 Hz, 1H), 7.74 (d, J = 2.0 Hz, 1H), 7.65 (dd, J = 8.4, 2.0 Hz, 1H), 7.55 (d, J = 0.8 Hz, 1H), 5.11-5.26 (m, 1H), 4.59-4.67 (m, 1H), 2.58-2.70 (m, 2H), 2.48-2.56 (m, 1H), 2.29 (s, 3H), 2.22-2.24 (m, 3H), 2.11-2.19 (m, 1H), 1.86-1.96 (m, 1H), 1.73-1.80 (m, 1H), 1.61-1.64 (m, 1H), 1.25-1.36 (m, 1H) |
| 174 | B | 367.1 | 1H NMR (400 MHz, DMSO-d6): δ 7.76 (d, J = 2.0 Hz, 1H), 7.70 (d, J = 8.0 Hz, 1H), 7.46 (d, J = 8.0 Hz, 1H), 6.64-6.92 (m, 3H), 4.00-4.10 (m, 1H), 2.80-2.90 (m, 1H), 2.54-2.59 (m, 1H), 2.17 (s, 3H), 1.97-2.03 (m, 1H), 1.94 (s, 3H), 1.80-1.91 (m, 2H), 1.67-1.74 (m, 1H), 1.49-1.58 (m, 1H), 1.24-1.34 (m, 1H). |
| 175 | B | 367.1 | 1H NMR (400 MHz, DMSO-d6): δ 7.67-7.79 (m, 2H), 7.62 (d, J = 8.4 Hz, 1H), 7.20-7.48 (m, 2H), 6.01 (d, J = 7.6 Hz, 1H), 4.21-4.37 (m, 1H), 2.87-2.99 (m, 1H), 2.57-2.63 (m, 1H), 2.19 (s, 3H), 2.16 (s, 3H), 1.84-1.98 (m, 3H), 1.66-1.74 (m, 1H), 1.51-1.61 (m, 1H), 1.38-1.48 (m, 1H) |
| 176 | B | 365.2 | 1H NMR (400 MHz, DMSO-d6): δ 8.22 (s, 1H), 7.82 (d, J = 8.4 Hz, 2H), 7.76 (d, J = 8.4 Hz, 2H), 6.73-6.78 (m, 2H), 4.16-4.25 (m, 1H), 2.82 (dd, J = 13.2, 3.6 Hz, 1H), 2.55-2.62 (m, 3H), 2.35 (s, 3H), 2.18 (s, 3H), 1.84-1.92 (m, 1H), 1.51-1.71 (m, 5H). |
| 177 | F | 352.2 | 1H NMR (400 MHz, DMSO-d6): δ 8.17 (s, 1H), 7.80-7.90 (m, 4H), 7.19 (s, 1H), 5.22-5.34 (m, 1H), 2.89-2.95 (m, 1H), 2.21-2.28 (m, 4H), 2.18 -2.21 (m, 4H), 1.98-2.14 (m, 3H), 1.72-1.79 (m, 1H), 1.46-1.62 (m, 2H). |
| 178 | F | 352.2 | 1H NMR (400 MHz, DMSO-d6): δ 8.28 (d, J = 8.0 Hz, 2H), 8.16-8.20 (m, 2H), 7.89 (d, J = 8.4 Hz, 2H), 5.30-5.36 (m, 1H), 2.95-2.99 (m, 1H), 2.21-2.29 (m, 8H), 2.02-2.16 (m, 2H), 1.74-1.83 (m, 1H), 1.47-1.65 (m, 2H). |
| 179 | F | 302.2 | 1H NMR (400 MHz, DMSO-d6): δ 7.59-7.63 (m, 2H), 7.30-7.35 (m, 2H), 7.14 (s, 1H), 5.23-5.28 (m, 1H), 2.90-3.00 (m, 1H), 2.01-2.25 (m, 10H), 1.73-1.75 (m, 1H), 1.40-1.64 (m, 2H). |
| 180 | F | 302.2 | 1H NMR (400 MHz, DMSO-d6): δ 8.16 (brs, 0.8H), 8.04-8.13 (m, 3H), 7.33-7.38 (m, 2H), 5.24-5.36 (m, 1H), 2.95-2.98 (m, 1H), 2.00-2.31 (m, 10H), 1.71-1.83 (m, 1H), 1.45-1.64 (m, 2H). |
| 181 | F | 332.2 | 1H NMR (400 MHz, DMSO-d6): δ 7.46 (d, J = 1.6 Hz, 1H), 7.36 (dd, J = 8.4, 2.4 Hz, 1H), 7.24 (d, J = 8.0 Hz, 1H), 7.15 (s, 1H), 5.22-5.29 (m, 1H), 2.91-2.94 (m, 1H), 2.53-2.55 (m, 1H), 2.16-2.23 (m, 4H), 1.98-2.11 (m, 8H), 1.73-1.77 (m, 1H), 1.44-1.61 (m, 2H). |
| 182 | B | 337.1 | 1H NMR (400 MHz, DMSO-d6) δ 7.80-7.84 (m, 2H), 7.74-7.78 (m, 2H), 7.08 (brd, J = 6.8 Hz, 1H), 6.72 (s, 1H), 4.38-4.49 (m, 1H), 2.72-2.78 (m, 1H), 2.64-2.69 (m, 1H), 2.58-2.64 (m, 2H), 2.30-2.36 (m, 1H), 2.27 (s, 3H), 2.19 (s, 3H), 1.60-1.72 (m, 1H). |

TABLE 2-continued

| Cmpd No | General Synthetic Route | LCMS [M + H]+ | Characterization |
|---|---|---|---|
| 183 | B | 287.2 | 1H NMR (400 MHz, DMSO-d6): δ 7.52-7.57 (m, 2H), 7.24-7.30 (m, 2H), 6.96 (brd, J = 6.4 Hz, 1H), 6.68 (s, 1H), 4.35-4.46 (m, 1H), 2.70-2.77 (m, 1H), 2.57-2.64 (m, 1H), 2.33-2.42 (m, 2H), 2.20-2.28 (m, 4H), 2.14 (s, 3H), 1.58-1.69 (m, 1H). |
| 184 | E | 301.2 | 1H NMR (400 MHz, DMSO-d6): δ 7.54-7.59 (m, 2H), 7.26-7.31 (m, 2H), 7.02 (s, 1H), 5.23-5.40 (m, 1H), 3.01 (s, 3H), 2.75-2.87 (m, 1H), 2.65-2.73 (m, 1H), 2.15-2.28 (m, 9H), 1.68-1.81 (m, 1H). |
| 185 | E | 351.2 | 1H NMR (400 MHz, DMSO-d6): δ 7.72-7.88 (m, 4H), 7.06 (s, 1H), 5.25-5.47 (m, 1H), 3.03 (s, 3H), 2.59-2.75 (m, 2H), 2.35-2.50 (m, 4H), 2.18-2.33 (m, 5H), 1.75-1.85 (m, 1H). |
| 186 | B | 337.1 | $^1$HNMR (400 MHz, DMSO-$d_6$) δ 7.80-7.84 (m, 2H), 7.74-7.78 (m, 2H), 7.08 (brd, J = 6.8 Hz, 1H), 6.72 (s, 1H), 4.38-4.49 (m, 1H), 2.72-2.78 (m, 1H), 2.64-2.69 (m, 1H), 2.58-2.64 (m, 2H), 2.30-2.36 (m, 1H), 2.27 (s, 3H), 2.19 (s, 3H), 1.60-1.72 (m, 1H). |
| 187 | B | 316.9 | $^1$H NMR (400 MHz, DMSO-$d_6$): δ 7.41 (s, 1H), 7.31 (dd, J = 8.0, 2.0 Hz, 1H), 7.18 (d, J = 8.4 Hz, 1H), 6.94 (d, J = 7.2 Hz, 1H), 6.70 (s, 1H), 4.37-4.46 (m, 1H), 2.74-2.80 (m, 1H), 2.61-2.67 (m, 1H), 2.40-2.44 (m, 2H), 2.22-2.29 (m, 4H), 2.02 (s, 3H), 1.88 (s, 3H), 1.62-1.69 (m, 1H). |
| 188 | B | 354.3 | $^1$H NMR (400 MHz, CDCl3): δ 7.63-7.74 (m, 4H), 6.56 (s, 1H), 5.22 (brs, 1H), 4.04-4.21 (s, 1H), 2.27-2.73 (m, 4H), 2.26 (s, 3H), 1.68-1.90 (m, 4H, overlap with H2O signal). |
| 189 | B | 333.2 | 1H NMR (400 MHz, DMSO-d6) δ 7.47-7.56 (m, 3H), 7.25 (d, J = 9.2 Hz, 1H), 6.87-6.94 (m, 2H), 6.64 (t, J = 55.2 Hz, 1H), 4.07-4.11 (m, 1H), 2.84-2.88 (m, 1H), 2.50-2.55 (m, 1H, overlap with DMSO-d6 signal), 2.18 (s, 3H), 1.98-2.10 (m, 4H), 1.82-1.92 (m, 2H), 1.69-1.74 (m, 1H), 151-1.57 (m, 1H), 1.30-1.47 (m, 1H). |
| 190 | D | 347.1 | $^1$H NMR (400 MHz, $CDCl_3$) δ 7.43-7.55 (m, 2H), 7.07-7.19 (m, 2H), 6.58 (s, 1H), 5.05-5.40 (m, 1H), 4.66-4.99 (m, 1H), 4.20-4.46 (m, 1H), 2.81-3.06 (m, 2H), 2.48-2.76 (m, 1H), 2.48-2.76 (m, 3H), 2.21-2.37 (m, 4H), 1.78-2.00 (m, 1H), 1.08 (d, J = 6.8 Hz, 6H). |
| 191 | B | 367.1 | 1H NMR (400 MHz, DMSO): δ 12.44 (brs, 1H), 7.91 (d, J = 8.0 Hz, 2H), 7.72 (d, J = 7.6 Hz, 2H), 6.13 (brd, J = 8.0 Hz, 1H), 3.75-3.86 (m, 1H), 2.62-2.69 (m, 1H), 2.31-2.37 (m, 1H), 2.12-2.23 (m, 5H), 1.81 (s, 3H), 1.61-1.69 (m, 2H), 1.46-1.54 (m, 2H). |
| 192 | B | 355.0 | 1H NMR (400 MHz, DMSO-d6): δ 7.40-7.51 (m, 2H), 7.27-7.40 (m, 4H), 4.12-4.28 (m, 1H), 2.77-2.83 (m, 1H), 2.50-2.57 (m, 1H), 2.19 (s, 3H), 2.10-2.16 (m, 1H), 2.00-2.08 (m, 1H), 1.78-1.88 (m, 1H), 1.68-1.77 (m, 1H), 1.51-1.60 (m, 1H), 1.34-1.44 (m, 1H). |
| 193 | E | 391.1 | $^1$H NMR (400 MHz, DMSO-$d_6$) δ 8.23 (brs, 1H), 7.82 (dd, J = 14.8 Hz, 8.0 Hz, 4H), 7.26 (s, 1H), 4.45-4.60 (m, 1H), 2.96-3.10 (m, 1H), 2.80-2.89 (m, 1H), 2.38-2.47 (m, 2H) (overlap with DMSO-$d_6$ signal), 2.29 (s, 6H), 1.85-2.04 (m, 3H), 1.72-1.81 (m, 1H), 1.55-1.68 (m, 1H), 0.95-1.05 (m, 2H), 0.62-0.72 (m, 1H), 0.52-0.61 (m, 1H) |
| 194 | B | 371.0 | 1H NMR (400 MHz, DMSO-d6): δ 7.54 (d, J = 8.4 Hz, 2H), 7.45 (d, J = 8.4 Hz, 2H), 7.41 (brd, J = 8.0 Hz 1H), 7.32 (s, 1H), 4.12-4.21 (m, 1H), 2.74-2.84 (m, 1H), 2.59-2.63 (m, 1H), 2.19 (s, 3H), 2.11-2.16 (m, 1H), 2.03-2.10 (m, 1H), 1.78-1.84 (m, 1H), 1.70-1.77 (m, 1H), 1.52-1.59 (m, 1H), 1.36-1.44 (m, 1H). |
| 195 | B | 369.2 | 1HNMR (400 MHz, DMSO-d6): δ 7.45-7.50 (m, 2H), 7.28-7.35 (m, 4H), 4.10-4.20 (m, 1H), 2.87-2.94 (m, 1H), 2.55-2.62 (m, 1H), 2.33-2.39 (m, 2H), 2.10-2.15 (m, 1H), 1.99-2.05 (m, 1H), 1.83-1.90 (m, 1H), 1.70-175 (m, 1H), 1.52-1.58 (m, 1H), 1.36-1.43 (m, 1H), 1.00 (t, J = 7.2 Hz, 3H) |
| 196 | B | 371.2 | 1H NMR (400 MHz, DMSO-d6): δ 8.19 (s, 1H), 8.31 (d, J = 8.4 Hz, 2H), 7.57 (d, J = 8.8 Hz, 2H), 6.22 (brd, J = 8.0 Hz, 1H), 4.48-4.55 (m, 1H), 2.64-2.69 (m, 1H), 2.19-2.35 (m, 6H), 1.64-1.73 (m, 3H), 1.52-1.59 (m, 1H). |

TABLE 2-continued

| Cmpd No | General Synthetic Route | LCMS [M + H]+ | Characterization |
|---|---|---|---|
| 197 | B | 369.1 | 1HNMR (400 MHz, DMSO-d6): δ 8.11-8.18 (m, 3H), 7.29-7.39 (m, 2H), 6.20 (d, J = 8.0 Hz, 1H), 4.45-4.56 (m, 1H), 2.60-2.66 (m, 2H), 2.36-2.43 (m, 4H), 1.62-1.80 (m, 3H), 1.50-1.58 (m, 1H), 1.01 (t, J = 7.2 Hz, 3H). |
| 198 | B | 367.1 | 1H NMR (400 MHz, DMSO): δ 11.85-12.25 (m, 1H), 7.60 (s, 1H), 7.55 (d, J = 8.0 Hz, 1H), 7.40 (d, J = 8.0 Hz, 1H), 6.50 (brd, J = 8.4 Hz, 1H), 5.59-5.62 (m, 1H), 3.55-3.68 (m, 1H), 2.51-2.63 (m, 2H), 2.29-2.37 (m, 1H), 2.18-2.25 (m, 7H), 1.63-1.71 (m, 2H), 1.35-1.55 (m, 2H). |
| 199 | B | 333.1 | $^1$H NMR (400 MHz, DMSO-$d_6$) δ 7.40-7.51 (m, 4H), 6.83-7.20 (m, 3H), 4.07-4.12 (m, 1H), 2.83-2.87 (m, 1H), 2.52-2.54 (m, 1H) (overlap with DMSO-$d_6$ signal), 2.35 (s, 3H), 2.18 (s, 1H), 1.75-2.08 (m, 3H), 1.66-1.72 (m, 1H), 1.47-1.58 (m, 1H), 1.21-1.35 (m, 1H) |
| 200 | B | 359.1 | $^1$H NMR (400 MHz, DMSO-$d_6$): 8 7.41 (s, 1H), 7.28-7.35 (m, 1H), 7.18 (d, J = 8.0 Hz, 1H), 6.72 (s, 1H), 6.58 (brd, J = 7.6 Hz, 1H), 3.92-4.03 (m, 1H), 3.25-3.29 (m, 1H), 2.89-2.92 (m, 1H), 2.61-2.70 (m, 1H), 2.15-2.23 (m, 1H), 2.00-2.09 (m, 4H), 1.83-1.90 (m, 4H), 1.65-1.73 (m, 1H), 1.39-1.51 (m, 1H), 1.22-1.35 (m, 1H), 0.94-0.98 (m, 6H). |
| 201 | B | 345.1 | $^1$H NMR (400 MHz, DMSO-$d_6$): δ 7.41 (d, J = 1.6 Hz, 1H), 7.37 (dd, J = 8.0, 2.0 Hz, 1H), 7.17 (d, J = 8.4 Hz, 1H), 6.72 (s, 1H), 6.61 (brd, J = 7.6 Hz, 1H), 3.95-4.06 (m, 1H), 2.89-2.97 (m, 1H), 2.66-2.71 (m, 1H), 2.34 (q, J = 7.2 Hz, 2H), 1.98-2.03 (m, 4H), 1.61-1.85 (m, 4H), 1.70-1.78 (m, 1H), 1.45-1.58 (m, 1H), 1.22-1.33 (m, 1H), 0.99 (t, J = 7.2 Hz, 2H). |
| 202 | E | 331.1 | $^1$H NMR (400 MHz, DMSO-$d_6$): δ 7.57 (d, J = 8.4 Hz, 2H), 7.52 (d, J = 8.4 Hz, 2H), 6.10 (s, 1H), 4.60-4.69 (m, H), 2.96 (s, 3H), 2.74 (d, 2H), 2.24 (s, 3H), 2.20 (s, 3H), 2.03 (t, J = 10.4, 1H), 1.79-1.86 (m, 1H), 1.61-1.74 (m, 2H), 1.51-1.64 (m, 2H). |
| 203 | B | 351.1 | 1H NMR (400 MHz, DMSO-d6) δ 7.45-7.57 (m, 3H), 6.62-6.90 (m, 3H), 3.98-4.12 (m, 1H), 2.81-2.92 (m, 1H), 2.19 (s, 3H), 1.81-2.04 (m, 6H), 1.66-1.76 (m, 1H), 1.47-1.61 (m, 1H), 1.23-1.37 (m, 1H). |
| 204 | E | 345.2 | $^1$H NMR (400 MHz, DMSO-$d_6$): δ 7.43 (d, J = 1.6 Hz 1H), 7.33 (dd, J = 8.0, 2.0 Hz, 1 H), 7.19 (d, J = 8.0 Hz, 1 H), 7.01 (s, 1H), 4.59-4.67 (m, 1H), 2.96 (s, 3H), 2.72-2.77 (m, 2H), 2.20 (s, 3H), 2.02-2.06 (m, 4H), 1.97 (s, 3H), 1.79-1.85 (m, 1H), 1.68-1.75 (m, 2H), 1.54-1.65 (m, 2H). |
| 205 | B | 322.1 | $^1$H NMR (400 MHz, DMSO-$d_6$): δ 7.53 (d, J = 8.0 Hz, 2H), 7.42 (d, J = 8.4 Hz, 2H), 6.72 (s, 1H), 6.63 (brd, J = 8.0 Hz, 1H), 4.10 (s, 2H), 4.08-4.03 (m, 1H), 2.86-2.84 (m, 1H), 2.50-2.54 (m, 1H), 2.15-2.20 (m, 6H), 1.89-1.99 (m, 1H), 1.84-1.85 (m, 2H), 1.70-1.82 (m, 1H), 1.68-1.69 (m, 1H), 1.19-1.36 (m, 1H). |
| 206 | B | 322.0 | $^1$H NMR (400 MHz, DMSO-$d_6$): δ 8.02 (d, J = 8.0 Hz, 2H), 7.73 (s, 1H), 7.44 (d, J = 8.0 Hz, 2H), 5.87 (brd, J = 8.0 Hz, 1H), 4.25-4.32 (m, 1H), 4.09 (s, 2H), 2.95-2.97 (m, 1H), 2.90-2.93 (m, 1H), 2.15-2.21 (m, 6H), 1.82-1.99 (m, 3H), 1.66-1.76 (m, 1H) , 1.51-1.62 (m, 1H), 1.36-1.49 (m, 1H). |
| 207 | | | |
| 208 | | | |
| 209 | | | |
| 210 | F | 318.2 | $^1$H NMR (400 MHz, DMSO-$d_6$) δ 7.58 (dd, J = 15.2 Hz, 8.8 Hz, 4H), 7.14 (s, 1H), 5.21-5.29 (m, 1H), 2.84-2.97 (m, 1H), 2.53-2.62 (m, 1H) (overlap with DMSO-$d_6$ signal), 2.25 (s, 3H), 2.14-2.22 (m, 4H), 2.05-2.13 (m, 1H), 1.96-2.04 (m, 1H), 1.71-1.80 (m, 1H), 1.45-1.61 (m, 2H). |

Example 8

NLRP3 Inflammasome Activation and Cell Viability Assessment in THP1 Macrophages THP1—Human acute monocytic leukemia cells were cultured (ATCC, cat #TIB-202) in Gibco RPMI-1640 medium (ThermoFisher cat #72400054) supplemented with 10% Heat Inactivated FBS at density between 3-8×10^5 viable cells/ml. The cells were then subcultured when the cell concentration reached $8\times10^5$ cells/mL (every 2-3 days).

To determine the compounds' $IC_{50}$, $1.75\times10^4$ cells/well were plated in CELLSTAR 384 well plates (Greiner cat #781091) in 50 ul/well DMEM (ThermoFisher, cat

#10393021), 10% FBS, 1×GlutaMax (ThermoFisher, cat #35050038)+20 nM PMA (Sigma, cat #P1585) and used in the inner 224 wells of a 384 well plate. The parameter wells were filled with 50 ul PBS and incubated at 37° C., 5% $CO_2$ for 48 hrs.

After 48 hrs incubation, the PMA containing media was removed, and changed for 40 ul/well of fresh DMEM, 10% FBS, 1×GlutMax and incubated at 37° C., 5% $CO_2$ for 24 hrs.

The following day the cells were primed with LPS (*E. coli*) (Sigma, cat #L3129) at 20 ng/ml in DMEM, 10% FBS, 1×GlutMax for 3 hrs at 37° C., 5% $CO_2$.

Following the LPS priming step, the cells were treated with compounds at 10 uM top final concentration, 1:4 dilution, 8 times: (10 uM, 2.5 uM, 0.625 uM, 0.156 uM, 0.039 uM, 0.0097 uM, 0.0024 uM, 0.0006 uM). DMSO was used as a vehicle control, and MCC950 (InvivGen, cat #inh-mcc) was used at 1 uM as a positive control, and incubated for 1 hrs at 37° C., 5% $CO_2$.

Following the 1 hr compound incubation, the NLRP3 inflammasome activation step was conducted by treating cells with Nigericin (InvivoGen, cat #tlrl-nig) at 6.7 uM final concentration for 3 hrs at 37° C., 5% $CO_2$.

Thereafter, 30 ul samples of cells' supernatants were collected for cytokine analysis which was conducted on Hu IL-1β AlphaLISA (Perkin Elemer, cat #AL220C) and Hu IL-6 AlphaLISA (Perkin Elemer, cat #AL220C). The cells' viability was assessed by performing CellTiter-Glo Luminescent Assay (Promega, cat #G7572) according to the manufacturer's protocol.

Cell viability assessment for select NLRP3 inflammasome modulators is displayed in Tables 3 and 4.

For Table 3—The activity ranges are as follows: "++++++" denotes IL-1β activity ≤10 nM; "+++++" denotes IL-1β activity >10 nM and ≤50 nM; "++++" denotes IL-1β activity >50 nM and ≤100 nM; "+++" denotes IL-1β activity >100 nM and ≤500 nM; and "++" denotes IL-1β activity >500 nM and ≤1,000 nM; "+" denotes IL-1β activity >1,000 nM. "*" denotes not yet tested.

For Table 4—The activity ranges are as follows: "++++" denotes IL-6 activity ≤1 μM; "+++" denotes IL-6 activity >1 μM and ≤5 μM; "++" denotes IL-6 activity >5 μM and ≤10 μM; and "+" denotes IL-6 activity of >10 μM. "*" denotes not yet tested.

TABLE 3

| Cpd No. | IL-1β Activity (nM) |
|---|---|
| 1 | ++++++ |
| 2 | ++++++ |
| 3 | +++++ |
| 4 | +++++ |
| 5 | +++++ |
| 6 | +++++ |
| 7 | +++++ |
| 8 | +++++ |
| 9 | +++++ |
| 10 | +++++ |
| 11 | +++++ |
| 12 | +++++ |
| 13 | ++++ |
| 14 | +++++ |
| 15 | +++++ |
| 16 | +++++ |
| 17 | ++++ |
| 18 | ++++ |
| 19 | +++ |
| 20 | +++ |
| 21 | +++ |
| 22 | ++++ |

TABLE 3-continued

| Cpd No. | IL-1β Activity (nM) |
|---|---|
| 23 | +++ |
| 24 | +++ |
| 25 | ++++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | ++ |
| 36 | ++ |
| 37 | ++ |
| 38 | ++ |
| 39 | ++ |
| 40 | ++++ |
| 41 | +++ |
| 42 | ++ |
| 43 | + |
| 44 | +++ |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | ++++ |
| 60 | +++ |
| 61 | +++++ |
| 62 | +++++ |
| 63 | +++ |
| 64 | +++ |
| 65 | ++ |
| 66 | ++++++ |
| 67 | +++ |
| 68 | ++++++ |
| 69 | ++++ |
| 70 | ++++++ |
| 71 | +++++ |
| 72 | +++ |
| 73 | +++ |
| 74 | + |
| 75 | + |
| 76 | + |
| 77 | + |
| 78 | + |
| 79 | + |
| 80 | + |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | +++++ |
| 94 | + |
| 95 | + |
| 96 | + |
| 97 | + |
| 98 | + |
| 99 | ++ |
| 100 | + |

TABLE 3-continued

| Cpd No. | IL-1β Activity (nM) |
|---|---|
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | ++++ |
| 121 | +++ |
| 122 | +++++ |
| 123 | ++++++ |
| 124 | +++++ |
| 125 | ++++ |
| 126 | + |
| 127 | ++++++ |
| 128 | +++ |
| 129 | ++++ |
| 130 | +++++ |
| 131 | ++ |
| 132 | +++++ |
| 133 | +++++ |
| 134 | +++ |
| 135 | +++++ |
| 136 | ++++ |
| 137 | +++ |
| 138 | + |
| 139 | ++ |
| 140 | + |
| 141 | + |
| 142 | +++ |
| 143 | +++++ |
| 144 | +++ |
| 145 | ++++ |
| 146 | ++++++ |
| 147 | + |
| 148 | + |
| 149 | +++ |
| 150 | + |
| 151 | + |
| 152 | +++++ |
| 153 | + |
| 154 | +++ |
| 155 | ++++++ |
| 156 | ++++++ |
| 157 | +++++ |
| 158 | +++ |
| 159 | ++ |
| 160 | ++ |
| 161 | +++ |
| 162 | +++++ |
| 163 | + |
| 164 | + |
| 165 | ++++++ |
| 166 | +++++ |
| 167 | +++ |
| 168 | +++++ |
| 169 | +++++ |
| 170 | +++++ |
| 171 | ++++++ |
| 172 | + |
| 173 | + |
| 174 | ++++++ |
| 175 | ++++++ |
| 176 | ++++ |
| 177 | +++ |
| 178 | + |

TABLE 3-continued

| Cpd No. | IL-1β Activity (nM) |
|---|---|
| 179 | + |
| 180 | + |
| 181 | ++ |
| 182 | ++++ |
| 183 | +++ |
| 184 | + |
| 185 | + |
| 186 | ++++++ |
| 187 | + |
| 188 | * |
| 189 | + |
| 190 | ++++ |
| 191 | +++++ |
| 192 | ++++++ |
| 193 | ++++++ |
| 194 | ++++++ |
| 195 | +++++ |
| 196 | ++ |
| 197 | + |
| 198 | ++ |
| 199 | ++++ |
| 200 | ++++++ |
| 201 | ++++++ |
| 202 | +++ |
| 203 | +++++ |
| 204 | ++ |
| 205 | * |
| 206 | * |
| 207 | * |
| 208 | * |
| 209 | * |
| 210 | +++ |

TABLE 4

| Cpd No. | IL-6 Activity (μM) |
|---|---|
| 1 | + |
| 2 | +++ |
| 3 | ++ |
| 4 | ++ |
| 5 | + |
| 6 | + |
| 7 | + |
| 8 | + |
| 9 | +++ |
| 10 | ++ |
| 11 | +++ |
| 12 | + |
| 13 | ++ |
| 14 | + |
| 15 | + |
| 16 | + |
| 17 | + |
| 18 | ++ |
| 19 | ++ |
| 20 | + |
| 21 | ++ |
| 22 | + |
| 23 | + |
| 24 | + |
| 25 | + |
| 26 | + |
| 27 | + |
| 28 | ++ |
| 29 | + |
| 30 | + |
| 31 | + |
| 32 | + |
| 33 | + |
| 34 | + |
| 35 | + |
| 36 | + |
| 37 | + |
| 38 | + |

TABLE 4-continued

| Cpd No. | IL-6 Activity (μM) |
|---|---|
| 39 | + |
| 40 | ++ |
| 41 | + |
| 42 | ++ |
| 43 | ++ |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | ++ |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | ++ |
| 76 | ++ |
| 77 | ++ |
| 78 | + |
| 79 | + |
| 80 | + |
| 81 | + |
| 82 | + |
| 83 | ++ |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | ++ |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | ++ |
| 111 | + |
| 112 | + |
| 113 | + |
| 114 | + |
| 115 | ++ |
| 116 | + |

TABLE 4-continued

| Cpd No. | IL-6 Activity (μM) |
|---|---|
| 117 | + |
| 118 | + |
| 119 | + |
| 120 | + |
| 121 | + |
| 122 | + |
| 123 | + |
| 124 | ++ |
| 125 | + |
| 126 | + |
| 127 | + |
| 128 | + |
| 129 | + |
| 130 | ++ |
| 131 | + |
| 132 | + |
| 133 | + |
| 134 | + |
| 135 | + |
| 136 | ++ |
| 137 | + |
| 138 | + |
| 139 | ++ |
| 140 | + |
| 141 | + |
| 142 | +++ |
| 143 | + |
| 144 | ++ |
| 145 | + |
| 146 | ++ |
| 147 | ++ |
| 148 | + |
| 149 | ++ |
| 150 | + |
| 151 | +++ |
| 152 | + |
| 153 | ++ |
| 154 | + |
| 155 | + |
| 156 | + |
| 157 | + |
| 158 | ++ |
| 159 | ++ |
| 160 | +++ |
| 161 | + |
| 162 | + |
| 163 | + |
| 164 | + |
| 165 | + |
| 166 | + |
| 167 | + |
| 168 | ++ |
| 169 | + |
| 170 | + |
| 171 | + |
| 172 | + |
| 173 | + |
| 174 | ++ |
| 175 | + |
| 176 | + |
| 177 | + |
| 178 | +++ |
| 179 | + |
| 180 | + |
| 181 | ++++ |
| 182 | + |
| 183 | + |
| 184 | ++ |
| 185 | +++ |
| 186 | + |
| 187 | + |
| 188 | * |
| 189 | + |
| 190 | + |
| 191 | + |
| 192 | + |
| 193 | ++ |
| 194 | + |

TABLE 4-continued

| Cpd No. | IL-6 Activity (μM) |
|---|---|
| 195 | + |
| 196 | +++ |
| 197 | + |
| 198 | + |
| 199 | + |
| 200 | + |
| 201 | + |
| 202 | + |
| 203 | + |
| 204 | + |
| 205 | * |
| 206 | * |
| 207 | * |
| 208 | * |
| 209 | * |
| 210 | + |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Application No. 63/294,619, filed Dec. 29, 2021, and U.S. Provisional Patent Application No. 63/341,955, filed on May 13, 2022, are incorporated herein by reference, in their entirety. Aspects of the embodiments can be modified, if necessary, to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A compound having structure (A):

(A)

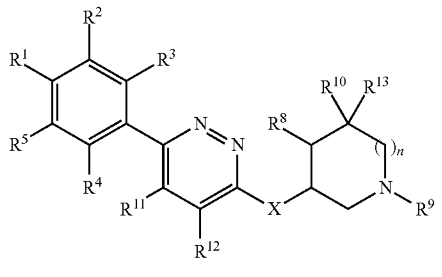

or a pharmaceutically acceptable salt, isomer, hydrate, solvate or isotope thereof, wherein:

X is O or $NR^{15}$;

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F, X is $NR^{15}$, and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

2. The compound of claim 1, having structure (B):

(B)

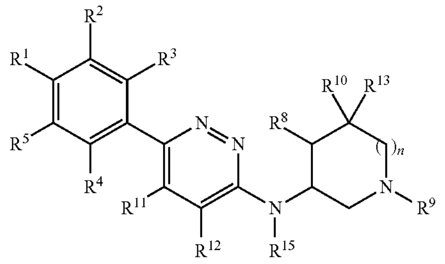

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or halo;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, H, halo, $CF_3$, $C_{1-6}$ alkyl, CN, OH or $OC_{1-6}$ alkyl;

$R^{15}$ is H, $C_{1-6}$ alkyl or $C_{3-5}$ cycloalkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

3. The compound of claim 1, having structure (C):

(C)

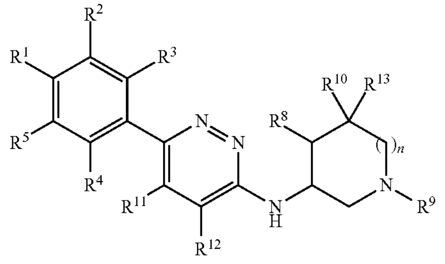

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl;

n is 1 or 2;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H or $CH_3$, then $R^9$ is not H.

4. The compound of claim 1, having structure (I):

(I)

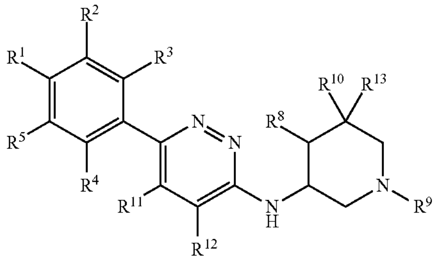

or a pharmaceutically acceptable salt, isomer, hydrate, solvate or isotope thereof, wherein:

$R^1$ is H, $CF_3$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $C_{1-6}$ alkyl, CN, F, Cl, C(O)OH or $OC_{1-6}$ alkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CF_2$, $CF_3$, or $C_{3-5}$ cycloalkyl;

$R^{10}$ and $R^{13}$ are independently H or F;

$R^{11}$ is H, $CF_3$, $C_{1-6}$ alkyl or CN;

$R^{12}$ is H, C1 or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

5. The compound of claim 4, wherein the compound has the following structure:

(Ia)

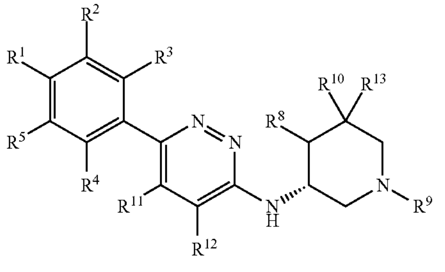

or a pharmaceutically acceptable salt, isomer, hydrate, solvate or isotope thereof, wherein:

$R^1$ is $CF_3$, $C_{1-6}$ alkyl, $C_{3-5}$ cycloalkyl, CN, $C_{1-6}$ cyanoalkyl, F, C(O)OH or $OCF_3$;

$R^2$, $R^3$, $R^4$, and $R^5$ are independently H, $CF_3$, $C_{1-6}$ alkyl, CN, F, Cl, C(O)OH or $OC_{1-6}$ alkyl;

$R^8$ is H or F;

$R^9$ is $C_{1-6}$ alkyl optionally substituted with one or more $R^{9'}$;

$R^{9'}$ is F or $C_{3-5}$ cycloalkyl;

$R^{10}$ and $R^{13}$ are independently H or F;

$R^{11}$ is H, $CF_3$, $C_{1-6}$ alkyl or CN; and $R^{12}$ is H, C1 or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not ethyl; and wherein if $R^1$ is H, then $R^{12}$ is not methyl or H.

6. The compound of claim 1, wherein the compound has the following structure:

(Ia')

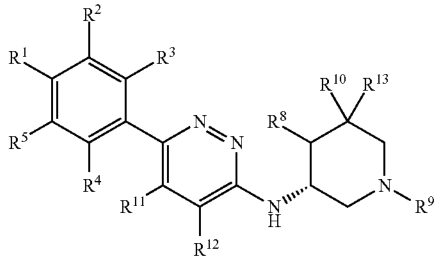

or a pharmaceutically acceptable salt, isomer, hydrate, solvate or isotope thereof, wherein:

$R^1$ is $CF_3$ or F;

$R^2$, $R^3$, $R^4$, and $R^5$ are independently H, $CF_3$, $C_{1-6}$ alkyl, CN, F, Cl, C(O)OH or $OC_{1-6}$ alkyl;

$R^8$ is H or F;

$R^9$ is $C_{1-6}$ alkyl optionally substituted with one or more $R^{9'}$;

$R^{9'}$ is F or $C_{3-5}$ cycloalkyl;

$R^{10}$ and $R^{13}$ are independently H or F;

$R^{11}$ is H, $CF_3$, $C_{1-6}$ alkyl or CN; and $R^{12}$ is H, Cl or $C_{1-6}$ alkyl.

7. The compound of claim 1, wherein the has the following structure (D):

(D)

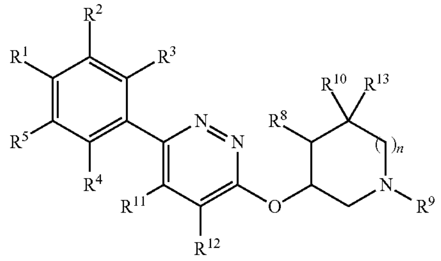

or a pharmaceutically acceptable salt, isomer, hydrate, solvate or isotope thereof, wherein:

$R^1$ is H, OH, $CF_3$, $CHF_2$, $C_{1-6}$ alkyl, $C_{3-5}$ cycloalkyl, CN, $C_{1-6}$ cyanoalkyl, F, Cl, C(O)OH, $OC_{1-6}$ alkyl or $OCF_3$;

$R^2$, $R^3$, $R^4$, and $R^5$ are independently H, $CF_3$, $CHF_2$, $C_{1-6}$ alkyl, CN, $C_{1-6}$ cyanoalkyl, F, Cl, C(O)OH, $OCF_3$, $OC_{1-6}$ alkyl or $C_{3-5}$ cycloalkyl;

$R^8$ is H or F;

$R^9$ is H, $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or F;

$R^{11}$ and $R^{12}$ are each, independently, H, F, Cl, $CF_3$, $C_{1-6}$ alkyl, CN, OH or $OC_{1-6}$ alkyl; and n is 1 or 2.

8. The compound of claim 1, or a pharmaceutically acceptable salt, isomer, hydrate, solvate or isotope thereof, wherein the compound has the following structure:

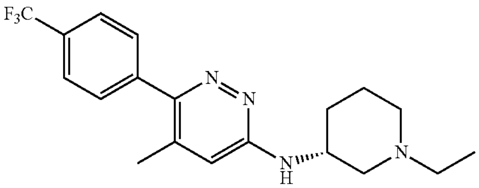
;
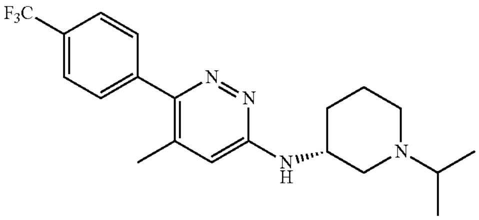
;
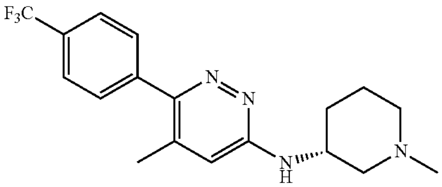
;
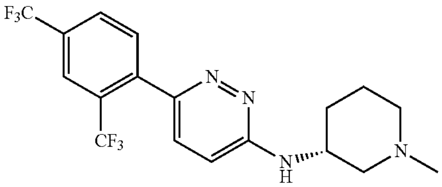
;
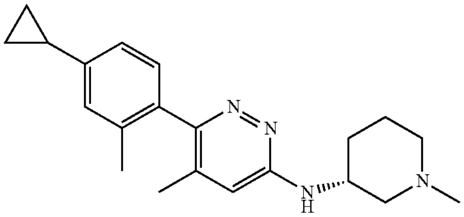
;
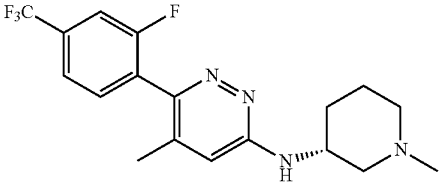
;
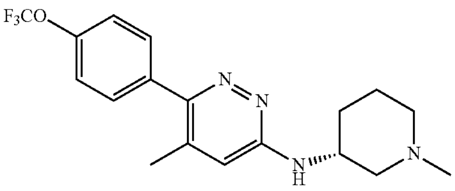
;
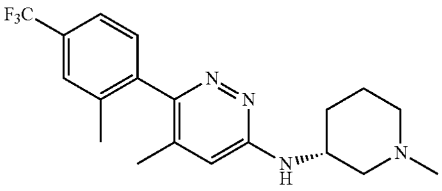
;
-continued
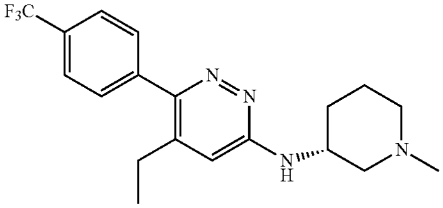
;
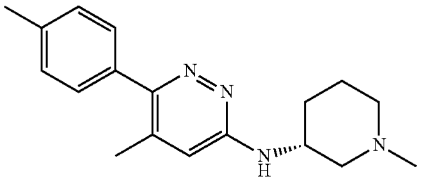
;
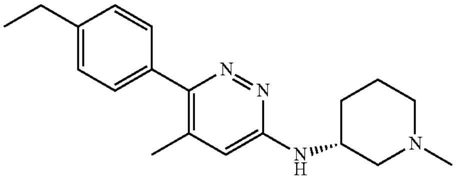
;
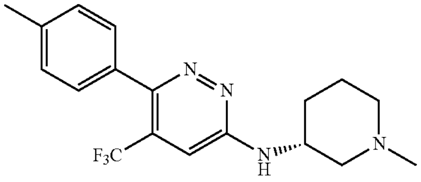
;
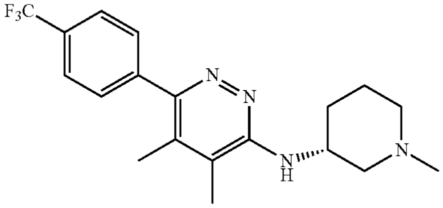
;
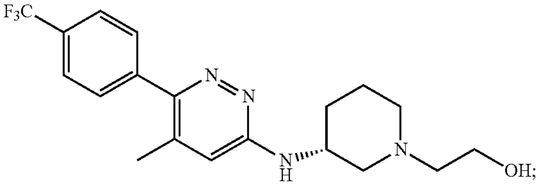
;
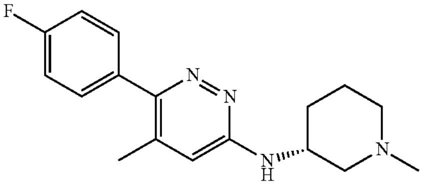
;
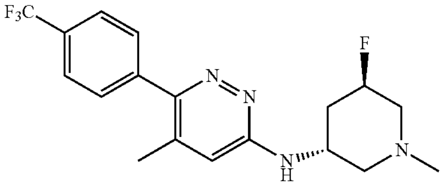
;
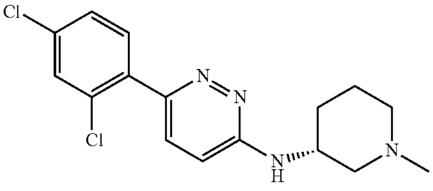
;

-continued
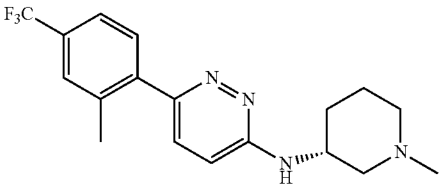
;
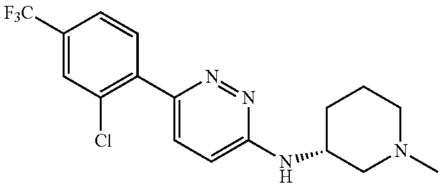
;
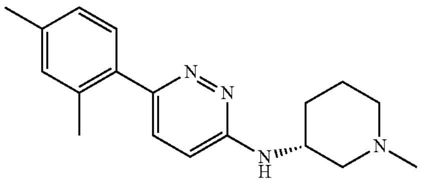
;
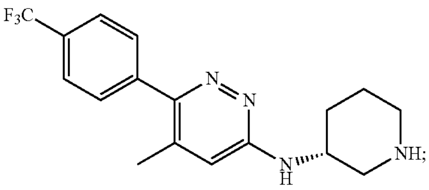
;
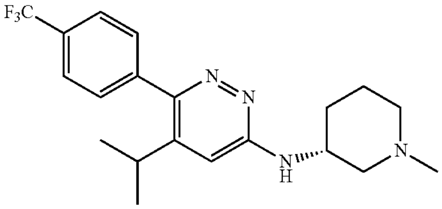
;
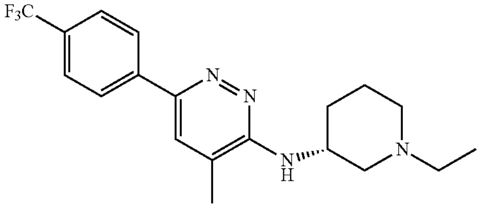
;
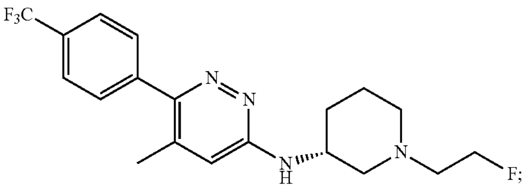
;
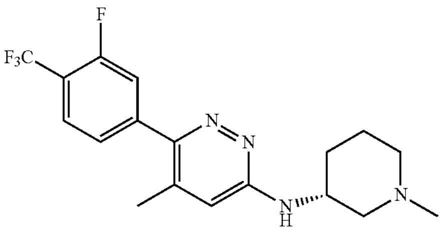
;
-continued
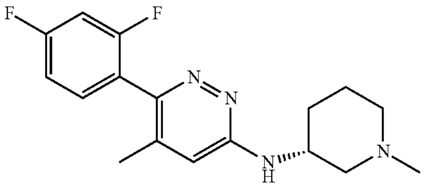
;
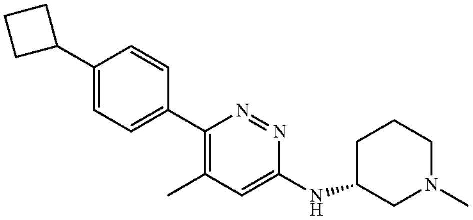
;
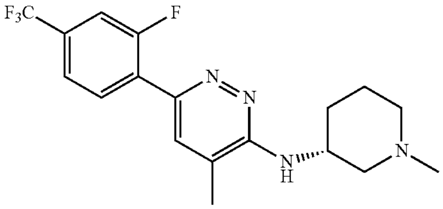
;
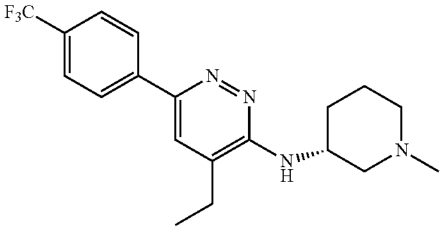
;
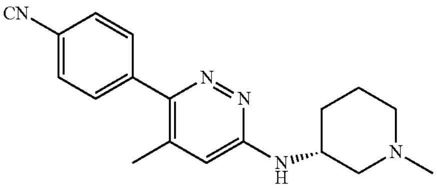
;
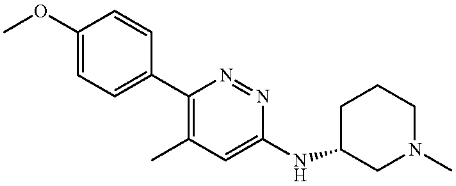
;
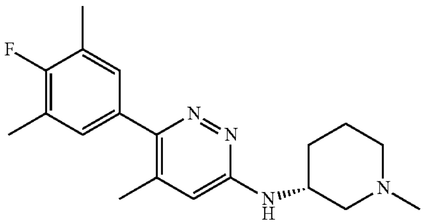
;
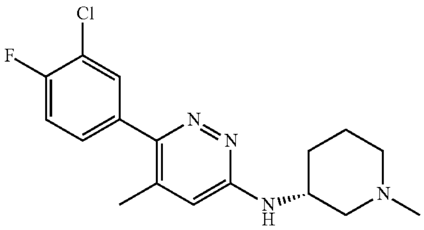
;

-continued
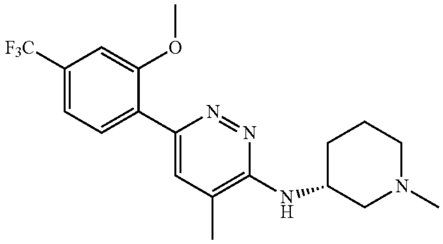
;
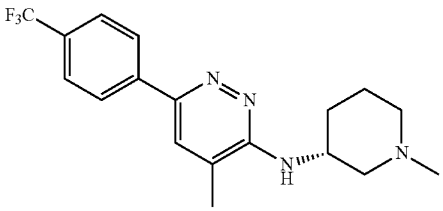
;
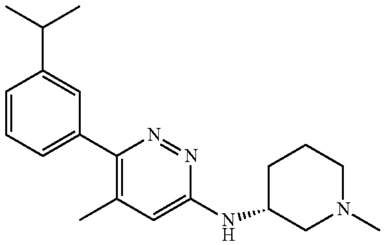
;
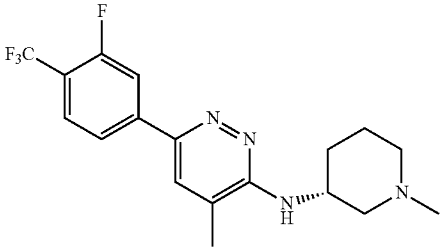
;
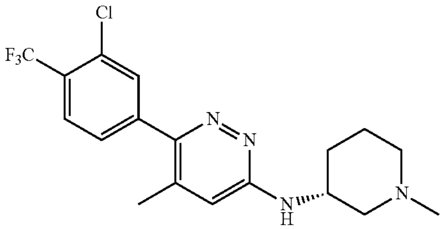
;
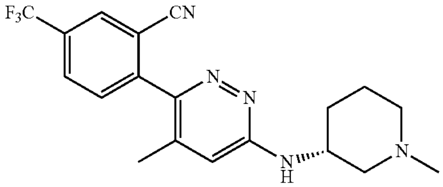
;
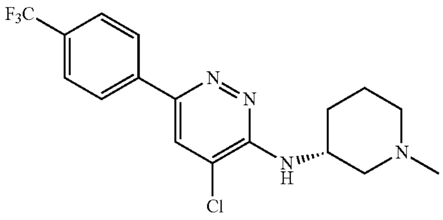
;
-continued
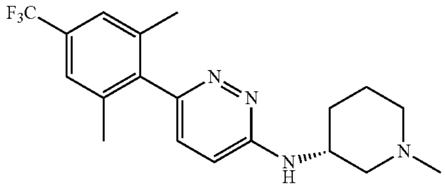
;
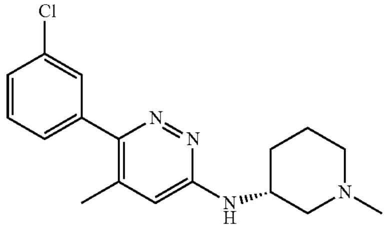
;
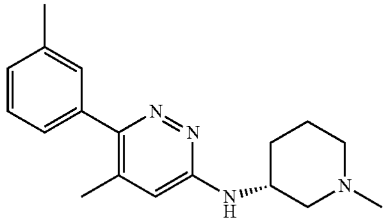
;
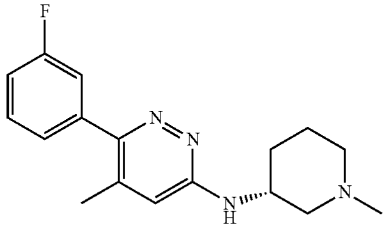
;
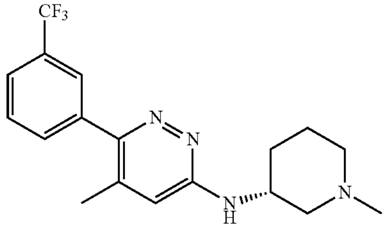
;
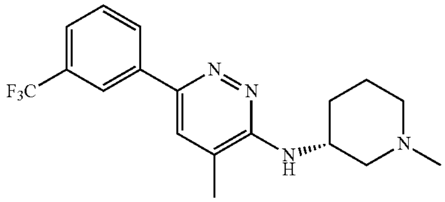
;
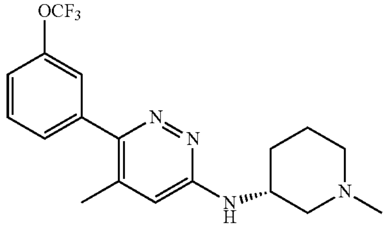
;
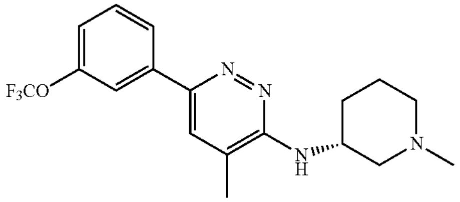
;

-continued
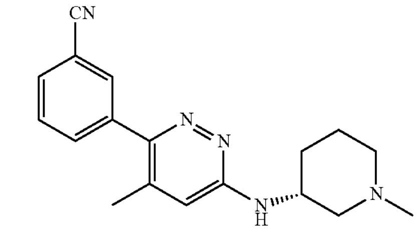
;
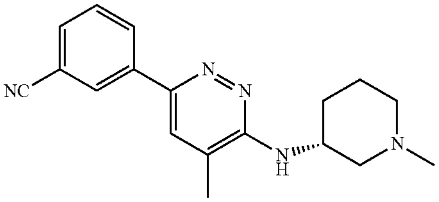
;
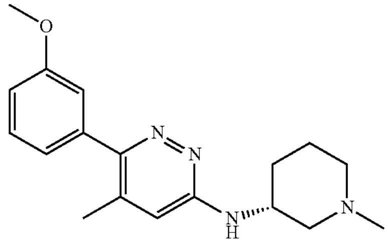
;
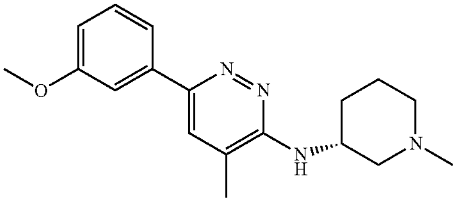
;
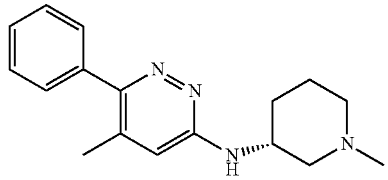
;
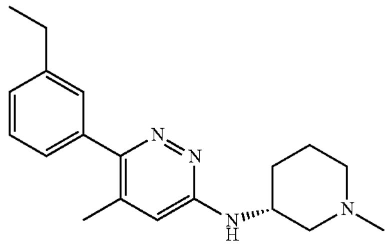
;
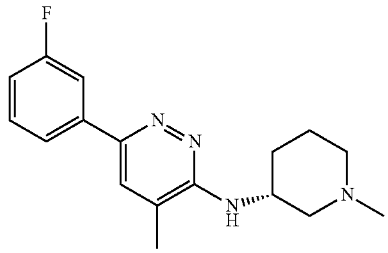
;
-continued
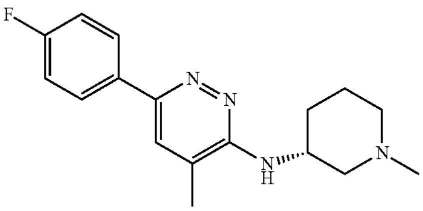
;
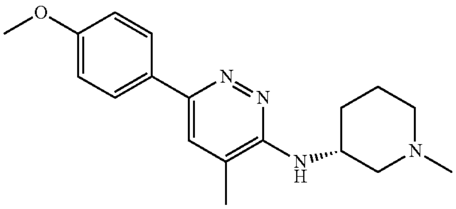
;
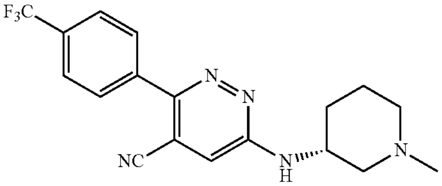
;
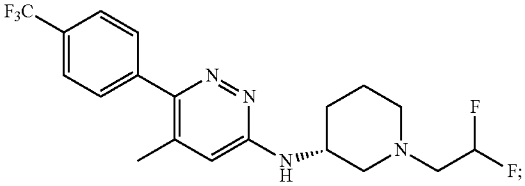
;
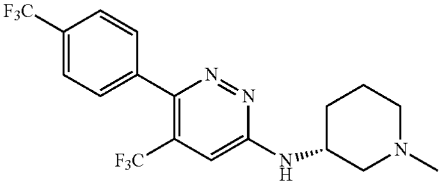
;
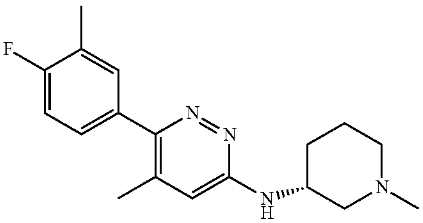
;
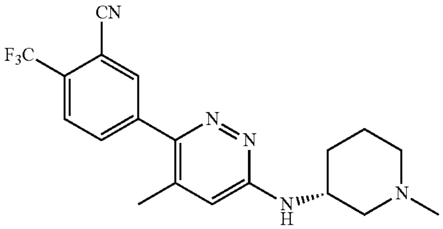
;
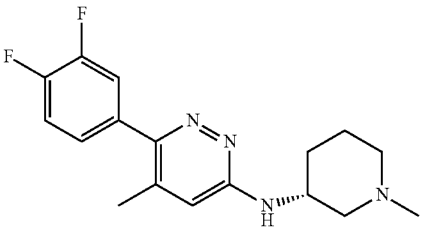
;

-continued
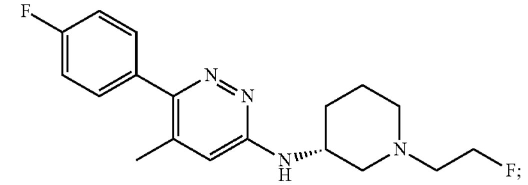
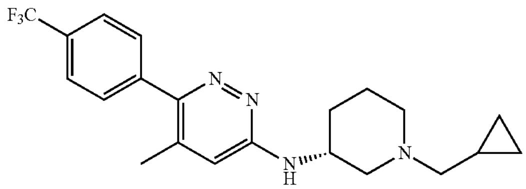
;
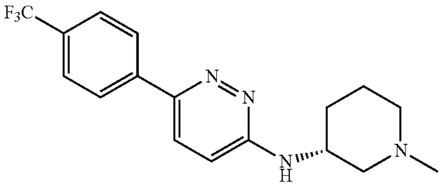
;
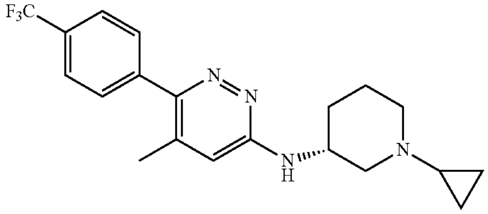
;
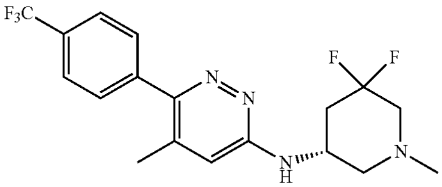
;
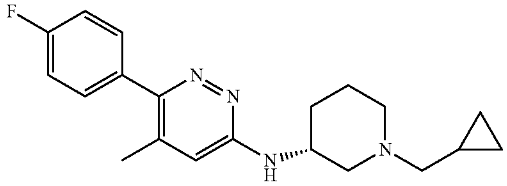
;
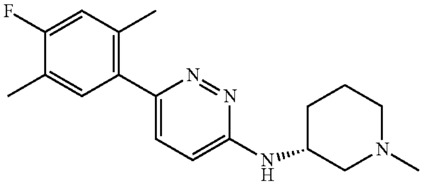
;
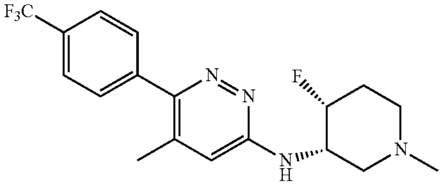
;
-continued
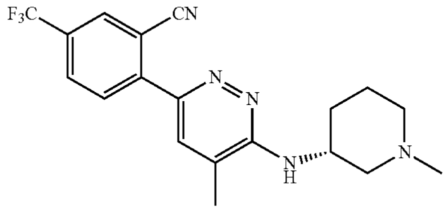
;
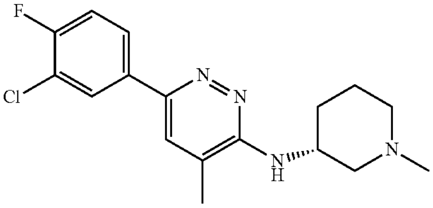
;
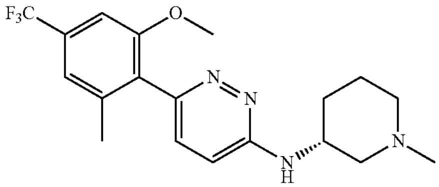
;
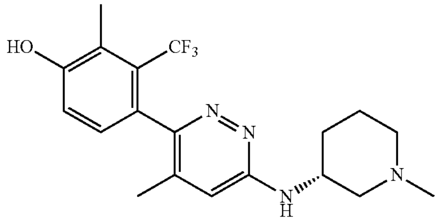
;
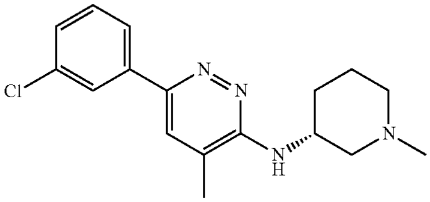
;
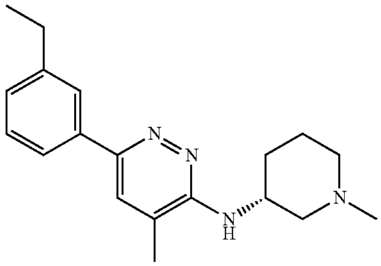
;
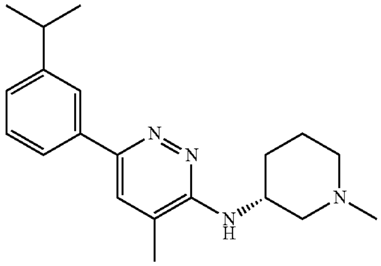
;

-continued
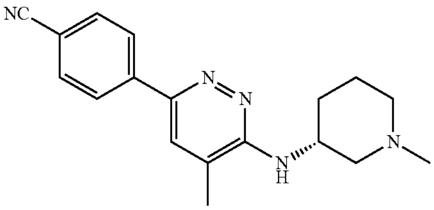
;
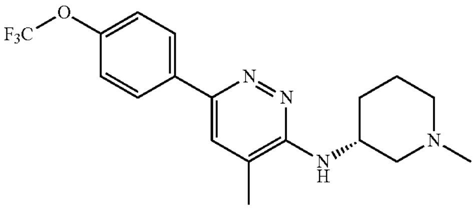
;
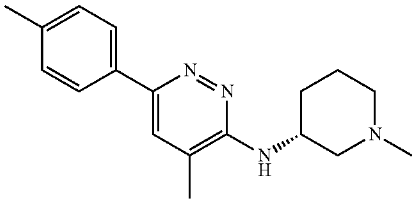
;
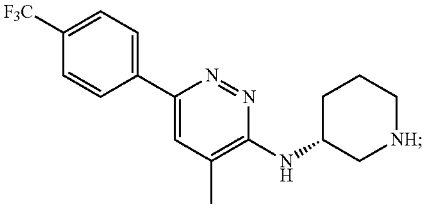
;
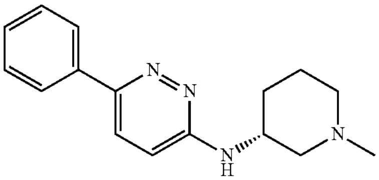
;
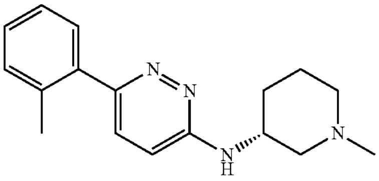
;
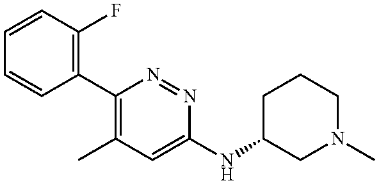
;
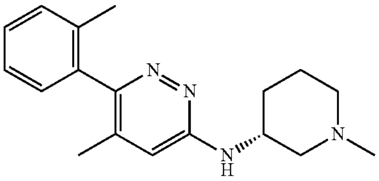
;
-continued
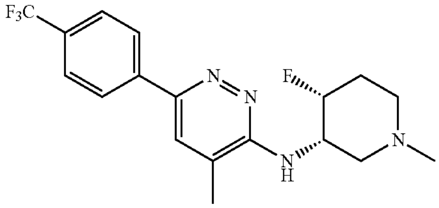
;
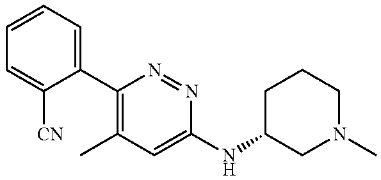
;
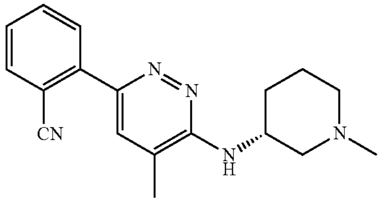
;
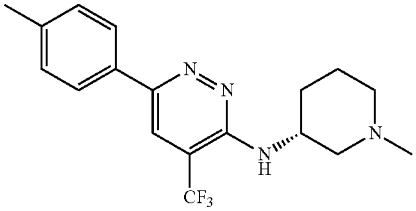
;
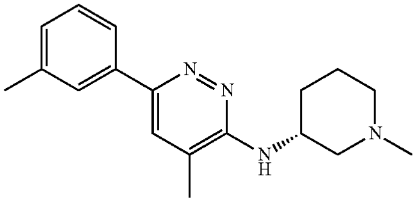
;
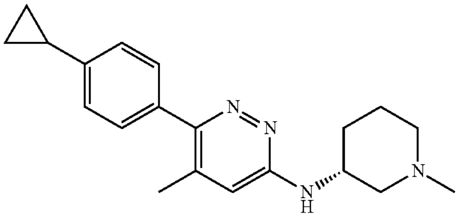
;
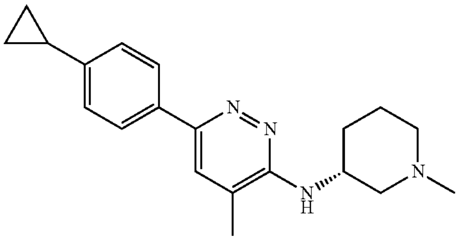
;
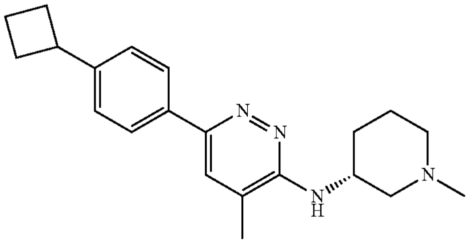
;

-continued
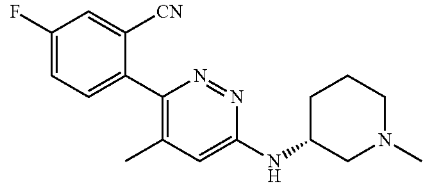
;
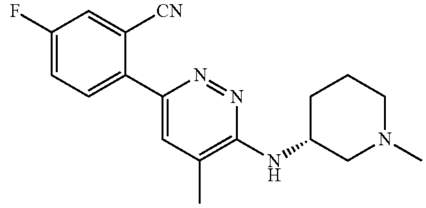
;
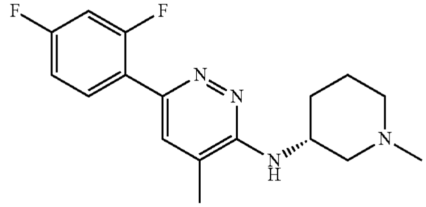
;
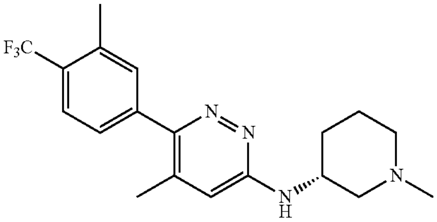
;
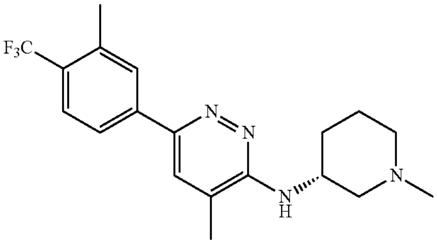
;
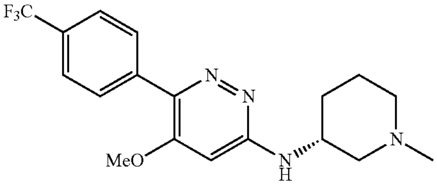
;
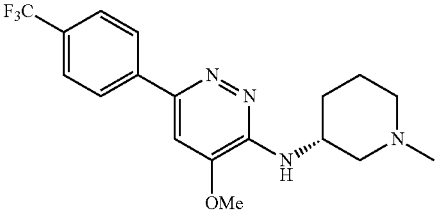
;
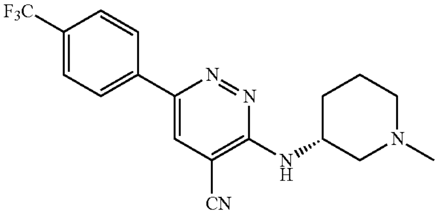
;
-continued
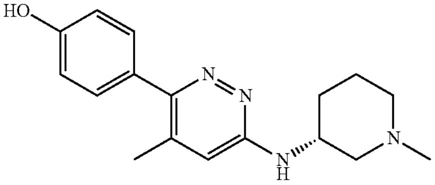
;
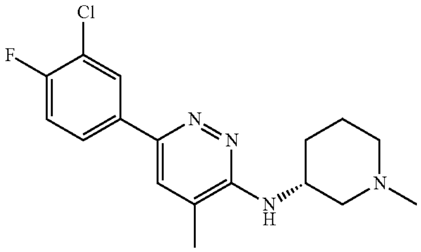
;
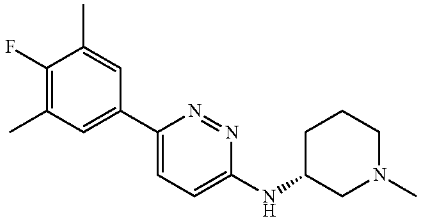
;
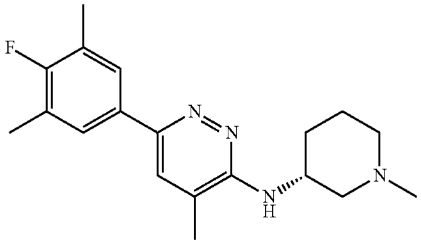
;
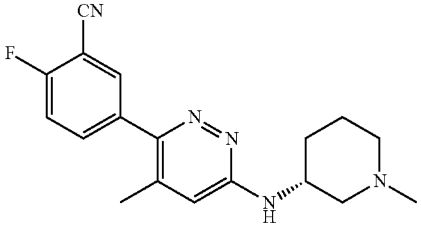
;
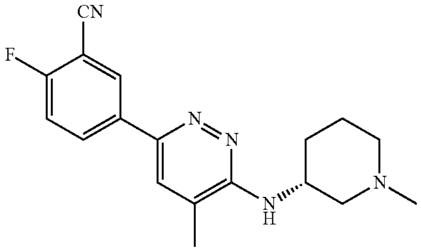
;
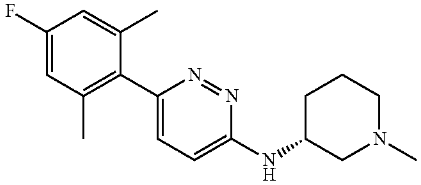
;

-continued
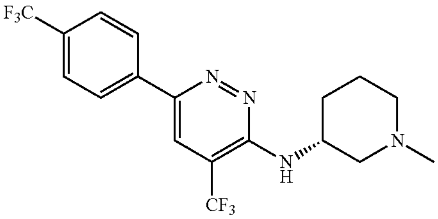
;
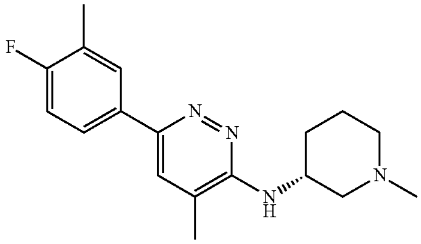
;
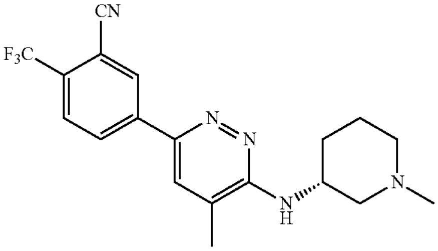
;
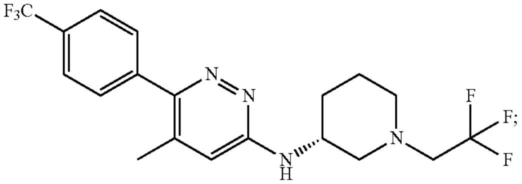
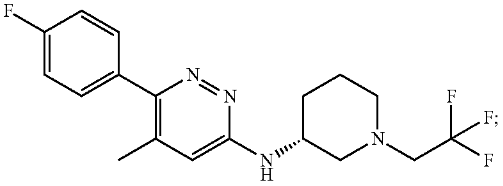
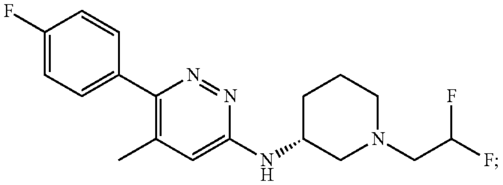
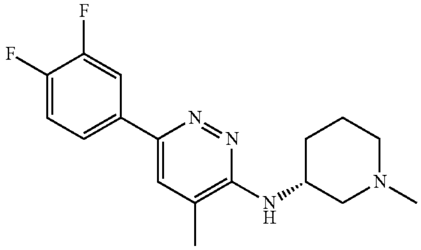
;
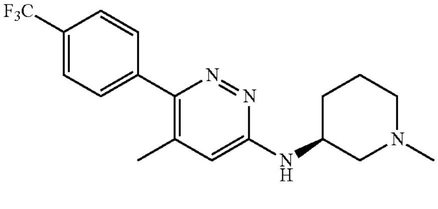
;
-continued
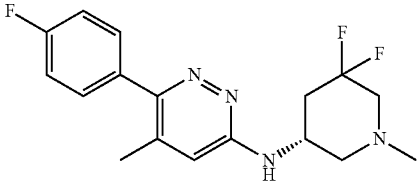
;
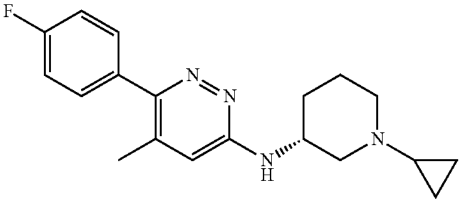
;
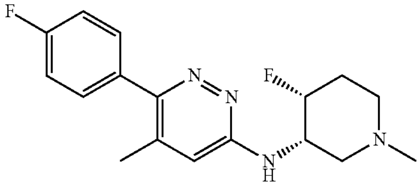
;
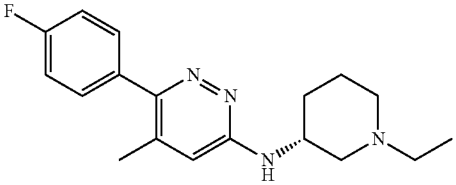
;
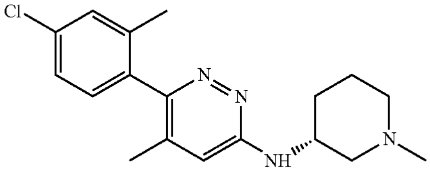
;
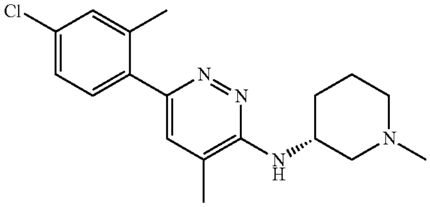
;
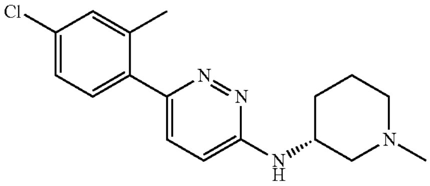
;
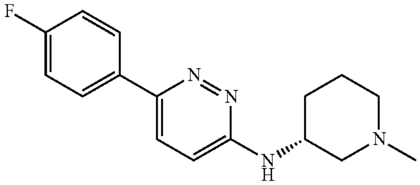
;
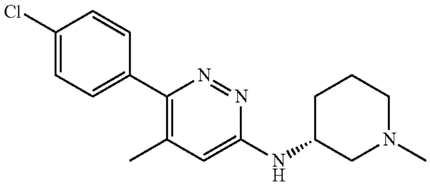
;

-continued
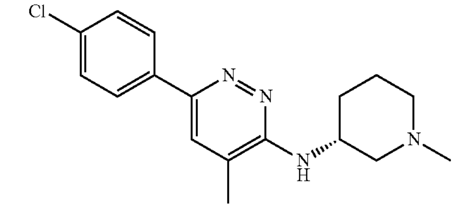
;
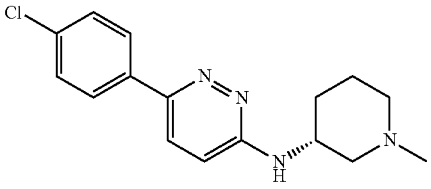
;
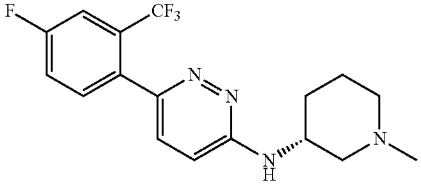
;
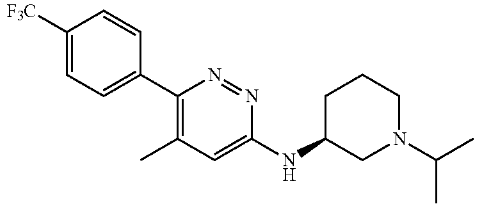
;
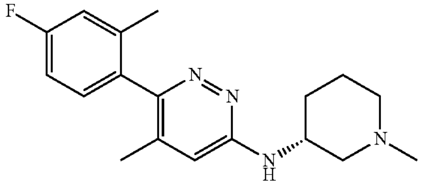
;
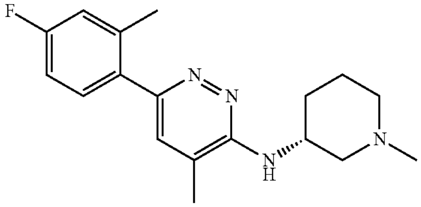
;
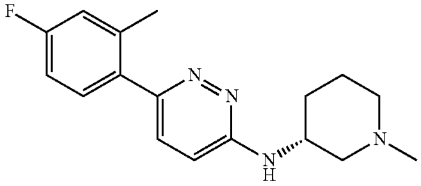
;
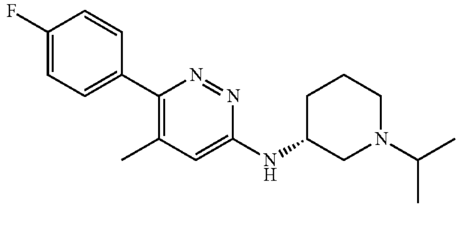
;
-continued
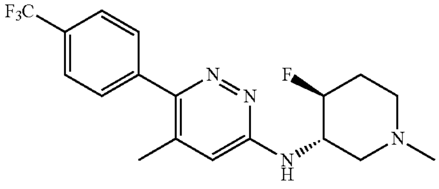
;
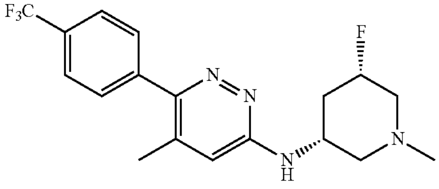
;
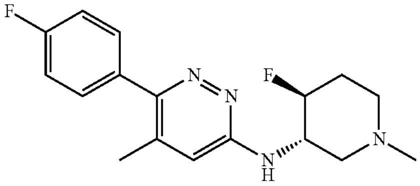
;
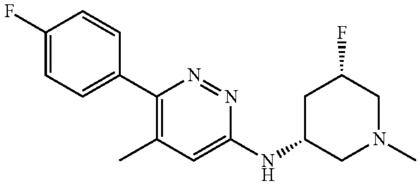
;
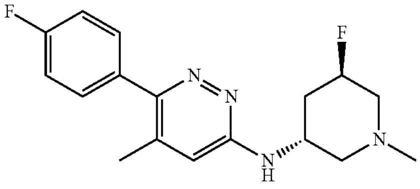
;
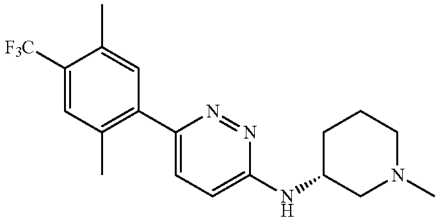
;
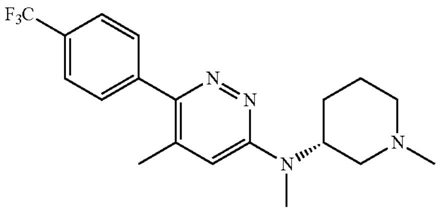
;
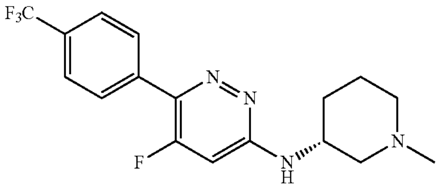
;

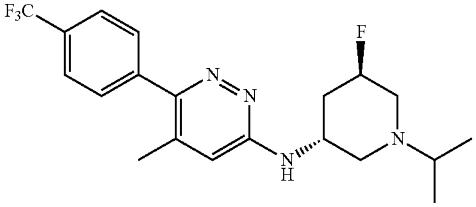
;
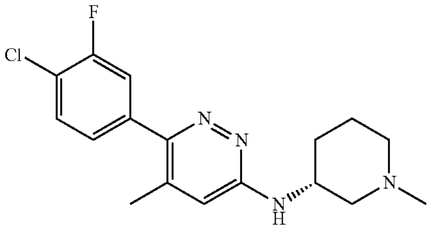
;
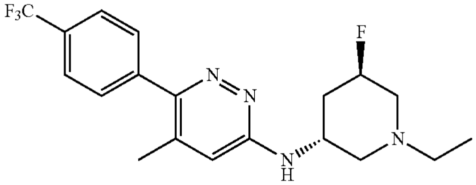
;
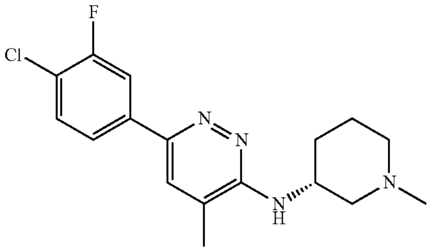
;
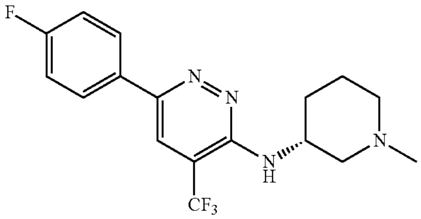
;
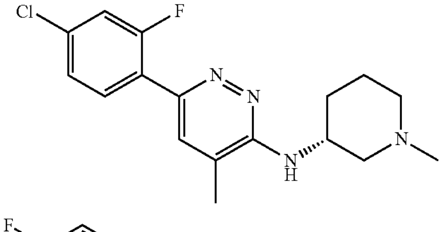
;
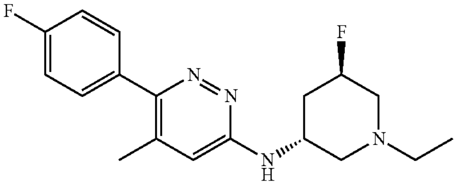
;
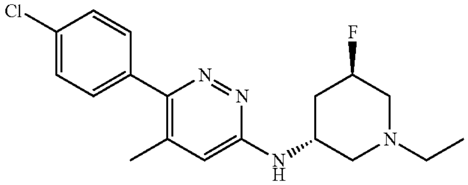
;
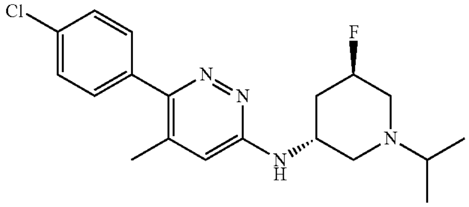
;
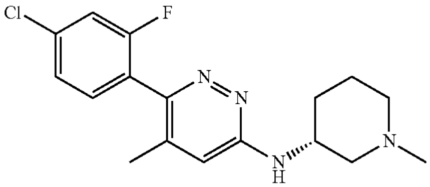
;
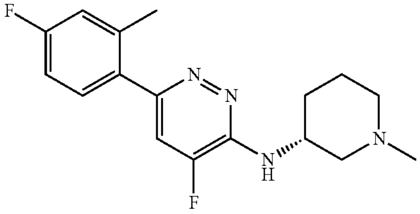
;
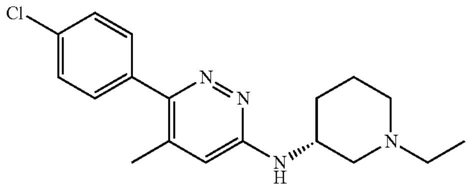
;
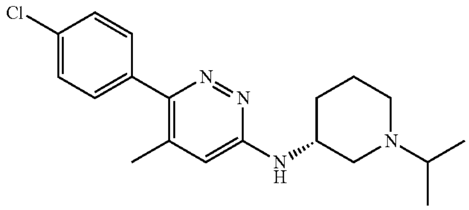
;
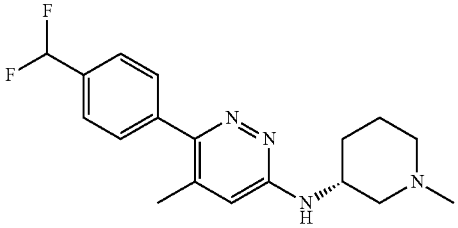
;
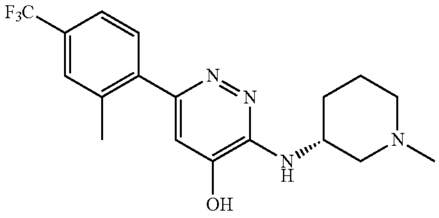
;
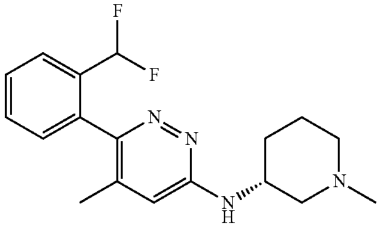
;

-continued
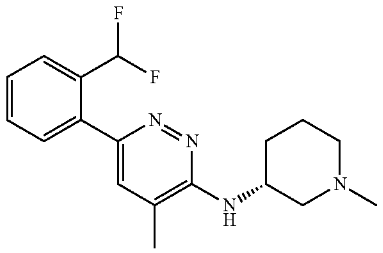
;
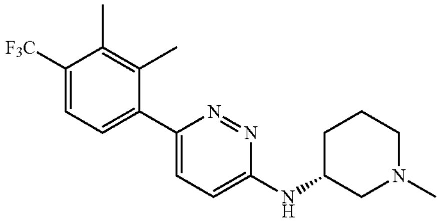
;
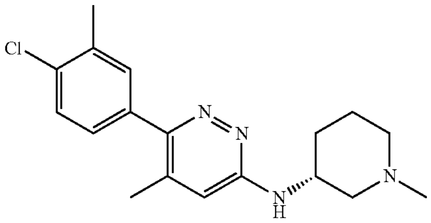
;
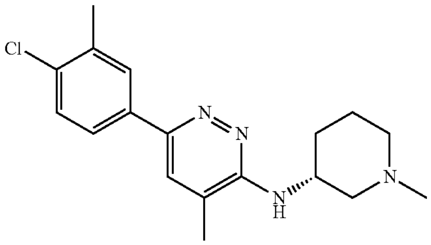
;
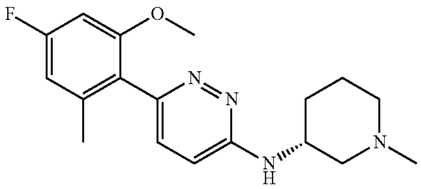
;
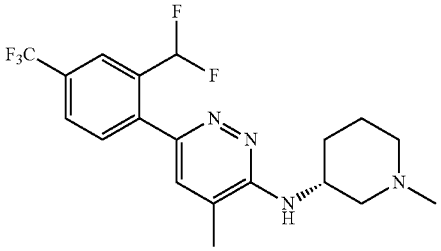
;
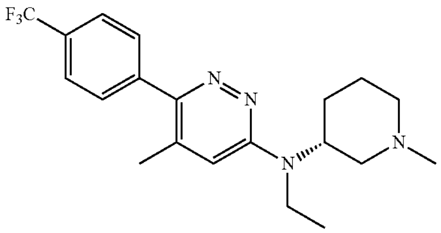
;
-continued
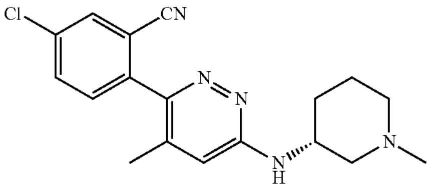
;
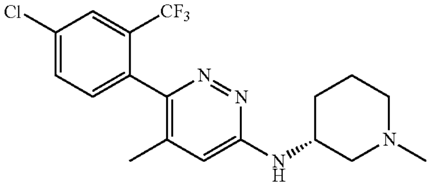
;
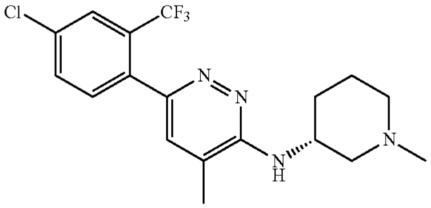
;
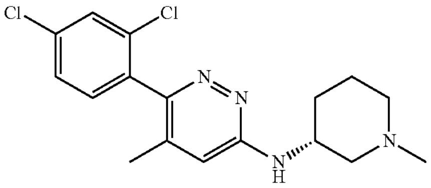
;
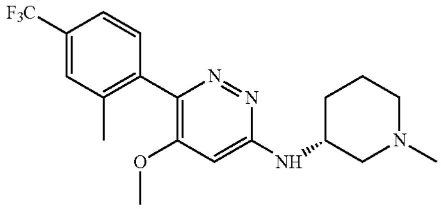
;
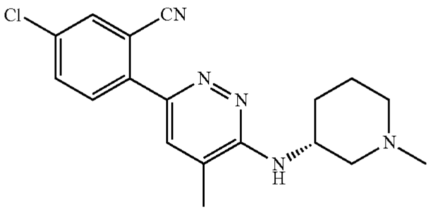
;
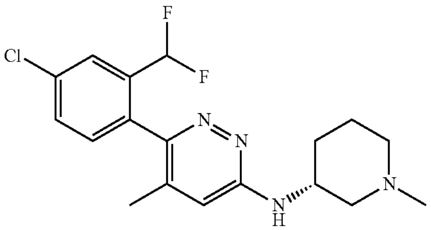
;
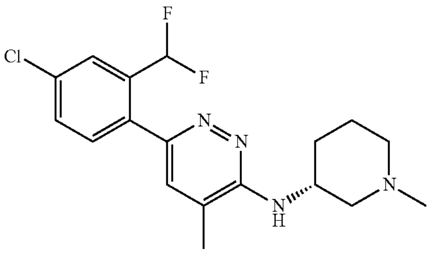
;

-continued
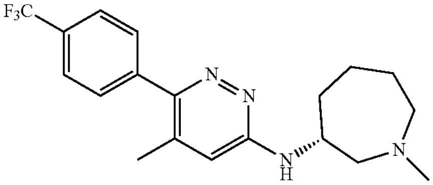
;
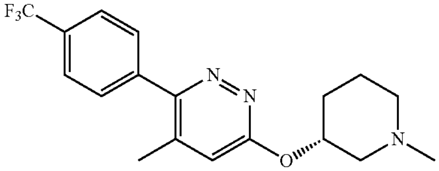 [SMILES: Cc1cc(O[C@@H]2CCCN(C)C2)nnc1-c1ccc(C(F)(F)F)cc1]
;
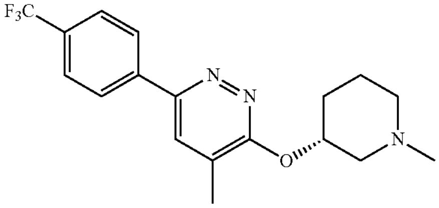
;
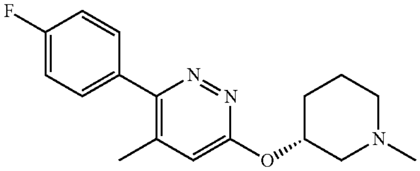
;
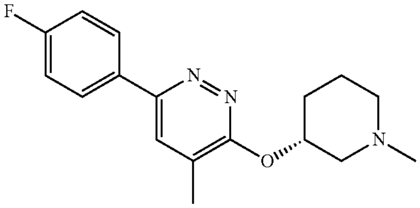
;
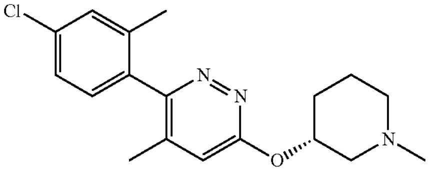
;
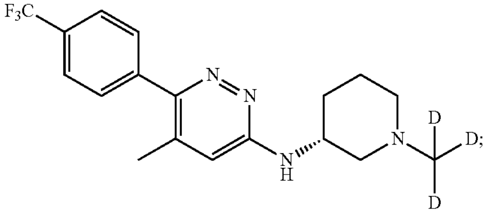
;
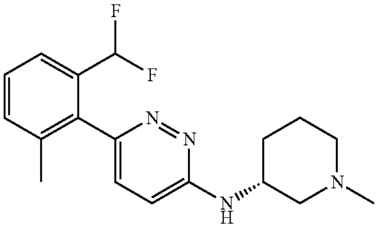
;
-continued
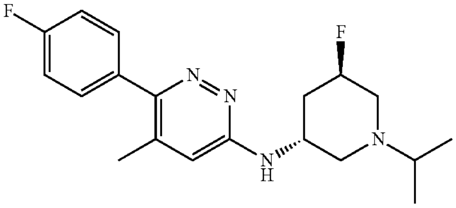
;
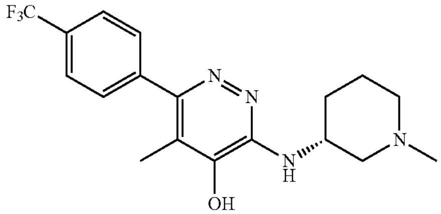
;
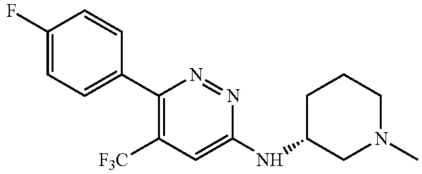
;
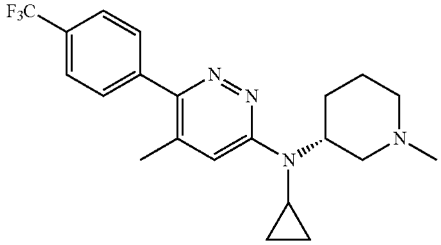
;
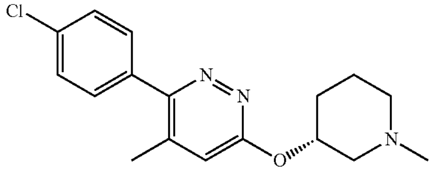
;
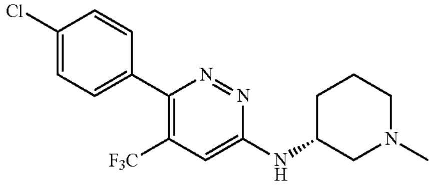
;
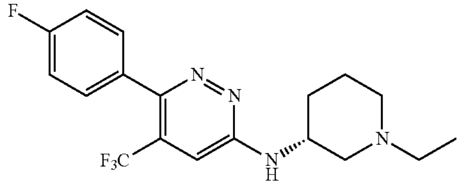
;
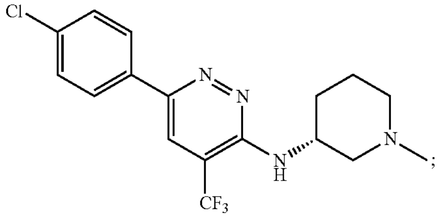
;

-continued

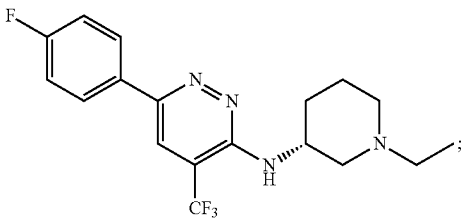

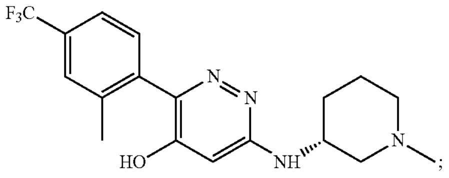

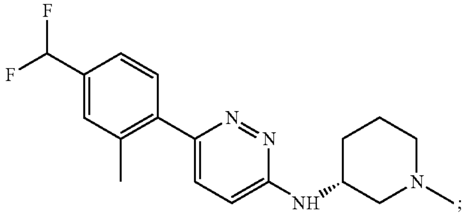

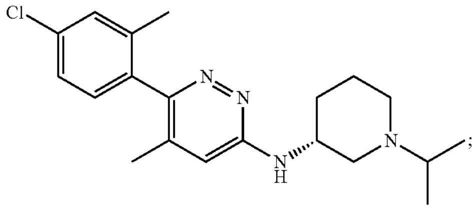

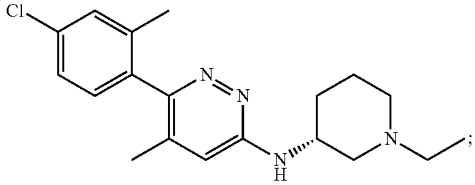

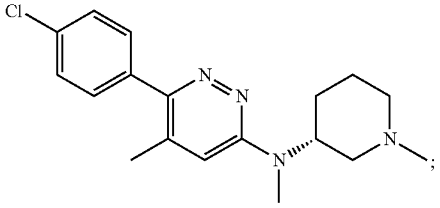

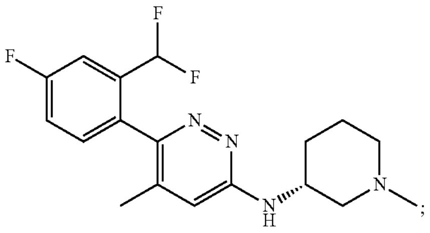

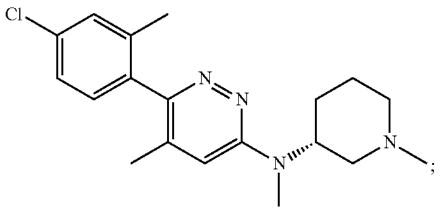

-continued

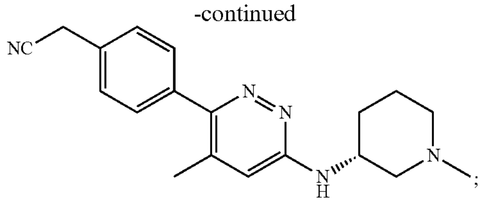

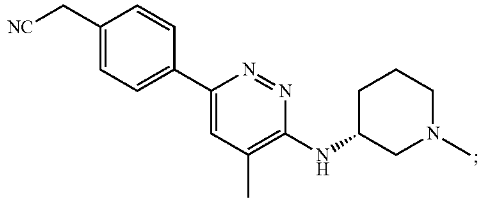

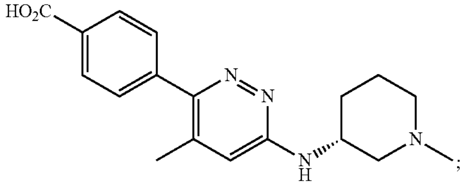

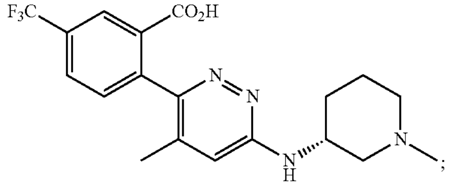

or

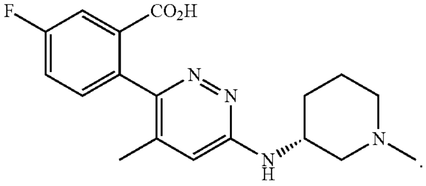

9. A pharmaceutical composition comprising the compound of claim 1, or a pharmaceutically acceptable salt, isomer, hydrate, solvate or isotope thereof, and at least one pharmaceutically acceptable excipient.

10. A method of modulating NLRP3 inflammasome activity by contacting NLRP3 inflammasome with an effective amount of the compound of claim 1, or a pharmaceutically acceptable salt, isomer, hydrate, solvate or isotope thereof.

11. A compound having structure (II):

(II)

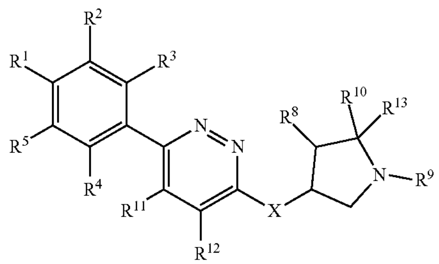

or a pharmaceutically acceptable salt, isomer, hydrate, solvate or isotope thereof, wherein:

X is O or $NR^{15}$;

$R^1$ is OH, $CF_3$, $CHF_2$, $C_{1-6}$ alkyl, $C_{3-5}$ cycloalkyl, CN, F, Cl, $OC_{1-6}$ alkyl or $OCF_3$;

$R^2$, $R^3$, $R^4$, and $R^5$ are independently H, $CF_3$, $CHF_2$, $C_{1-6}$ alkyl, CN, F, Cl, $OCF_3$ or $OC_{1-6}$ alkyl;

$R^8$ is H or halo;

$R^9$ is $C_{3-5}$ cycloalkyl, or $C_{1-6}$ alkyl optionally substituted with one or more $R^{9'}$;

$R^{9'}$ is OH, F, $CHF_2$, $CF_3$ or $C_{3-5}$ cycloalkyl;

$R^{10}$ and $R^{13}$ are independently H or halo;

$R^{11}$ and $R^{12}$ are each, independently, is H, halo, $CF_3$, $C_{1-6}$ alkyl, CN, OH or $OC_{1-6}$ alkyl; and $R^{15}$ is H or $C_{1-6}$ alkyl;

wherein if $R^1$ is F and $R^2$, $R^3$, $R^4$, $R^5$, $R^8$, $R^{11}$ and $R^{12}$ are each H, then $R^9$ is not tert-butyl.

12. The compound of claim 11, wherein the compound has the following structure (IIa'):

(IIa')

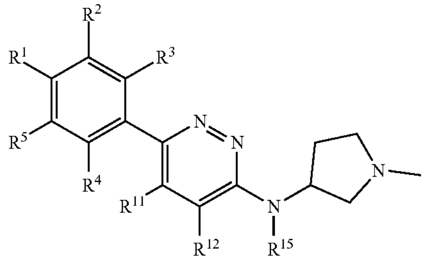

or a pharmaceutically acceptable salt, isomer, hydrate, solvate or isotope thereof, wherein:

$R^1$ is $CF_3$ or F $R^2$, $R^3$, $R^4$, and $R^5$ are independently H, $CF_3$, $CHF_2$, $C_{1-6}$ alkyl, CN, F, Cl, $OCF_3$ or $OC_{1-6}$ alkyl;

$R^{11}$ and $R^{12}$ are each, independently, is H, halo, $CF_3$, $C_{1-6}$ alkyl, CN, OH or $OC_{1-6}$ alkyl; and $R^{15}$ is H or $C_{1-6}$ alkyl.

13. The compound of claim 11, or a pharmaceutically acceptable salt, isomer, hydrate, solvate or isotope thereof, wherein the compound has the following structure:

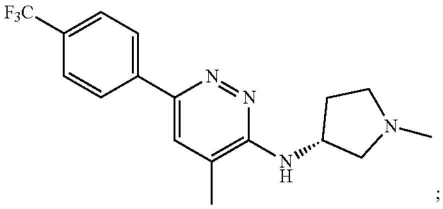

;

-continued

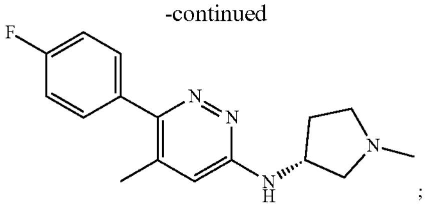

;

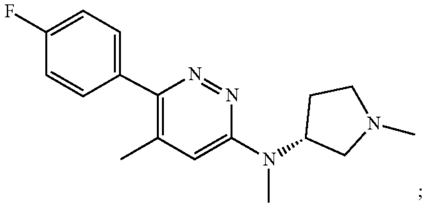

;

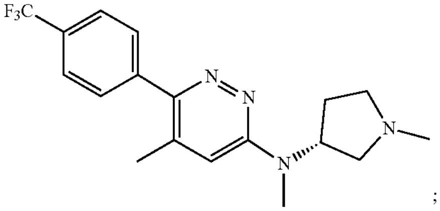

;

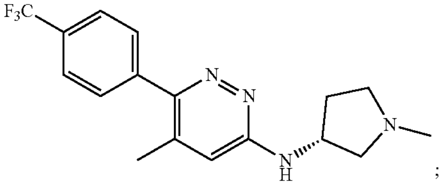

; or

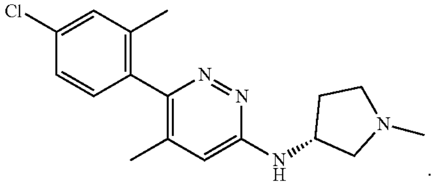

.

14. A pharmaceutical composition comprising the compound of claim 11, or a pharmaceutically acceptable salt, isomer, hydrate, solvate or isotope thereof, and at least one pharmaceutically acceptable excipient.

15. A method of modulating NLRP3 inflammasome activity by contacting NLRP3 inflammasome with an effective amount of the compound of claim 11, or a pharmaceutically acceptable salt, isomer, hydrate, solvate or isotope thereof.

* * * * *